(12) United States Patent
Kuksa et al.

(10) Patent No.: US 9,447,078 B2
(45) Date of Patent: Sep. 20, 2016

(54) SUBSTITUTED HETEROCYCLIC COMPOUNDS FOR DISEASE TREATMENT

(71) Applicant: Acucela Inc., Seattle, WA (US)

(72) Inventors: Vladimir A. Kuksa, Bothell, WA (US); Mark W. Orme, Seattle, WA (US); Feng Hong, Bellevue, WA (US); Ryo Kubota, Seattle, WA (US)

(73) Assignee: ACUCELA INC., Seattle, WA (US)

( * ) Notice: Subject to any disclaimer, the term of this patent is extended or adjusted under 35 U.S.C. 154(b) by 22 days.

(21) Appl. No.: 13/745,675

(22) Filed: Jan. 18, 2013

(65) Prior Publication Data

US 2013/0225619 A1     Aug. 29, 2013

Related U.S. Application Data

(60) Provisional application No. 61/589,108, filed on Jan. 20, 2012.

(51) Int. Cl.

| | |
|---|---|
| C07D 213/36 | (2006.01) |
| C07D 213/42 | (2006.01) |
| C07D 405/12 | (2006.01) |
| C07D 207/36 | (2006.01) |
| C07D 213/38 | (2006.01) |
| C07D 213/64 | (2006.01) |
| C07D 213/71 | (2006.01) |
| C07D 239/34 | (2006.01) |
| C07D 249/04 | (2006.01) |
| C07D 277/28 | (2006.01) |
| C07D 307/52 | (2006.01) |
| C07D 307/58 | (2006.01) |
| C07D 307/66 | (2006.01) |
| C07D 333/20 | (2006.01) |
| C07D 333/32 | (2006.01) |
| C07D 333/36 | (2006.01) |
| C07D 401/12 | (2006.01) |
| C07D 213/74 | (2006.01) |
| C07D 333/16 | (2006.01) |
| C07D 333/34 | (2006.01) |
| C07D 213/30 | (2006.01) |
| C07D 213/65 | (2006.01) |
| C07D 213/68 | (2006.01) |
| C07D 213/70 | (2006.01) |
| C07D 307/42 | (2006.01) |

(52) U.S. Cl.
CPC .......... *C07D 405/12* (2013.01); *C07D 207/36* (2013.01); *C07D 213/30* (2013.01); *C07D 213/38* (2013.01); *C07D 213/64* (2013.01); *C07D 213/65* (2013.01); *C07D 213/68* (2013.01); *C07D 213/70* (2013.01); *C07D 213/71* (2013.01); *C07D 213/74* (2013.01); *C07D 239/34* (2013.01); *C07D 249/04* (2013.01); *C07D 277/28* (2013.01); *C07D 307/42* (2013.01); *C07D 307/52* (2013.01); *C07D 307/58* (2013.01); *C07D 307/66* (2013.01); *C07D 333/16* (2013.01); *C07D 333/20* (2013.01); *C07D 333/32* (2013.01); *C07D 333/34* (2013.01); *C07D 333/36* (2013.01); *C07D 401/12* (2013.01)

(58) Field of Classification Search
CPC .......................... C07D 213/36; C07D 213/42
USPC ....... 546/293, 294, 300, 290, 314, 316, 329, 546/336, 337; 514/346, 351
See application file for complete search history.

(56) References Cited

U.S. PATENT DOCUMENTS

| | | |
|---|---|---|
| 3,509,153 A | 4/1970 | Shin et al. |
| 3,644,353 A | 2/1972 | Lunts et al. |
| 4,214,001 A | 7/1980 | Engelhardt et al. |
| 4,569,354 A | 2/1986 | Shapiro et al. |
| 5,049,587 A | 9/1991 | Okamoto et al. |
| 5,135,955 A | 8/1992 | Campbell et al. |
| 5,641,750 A | 6/1997 | Louis |
| 5,736,516 A | 4/1998 | Louis |
| 5,958,973 A | 9/1999 | Bischofberger et al. |
| 6,051,605 A | 4/2000 | Capiris et al. |
| 6,090,624 A | 7/2000 | Greenwood et al. |
| 6,117,675 A | 9/2000 | Van Der Kooy et al. |
| 6,162,943 A | 12/2000 | Lui et al. |
| 6,183,735 B1 | 2/2001 | Greenwood et al. |
| 6,406,840 B1 | 6/2002 | Li et al. |

(Continued)

FOREIGN PATENT DOCUMENTS

| | | |
|---|---|---|
| CH | 396941 | 8/1965 |
| EP | 0525360 | 2/1993 |

(Continued)

OTHER PUBLICATIONS

Dorwald, Side Reactions in Organic Synthesis, 2005, Wiley: VCH Weinheim Preface, pp. 1-15 & Chapter 8, pp. 279-308.*

(Continued)

*Primary Examiner* — Patricia L Morris

(74) *Attorney, Agent, or Firm* — Wilson, Sonsini, Goodrich & Rosati

(57) ABSTRACT

The present invention relates generally to compositions and methods for treating neurodegenerative diseases and disorders, particularly ophthalmic diseases and disorders. Provided herein are substituted heterocyclic amine derivative compound and pharmaceutical compositions comprising these compounds. The subject compositions are useful for treating and preventing ophthalmic diseases and disorders, including age-related macular degeneration (AMD) and Stargardt's Disease.

18 Claims, No Drawings

(56) References Cited

U.S. PATENT DOCUMENTS

| | | | |
|---|---|---|---|
| 6,713,300 B1 | 3/2004 | Allikmets et al. | |
| 6,713,458 B1 | 3/2004 | Yerxa et al. | |
| 7,982,071 B2 | 7/2011 | Scott et al. | |
| 8,076,516 B2 | 12/2011 | Scott et al. | |
| 8,299,307 B2 | 10/2012 | Scott et al. | |
| 8,389,771 B2 | 3/2013 | Scott et al. | |
| 8,420,863 B2 | 4/2013 | Scott et al. | |
| 8,445,476 B2 * | 5/2013 | Wagman et al. | 514/210.04 |
| 8,450,527 B2 | 5/2013 | Scott et al. | |
| 8,492,589 B2 | 7/2013 | Scott et al. | |
| 8,653,142 B2 | 2/2014 | Scott et al. | |
| 8,674,137 B2 | 3/2014 | Scott et al. | |
| 8,716,529 B2 | 5/2014 | Scott et al. | |
| 8,766,007 B2 | 7/2014 | Scott et al. | |
| 2002/0009713 A1 | 1/2002 | Miller et al. | |
| 2002/0058685 A1 | 5/2002 | Hamilton | |
| 2003/0032078 A1 | 2/2003 | Travis | |
| 2003/0050283 A1 | 3/2003 | Richter et al. | |
| 2003/0186961 A1 | 10/2003 | Hamilton et al. | |
| 2004/0116403 A1 | 6/2004 | Klimko et al. | |
| 2004/0147019 A1 | 7/2004 | Kubota et al. | |
| 2005/0043386 A1 | 2/2005 | Nishi et al. | |
| 2005/0059148 A1 | 3/2005 | Kubota | |
| 2005/0159662 A1 | 7/2005 | Imanishi et al. | |
| 2006/0069078 A1 | 3/2006 | Rando | |
| 2006/0252107 A1 | 11/2006 | Kubota | |
| 2006/0281821 A1 | 12/2006 | Palczewski et al. | |
| 2007/0002275 A1 | 1/2007 | Yan et al. | |
| 2008/0167307 A1 | 7/2008 | Tozawa et al. | |
| 2009/0062353 A1 | 3/2009 | Scott et al. | |
| 2009/0088435 A1 | 4/2009 | Mata et al. | |
| 2009/0170841 A1 | 7/2009 | Scott et al. | |
| 2009/0281149 A1 | 11/2009 | Scott et al. | |
| 2009/0326074 A1 | 12/2009 | Scott et al. | |
| 2010/0081702 A1 | 4/2010 | Shimozato et al. | |
| 2010/0093865 A1 | 4/2010 | Scott et al. | |
| 2010/0113539 A1 | 5/2010 | Scott et al. | |
| 2011/0003895 A1 | 1/2011 | Kubota et al. | |
| 2011/0082181 A1 | 4/2011 | Seiders et al. | |
| 2012/0004269 A1 | 1/2012 | Scott et al. | |
| 2012/0041038 A1 | 2/2012 | Scott et al. | |
| 2012/0041039 A1 | 2/2012 | Scott et al. | |
| 2012/0122938 A1 | 5/2012 | Scott et al. | |
| 2012/0129860 A1 | 5/2012 | Scott et al. | |
| 2012/0129894 A1 | 5/2012 | Scott et al. | |
| 2012/0214852 A1 | 8/2012 | Scott et al. | |
| 2013/0018077 A1 | 1/2013 | Scott et al. | |
| 2013/0030026 A1 | 1/2013 | Scott et al. | |
| 2013/0197096 A1 | 8/2013 | Scott et al. | |
| 2013/0225619 A1 | 8/2013 | Kuksa et al. | |
| 2013/0253064 A1 | 9/2013 | Scott et al. | |
| 2014/0039048 A1 | 2/2014 | Scott et al. | |

FOREIGN PATENT DOCUMENTS

| | | |
|---|---|---|
| EP | 0706994 A1 | 4/1996 |
| EP | 1300405 A1 | 4/2003 |
| EP | 1661881 A2 | 5/2006 |
| GB | 884663 | 11/1959 |
| JP | H07-41468 | 2/1995 |
| WO | WO-93-15045 A1 | 8/1993 |
| WO | WO-95-19952 | 7/1995 |
| WO | WO-98-12303 | 3/1998 |
| WO | WO-99-16783 | 4/1999 |
| WO | WO-99-29279 A2 | 6/1999 |
| WO | WO-00-40699 | 7/2000 |
| WO | WO-01-09327 | 2/2001 |
| WO | WO-01-42784 | 6/2001 |
| WO | WO-0153297 A1 | 7/2001 |
| WO | WO-01-81551 | 11/2001 |
| WO | WO-01-83714 | 11/2001 |
| WO | WO-2004-013082 | 2/2004 |
| WO | WO-2005-020882 | 3/2005 |
| WO | WO-2006021884 A2 | 3/2006 |
| WO | WO-2007-038372 A1 | 4/2007 |
| WO | WO-2007053345 A1 | 5/2007 |
| WO | WO-2007-079593 | 7/2007 |
| WO | WO-2007-120528 A2 | 10/2007 |
| WO | WO-2007140117 A1 | 12/2007 |
| WO | WO-2009-045479 | 4/2009 |
| WO | WO-2011-003103 | 1/2011 |

OTHER PUBLICATIONS

Guillory (in Brittain ed.), "Polymorphism in Pharmaceutical Solids.," NY: Marcel Dekker, Inc., 1999, 1-2, 125-181, 183-226.*

Yu et al., "Physical characterization of, etc.,", PSTT, vl. 1(3), 118-127 (1998).*

Vippagunta et al., "Crystalline Solids", Advanced Drug Delivery Reviews 48 (2001) 3-26.*

Ahmed et al., "Oxygen distribution in the macaque retina," Invest. Ophthalmol. Vis. Sci. 34(3):516-521 (1993).

Akula et al., "Rod photoreceptor function predicts blood vessel abnormality in retinopathy of prematurity," Invest. Ophthalmol. Vis. Sci. 48(9):4351-4359 (2007).

Allikmets et al., "A photoreceptor cell-specific ATP-binding transporter gene (ABCR) is mutated in recessive Stargardt macular dystrophy," Nat. Genet. 15(3):236-246 (1997).

Ambati et al., "An animal model of age-related macular degeneration in senescent Ccl-2- or Ccr-2-deficient mice," Nat. Med. 9(11):1390-1397 (2003); Epub Oct. 19, 2003.

Arden et al., "Spare the rod and spoil the eye," Br. J. Ophthalmol. 89(6):764-769 (2005).

Asi et al., "Relationships between the electroretinogram a-wave, b-wave and oscillatory potentials and their application to clinical diagnosis," Documenta Ophthalmologica 79(2):125-139 (1992).

Berge, SM et al. "Pharmaceutical Salts," Journal of Pharmaceutical Science, vol. 66, Issue 1, pp. 1-19, Jan. 1977.

Chemical Encyclopedia, scientific publishing house, Big Russian Encyclopedia, Moscow, 1985, vol. 4, p. 380, col. 752.

Chen et al., "RPE65 gene delivery restores isomerohydrolase activity and prevents early cone loss in RPE65−/− mice," Invest. Ophthalmol. Vis. Sci. 47(3):1177-1184 (2006).

Crabb et al., "Cloning of the cDNAs encoding the cellular retinaldehyde-binding protein from bovine and human retina and comparison of the protein structures," J. Biol. Chem. 263(35):18688-18692 (1988).

Crabb et al., "Structural and functional characterization of recombinant human cellular retinaldehyde-binding protein," Protein Sci. 7(3):746-757 (1998).

Cringle et al., "Intraretinal oxygen consumption in the rat in vivo," Invest. Ophthalmol. Vis Sci. 43(6):1922-1927 (2002).

De Gooyer et al., "Rod photoreceptor loss in Rho−/− mice reduces retinal hypoxia and hypoxia-regulated gene expression," Invest. Ophthalmol. Vis Sci. 47(12):5553-5560 (2006).

De Laey, et al. Hyperlipofuscinosis and subretinal fibrosis in Stargardt's disease. Retina 15(5):399-406 (1995).

Deigner et al., "Membranes as the energy source in the endergonic transformation of vitamin A to 11-cis-retinol," Science 244(4907):968-971 (1989).

Dembinska et al., "Evidence for a brief period of enhanced oxygen susceptibility in the rat model of oxygen-induced retinopathy," Invest. Ophthalmol. Vis. Sci. 43(7):2481-2490 (2002).

Dentchev et al., "Amyloid-beta is found in drusen from some age-related macular degeneration retinas, but not in drusen from normal retinas," Mol. Vis. 9:184-190 (2003).

Eldred et al., "Retinal age pigments generated by self-assembling lysosomotropic detergents," Nature 361(6414):724-726 (1993).

Epstein, E., "Alkoxyphenyl N-Substituted Aminopropanols," J. Am. Chem. Soc. 81(23):6207-6209 (1959).

Envision Clarity Trial 2010 [online] [retrieved on Feb. 16, 2012]. Retrieved from the Internet: http://www.envisiontrial.com, Acucela, Inc.

Ettmayer, Peter, "Lessons Learned from Marketed and Investigational Prodrugs," Medicinal Chemistry, 47(10):2394-2404 (2004).

Experimental Treatments for Macular Degeneration. [online] The New York Times: Consults, Experts on the Front Lines of Medicine, Sep. 21, 2011, [retrieved on Feb. 17, 2012], Retrieved from the

(56) References Cited

OTHER PUBLICATIONS

Internet: http://consults.blogs.nytimes.com/2011/09/21/experimental-treatments-for-macular-degeneration/.
Filipek et al., "G protein-coupled receptor rhodopsin: a prospectus," Annu. Rev. Physiol. vol. 65, pp. 851-879 (2003).
Finnemann et al., "The lipofuscin component A2E selectively inhibits phagolysosomal degradation of photoreceptor phospholipid by the retinal pigment epithelium," Proc. Natl. Acad. Sci. USA 99(6):3842-3847 (2002).
Giasson et al., "The relationship between oxidative/nitrative stress and pathological inclusions in Alzheimer's and Parkinson's diseases," Free Radic. Biol. Med. 32(12):1264-1275 (2002).
Glazer et al., "Understanding the etiology of Stargardt's disease," Ophthalmol. Clin. North Am. 15(1):93-100, viii (2002).
Golczak et al., "Positively charged retinoids are potent and selective inhibitors of the trans-cis isomerization in the retinoid (visual) cycle," Proc. Natl. Acad. Sci. USA 102(23):8162-8167 (2005).
Gollapalli et al., "Specific inactivation of isomerohydrolase activity by 11-cis-retinoids," Biochim Biophys Acta. 1651(1-2):93-101 (2003).
Gollapalli et al., "The specific binding of retinoic acid to RPE65 and approaches to the treatment of macular degeneration," Proc. Natl. Acad. Sci. USA 101(27):10030-10035 (2004).
Gorin et al., "The genetics of age-related macular degeneration," Mol. Vis. 5:29 (1999).
Groenendijk, et al, "Quantitative determination of retinals with complete retention of their geometric configuration," Biochim Biophys. Acta. 617(3):430-438 (1980).
Gwiazda et al., "Myopia and ambient night-time lighting," Nature 404(6774):144 (2000).
Haeseleer et al., "Essential role of Ca2+-binding protein 4, a Cav1.4 channel regulator, in photoreceptor synaptic function," Nat. Neurosci. 7(10):1079-1087 (2004).
Hancock et al., "Oscillatory potential analysis and ERGs of normal and diabetic rats," Invest. Ophthalmol. Vis. Sci. 45(3):1002-1008 (2004).
Holz et al., "Inhibition of lysosomal degradative functions in RPE cells by a retinoid component of lipofuscin," Invest. Ophthalmol. Vis. Sci. 40(3):737-743 (1999).
Imanishi et al., "Noninvasive two-photon imaging reveals retinyl ester storage structures in the eye," J Cell Biol. 164(3):373-383 (2004).
Intres et al., "Molecular cloning and structural analysis of the human gene encoding cellular retinaldehyde-binding protein," J. Biol. Chem. 269(41):25411-25418 (1994).
Iyengar et al., "Dissection of genomewide-scan data in extended families reveals a major locus and oligogenic susceptibility for age-related macular degeneration," Am. J. Hum. Genet. 74(1):20-39 (2004); Epub Dec. 19, 2003.
Jaakson et al., "Genotyping microarray (gene chip) for the ABCR (ABCA4) gene," Hum. Mutat. 22(5):395-403 (2003).
Johnson et al, "The Alzheimer's amyloid beta-peptide is deposited at sites of complement activation in pathologic deposits associated with aging and age-related macular degeneration," Proc. Natl. Acad. Sci. USA 99(18):11830-11835 (2002).
Kano et al., "A synthesis of dibenz[b,f]azecines from 1-halogenobenzyl-1H-2-benzazepines," Chem. Pharm. Bull. 25(9):2401-2409 (1977).
Karan et al., "Lipofuscin accumulation, abnormal electrophysiology, and photoreceptor degeneration in mutant ELOVL4 transgenic mice: a model for macular degeneration," Proc. Natl. Acad. Sci. 102(11):4164-4169 (2005).
Keating et al., "Technical aspects of multifocal ERG recording," Documenta Ophthalmologica 100(2-3):77-98 (2000).
Kenealy et al., "Linkage analysis for age-related macular degeneration supports a gene on chromosome 10q26," Mol. Vis. 10:57-61 (2004).
Kermani et al., "Refined genetic and physical positioning of the gene for Doyne honeycomb retinal dystrophy (DHRD)," 104:77-82 (1999).

Kljavin et al., "Müller cells are a preferred substrate for in vitro neurite extension by rod photoreceptor cells," J. Neurosci. 11(10):2985-9294 (1991).
Koevary, "Pharmacokinetics of topical ocular drug delivery:potential uses for the treatment of diseases of the posterior segement and beyond," Curr. Drug Metab. 4(3):213-222 (2003).
Lamb et al., "Dark adaptation and the retinoid cycle of vision," Prog. Retin. Eye Res. 23(3):307-380 (2004).
Law et al., "The molecular basis of retinoic acid induced night blindness," Biochem. Biophys. Res. Commun. 161(2):825-829 (1989).
Lee et al., "Review on the systemic delivery of insulin via the ocular route," Int. J. Pharm. 233(1-2):1-18 (2002).
Li, et al., "Integrin alpha(1) beta(1)-mediated activation of cyclin-dependent kinase 5 activity is involved in neurite outgrowth and human neurofilament protein H Lys-Ser-Pro tail domain phosphorylation," J. Neurosci. 20(16):6055-6062 (2000).
Liang et al., "Rhodopsin signaling and organization in heterozygote rhodopsin knockout mice," J. Biol. Chem. 279: 48189-48196 (2004).
Liu et al., "The retinal vasculature and function of the neural retina in a rat model of retinopathy of prematurity," Invest. Ophthalmol. Vis. Sci. 47(6):2639-2647 (2006).
Liu et al., "Development of the electroretinographic oscillatory potentials in normal and ROP rats," Invest. Ophthalmol. Vis Sci. 47(12):5447-5452 (2006).
Luan et al., "Retinal thickness and subnormal retinal oxygenation response in experimental diabetic retinopathy," Invest. Ophthalmol. Vis. Sci. 47(1):320-328 (2006).
Maeda A., et al., "Effects of potent inhibitors of the retinoid cycle on visual function and photoreceptor protection from light damage in mice," Molecular Pharmacology, American Society for Pharmacology and Experimental Therapeutics, vol. 70, No. 4, Oct. 1, 2006, p. 1220-1229.
Maeda et al., "Evaluation of the role of the retinol G protein-coupled receptor (RGR) in the vertebrate retina in vivo," J. Neurochem. 85(4):944-956 (2003).
Mata et al., "Biosynthesis of a major lipofuscin fluorophore in mice and humans with ABCR-mediated retinal and macular degeneration," Proc. Natl. Acad. Sci. USA 97(13):7154-7159 (2000).
Mata et al., "Delayed dark-adaptation and lipofuscin accumulation in abcr+/− mice: implications for involvement of ABCR in age-related macular degeneration," Invest. Ophthalmol. Vis. Sci. 42(8):1685-1690 (2001).
Mata et al., "Isomerization and oxidation of vitamin A in cone-dominant retinas: a novel pathway for visual-pigment regeneration in daylight," Neuron 36(1):69-80 (2002).
Mcbee et al., "Confronting complexity: the interlink of phototransduction and retinoid metabolism in the vertebrate retina," Prog. Retin. Eye Res. 20(4):469-529 (2001).
Moiseyev et al., "RPE65 is the isomerohydrolase in the retinoid visual cycle." Proc. Natl. Acad. Sci. USA 102(35):12413-12418 (2005).
Morisette et al., "High-throughput crystallization: polymorphs, slats, co-crystals, and solvates of pharmaceutical solids," Advanced Drug Delivery Reviews, 56, 275-300 (2004).
N.A. Tyukavina, Yu I. Baukov, Bio Organic Chemistry, DROFA, M. 2005, p. 83-85.
Oglivie, et al., "Growth factors in combination, but not individually, rescue rd mouse photoreceptors in organ culture", Exp. Neurol. 161(2):676-685 (2000).
Okajima et al., "Retinol kinetics in the isolated retina determined by retinoid extraction and HPLC," Exp. Eye Res. 65(3):331-340 (1997).
Parish et al., "Isolation and one-step preparation of A2E and iso-A2E, fluorophores from human retinal pigment epithelium," Proc. Natl. Acad. Sci. USA 95(25):14609-14613 (1998).
PCT/US2013/022304 International Search Report dated Mar. 25, 2013.
Penn et al., "Oxygen-induced retinopathy in the rat: relationship of retinal nonperfusion to subsequent neovascularization," Invest. Ophthalmol. Vis. Sci. 35(9):3429-3435 (1994).

(56) References Cited

OTHER PUBLICATIONS

Phipps et al., "Rod photoreceptor dysfunction in diabetes: activation, deactivation, and dark adaptation," Invest. Ophthalmol. Vis. Sci. 47(7):3187-3194 (2006).
Prasad P.S., et al. "Age-related macular degeneration: Current and novel therapies," Maturitas, Elsevier Science Publishers, Ireland Ltd., vol. 66, No. 1, May 1, 2012, pp. 46-50.
Quinn et al., "Myopia and ambient lighting at night," Nature 399(6732):113-114 (1999).
Radu et al., "Treatment with isotretinoin inhibits lipofuscin accumulation in a mouse model of recessive Stargardt's macular degeneration," Proc. Natl. Acad. Sci. USA, 100(8):4742-4747 (Apr. 15, 2003).
Radu et al., "Light exposure stimulates formation of A2E oxiranes in a mouse model of Stargardt's macular degeneration," Proc. Natl. Acad. Sci. USA 101(16):5928-5933 (2004).
Ramsey et al., "An electrophysiological study of retinal function in the diabetic female rat," Invest. Ophthalmol. Vis. Sci. 47(11):5116-5124 (2006).
Seddon et al., "Assessment of mutations in the Best macular dystrophy (VMD2) gene in patients with adult-onset foveomacular vitelliform dystrophy, age-related maculopathy, and bull's-eye maculopathy," Ophthalmology 108(11):2060-2067 (2001).
Sharma et al., "Identification of substrate binding site of cyclin-dependent kinase 5," J. Biol. Chem. 274(14):9600-9606 (1999).
Sieving et al., "Inhibition of the visual cycle in vivo by 13-*cis* retinoic acid protects from light damage and provides a mechanism for night blindness in isotretinoin therapy," *Proc. Natl. Acad. Sci. USA*, 98(4):1835-1840 (Feb. 13, 2001).
Spaeth, Ed., "Ophthalmic Surgery: Principles of Practice," W. B. Sanders Co., Philadelphia, Pa., 85-87 (1990).
Sparrow et al., "A2E, a lipofuscin fluorophore, in human retinal pigmented epithelial cells in culture," Invest. Ophthalmol. Vis. Sci. 40(12):2988-2995 (1999).
Sparrow et al., "Involvement of Oxidative Mechanisms in Blue-Light Induced Damage to A2E-Laden RPE" Invest. Ophthalmol. Vis. Sci. Apr. 2002, vol. 43, No. 4, pp. 1222-1227.
Sparrow et al., "A2E-epoxides damage DNA in retinal pigment epithelial cells. Vitamin E and other antioxidants inhibit A2E-epoxide formation," J. Biol. Chem. 278(20):18207-18213 (2003).
Sparrow, "Therapy for macular degeneration: insights from acne," Proc. Natl. Acad. Sci. USA 100(8):4353-4354 (2003).
Stella, V.J, "Prodrugs as therapeutics," Expert Opinion of Therapeutic Patents 14(3):277-280 (2004).
Stecher et al., "Preferential release of 11-cis-retinol from retinal pigment epithelial cells in the presence of cellular retinaldehyde-binding protein," J. Biol. Chem. 274(13):8577-8585 (1999).
Sugitomo et al., "A procedure for electroretinogram (ERG) recording in mice—effect of monoiodoacetic acid on the ERG in pigmented mice," J. Toxicol. Sci. 22 Suppl 2:315-325 (1997).
Suter et al., "Age-related macular degeneration. The lipofusion component N-retinyl-N-retinylidene ethanolamine detaches proapoptotic proteins from mitochondria and induces apoptosis in mammalian retinal pigment epithelial cells," J. Biol. Chem. 275(50):39625-39630 (2000).
Suzuki et al., "Retinyl and 3-dehydroretinyl esters in the crayfish retina," Vision Res. 28(10):1061-1070 (1988).
Testa, Bernard, "Prodrug Research: futile or fertile?" Biochemical Pharmacology, 68:2097-2106 (2004).
Trevino et al.,"Retinoid cycles in the cone-dominated chicken retina," J. Exp. Biol. 208(21):4151-4157 (2005).
Van Hooser et al., "Recovery of visual functions in a mouse model of Leber congenital amaurosis," J. Biol. Chem. 277(21):19173-19182 (2002).
Vippagunta et al., "Crystalline Solids," Advanced Drug Delivery Reviews 48:3-26 (2001).
Weng et al., "Insights into the function of Rim protein in photoreceptors and etiology of Stargardt's disease from the phenotype in abcr knockout mice," Cell 98(1):13-23 (1999).
Wentzel et al., "Molecular mechanisms of light-induced photoreceptor apoptosis and neuroprotection for retinal degeneration," Prog. Retin. Eye Res. 24(1):275-306 (2005).
Werdich et al., "Variable oxygen and retinal VEGF levels: correlation with incidence and severity of pathology in a rat model of oxygen-induced retinopathy," Exp. Eye Res. 79(5):623-630 (2004).
Wolff et al., Burger's Medicinal Chemistry, 5th Ed., vol. 1, pp. 975-977, 1994.
Woodruff et al., "Spontaneous activity of opsin apoprotein is a cause of Leber congenital amaurosis," Nat. Genet. 35(2):158-164 (2003).
Yates et al., "Genetic susceptibility to age related macular degeneration," J. Med. Genet. 37(2):83-87 (2000).
Zadnik et al., "Myopia and ambient night-time lighting," Nature 404(6774):143-1444 (2000).
PCT/US2013/022304 International Prelimianry Report on Patentability dated Jul. 31, 2014.
Adlington et al. A versatile approach to pyrimidin-4-yl substituted α-aminoacids from alkynyl ketones; the total synthesis of I-lathyrine. Chemical Communications 18:1575-1758 (1997).
Hoye et al. Synthesis of the C2-Symmetric, Macrocyclic Alkaloid, (+)-Xestospongin A and Its C (9)-Epimer, (−)-Xestospongin C: Impact of Substrate Rigidity and Reaction Conditions on the Efficiency of the Macrocyclic Dimerization Reaction. J Am Chem Soc 118(48):12074-12081 (1996).

* cited by examiner

SUBSTITUTED HETEROCYCLIC COMPOUNDS FOR DISEASE TREATMENT

CROSS REFERENCE

This application claims the benefit of U.S. Provisional Application No. 61/589,108, filed Jan. 20, 2012, which is incorporated herein by reference in its entirety.

BACKGROUND

Neurodegenerative diseases, such as glaucoma, macular degeneration, and Alzheimer's disease, affect millions of patients throughout the world. Because the loss of quality of life associated with these diseases is considerable, drug research and development in this area is of great importance. Age-related macular degeneration (AMD) affects between ten and fifteen million patients in the United States, and it is the leading cause of blindness in aging populations worldwide. AMD affects central vision and causes the loss of photoreceptor cells in the central part of retina called the macula. Due to the great unmet medical need of patients suffering from AMD, new treatments are in great demand.

BRIEF SUMMARY OF THE INVENTION

A need exists in the art for an effective treatment of ophthalmic diseases or disorders resulting in ophthalmic dysfunction including those described above. In particular, there exists a pressing need for compositions and methods for treating Stargardt's disease and age-related macular degeneration (AMD) without causing further unwanted side effects such as progressive retinal degeneration, LCA-like conditions, night blindness, or systemic vitamin A deficiency. A need also exists in the art for effective treatments for other ophthalmic diseases and disorders that adversely affect the retina.

One embodiment provides a compound of Formula (A) or tautomer, stereoisomer, geometric isomer or a pharmaceutically acceptable solvate, hydrate, salt, or N-oxide thereof:

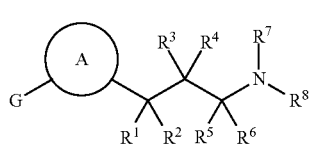

Formula (A)

wherein,
Ring A is selected from a 1,3-disubstituted heterocycle;
G is —X—Y;
X is selected from —O—C($R^9$)$_2$—, —O—C(=O)—, —S—C($R^9$)$_2$—, —S(O)—C($R^9$)$_2$—, —S(O)$_2$—C($R^9$)$_2$—, —SO$_2$(NR$^9$)—, —NR$^9$—C($R^9$)$_2$—, —NR$^9$—C(=O)—, —NR$^9$—S(O)$_2$—, —C($R^9$)$_2$—C($R^9$)$_2$—, —C(=O)—C($R^9$)$_2$—, —C($R^9$)$_2$—C(=O)—, —C($R^9$)=C($R^9$)—, —C≡C—, —C(=O)—N($R^9$)—, —C(=O)—O—, —C($R^9$)$_2$—O—, and —C($R^9$)$_2$—NR$^9$—;
Y is selected from $C_3$-$C_{15}$ alkyl, carbocyclyl, carbocyclylalkyl, heterocyclyl, heterocyclylalkyl, aryl or aralkyl;
$R^1$ and $R^2$ are each independently selected from hydrogen, halogen, alkyl, fluoroalkyl, —OR$^9$, —NR$^{10}$R$^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;
$R^3$ and $R^4$ are each independently selected from hydrogen, halogen, $C_1$-$C_5$ alkyl, fluoroalkyl, —OR$^9$ or —NR$^{10}$R$^{11}$; or $R^3$ and $R^4$ together form an oxo;
$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;
$R^7$ and $R^8$ are each independently selected from hydrogen, alkyl, carbocyclyl, —C(=O)R$^{13}$, SO$_2$R$^{13}$, CO$_2$R$^{13}$ or SO$_2$NR$^{10}$R$^{11}$; or $R^7$ and $R^8$, together with the nitrogen atom to which they are attached, form an N-heterocyclyl;
each $R^9$ independently hydrogen or alkyl;
each $R^{10}$ and $R^{11}$ is independently selected from hydrogen, alkyl, carbocyclyl, heterocyclyl, —C(=O)R$^{13}$, SO$_2$R$^{13}$, CO$_2$R$^{13}$ or SO$_2$NR$^{10}$R$^{11}$; or $R^{10}$ and $R^{11}$ together with the nitrogen atom to which they are attached, form an N-heterocyclyl; and
each $R^{13}$ is independently selected from alkyl, heteroalkyl, alkenyl, aryl, aralkyl, carbocyclyl, heteroaryl or heterocyclyl.

One embodiment provides a compound, or tautomer, stereoisomer, geometric isomer, or pharmaceutically acceptable solvate, hydrate, salt, or N-oxide thereof, selected from the group consisting of:

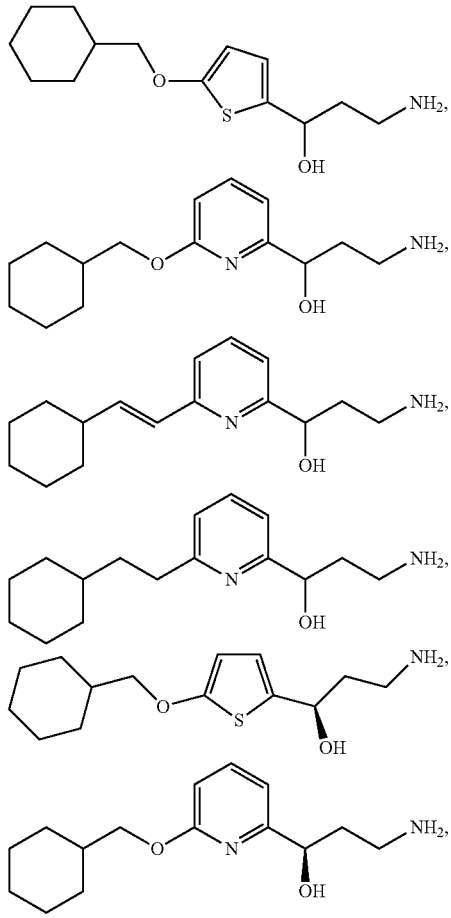

-continued

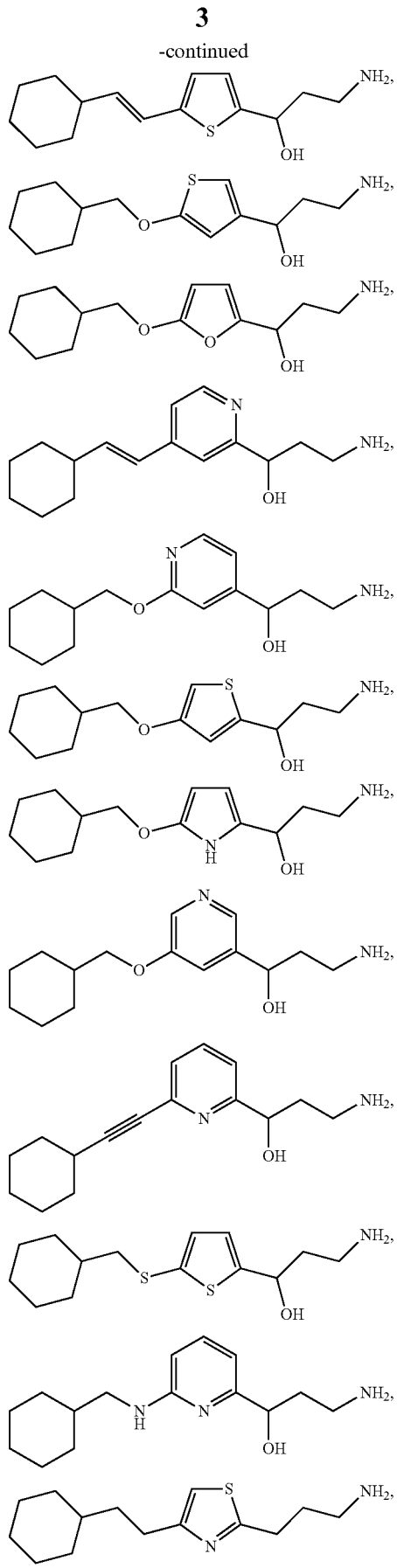

-continued

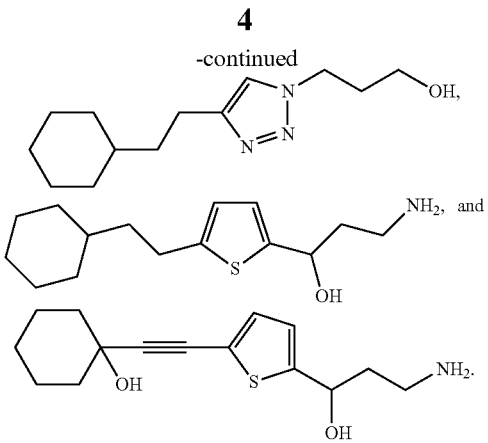

One embodiment provides a pharmaceutical composition comprising a pharmaceutically acceptable carrier and a compound of Formula (A) or tautomer, stereoisomer, geometric isomer, or pharmaceutically acceptable solvate, hydrate, salt, or N-oxide thereof:

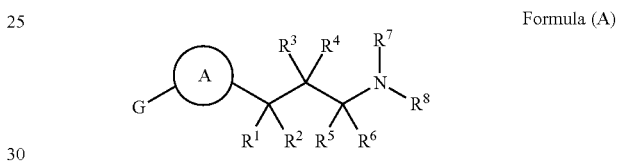

Formula (A)

wherein,
Ring A is selected from a 1,3-disubstituted heterocycle;
G is —X—Y;
X is selected from —O—C($R^9$)$_2$—, —O—C(=O)—, —S—C($R^9$)$_2$—, —S(O)—C($R^9$)$_2$—, —S(O)$_2$—C($R^9$)$_2$—, —SO$_2$(N$R^9$)—, —N$R^9$—C($R^9$)$_2$—, —N$R^9$—C(=O)—, —N$R^9$—S(O)$_2$—, —C($R^9$)$_2$—C($R^9$)$_2$—, —C(=O)—C($R^9$)$_2$—, —C($R^9$)$_2$—C(=O)—, —C($R^9$)=C($R^9$)—, —C≡C—, —C(=O)—N($R^9$)—, —C(=O)—O—, —C($R^9$)$_2$—O—, and —C($R^9$)$_2$—N$R^9$—;
Y is selected from $C_3$-$C_{15}$ alkyl, carbocyclyl, carbocyclylalkyl, heterocyclyl, heterocyclylalkyl, aryl or aralkyl;
$R^1$ and $R^2$ are each independently selected from hydrogen, halogen, alkyl, fluoroalkyl, —O$R^9$, —N$R^{10}R^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;
$R^3$ and $R^4$ are each independently selected from hydrogen, halogen, $C_1$-$C_5$ alkyl, fluoroalkyl, —O$R^9$ or —N$R^{10}R^{11}$; or $R^3$ and $R^4$ together form an oxo;
$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;
$R^7$ and $R^8$ are each independently selected from hydrogen, alkyl, carbocyclyl, —C(=O)$R^{13}$, SO$_2R^{13}$, CO$_2R^{13}$ or SO$_2$N$R^{10}R^{11}$; or $R^7$ and $R^8$, together with the nitrogen atom to which they are attached, form an N-heterocyclyl;
each $R^9$ independently hydrogen or alkyl;

each $R^{10}$ and $R^{11}$ is independently selected from hydrogen, alkyl, carbocyclyl, heterocyclyl, —C(=O)$R^{13}$, $SO_2R^{13}$, $CO_2R^{13}$ or $SO_2NR^{10}R^{11}$; or $R^{10}$ and $R^{11}$ together with the nitrogen atom to which they are attached, form an N-heterocyclyl; and each $R^{13}$ is independently selected from alkyl, heteroalkyl, alkenyl, aryl, aralkyl, carbocyclyl, heteroaryl or heterocyclyl.

One embodiment provides a method for treating an ophthalmic disease or disorder in a subject, comprising administering to the subject a pharmaceutical composition comprising a compound of Formula (A) or tautomer, stereoisomer, geometric isomer, or pharmaceutically acceptable solvate, hydrate, salt, or N-oxide thereof:

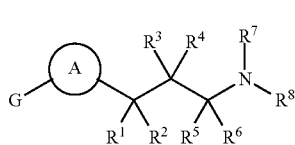

Formula (A)

wherein,
Ring A is selected from a 1,3-disubstituted heterocycle;
G is —X—Y;
X is selected from —O—C($R^9$)$_2$—, —O—C(=O)—, —S—C($R^9$)$_2$—, —S(O)—C($R^9$)$_2$—, —S(O)$_2$—C($R^9$)$_2$—, —SO$_2$(N$R^9$)—, —$NR^9$—C($R^9$)$_2$—, —$NR^9$—C(=O)—, —$NR^9$—S(O)$_2$—, —C($R^9$)$_2$—C($R^9$)$_2$—, —C(=O)—C($R^9$)$_2$—, —C($R^9$)$_2$—C(=O)—, —C($R^9$)=C($R^9$)—, —C≡C—, —C(=O)—N($R^9$)—, —C(=O)—O—, —C($R^9$)$_2$—O—, and —C($R^9$)$_2$—$NR^9$—;
Y is selected from $C_3$-$C_{15}$ alkyl, carbocyclyl, carbocyclylalkyl, heterocyclyl, heterocyclylalkyl, aryl or aralkyl;
$R^1$ and $R^2$ are each independently selected from hydrogen, halogen, alkyl, fluoroalkyl, —$OR^9$, —$NR^{10}R^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;
$R^3$ and $R^4$ are each independently selected from hydrogen, halogen, $C_1$-$C_5$ alkyl, fluoroalkyl, —$OR^9$ or —$NR^{10}R^{11}$; or $R^3$ and $R^4$ together form an oxo;
$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;
$R^7$ and $R^8$ are each independently selected from hydrogen, alkyl, carbocyclyl, —C(=O)$R^{13}$, $SO_2R^{13}$, $CO_2R^{13}$ or $SO_2NR^{10}R^{11}$; or $R^7$ and $R^8$, together with the nitrogen atom to which they are attached, form an N-heterocyclyl;
each $R^9$ independently hydrogen or alkyl;
each $R^{10}$ and $R^{11}$ is independently selected from hydrogen, alkyl, carbocyclyl, heterocyclyl, —C(=O)$R^{13}$, $SO_2R^{13}$, $CO_2R^{13}$ or $SO_2NR^{10}R^{11}$; or $R^{10}$ and $R^{11}$ together with the nitrogen atom to which they are attached, form an N-heterocyclyl; and
each $R^{13}$ is independently selected from alkyl, heteroalkyl, alkenyl, aryl, aralkyl, carbocyclyl, heteroaryl or heterocyclyl.

One embodiment provides a method for treating an ophthalmic disease or disorder in a subject, wherein the ophthalmic disease or disorder is age-related macular degeneration or Stargardt's macular dystrophy.

One embodiment provides a method for treating an ophthalmic disease or disorder in a subject, wherein the ophthalmic disease or disorder is selected from retinal detachment, hemorrhagic retinopathy, retinitis pigmentosa, conerod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS.

One embodiment provides a method of modulating chromophore flux in a retinoid cycle comprising administering to the subject a pharmaceutical composition comprising a compound of Formula (A) or tautomer, stereoisomer, geometric isomer, or pharmaceutically acceptable solvate, hydrate, salt, or N-oxide thereof:

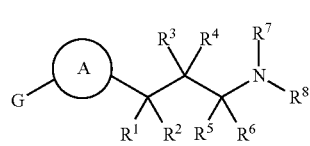

Formula (A)

wherein,
Ring A is selected from a 1,3-disubstituted heterocycle;
G is —X—Y;
X is selected from —O—C($R^9$)$_2$—, —O—C(=O)—, —S—C($R^9$)$_2$—, —S(O)—C($R^9$)$_2$—, —S(O)$_2$—C($R^9$)$_2$—, —SO$_2$(N$R^9$)—, —$NR^9$—C($R^9$)$_2$—, —$NR^9$—C(=O)—, —$NR^9$—S(O)$_2$—, —C($R^9$)$_2$—C($R^9$)$_2$—, —C(=O)—C($R^9$)$_2$—, —C($R^9$)$_2$—C(=O)—, —C($R^9$)=C($R^9$)—, —C≡C—, —C(=O)—N($R^9$)—, —C(=O)—O—, —C($R^9$)$_2$—O—, and —C($R^9$)$_2$—$NR^9$—;
Y is selected from $C_3$-$C_{15}$ alkyl, carbocyclyl, carbocyclylalkyl, heterocyclyl, heterocyclylalkyl, aryl or aralkyl;
$R^1$ and $R^2$ are each independently selected from hydrogen, halogen, alkyl, fluoroalkyl, —$OR^9$, —$NR^{10}R^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;
$R^3$ and $R^4$ are each independently selected from hydrogen, halogen, $C_1$-$C_5$ alkyl, fluoroalkyl, —$OR^9$ or —$NR^{10}R^{11}$; or $R^3$ and $R^4$ together form an oxo;
$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;
$R^7$ and $R^8$ are each independently selected from hydrogen, alkyl, carbocyclyl, —C(=O)$R^{13}$, $SO_2R^{13}$, $CO_2R^{13}$ or $SO_2NR^{10}R^{11}$; or $R^7$ and $R^8$, together with the nitrogen atom to which they are attached, form an N-heterocyclyl;

each $R^9$ independently hydrogen or alkyl;

each $R^{10}$ and $R^{11}$ is independently selected from hydrogen, alkyl, carbocyclyl, heterocyclyl, $-C(=O)R^{13}$, $SO_2R^{13}$, $CO_2R^{13}$ or $SO_2NR^{10}R^{11}$; or $R^{10}$ and $R^{11}$ together with the nitrogen atom to which they are attached, form an N-heterocyclyl; and each $R^{13}$ is independently selected from alkyl, heteroalkyl, alkenyl, aryl, aralkyl, carbocyclyl, heteroaryl or heterocyclyl.

One embodiment provides a method of inhibiting dark adaptation of a rod photoreceptor cell of the retina comprising contacting the retina with a compound of Formula (A) or tautomer, stereoisomer, geometric isomer, or pharmaceutically acceptable solvate, hydrate, salt, or N-oxide thereof:

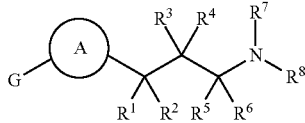

Formula (A)

wherein,

Ring A is selected from a 1,3-disubstituted heterocycle;

G is —X—Y;

X is selected from $-O-C(R^9)_2-$, $-O-C(=O)-$, $-S-C(R^9)_2-$, $-S(O)-C(R^9)_2-$, $-S(O)_2-C(R^9)_2-$, $-SO_2(NR^9)-$, $-NR^9-C(R^9)_2-$, $-NR^9-C(=O)-$, $-NR^9-S(O)_2-$, $-C(R^9)_2-C(R^9)_2-$, $-C(=O)-C(R^9)_2-$, $-C(R^9)_2-C(=O)-$, $-C(R^9)=C(R^9)-$, $-C\equiv C-$, $-C(=O)-N(R^9)-$, $-C(=O)-O-$, $-C(R^9)_2-O-$, and $-C(R^9)_2-NR^9-$;

Y is selected from $C_3$-$C_{15}$ alkyl, carbocyclyl, carbocyclylalkyl, heterocyclyl, heterocyclylalkyl, aryl or aralkyl;

$R^1$ and $R^2$ are each independently selected from hydrogen, halogen, alkyl, fluoroalkyl, $-OR^9$, $-NR^{10}R^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;

$R^3$ and $R^4$ are each independently selected from hydrogen, halogen, $C_1$-$C_5$ alkyl, fluoroalkyl, $-OR^9$ or $-NR^{10}R^{11}$; or $R^3$ and $R^4$ together form an oxo;

$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;

$R^7$ and $R^8$ are each independently selected from hydrogen, alkyl, carbocyclyl, $-C(=O)R^{13}$, $SO_2R^{13}$, $CO_2R^{13}$ or $SO_2NR^{10}R^{11}$; or $R^7$ and $R^8$, together with the nitrogen atom to which they are attached, form an N-heterocyclyl;

each $R^9$ independently hydrogen or alkyl;

each $R^{10}$ and $R^{11}$ is independently selected from hydrogen, alkyl, carbocyclyl, heterocyclyl, $-C(=O)R^{13}$, $SO_2R^{13}$, $CO_2R^{13}$ or $SO_2NR^{10}R^{11}$; or $R^{10}$ and $R^{11}$ together with the nitrogen atom to which they are attached, form an N-heterocyclyl; and each $R^{13}$ is independently selected from alkyl, heteroalkyl, alkenyl, aryl, aralkyl, carbocyclyl, heteroaryl or heterocyclyl.

One embodiment provides a method of inhibiting regeneration of rhodopsin in a rod photoreceptor cell of the retina comprising contacting the retina with a compound of Formula (A) or tautomer, stereoisomer, geometric isomer, or pharmaceutically acceptable solvate, hydrate, salt, or N-oxide thereof:

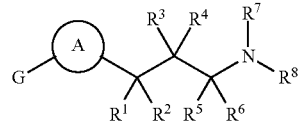

Formula (A)

wherein,

Ring A is selected from a 1,3-disubstituted heterocycle;

G is —X—Y;

X is selected from $-O-C(R^9)_2-$, $-O-C(=O)-$, $-S-C(R^9)_2-$, $-S(O)-C(R^9)_2-$, $-S(O)_2-C(R^9)_2-$, $-SO_2(NR^9)-$, $-NR^9-C(R^9)_2-$, $-NR^9-C(=O)-$, $-NR^9-S(O)_2-$, $-C(R^9)_2-C(R^9)_2-$, $-C(=O)-C(R^9)_2-$, $-C(R^9)_2-C(=O)-$, $-C(R^9)=C(R^9)-$, $-C\equiv C-$, $-C(=O)-N(R^9)-$, $-C(=O)-O-$, $-C(R^9)_2-O-$, and $-C(R^9)_2-NR^9-$;

Y is selected from $C_3$-$C_{15}$ alkyl, carbocyclyl, carbocyclylalkyl, heterocyclyl, heterocyclylalkyl, aryl or aralkyl;

$R^1$ and $R^2$ are each independently selected from hydrogen, halogen, alkyl, fluoroalkyl, $-OR^9$, $-NR^{10}R^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;

$R^3$ and $R^4$ are each independently selected from hydrogen, halogen, $C_1$-$C_5$ alkyl, fluoroalkyl, $-OR^9$ or $-NR^{10}R^{11}$; or $R^3$ and $R^4$ together form an oxo;

$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;

$R^7$ and $R^8$ are each independently selected from hydrogen, alkyl, carbocyclyl, $-C(=O)R^{13}$, $SO_2R^{13}$, $CO_2R^{13}$ or $SO_2NR^{10}R^{11}$; or $R^7$ and $R^8$, together with the nitrogen atom to which they are attached, form an N-heterocyclyl;

each $R^9$ independently hydrogen or alkyl;

each $R^{10}$ and $R^{11}$ is independently selected from hydrogen, alkyl, carbocyclyl, heterocyclyl, $-C(=O)R^{13}$, $SO_2R^{13}$, $CO_2R^{13}$ or $SO_2NR^{10}R^{11}$; or $R^{10}$ and $R^{11}$ together with the nitrogen atom to which they are attached, form an N-heterocyclyl; and each $R^{13}$ is independently selected from alkyl, heteroalkyl, alkenyl, aryl, aralkyl, carbocyclyl, heteroaryl or heterocyclyl.

One embodiment provides a method of reducing ischemia in an eye of a subject comprising administering to the subject a pharmaceutical composition comprising a compound of Formula (A) or tautomer, stereoisomer, geometric isomer, or pharmaceutically acceptable solvate, hydrate, salt, or N-oxide thereof:

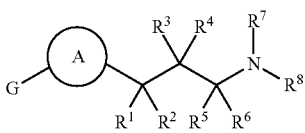

Formula (A)

wherein,
Ring A is selected from a 1,3-disubstituted heterocycle;
G is —X—Y;
X is selected from —O—C($R^9$)$_2$—, —O—C(=O)—, —S—C($R^9$)$_2$—, —S(O)—C($R^9$)$_2$—, —S(O)$_2$—C($R^9$)$_2$—, —SO$_2$(N$R^9$)—, —N$R^9$—C($R^9$)$_2$—, —N$R^9$—C(=O)—, —N$R^9$—S(O)$_2$—, —C($R^9$)$_2$—C($R^9$)$_2$—, —C(=O)—C($R^9$)$_2$—, —C($R^9$)$_2$—C(=O)—, —C($R^9$)=C($R^9$)—, —C≡C—, —C(=O)—N($R^9$)—, —C(=O)—O—, —C($R^9$)$_2$—O—, and —C($R^9$)$_2$—N$R^9$—;

Y is selected from $C_3$-$C_{15}$ alkyl, carbocyclyl, carbocyclyalkyl, heterocyclyl, heterocyclylalkyl, aryl or aralkyl;

$R^1$ and $R^2$ are each independently selected from hydrogen, halogen, alkyl, fluoroalkyl, —O$R^9$, —N$R^{10}R^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;

$R^3$ and $R^4$ are each independently selected from hydrogen, halogen, $C_1$-$C_5$ alkyl, fluoroalkyl, —O$R^9$ or —N$R^{10}R^{11}$; or $R^3$ and $R^4$ together form an oxo;

$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;

$R^7$ and $R^8$ are each independently selected from hydrogen, alkyl, carbocyclyl, —C(=O)$R^{13}$, SO$_2R^{13}$, CO$_2R^{13}$ or SO$_2$N$R^{10}R^{11}$; or $R^7$ and $R^8$, together with the nitrogen atom to which they are attached, form an N-heterocyclyl;

each $R^9$ independently hydrogen or alkyl;

each $R^{10}$ and $R^{11}$ is independently selected from hydrogen, alkyl, carbocyclyl, heterocyclyl, —C(=O)$R^{13}$, SO$_2R^{13}$, CO$_2R^{13}$ or SO$_2$N$R^{10}R^{11}$; or $R^{10}$ and $R^{11}$ together with the nitrogen atom to which they are attached, form an N-heterocyclyl; and each $R^{13}$ is independently selected from alkyl, heteroalkyl, alkenyl, aryl, aralkyl, carbocyclyl, heteroaryl or heterocyclyl.

One embodiment provides a method of inhibiting neovascularization in the retina of an eye of a subject comprising administering to the subject a pharmaceutical composition comprising a compound of Formula (A) or tautomer, stereoisomer, geometric isomer, or pharmaceutically acceptable solvate, hydrate, salt, or N-oxide thereof:

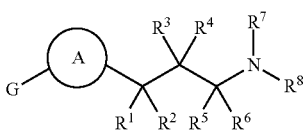

Formula (A)

wherein,
Ring A is selected from a 1,3-disubstituted heterocycle;
G is —X—Y;
X is selected from —O—C($R^9$)$_2$—, —O—C(=O)—, —S—C($R^9$)$_2$—, —S(O)—C($R^9$)$_2$—, —S(O)$_2$—C($R^9$)$_2$—, —SO$_2$(N$R^9$)—, —N$R^9$—C($R^9$)$_2$—, —N$R^9$—C(=O)—, —N$R^9$—S(O)$_2$—, —C($R^9$)$_2$—C($R^9$)$_2$—, —C(=O)—C($R^9$)$_2$—, —C($R^9$)$_2$—C(=O)—, —C($R^9$)=C($R^9$)—, —C≡C—, —C(=O)—N($R^9$)—, —C(=O)—O—, —C($R^9$)$_2$—O—, and —C($R^9$)$_2$—N$R^9$—;

Y is selected from $C_3$-$C_{15}$ alkyl, carbocyclyl, carbocyclyalkyl, heterocyclyl, heterocyclylalkyl, aryl or aralkyl;

$R^1$ and $R^2$ are each independently selected from hydrogen, halogen, alkyl, fluoroalkyl, —O$R^9$, —N$R^{10}R^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;

$R^3$ and $R^4$ are each independently selected from hydrogen, halogen, $C_1$-$C_5$ alkyl, fluoroalkyl, —O$R^9$ or —N$R^{10}R^{11}$; or $R^3$ and $R^4$ together form an oxo;

$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;

$R^7$ and $R^8$ are each independently selected from hydrogen, alkyl, carbocyclyl, —C(=O)$R^{13}$, SO$_2R^{13}$, CO$_2R^{13}$ or SO$_2$N$R^{10}R^{11}$; or $R^7$ and $R^8$, together with the nitrogen atom to which they are attached, form an N-heterocyclyl;

each $R^9$ independently hydrogen or alkyl;

each $R^{10}$ and $R^{11}$ is independently selected from hydrogen, alkyl, carbocyclyl, heterocyclyl, —C(=O)$R^{13}$, SO$_2R^{13}$, CO$_2R^{13}$ or SO$_2$N$R^{10}R^{11}$; or $R^{10}$ and $R^{11}$ together with the nitrogen atom to which they are attached, form an N-heterocyclyl; and each $R^{13}$ is independently selected from alkyl, heteroalkyl, alkenyl, aryl, aralkyl, carbocyclyl, heteroaryl or heterocyclyl.

One embodiment provides a method of inhibiting degeneration of a retinal cell in a retina comprising contacting the retina with a compound of Formula (A) or tautomer, stereoisomer, geometric isomer, or pharmaceutically acceptable solvate, hydrate, salt, or N-oxide thereof:

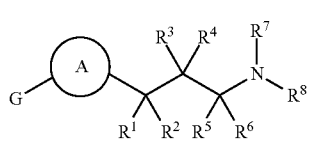

Formula (A)

wherein,
Ring A is selected from a 1,3-disubstituted heterocycle;
G is —X—Y;
X is selected from —O—C($R^9$)$_2$—, —O—C(=O)—, —S—C($R^9$)$_2$—, —S(O)—C($R^9$)$_2$—, —S(O)$_2$—C($R^9$)$_2$—, —SO$_2$(N$R^9$)—, —N$R^9$—C($R^9$)$_2$—, —N$R^9$—C(=O)—, —N$R^9$—S(O)$_2$—, —C($R^9$)$_2$—C($R^9$)$_2$—, —C(=O)—C($R^9$)$_2$—, —C($R^9$)$_2$—C(=O)—, —C($R^9$)=C($R^9$)—, —C≡C—, —C(=O)—N($R^9$)—, —C(=O)—O—, —C($R^9$)$_2$—O—, and —C($R^9$)$_2$—N$R^9$—;

Y is selected from $C_3$-$C_{15}$ alkyl, carbocyclyl, carbocyclylalkyl, heterocyclyl, heterocyclylalkyl, aryl or aralkyl;

$R^1$ and $R^2$ are each independently selected from hydrogen, halogen, alkyl, fluoroalkyl, —$OR^9$, —$NR^{10}R^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;

$R^3$ and $R^4$ are each independently selected from hydrogen, halogen, $C_1$-$C_5$ alkyl, fluoroalkyl, —$OR^9$ or —$NR^{10}R^{11}$; or $R^3$ and $R^4$ together form an oxo;

$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;

$R^7$ and $R^8$ are each independently selected from hydrogen, alkyl, carbocyclyl, —C(=O)$R^{13}$, $SO_2R^{13}$, $CO_2R^{13}$ or $SO_2NR^{10}R^{11}$; or $R^7$ and $R^8$, together with the nitrogen atom to which they are attached, form an N-heterocyclyl;

each $R^9$ independently hydrogen or alkyl;

each $R^{10}$ and $R^{11}$ is independently selected from hydrogen, alkyl, carbocyclyl, heterocyclyl, —C(=O)$R^{13}$, $SO_2R^{13}$, $CO_2R^{13}$ or $SO_2NR^{10}R^{11}$; or $R^{10}$ and $R^{11}$ together with the nitrogen atom to which they are attached, form an N-heterocyclyl; and each $R^{13}$ is independently selected from alkyl, heteroalkyl, alkenyl, aryl, aralkyl, carbocyclyl, heteroaryl or heterocyclyl.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

DEFINITIONS

As used in the specification and appended claims, unless specified to the contrary, the following terms have the meaning indicated below.

As used herein and in the appended claims, the singular forms "a," "and," and "the" include plural referents unless the context clearly dictates otherwise. Thus, for example, reference to "a compound" includes a plurality of such compounds, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

"Amino" refers to the —$NH_2$ radical.

"Cyano" refers to the —CN radical.

"Nitro" refers to the —$NO_2$ radical.

"Oxa" refers to the —O— radical.

"Oxo" refers to the =O radical.

"Thioxo" refers to the =S radical.

"Imino" refers to the =N—H radical.

"Hydrazino" refers to the =N—$NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl (Me), ethyl (Et), 1-propyl (n-propyl), 1-methylethyl (iso-propyl), 1-butyl (n-butyl), 1-methylpropyl (s-butyl), 2-methylpropyl (i-butyl), 1,1-dimethylethyl (t-butyl), or n-pentyl. The alkyl is attached to the rest of the molecule by a single bond. Unless stated otherwise specifically in the specification, an alkyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butyryl, pentynyl, hexynyl, and the like. Unless stated otherwise specifically in the specification, an alkynyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. In some embodiments the point of attachment of the alkylene chain to the rest of the molecule and to the radical group is through one carbon in the alkylene chain. In other embodiments the point of attachment of the alkylene chain to the rest of the molecule and to the radical group is through any two carbons within the alkylene chain. Unless stated otherwise specifically in the specification, an alkylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. In some embodiments, the point of attachment of the alkenylene chain to the rest of the molecule and to the radical group is through one carbon. In other embodiments, the point of attachment of the alkenylene chain to the rest of the molecule and to the radical group is through any two carbons within the chain. Unless stated otherwise specifically in the specification, an alkenylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. Aryl groups include, but are not limited to, groups such as phenyl, fluorenyl, and naphthyl. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, benzyl, diphenylmethyl and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl are saturated, (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, including fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

The compounds, or their pharmaceutically acceptable salts, in some embodiments, contain one or more asymmetric centers and thus give rise to enantiomers, diastereomers, and other stereoisomeric forms that are defined, in terms of absolute stereochemistry, as (R)- or (S)- or, as (D)- or (L)- for amino acids. When the compounds described herein contain olefinic double bonds or other centers of geometric asymmetry, and unless specified otherwise, it is intended that the compounds include both E and Z geometric isomers (e.g., cis or trans.) Likewise, all possible isomers, as well as their racemic and optically pure forms, and all tautomeric forms are also intended to be included.

A "stereoisomer" refers to a compound made up of the same atoms bonded by the same bonds but having different three-dimensional structures, which are not interchangeable. It is therefore contemplated that various stereoisomers and mixtures thereof and includes "enantiomers," which refers to two stereoisomers whose molecules are nonsuperimposeable mirror images of one another.

The compounds presented herein, in some embodiments, exist as tautomers. A "tautomer" refers to a proton shift from one atom of a molecule to another atom of the same molecule, accompanied by an isomerization of an adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

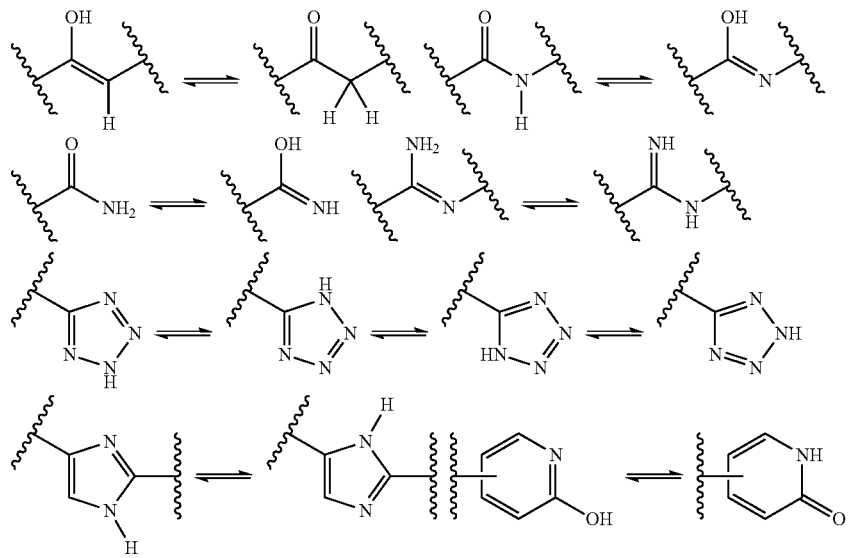

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted heterocyclic amine derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997), which is hereby incorporated by reference in its entirety). Acid addition salts of basic compounds are prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Non-retinoid compound" refers to any compound that is not a retinoid. A retinoid is a compound that has a diterpene skeleton possessing a trimethylcyclohexenyl ring and a polyene chain that terminates in a polar end group. Examples of retinoids include retinaldehyde and derived imine/hydrazide/oxime, retinol and any derived ester, retinol amine and any derived amide, retinoic acid and any derived ester or amide. In some embodiments, a non-retinoid compound optionally comprises an internal cyclic group (e.g., aromatic group).

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Age-related macular degeneration (AMD) affects between ten and fifteen million patients in the United States, and it is the leading cause of blindness in aging populations worldwide. AMD affects central vision and causes the loss of photoreceptor cells in the central part of retina called the macula. Macular degeneration can be classified into two types: dry-form and wet-form. The dry-form is more common than the wet; about 90% of age-related macular degeneration patients are diagnosed with the dry-form. The wet-form of the disease and geographic atrophy, which is the end-stage phenotype of dry-form AMD, causes the most serious vision loss. All patients who develop wet-form AMD are believed to previously have developed dry-form AMD for a prolonged period of time. The exact causes of AMD are still unknown. The dry-form of AMD may result from the senescence and thinning of macular tissues associated with the deposition of pigment in the macular retinal pigment epithelium. In wet-form AMD, new blood vessels grow beneath the retina, form scar tissue, bleed, and leak fluid. The overlying retina can be severely damaged, creating "blind" areas in the central vision.

For the vast majority of patients who have the dry-form of AMD, no effective treatment is yet available. Because the dry-form of AMD precedes development of the wet-form of AMD, therapeutic intervention to prevent or delay disease progression in the dry-form AMD would benefit patients with dry-form of AMD and might reduce the incidence of the wet-form of AMD.

Decline of vision noticed by the patient or characteristic features detected by an ophthalmologist during a routine eye exam may be the first indicator of AMD. The formation of "drusen," or membranous debris beneath the retinal pigment epithelium of the macula is often the first physical sign that AMD is developing. Late symptoms include the perceived distortion of straight lines and, in advanced cases, a dark, blurry area or area with absent vision appears in the center of vision; and/or there may be color perception changes.

Different forms of genetically-linked macular degenerations may also occur in younger patients. In other maculopathies, factors in the disease are heredity, nutritional, traumatic, infection, or other ecologic factors.

Glaucoma is a broad term used to describe a group of diseases that causes a slowly progressive visual field loss, usually asymptomatically. The lack of symptoms may lead to a delayed diagnosis of glaucoma until the terminal stages of the disease. The prevalence of glaucoma is estimated to be 2.2 million in the United States, with about 120,000 cases of blindness attributable to the condition. The disease is particularly prevalent in Japan, which has four million reported cases. In many parts of the world, treatment is less accessible than in the United States and Japan, thus glaucoma ranks as a leading cause of blindness worldwide. Even if subjects afflicted with glaucoma do not become blind, their vision is often severely impaired.

The progressive loss of peripheral visual field in glaucoma is caused by the death of ganglion cells in the retina. Ganglion cells are a specific type of projection neuron that connects the eye to the brain. Glaucoma is usually accompanied by an increase in intraocular pressure. Current treatment includes use of drugs that lower the intraocular pressure; however, contemporary methods to lower the intraocular pressure are often insufficient to completely stop disease progression. Ganglion cells are believed to be susceptible to pressure and may suffer permanent degeneration prior to the lowering of intraocular pressure. An increasing number of cases of normal-tension glaucoma are observed in which ganglion cells degenerate without an observed increase in the intraocular pressure. Current glaucoma drugs only treat intraocular pressure and are ineffective in preventing or reversing the degeneration of ganglion cells.

Recent reports suggest that glaucoma is a neurodegenerative disease, similar to Alzheimer's disease and Parkinson's disease in the brain, except that it specifically affects retinal neurons. The retinal neurons of the eye originate from diencephalon neurons of the brain. Though retinal neurons are often mistakenly thought not to be part of the brain, retinal cells are key components of the central nervous system, interpreting the signals from the light-sensing cells.

Alzheimer's disease (AD) is the most common form of dementia among the elderly. Dementia is a brain disorder that seriously affects a person's ability to carry out daily activities. Alzheimer's is a disease that affects four million people in the United States alone. It is characterized by a loss of nerve cells in areas of the brain that are vital to memory and other mental functions. Currently available drugs can ameliorate AD symptoms for a relatively finite period of time, but no drugs are available that treat the disease or completely stop the progressive decline in mental function. Recent research suggests that glial cells that support the neurons or nerve cells may have defects in AD sufferers, but the cause of AD remains unknown. Individuals with AD seem to have a higher incidence of glaucoma and age-related macular degeneration, indicating that similar pathogenesis may underlie these neurodegenerative diseases of the eye and brain. (See Giasson et al., *Free Radic. Biol. Med.* 32:1264-75 (2002); Johnson et al., *Proc. Natl. Acad. Sci. USA* 99:11830-35 (2002); Dentchev et al., *Mol. Vis.* 9:184-90 (2003)).

Neuronal cell death underlies the pathology of these diseases. Unfortunately, very few compositions and methods that enhance retinal neuronal cell survival, particularly photoreceptor cell survival, have been discovered. A need therefore exists to identify and develop compositions that can be used for treatment and prophylaxis of a number of retinal diseases and disorders that have neuronal cell death as a primary, or associated, element in their pathogenesis.

In vertebrate photoreceptor cells, the irradiance of a photon causes isomerization of 11-cis-retinylidene chromophore to all-trans-retinylidene and uncoupling from the visual opsin receptors. This photoisomerization triggers conformational changes of opsins, which, in turn, initiate the biochemical chain of reactions termed phototransduction (Filipek et al., *Annu. Rev. Physiol.* 65:851-79 (2003)). Regeneration of the visual pigments requires that the chromophore be converted back to the 11-cis-configuration in the processes collectively called the retinoid (visual) cycle (see, e.g., McBee et al., *Prog. Retin. Eye Res.* 20:469-52 (2001)). First, the chromophore is released from the opsin and reduced in the photoreceptor by retinol dehydrogenases. The product, all-trans-retinol, is trapped in the adjacent retinal pigment epithelium (RPE) in the form of insoluble fatty acid esters in subcellular structures known as retinosomes (Imanishi et al., *J. Cell Biol.* 164:373-87 (2004)).

In Stargardt's disease (Allikmets et al., *Nat. Genet.* 15:236-46 (1997)), a disease associated with mutations in the ABCR transporter that acts as a flippase, the accumulation of all-trans-retinal may be responsible for the formation of a lipofuscin pigment, A2E, which is toxic towards retinal pigment epithelial cells and causes progressive retinal degeneration and, consequently, loss of vision (Mata et al., *Proc. Natl. Acad. Sci. USA* 97:7154-59 (2000); Weng et al., *Cell* 98:13-23 (1999)). Treating patients with an inhibitor of retinol dehydrogenases, 13-cis-RA (Isotretinoin, Accutane®, Roche), has been considered as a therapy that might prevent or slow the formation of A2E and might have protective properties to maintain normal vision (Radu et al., *Proc. Natl. Acad. Sci. USA* 100:4742-47 (2003)). 13-cis-RA has been used to slow the synthesis of 11-cis-retinal by inhibiting 11-cis-RDH (Law et al., *Biochem. Biophys. Res. Commun.* 161:825-9 (1989)), but its use can also be associated with significant night blindness. Others have proposed that 13-cis-RA works to prevent chromophore regeneration by binding RPE65, a protein essential for the isomerization process in the eye (Gollapalli et al., *Proc. Natl. Acad. Sci. USA* 101:10030-35 (2004)). Gollapalli et al. reported that 13-cis-RA blocked the formation of A2E and suggested that this treatment may inhibit lipofuscin accumulation and, thus, delay either the onset of visual loss in Stargardt's disease or age-related macular degeneration, which are both associated with retinal pigment-associated lipofuscin accumulation. However, blocking the retinoid cycle and forming unliganded opsin may result in more severe consequences and worsening of the patient's prognosis (see, e.g., Van Hooser et al., *J. Biol. Chem.* 277:19173-82 (2002); Woodruff et al., *Nat. Genet.* 35:158-164 (2003)). Failure of the chromophore to form may lead to progressive retinal degeneration and may produce a phenotype similar to Leber Congenital Amaurosis (LCA), which is a very rare genetic condition affecting children shortly after birth.

Substituted Heterocyclic Amine Derivative Compounds

Substituted heterocyclic amine derivative compounds are described herein that inhibit an isomerization step of the retinoid cycle. These compounds, and compositions comprising these compounds, are useful for inhibiting degeneration of retinal cells or for enhancing retinal cell survival. The compounds described herein are, therefore, useful for treating ophthalmic diseases and disorders, including retinal diseases or disorders, such as age related macular degeneration and Stargardt's disease.

One embodiment provides a compound of Formula (A) or tautomer, stereoisomer, geometric isomer or a pharmaceutically acceptable solvate, hydrate, salt, or N-oxide thereof:

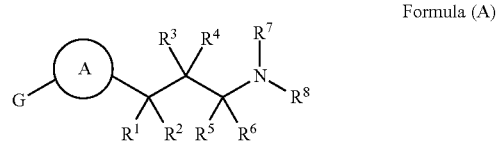

Formula (A)

wherein,

Ring A is selected from a 1,3-disubstituted heterocycle;

G is —X—Y;

X is selected from —O—C($R^9$)$_2$—, —O—C(=O)—, —S—C($R^9$)$_2$—, —S(O)—C($R^9$)$_2$—, —S(O)$_2$—C($R^9$)$_2$—, —SO$_2$(NR$^9$)—, —NR$^9$—C($R^9$)$_2$—, —NR$^9$—C(=O)—, —NR$^9$—S(O)$_2$—, —C($R^9$)$_2$—C($R^9$)$_2$—, —C(=O)—C($R^9$)$_2$—, —C($R^9$)$_2$—C(=O)—, —C($R^9$)=C($R^9$)—, —C≡C—, —C(=O)—N($R^9$)—, —C(=O)—O—, —C($R^9$)$_2$—O—, and —C($R^9$)$_2$—NR$^9$—;

Y is selected from $C_3$-$C_{15}$ alkyl, carbocyclyl, carbocyclylalkyl, heterocyclyl, heterocyclylalkyl, aryl or aralkyl;

$R^1$ and $R^2$ are each independently selected from hydrogen, halogen, alkyl, fluoroalkyl, —OR$^9$, —NR$^{10}$R$^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;

$R^3$ and $R^4$ are each independently selected from hydrogen, halogen, $C_1$-$C_5$ alkyl, fluoroalkyl, —OR$^9$ or —NR$^{10}$R$^{11}$; or $R^3$ and $R^4$ together form an oxo;

$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;

$R^7$ and $R^8$ are each independently selected from hydrogen, alkyl, carbocyclyl, —C(=O)R$^{13}$, SO$_2$R$^{13}$, CO$_2$R$^{13}$ or SO$_2$NR$^{10}$R$^{11}$; or $R^7$ and $R^8$, together with the nitrogen atom to which they are attached, form an N-heterocyclyl;

each $R^9$ independently hydrogen or alkyl;

each $R^{10}$ and $R^{11}$ is independently selected from hydrogen, alkyl, carbocyclyl, heterocyclyl, —C(=O)$R^{13}$, $SO_2R^{13}$, $CO_2R^{13}$ or $SO_2NR^{10}R^{11}$; or $R^{10}$ and $R^{11}$ together with the nitrogen atom to which they are attached, form an N-heterocyclyl; and each $R^{13}$ is independently selected from alkyl, heteroalkyl, alkenyl, aryl, aralkyl, carbocyclyl, heteroaryl or heterocyclyl.

For any and all of the embodiments, substituents are selected from among from a subset of the listed alternatives. For example, in some embodiments is provided a compound of Formula (A) or tautomer, stereoisomer, geometric isomer or a pharmaceutically acceptable solvate, hydrate, salt, or N-oxide thereof, wherein Ring A is selected from:

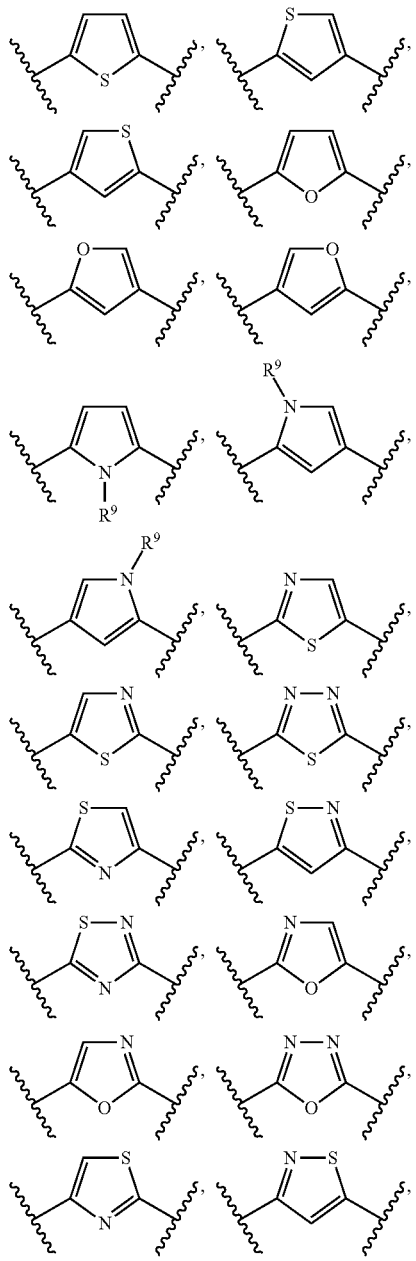

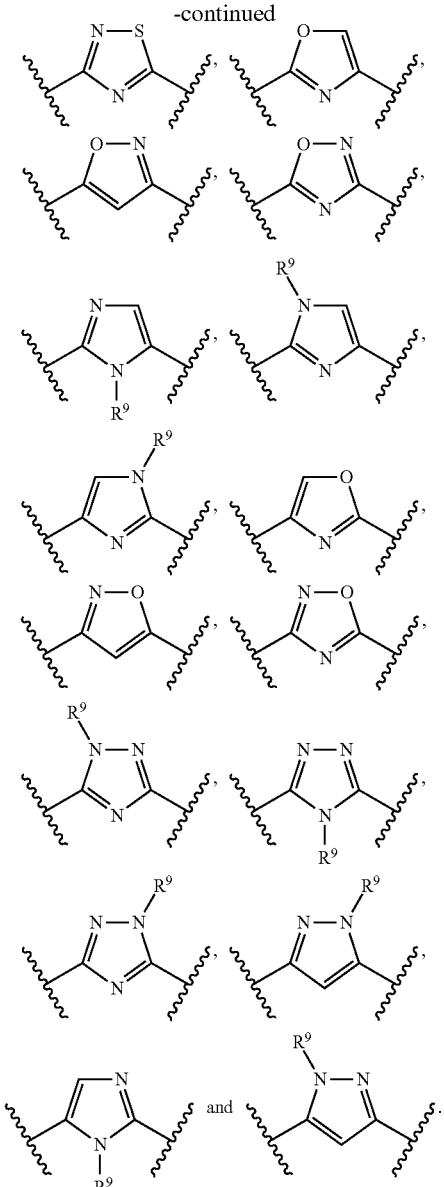

Another embodiment provides a compound of Formula (A) or tautomer, stereoisomer, geometric isomer or a pharmaceutically acceptable solvate, hydrate, salt, or N-oxide thereof, wherein Ring A is selected from:

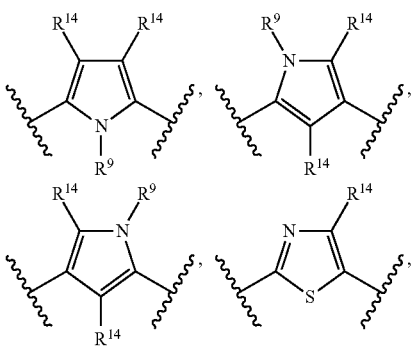

-continued

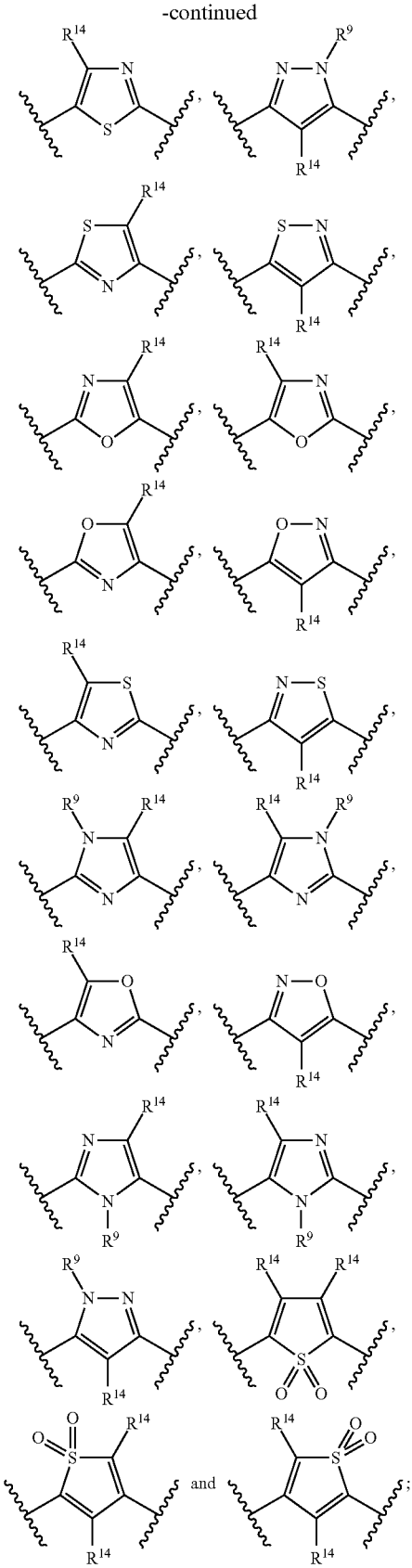

and each $R^{14}$ is independently selected from hydrogen, halogen, $OR^9$, alkyl, or fluoroalkyl.

Another embodiment provides a compound of Formula (A) or tautomer, stereoisomer, geometric isomer or a pharmaceutically acceptable solvate, hydrate, salt, or N-oxide thereof, wherein Ring A is selected from:

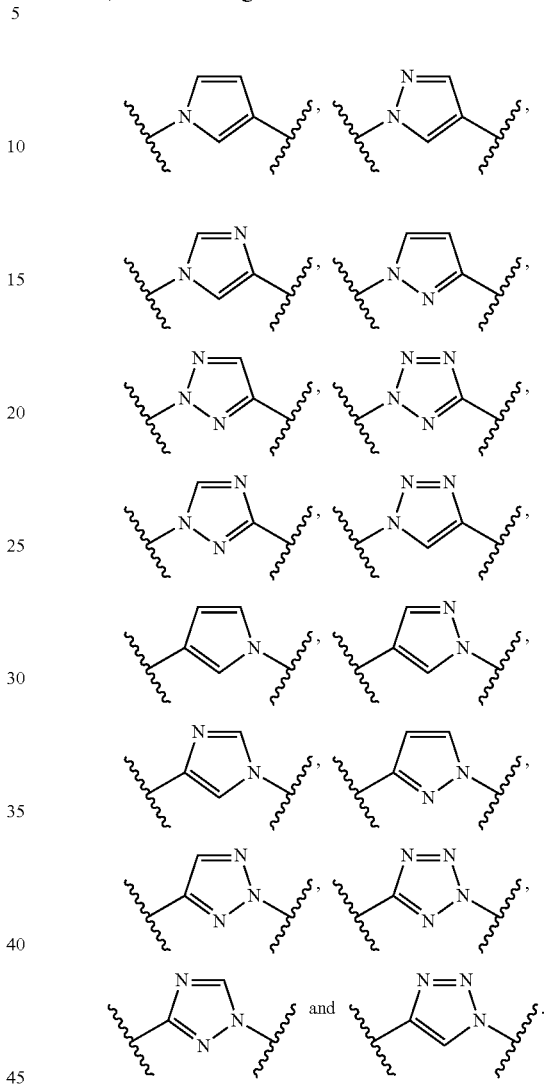

Another embodiment provides a compound of Formula (A) or tautomer, stereoisomer, geometric isomer or a pharmaceutically acceptable solvate, hydrate, salt, or N-oxide thereof, wherein Ring A is selected from:

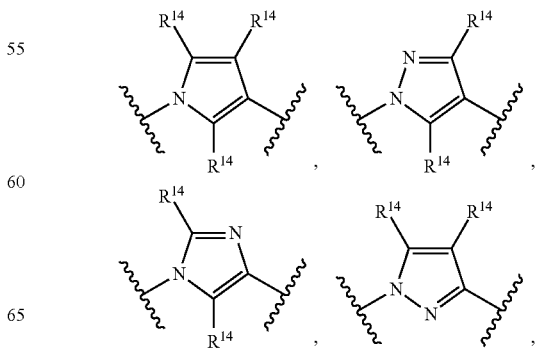

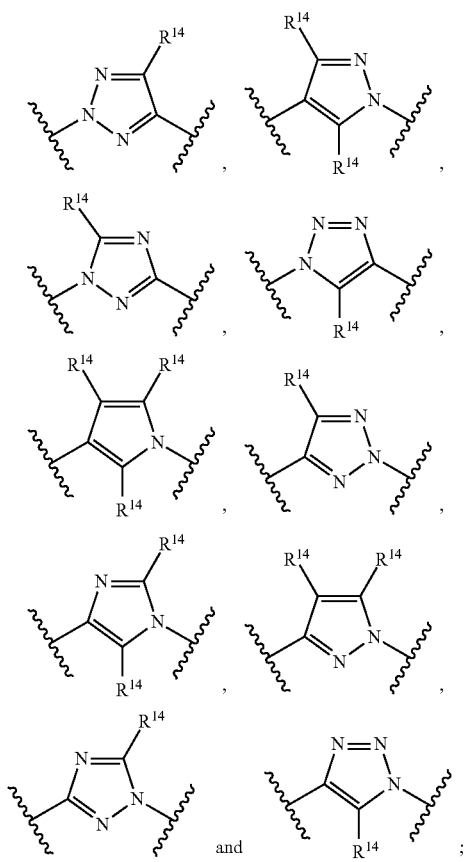

and each $R^{14}$ is independently selected from hydrogen, halogen, $OR^9$, alkyl, or fluoroalkyl.

Another embodiment provides a compound of Formula (A) or tautomer, stereoisomer, geometric isomer or a pharmaceutically acceptable solvate, hydrate, salt, or N-oxide thereof, wherein Ring A is selected from:

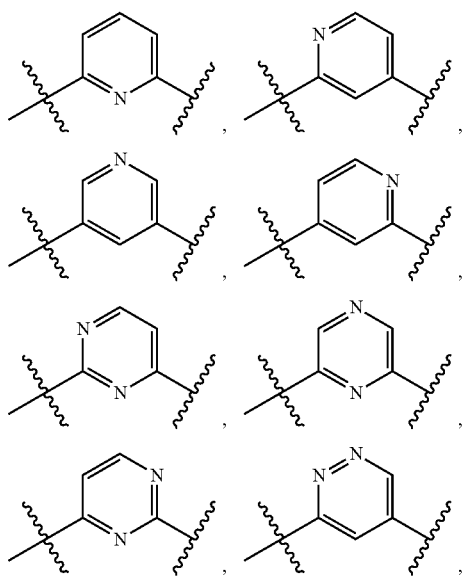

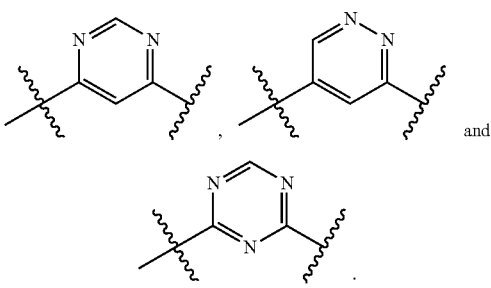

Another embodiment provides a compound of Formula (A) or tautomer, stereoisomer, geometric isomer or a pharmaceutically acceptable solvate, hydrate, salt, or N-oxide thereof, wherein Ring A is selected from:

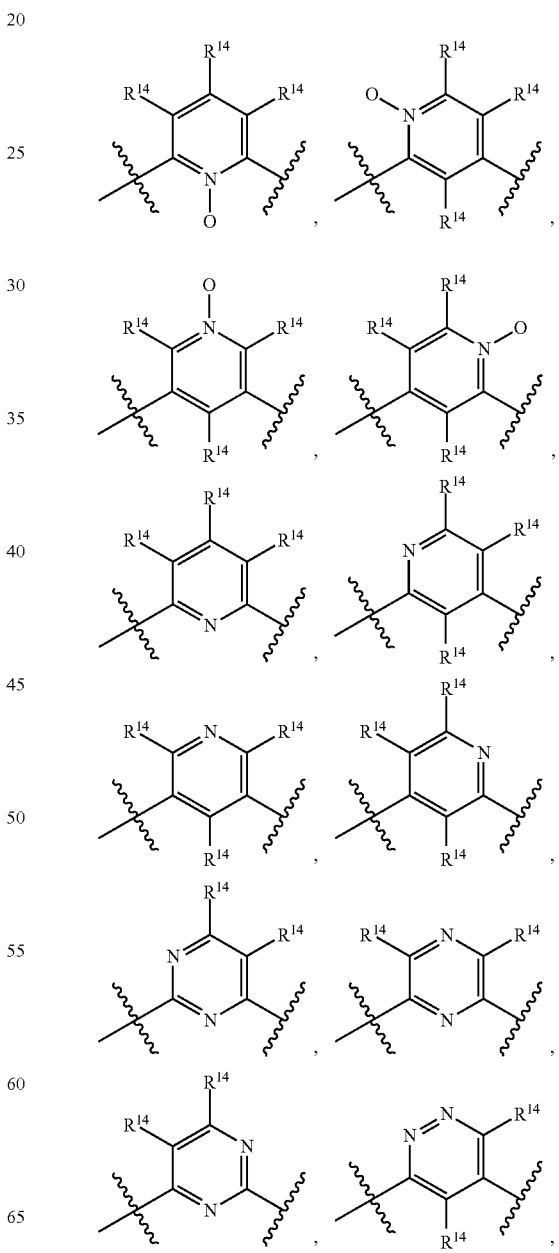

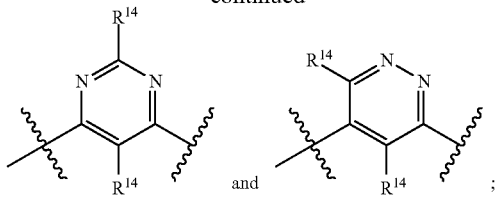

and each $R^{14}$ is independently selected from hydrogen, halogen, $OR^9$, alkyl, or fluoroalkyl.

Another embodiment provides a compound of Formula (A) or tautomer, stereoisomer, geometric isomer or a pharmaceutically acceptable solvate, hydrate, salt, or N-oxide thereof, wherein Ring A is selected from:

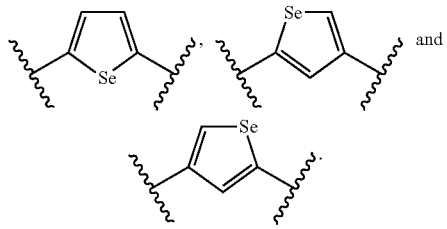

Another embodiment provides a compound of Formula (A) or tautomer, stereoisomer, geometric isomer or a pharmaceutically acceptable solvate, hydrate, salt, or N-oxide thereof, wherein Ring A is selected from:

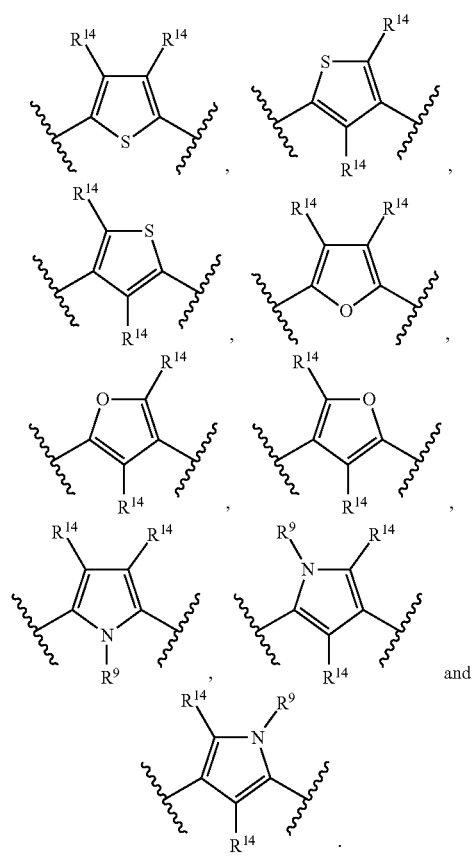

Another embodiment provides a compound of Formula (A) or tautomer, stereoisomer, geometric isomer or a pharmaceutically acceptable solvate, hydrate, salt, or N-oxide thereof, wherein Ring A is selected from:

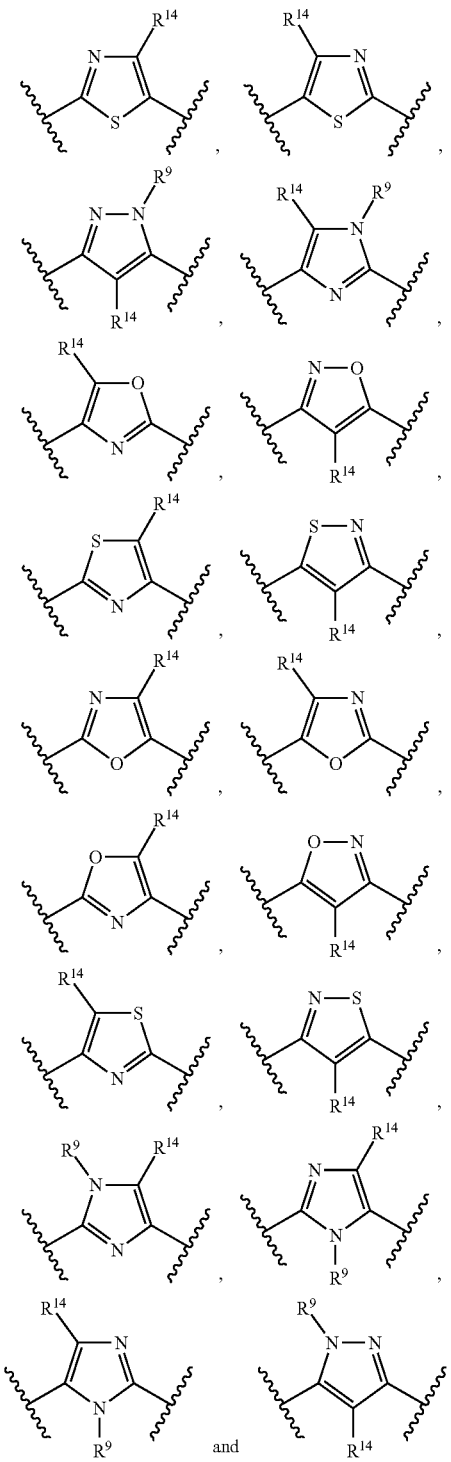

Another embodiment provides a compound of Formula (A) or tautomer, stereoisomer, geometric isomer or a pharmaceutically acceptable solvate, hydrate, salt, or N-oxide thereof, wherein Ring A is selected from:

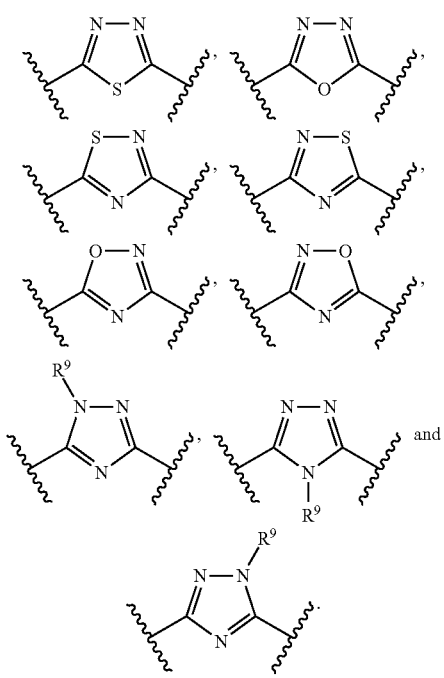

Another embodiment provides a compound of Formula (A) or tautomer, stereoisomer, geometric isomer or a pharmaceutically acceptable solvate, hydrate, salt, or N-oxide thereof, wherein Ring A is selected from:

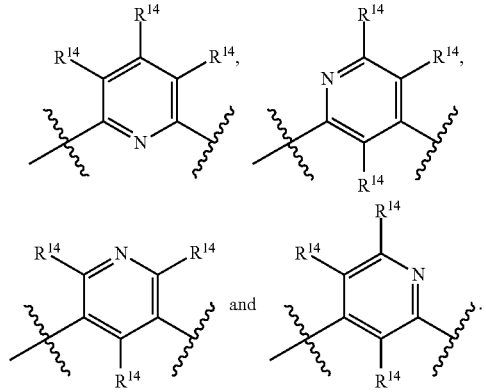

Another embodiment provides a compound of Formula (A) or tautomer, stereoisomer, geometric isomer or a pharmaceutically acceptable solvate, hydrate, salt, or N-oxide thereof, wherein Ring A is selected from:

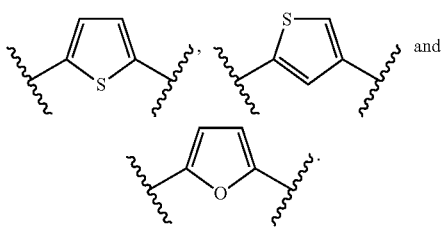

For any and all of the embodiments, substituents are selected from among from a subset of the listed alternatives. For example, in some embodiments is provided a compound of Formula (A) or tautomer, stereoisomer, geometric isomer or a pharmaceutically acceptable solvate, hydrate, salt, or N-oxide thereof, wherein Ring A is:

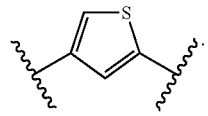 [SMILES: *c1csc(*)c1]

Another embodiment provides a compound of Formula (A) or tautomer, stereoisomer, geometric isomer or a pharmaceutically acceptable solvate, hydrate, salt, or N-oxide thereof, wherein Ring A is:

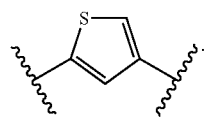

Another embodiment provides a compound of Formula (A) or tautomer, stereoisomer, geometric isomer or a pharmaceutically acceptable solvate, hydrate, salt, or N-oxide thereof, wherein Ring A is:

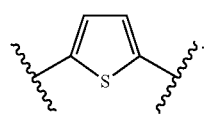

Another embodiment provides a compound of Formula (A) or tautomer, stereoisomer, geometric isomer or a pharmaceutically acceptable solvate, hydrate, salt, or N-oxide thereof, wherein Ring A is:

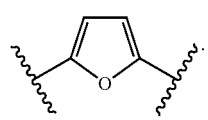

Another embodiment provides a compound of Formula (A) or tautomer, stereoisomer, geometric isomer or a pharmaceutically acceptable solvate, hydrate, salt, or N-oxide thereof, wherein Ring A is:

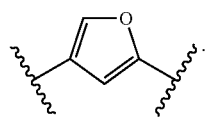

Another embodiment provides a compound of Formula (A) or tautomer, stereoisomer, geometric isomer or a pharmaceutically acceptable solvate, hydrate, salt, or N-oxide thereof, wherein Ring A is:

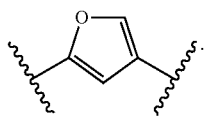 [SMILES: *c1coc(*)c1]

Another embodiment provides a compound of Formula (A) or tautomer, stereoisomer, geometric isomer or a pharmaceutically acceptable solvate, hydrate, salt, or N-oxide thereof, wherein Ring A is:

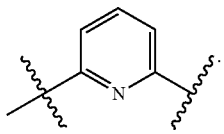 [SMILES: *c1cccc(*)n1]

Another embodiment provides a compound of Formula (A) or tautomer, stereoisomer, geometric isomer or a pharmaceutically acceptable solvate, hydrate, salt, or N-oxide thereof, wherein Ring A is:

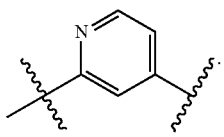 [SMILES: *c1ccnc(*)c1]

Another embodiment provides a compound of Formula (A) or tautomer, stereoisomer, geometric isomer or a pharmaceutically acceptable solvate, hydrate, salt, or N-oxide thereof, wherein Ring A is:

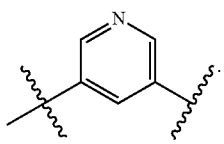 [SMILES: *c1cncc(*)c1]

Another embodiment provides a compound of Formula (A) or tautomer, stereoisomer, geometric isomer or a pharmaceutically acceptable solvate, hydrate, salt, or N-oxide thereof, wherein Ring A is:

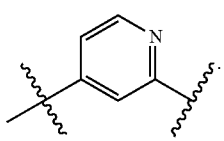 [SMILES: *c1ccnc(*)c1]

For any and all of the embodiments, substituents are selected from among from a subset of the listed alternatives. For example, in some embodiments is provided a compound of Formula (A) or tautomer, stereoisomer, geometric isomer or a pharmaceutically acceptable solvate, hydrate, salt, or N-oxide thereof, wherein Y is alkyl, carbocyclyl or heterocyclyl.

Another embodiment provides a compound of Formula (A) or tautomer, stereoisomer, geometric isomer or a pharmaceutically acceptable solvate, hydrate, salt, or N-oxide thereof, wherein Y is alkyl, carbocyclyl or heterocyclyl.

Another embodiment provides a compound of Formula (A) or tautomer, stereoisomer, geometric isomer or a pharmaceutically acceptable solvate, hydrate, salt, or N-oxide thereof, wherein Y is —$C(R^{16})(R^{17})(R^{18})$;

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl; and $R^{18}$ is selected from a hydrogen, alkyl, alkoxy, hydroxy, halo or fluoroalkyl.

Another embodiment provides a compound of Formula (A) or tautomer, stereoisomer, geometric isomer or a pharmaceutically acceptable solvate, hydrate, salt, or N-oxide thereof, wherein $R^{16}$ and $R^{17}$, together with the carbon to which they are attached, form a carbocyclyl or heterocyclyl.

Another embodiment provides a compound of Formula (A) or tautomer, stereoisomer, geometric isomer or a pharmaceutically acceptable solvate, hydrate, salt, or N-oxide thereof, wherein $R^{16}$ and $R^{17}$, together with the carbon to which they are attached, form a cyclobutyl, cyclopentyl, cyclohexyl, cycloheptyl, or cyclooctyl, and $R^{18}$ is hydrogen or hydroxy.

Another embodiment provides a compound of Formula (A) or tautomer, stereoisomer, geometric isomer or a pharmaceutically acceptable solvate, hydrate, salt, or N-oxide thereof, wherein $R^{16}$ and $R^{17}$, together with the carbon to which they are attached, form a cyclopentyl, cyclohexyl, or cycloheptyl, and $R^{18}$ is hydrogen or hydroxy.

Another embodiment provides a compound of Formula (A) or tautomer, stereoisomer, geometric isomer or a pharmaceutically acceptable solvate, hydrate, salt, or N-oxide thereof, wherein $R^{16}$ and $R^{17}$ is independently selected from $C_1$-$C_{13}$ alkyl; and $R^{18}$ is hydrogen, hydroxy or alkoxy.

Another embodiment provides a compound of Formula (A) or tautomer, stereoisomer, geometric isomer or a pharmaceutically acceptable solvate, hydrate, salt, or N-oxide thereof, wherein X is selected from —O—$C(R^9)_2$—, —$S(O)_2$—$C(R^9)_2$—, —$SO_2(NR^9)$—, —$NR^9$—$C(R^9)_2$—, —$NR^9$—C(=O)—, and —$NR^9$—$S(O)_2$—.

Another embodiment provides a compound of Formula (A) or tautomer, stereoisomer, geometric isomer or a pharmaceutically acceptable solvate, hydrate, salt, or N-oxide thereof, wherein X is selected from —$C(R^9)_2$—$C(R^9)_2$—, —$C(R^9)$=$C(R^9)$—, —C≡C—, —C(=O)—N($R^9$)—, —$C(R^9)_2$—O—, and —$C(R^9)_2$—$NR^9$—.

Another embodiment provides a compound of Formula (A) or tautomer, stereoisomer, geometric isomer or a pharmaceutically acceptable solvate, hydrate, salt, or N-oxide thereof, wherein X is selected from —O—$C(R^9)_2$—, or —$C(R^9)_2$—$C(R^9)_2$—.

Another embodiment provides a compound of Formula (A) or tautomer, stereoisomer, geometric isomer or a pharmaceutically acceptable solvate, hydrate, salt, or N-oxide thereof, wherein X is —$C(R^9)_2$—$C(R^9)_2$—.

Another embodiment provides a compound of Formula (A) or tautomer, stereoisomer, geometric isomer or a pharmaceutically acceptable solvate, hydrate, salt, or N-oxide thereof, wherein X is —O—$C(R^9)_2$—.

For any and all of the embodiments, substituents are selected from among from a subset of the listed alternatives. For example, in some embodiments is provided a compound of Formula (A) or tautomer, stereoisomer, geometric isomer or a pharmaceutically acceptable solvate, hydrate, salt, or N-oxide thereof, wherein $R^3$ and $R^4$ are both hydrogen.

Another embodiment provides a compound of Formula (A) or tautomer, stereoisomer, geometric isomer or a pharmaceutically acceptable solvate, hydrate, salt, or N-oxide thereof, wherein $R^5$ and $R^6$ are both hydrogen.

Another embodiment provides a compound of Formula (A) or tautomer, stereoisomer, geometric isomer or a pharmaceutically acceptable solvate, hydrate, salt, or N-oxide thereof, wherein $R^3$, $R^4$, $R^5$ and $R^6$ are hydrogen.

Another embodiment provides a compound of Formula (A) or tautomer, stereoisomer, geometric isomer or a pharmaceutically acceptable solvate, hydrate, salt, or N-oxide thereof, wherein $R^1$ and $R^2$ are both hydrogen.

Another embodiment provides a compound of Formula (A) or tautomer, stereoisomer, geometric isomer or a pharmaceutically acceptable solvate, hydrate, salt, or N-oxide thereof, wherein $R^1$ is hydrogen and $R^2$ is —OH.

Another embodiment provides a compound of Formula (A) or tautomer, stereoisomer, geometric isomer or a pharmaceutically acceptable solvate, hydrate, salt, or N-oxide thereof, wherein $R^1$ and $R^2$ together form an oxo.

Another embodiment provides a compound of Formula (A) or tautomer, stereoisomer, geometric isomer or a pharmaceutically acceptable solvate, hydrate, salt, or N-oxide thereof, wherein $R^7$ and $R^8$ are both hydrogen.

Another embodiment provides a compound of Formula (A) or tautomer, stereoisomer, geometric isomer or a pharmaceutically acceptable solvate, hydrate, salt, or N-oxide thereof, wherein $R^7$ is hydrogen and $R^8$ is —C(=O)$R^{13}$ or CO$_2R^{13}$.

Another embodiment provides a compound of Formula (A) or tautomer, stereoisomer, geometric isomer or a pharmaceutically acceptable solvate, hydrate, salt, or N-oxide thereof, wherein $R^{13}$ is an alkyl.

Another embodiment provides a compound of Formula (A) or tautomer, stereoisomer, geometric isomer or a pharmaceutically acceptable solvate, hydrate, salt, or N-oxide thereof, wherein $R^8$ is CO$_2R^{13}$ and $R^{13}$ is

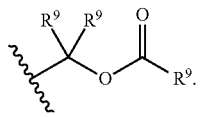

Any combination of the groups described above for the various variables is contemplated herein. Throughout the specification, groups and substituents thereof are chosen by one skilled in the field to provide stable moieties and compounds.

For any and all of the embodiments, substituents are selected from among from a subset of the listed alternatives. For example, in some embodiments is provided a compound of Formula (A) or tautomer, stereoisomer, geometric isomer or a pharmaceutically acceptable solvate, hydrate, salt, or N-oxide thereof, wherein Y is —C($R^{16}$)($R^{17}$)($R^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C($R^9$)$_2$—, or —C($R^9$)$_2$—C($R^9$)$_2$—; and ring A is:

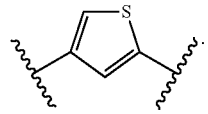

Another embodiment provides a compound of Formula (A) or tautomer, stereoisomer, geometric isomer or a pharmaceutically acceptable solvate, hydrate, salt, or N-oxide thereof, wherein Y is —C($R^{16}$)($R^{17}$)($R^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C($R^9$)$_2$—, or —C($R^9$)$_2$—C($R^9$)$_2$—; and ring A is:

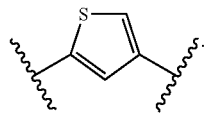 [SMILES: *c1csc(*)c1]

Another embodiment provides a compound of Formula (A) or tautomer, stereoisomer, geometric isomer or a pharmaceutically acceptable solvate, hydrate, salt, or N-oxide thereof, wherein Y is —C($R^{16}$)($R^{17}$)($R^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C($R^9$)$_2$—, or —C($R^9$)$_2$—C($R^9$)$_2$—; and ring A is:

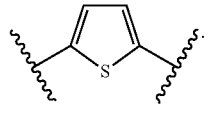

Another embodiment provides a compound of Formula (A) or tautomer, stereoisomer, geometric isomer or a pharmaceutically acceptable solvate, hydrate, salt, or N-oxide thereof, wherein Y is —C($R^{16}$)($R^{17}$)($R^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C($R^9$)$_2$—, or —C($R^9$)$_2$—C($R^9$)$_2$—; and ring A is:

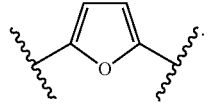

Another embodiment provides a compound of Formula (A) or tautomer, stereoisomer, geometric isomer or a pharmaceutically acceptable solvate, hydrate, salt, or N-oxide thereof, wherein Y is —C(R$^{16}$)(R$^{17}$)(R$^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C(R$^9$)$_2$—, or —C(R$^9$)$_2$—C(R$^9$)$_2$—; and ring A is:

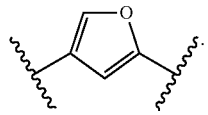

Another embodiment provides a compound of Formula (A) or tautomer, stereoisomer, geometric isomer or a pharmaceutically acceptable solvate, hydrate, salt, or N-oxide thereof, wherein Y is —C(R$^{16}$)(R$^{17}$)(R$^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C(R$^9$)$_2$—, or —C(R$^9$)$_2$—C(R$^9$)$_2$—; and ring A is:

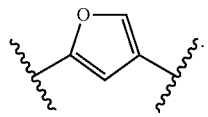

Another embodiment provides a compound of Formula (A) or tautomer, stereoisomer, geometric isomer or a pharmaceutically acceptable solvate, hydrate, salt, or N-oxide thereof, wherein Y is —C(R$^{16}$)(R$^{17}$)(R$^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C(R$^9$)$_2$—, or —C(R$^9$)$_2$—C(R$^9$)$_2$—; and ring A is:

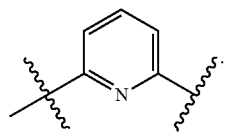

Another embodiment provides a compound of Formula (A) or tautomer, stereoisomer, geometric isomer or a pharmaceutically acceptable solvate, hydrate, salt, or N-oxide thereof, wherein Y is —C(R$^{16}$)(R$^{17}$)(R$^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C(R$^9$)$_2$—, or —C(R$^9$)$_2$—C(R$^9$)$_2$—; and ring A is:

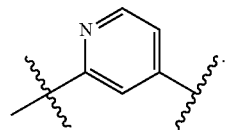 [SMILES: *c1ccnc(*)c1]

Another embodiment provides a compound of Formula (A) or tautomer, stereoisomer, geometric isomer or a pharmaceutically acceptable solvate, hydrate, salt, or N-oxide thereof, wherein Y is —C(R$^{16}$)(R$^{17}$)(R$^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C(R$^9$)$_2$—, or —C(R$^9$)$_2$—C(R$^9$)$_2$—; and ring A is:

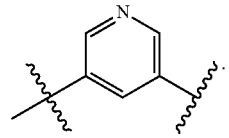 [SMILES: *c1cncc(*)c1]

Another embodiment provides a compound of Formula (A) or tautomer, stereoisomer, geometric isomer or a pharmaceutically acceptable solvate, hydrate, salt, or N-oxide thereof, wherein Y is —C(R$^{16}$)(R$^{17}$)(R$^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C(R$^9$)$_2$—, or —C(R$^9$)$_2$—C(R$^9$)$_2$—; and ring A is:

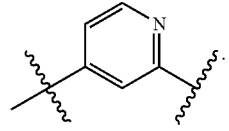

For any and all of the embodiments, substituents are selected from among from a subset of the listed alternatives. For example, in some embodiments is provided a compound of Formula (A) or tautomer, stereoisomer, geometric isomer or a pharmaceutically acceptable solvate, hydrate, salt, or N-oxide thereof, wherein $R^1$ is hydrogen, $R^2$ is —OH, $R^3$, $R^4$, $R^5$ and $R^6$ are hydrogen;

Y is —C($R^{16}$)($R^{17}$)($R^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C($R^9$)$_2$—, or —C($R^9$)$_2$—C($R^9$)$_2$—; and ring A is:

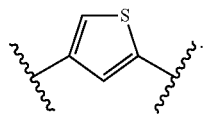

Another embodiment provides a compound of Formula (A) or tautomer, stereoisomer, geometric isomer or a pharmaceutically acceptable solvate, hydrate, salt, or N-oxide thereof, wherein, $R^1$ is hydrogen, $R^2$ is —OH, $R^3$, $R^4$, $R^5$ and $R^6$ are hydrogen;

Y is —C($R^{16}$)($R^{17}$)($R^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C($R^9$)$_2$—, or —C($R^9$)$_2$—C($R^9$)$_2$—; and ring A is:

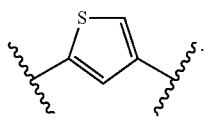 [SMILES: *c1csc(*)c1]

Another embodiment provides a compound of Formula (A) or tautomer, stereoisomer, geometric isomer or a pharmaceutically acceptable solvate, hydrate, salt, or N-oxide thereof, wherein, $R^1$ is hydrogen, $R^2$ is —OH, $R^3$, $R^4$, $R^5$ and $R^6$ are hydrogen;

Y is —C($R^{16}$)($R^{17}$)($R^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C($R^9$)$_2$—, or —C($R^9$)$_2$—C($R^9$)$_2$—; and ring A is:

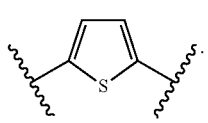 [SMILES: *c1ccc(*)s1]

Another embodiment provides a compound of Formula (A) or tautomer, stereoisomer, geometric isomer or a pharmaceutically acceptable solvate, hydrate, salt, or N-oxide thereof, wherein, $R^1$ is hydrogen, $R^2$ is —OH, $R^3$, $R^4$, $R^5$ and $R^6$ are hydrogen;

Y is —C($R^{16}$)($R^{17}$)($R^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C($R^9$)$_2$—, or —C($R^9$)$_2$—C($R^9$)$_2$—; and ring A is:

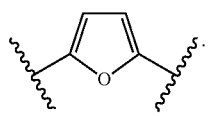

Another embodiment provides a compound of Formula (A) or tautomer, stereoisomer, geometric isomer or a pharmaceutically acceptable solvate, hydrate, salt, or N-oxide thereof, wherein, $R^1$ is hydrogen, $R^2$ is —OH, $R^3$, $R^4$, $R^5$ and $R^6$ are hydrogen;

Y is —C($R^{16}$)($R^{17}$)($R^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C($R^9$)$_2$—, or —C($R^9$)$_2$—C($R^9$)$_2$—; and ring A is:

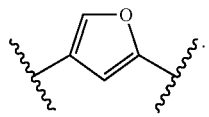 [SMILES: *c1coc(*)c1]

Another embodiment provides a compound of Formula (A) or tautomer, stereoisomer, geometric isomer or a pharmaceutically acceptable solvate, hydrate, salt, or N-oxide thereof, wherein, $R^1$ is hydrogen, $R^2$ is —OH, $R^3$, $R^4$, $R^5$ and $R^6$ are hydrogen;

Y is —C($R^{16}$)($R^{17}$)($R^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C($R^9$)$_2$—, or —C($R^9$)$_2$—C($R^9$)$_2$—; and ring A is:

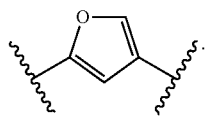 [SMILES: *c1coc(*)c1]

Another embodiment provides a compound of Formula (A) or tautomer, stereoisomer, geometric isomer or a pharmaceutically acceptable solvate, hydrate, salt, or N-oxide thereof, wherein, $R^1$ is hydrogen, $R^2$ is —OH, $R^3$, $R^4$, $R^5$ and $R^6$ are hydrogen;

Y is —C($R^{16}$)($R^{17}$)($R^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C($R^9$)$_2$—, or —C($R^9$)$_2$—C($R^9$)$_2$—; and ring A is:

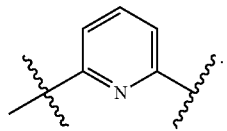 [SMILES: *c1cccc(*)n1]

Another embodiment provides a compound of Formula (A) or tautomer, stereoisomer, geometric isomer or a pharmaceutically acceptable solvate, hydrate, salt, or N-oxide thereof, wherein, $R^1$ is hydrogen, $R^2$ is —OH, $R^3$, $R^4$, $R^5$ and $R^6$ are hydrogen;

Y is —C($R^{16}$)($R^{17}$)($R^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C($R^9$)$_2$—, or —C($R^9$)$_2$—C($R^9$)$_2$—; and ring A is:

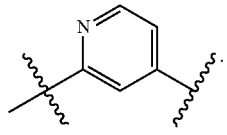 [SMILES: *c1ccnc(*)c1]

Another embodiment provides a compound of Formula (A) or tautomer, stereoisomer, geometric isomer or a pharmaceutically acceptable solvate, hydrate, salt, or N-oxide thereof, wherein, $R^1$ is hydrogen, $R^2$ is —OH, $R^3$, $R^4$, $R^5$ and $R^6$ are hydrogen;

Y is —C($R^{16}$)($R^{17}$)($R^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C($R^9$)$_2$—, or —C($R^9$)$_2$—C($R^9$)$_2$—; and ring A is:

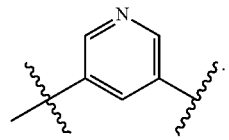 [SMILES: *c1cncc(*)c1]

Another embodiment provides a compound of Formula (A) or tautomer, stereoisomer, geometric isomer or a pharmaceutically acceptable solvate, hydrate, salt, or N-oxide thereof, wherein, $R^1$ is hydrogen, $R^2$ is —OH, $R^3$, $R^4$, $R^5$ and $R^6$ are hydrogen;

Y is —C($R^{16}$)($R^{17}$)($R^{18}$);

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocyclyl;

$R^{18}$ is selected from a hydrogen, alkyl, alkoxy, hydroxy, halo or fluoroalkyl;

X is selected from —O—C($R^9$)$_2$—, or —C($R^9$)$_2$—C($R^9$)$_2$—; and ring A is:

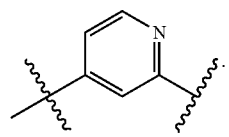 [SMILES: *c1ccnc(*)c1]

One embodiment provides a compound, or tautomer, stereoisomer, geometric isomer, or pharmaceutically acceptable solvate, hydrate, salt, or N-oxide thereof, selected from the group consisting of:

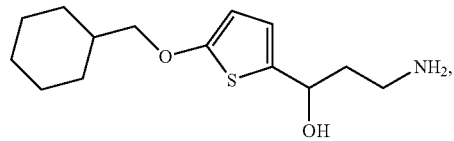

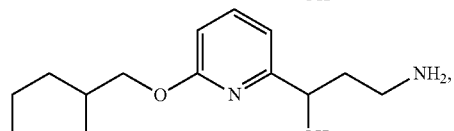

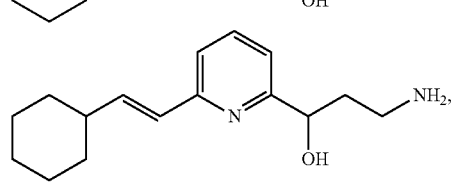

-continued
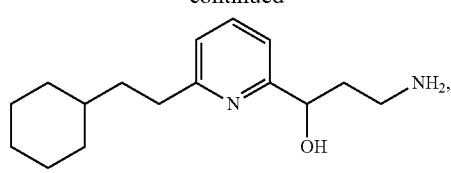
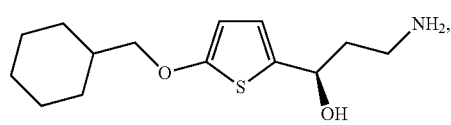
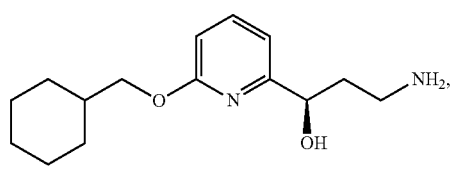
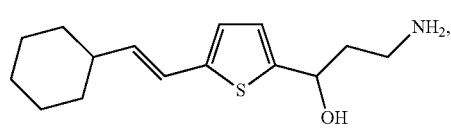
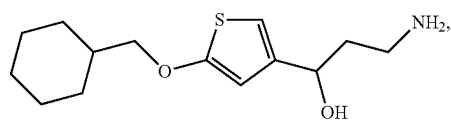
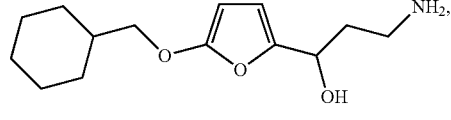
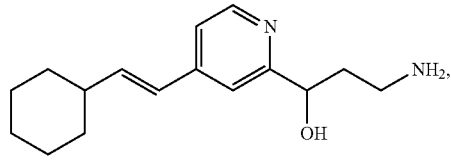
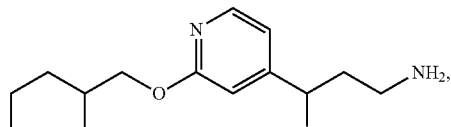
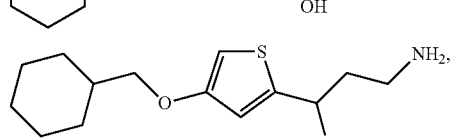
-continued
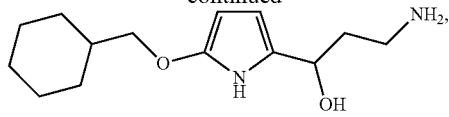
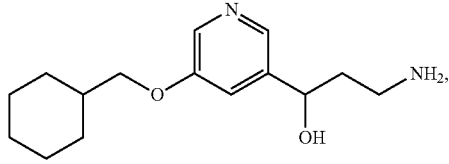
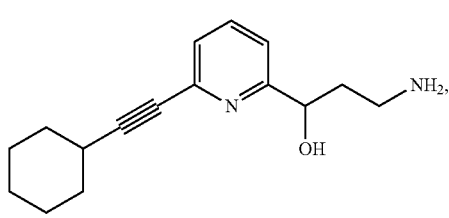
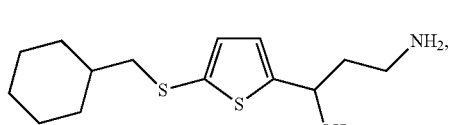
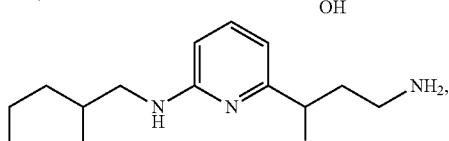
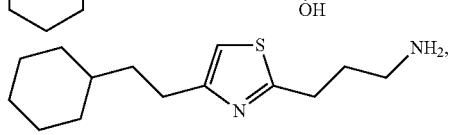
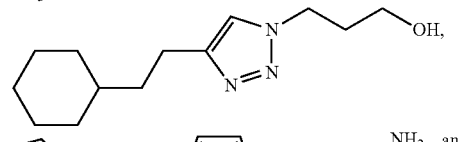
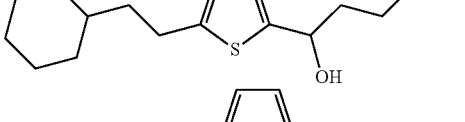
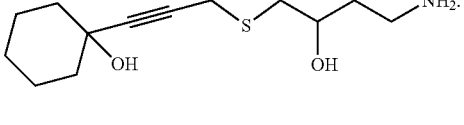
In some embodiments the compounds of Formula (A) disclosed herein have the structure provided in Table 1A.
TABLE 1A
| Synthesis Example | Structure | Name |
|---|---|---|
| 1 | 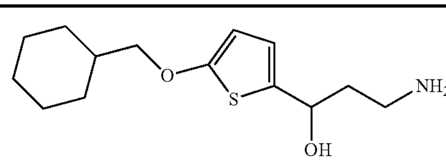 | 3-Amino-1-(5-(cyclohexylmethoxy)-thiophen-2-yl)propan-1-ol |

TABLE 1A-continued

| Synthesis Example | Structure | Name |
|---|---|---|
| 2 | 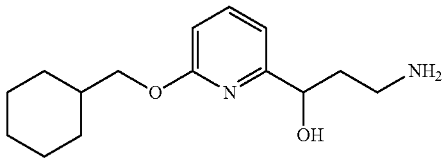 [SMILES: NCCC(O)c1cccc(OCC2CCCCC2)n1] | 3-Amino-1-(6-(cyclohexylmethoxy)-pyridin-2-yl)propan-1-ol |
| 3 | 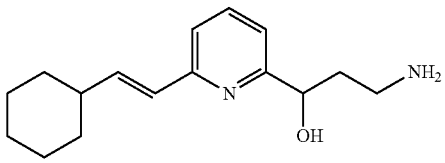 [SMILES: NCCC(O)c1cccc(/C=C/C2CCCCC2)n1] | (E)-3-Amino-1-(6-(2-cyclohexylvinyl)pyridin-2-yl)propan-1-ol |
| 4 | 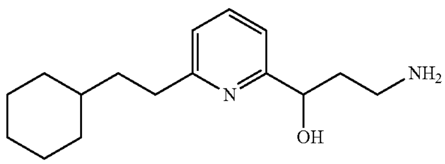 [SMILES: NCCC(O)c1cccc(CCC2CCCCC2)n1] | 3-Amino-1-(6-(2-cyclohexylethyl)pyridin-2-yl)propan-1-ol |
| 5 | 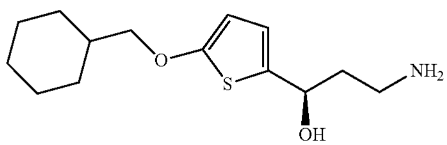 [SMILES: NCC[C@@H](O)c1ccc(OCC2CCCCC2)s1] | (R)-3-Amino-1-(5-(cyclohexylmethoxy)thiophen-2-yl)propan-1-ol |
| 6 | 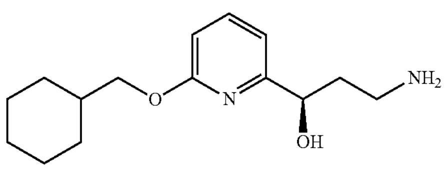 | (R)-3-Amino-1-(6-(cyclohexylmethoxy)pyridin-2-yl)propan-1-ol |
| 7 | 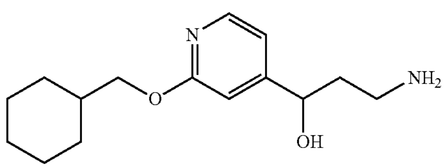 [SMILES: NCCC(O)c1ccnc(OCC2CCCCC2)c1] | 3-Amino-1-(2-(cyclohexylmethoxy)pyridin-4-yl)propan-1-ol |
| 8 | 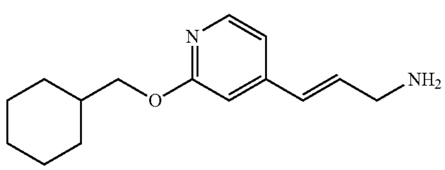 [SMILES: NC/C=C/c1ccnc(OCC2CCCCC2)c1] | (E)-3-(2-(Cyclohexylmethoxy)pyridin-4-yl)prop-2-en-1-amine |
| 9 | 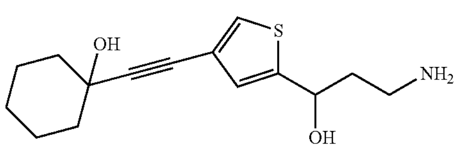 [SMILES: NCCC(O)c1cc(C#CC2(O)CCCCC2)cs1] | 1-((5-(3-Amino-1-hydroxypropyl)thiophen-3-yl)ethynyl)cyclohexanol |
| 10 | 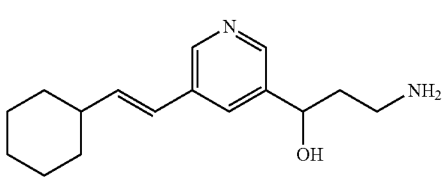 [SMILES: NCCC(O)c1cncc(/C=C/C2CCCCC2)c1] | (E)-3-Amino-1-(5-(2-cyclohexylvinyl)pyridin-3-yl)propan-1-ol |

TABLE 1A-continued

| Synthesis Example | Structure | Name |
|---|---|---|
| 11 | 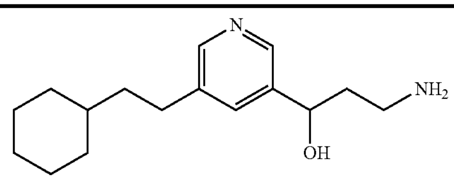 | 3-Amino-1-(5-(2-cyclohexylethyl)pyridin-3-yl)propan-1-ol |
| 12 | 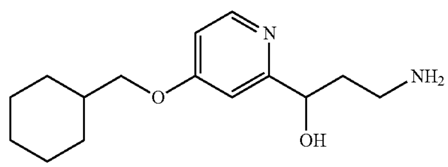 [SMILES: NCCC(O)c1cc(OCC2CCCCC2)ccn1] | 3-Amino-1-(4-(cyclohexylmethoxy)pyridin-2-yl)propan-1-ol |
| 13 | 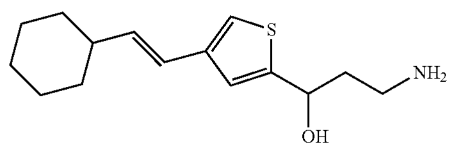 | (E)-3-Amino-1-(4-(2-cyclohexylvinyl)thiophen-2-yl)propan-1-ol |
| 14 | 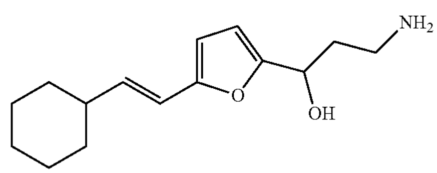 [SMILES: NCCC(O)c1ccc(/C=C/C2CCCCC2)o1] | (E)-3-Amino-1-(5-(2-cyclohexylvinyl)furan-2-yl)propan-1-ol |
| 15 | 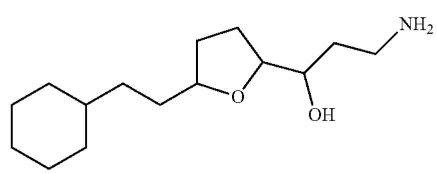 [SMILES: NCCC(O)C1CCC(CCC2CCCCC2)O1] | 3-Amino-1-(5-(2-cyclohexylethyl)tetrahydrofuran-2-yl)propan-1-ol |
| 16 | 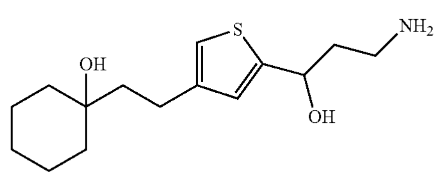 [SMILES: NCCC(O)c1cc(CCC2(O)CCCCC2)cs1] | 1-(2-(5-(3-Amino-1-hydroxypropyl)thiophen-3-yl)ethyl)cyclohexanol |
| 17 | 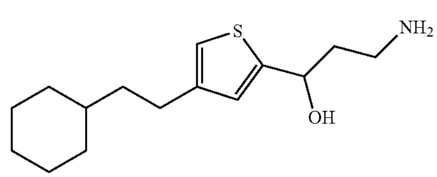 [SMILES: NCCC(O)c1cc(CCC2CCCCC2)cs1] | 3-Amino-1-(4-(2-cyclohexylethyl)thiophen-2-yl)propan-1-ol |
| 18 | 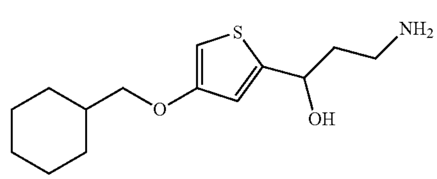 [SMILES: NCCC(O)c1cc(OCC2CCCCC2)cs1] | 3-Amino-1-(4-(cyclohexylmethoxy)thiophen-2-yl)propan-1-ol |
| 19 | 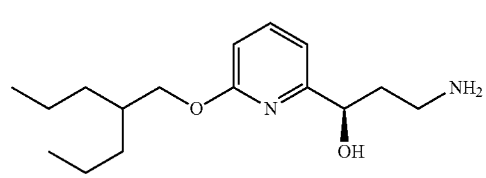 [SMILES: CCCC(CCC)COc1cccc([C@H](O)CCN)n1] | (R)-3-Amino-1-(6-((2-propylpentyl)oxy)pyridin-2-yl)propan-1-ol |

TABLE 1A-continued

| Synthesis Example | Structure | Name |
|---|---|---|
| 20 | 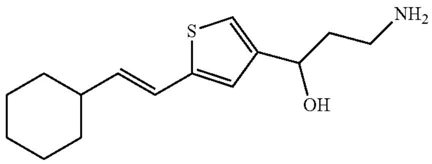 [SMILES: NCCC(O)c1csc(/C=C/C2CCCCC2)c1] | (E)-3-Amino-1-(5-(2-cyclohexylvinyl)thiophen-3-yl)propan-1-ol |
| 21 | 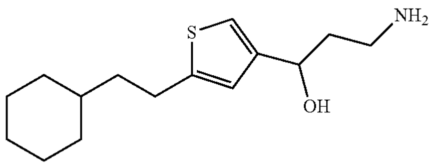 [SMILES: NCCC(O)c1csc(CCC2CCCCC2)c1] | 3-Amino-1-(5-(2-cyclohexylethyl)thiophen-3-yl)propan-1-ol |
| 22 | 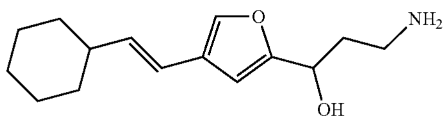 [SMILES: NCCC(O)c1cc(/C=C/C2CCCCC2)co1] | (E)-3-Amino-1-(4-(2-cyclohexylvinyl)furan-2-yl)propan-1-ol |
| 23 | 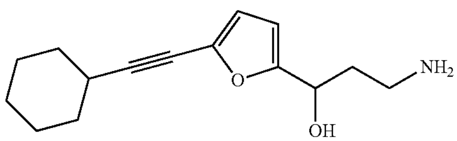 [SMILES: NCCC(O)c1ccc(C#CC2CCCCC2)o1] | 3-Amino-1-(5-(cyclohexylethynyl)furan-2-yl)propan-1-ol |
| 24 | 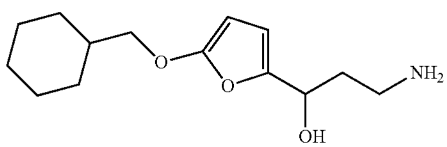 | 3-Amino-1-(5-(cyclohexylmethoxy)furan-2-yl)propan-1-ol |
| 25 | 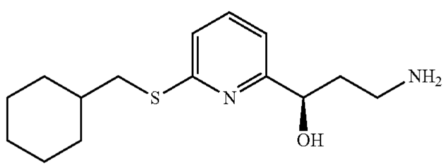 [SMILES: NCC[C@@H](O)c1cccc(SCC2CCCCC2)n1] | (R)-3-Amino-1-(6-((cyclohexylmethyl)thio)pyridin-2-yl)propan-1-ol |
| 26 | 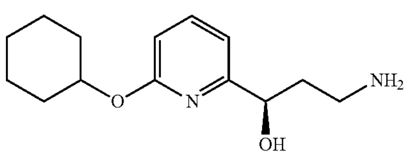 [SMILES: NCC[C@@H](O)c1cccc(OC2CCCCC2)n1] | (R)-3-Amino-1-(6-(cyclohexyloxy)pyridin-2-yl)propan-1-ol |
| 27 | 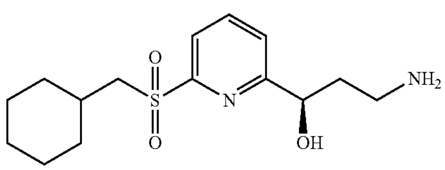 [SMILES: NCC[C@@H](O)c1cccc(S(=O)(=O)CC2CCCCC2)n1] | (R)-3-Amino-1-(6-((cyclohexylmethyl)sulfonyl)pyridin-2-yl)propan-1-ol |
| 28 | 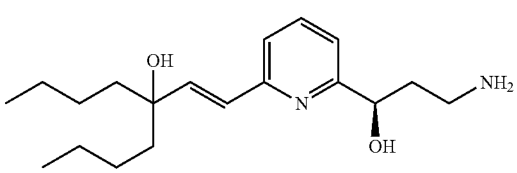 [SMILES: CCCCC(O)(/C=C/c1cccc([C@H](O)CCN)n1)CCCC] | (R,E)-5-(2-(6-(3-Amino-1-hydroxypropyl)pyridin-2-yl)vinyl)nonan-5-ol |

TABLE 1A-continued

| Synthesis Example | Structure | Name |
|---|---|---|
| 29 | 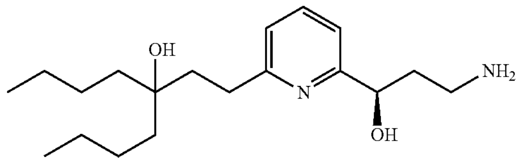 [SMILES: CCCCC(O)(CCCC)CCc1cccc([C@H](O)CCN)n1] | (R)-5-(2-(6-(3-Amino-1-hydroxypropyl)pyridin-2-yl)ethyl)nonan-5-ol |
| 30 | 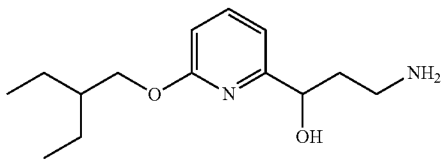 [SMILES: CCC(CC)COc1cccc(C(O)CCN)n1] | 3-Amino-1-(6-(2-ethylbutoxy)pyridin-2-yl)propan-1-ol |
| 31 | 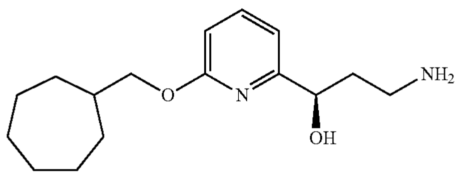 [SMILES: NCC[C@@H](O)c1cccc(OCC2CCCCCC2)n1] | (R)-3-Amino-1-(6-(cycloheptylmethoxy)pyridin-2-yl)propan-1-ol |
| 32 | 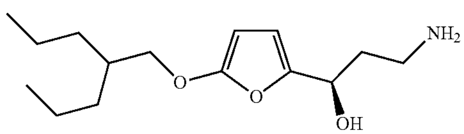 [SMILES: CCCC(CCC)COc1ccc([C@H](O)CCN)o1] | (R)-3-Amino-1-(5-((2-propylpentyl)oxy)furan-2-yl)propan-1-ol |
| 33 | 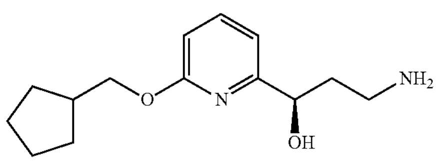 [SMILES: NCC[C@@H](O)c1cccc(OCC2CCCC2)n1] | (R)-3-Amino-1-(6-(cyclopentylmethoxy)pyridin-2-yl)propan-1-ol |
| 34 | 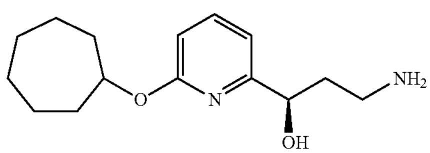 [SMILES: NCC[C@@H](O)c1cccc(OC2CCCCCC2)n1] | (R)-3-Amino-1-(6-(cycloheptyloxy)pyridin-2-yl)propan-1-ol |
| 35 | 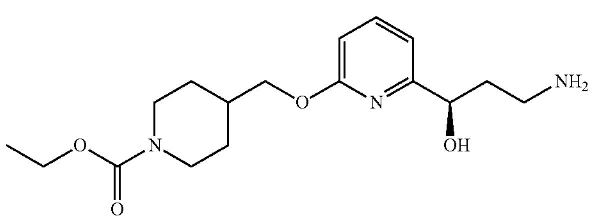 [SMILES: CCOC(=O)N1CCC(COc2cccc([C@H](O)CCN)n2)CC1] | (R)-Ethyl 4-(((6-(3-amino-1-hydroxypropyl)pyridin-2-yl)oxy)methyl)piperidine-1-carboxylate |
| 36 | 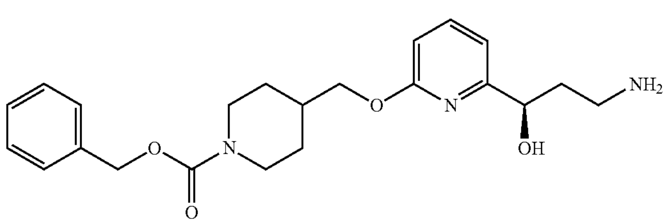 [SMILES: NCC[C@@H](O)c1cccc(OCC2CCN(C(=O)OCc3ccccc3)CC2)n1] | (R)-Benzyl 4-(((6-(3-amino-1-hydroxypropyl)pyridin-2-yl)oxy)methyl)piperidine-1-carboxylate |

TABLE 1A-continued

| Synthesis Example | Structure | Name |
|---|---|---|
| 37 | 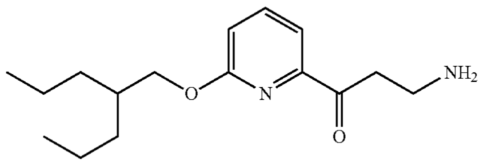 [SMILES: CCCC(CCC)COc1cccc(C(=O)CCN)n1] | 3-Amino-1-(6-((2-propylpentyl)oxy)pyridin-2-yl)propan-1-one |
| 38 | 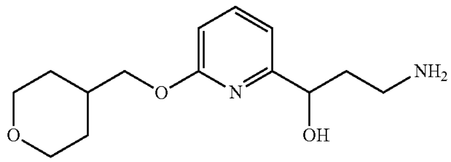 [SMILES: NCCC(O)c1cccc(OCC2CCOCC2)n1] | 3-Amino-1-(6-((tetrahydro-2H-pyran-4-yl)methoxy)pyridin-2-yl)propan-1-ol |
| 39 | 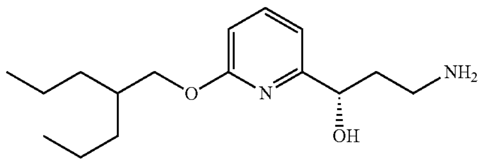 [SMILES: CCCC(CCC)COc1cccc([C@@H](O)CCN)n1] | (S)-3-Amino-1-(6-((2-propylpentyl)oxy)pyridin-2-yl)propan-1-ol |
| 40 | 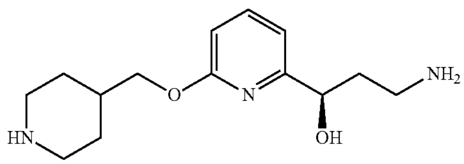 [SMILES: NCC[C@@H](O)c1cccc(OCC2CCNCC2)n1] | (R)-3-Amino-1-(6-(piperidin-4-ylmethoxy)pyridin-2-yl)propan-1-ol |
| 41 | 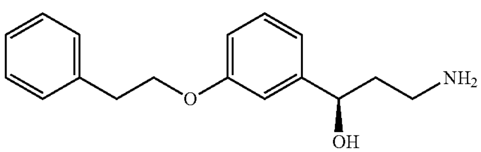 [SMILES: NCC[C@@H](O)c1cccc(OCCc2ccccc2)c1] | (R)-3-Amino-1-(6-phenethoxypyridin-2-yl)propan-1-ol |
| 42 | 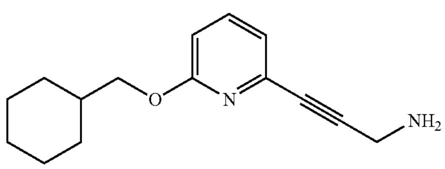 [SMILES: NCC#Cc1cccc(OCC2CCCCC2)n1] | 3-(6-(Cyclohexylmethoxy)pyridin-2-yl)prop-2-yn-1-amine |
| 43 | 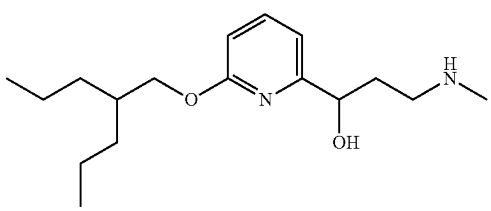 [SMILES: CCCC(CCC)COc1cccc(C(O)CCNC)n1] | 3-(Methylamino)-1-(6-((2-propylpentyl)oxy)pyridin-2-yl)propan-1-ol |
| 44 | 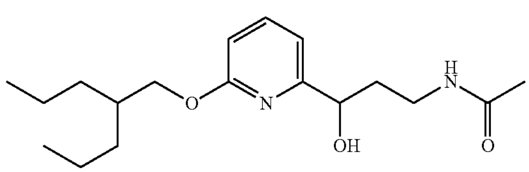 [SMILES: CCCC(CCC)COc1cccc(C(O)CCNC(C)=O)n1] | N-(3-Hydroxy-3-(6-((2-propylpentyl)oxy)pyridin-2-yl)propyl)acetamide |
| 45 | 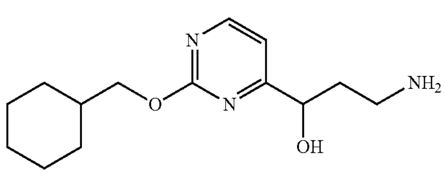 [SMILES: NCCC(O)c1ccnc(OCC2CCCCC2)n1] | 3-Amino-1-(2-(cyclohexylmethoxy)pyrimidin-4-yl)propan-1-ol |

TABLE 1A-continued

| Synthesis Example | Structure | Name |
|---|---|---|
| 46 | (structure) | (R)-3-amino-1-(4-(cyclohexylmethoxy)pyrimidin-2-yl)propan-1-ol |

In another embodiment is a compound selected from the group consisting of:
3-Amino-1-(5-(cyclohexylmethoxy)thiophen-2-yl)propan-1-ol;
3-Amino-1-(6-(cyclohexylmethoxy)pyridin-2-yl)propan-1-ol;
(E)-3-Amino-1-(6-(2-cyclohexylvinyl)pyridin-2-yl)propan-1-ol;
3-Amino-1-(6-(2-cyclohexylethyl)pyridin-2-yl)propan-1-ol;
(R)-3-Amino-1-(5-(cyclohexylmethoxy)thiophen-2-yl)propan-1-ol;
(R)-3-Amino-1-(6-(cyclohexylmethoxy)pyridin-2-yl)propan-1-ol;
3-Amino-1-(2-(cyclohexylmethoxy)pyridin-4-yl)propan-1-ol;
(E)-3-(2-(Cyclohexylmethoxy)pyridin-4-yl)prop-2-en-1-amine;
1-((5-(3-Amino-1-hydroxypropyl)thiophen-3-yl)ethynyl)cyclohexanol;
(E)-3-Amino-1-(5-(2-cyclohexylvinyl)pyridin-3-yl)propan-1-ol;
3-Amino-1-(5-(2-cyclohexylethyl)pyridin-3-yl)propan-1-ol;
3-Amino-1-(4-(cyclohexylmethoxy)pyridin-2-yl)propan-1-ol;
(E)-3-Amino-1-(4-(2-cyclohexylvinyl)thiophen-2-yl)propan-1-ol;
(E)-3-Amino-1-(5-(2-cyclohexylvinyl)furan-2-yl)propan-1-ol;
3-Amino-1-(5-(2-cyclohexylethyl)tetrahydrofuran-2-yl)propan-1-ol;
1-(2-(5-(3-Amino-1-hydroxypropyl)thiophen-3-yl)ethyl)cyclohexanol;
3-Amino-1-(4-(2-cyclohexylethyl)thiophen-2-yl)propan-1-ol;
3-Amino-1-(4-(cyclohexylmethoxy)thiophen-2-yl)propan-1-ol;
(R)-3-Amino-1-(6-((2-propylpentyl)oxy)pyridin-2-yl)propan-1-ol;
(E)-3-Amino-1-(5-(2-cyclohexylvinyl)thiophen-3-yl)propan-1-ol;
3-Amino-1-(5-(2-cyclohexylethyl)thiophen-3-yl)propan-1-ol;
(E)-3-Amino-1-(4-(2-cyclohexylvinyl)furan-2-yl)propan-1-ol;
3-Amino-1-(5-(cyclohexylethynyl)furan-2-yl)propan-1-ol;
3-Amino-1-(5-(cyclohexylmethoxy)furan-2-yl)propan-1-ol;
(R)-3-Amino-1-(6-(((cyclohexylmethyl)thio)pyridin-2-yl)propan-1-ol;
(R)-3-Amino-1-(6-(cyclohexyloxy)pyridin-2-yl)propan-1-ol;
(R)-3-Amino-1-(6-(((cyclohexylmethyl)sulfonyl)pyridin-2-yl)propan-1-ol;
(R,E)-5-(2-(6-(3-Amino-1-hydroxypropyl)pyridin-2-yl)vinyl)nonan-5-ol;
(R)-5-(2-(6-(3-Amino-1-hydroxypropyl)pyridin-2-yl)ethyl)nonan-5-ol;
3-Amino-1-(6-(2-ethylbutoxy)pyridin-2-yl)propan-1-ol;
(R)-3-Amino-1-(6-(cycloheptylmethoxy)pyridin-2-yl)propan-1-ol;
(R)-3-Amino-1-(5-((2-propylpentyl)oxy)furan-2-yl)propan-1-ol;
(R)-3-Amino-1-(6-(cyclopentylmethoxy)pyridin-2-yl)propan-1-ol;
(R)-3-Amino-1-(6-(cycloheptyloxy)pyridin-2-yl)propan-1-ol;
(R)-Ethyl 4-(((6-(3-amino-1-hydroxypropyl)pyridin-2-yl)oxy)methyl)piperidine-1-carboxylate;
(R)-Benzyl 4-(((6-(3-amino-1-hydroxypropyl)pyridin-2-yl)oxy)methyl)piperidine-1-carboxylate;
3-Amino-1-(6-((2-propylpentyl)oxy)pyridin-2-yl)propan-1-one;
3-Amino-1-(6-((tetrahydro-2H-pyran-4-yl)methoxy)pyridin-2-yl)propan-1-ol;
(S)-3-Amino-1-(6-((2-propylpentyl)oxy)pyridin-2-yl)propan-1-ol;
(R)-3-Amino-1-(6-(piperidin-4-ylmethoxy)pyridin-2-yl)propan-1-ol;
(R)-3-Amino-1-(6-phenethoxypyridin-2-yl)propan-1-ol;
3-(6-(Cyclohexylmethoxy)pyridin-2-yl)prop-2-yn-1-amine;
3-(Methylamino)-1-(6-((2-propylpentyl)oxy)pyridin-2-yl)propan-1-ol;
N-(3-Hydroxy-3-(6-((2-propylpentyl)oxy)pyridin-2-yl)propyl)acetamide;
3-Amino-1-(2-(cyclohexylmethoxy)pyrimidin-4-yl)propan-1-ol; and
(R)-3-amino-1-(4-(cyclohexylmethoxy)pyrimidin-2-yl)propan-1-ol.

In additional embodiments, the compound of Formula (A) is selected from the group consisting of:

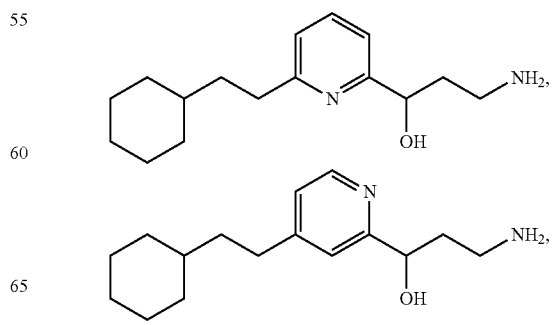

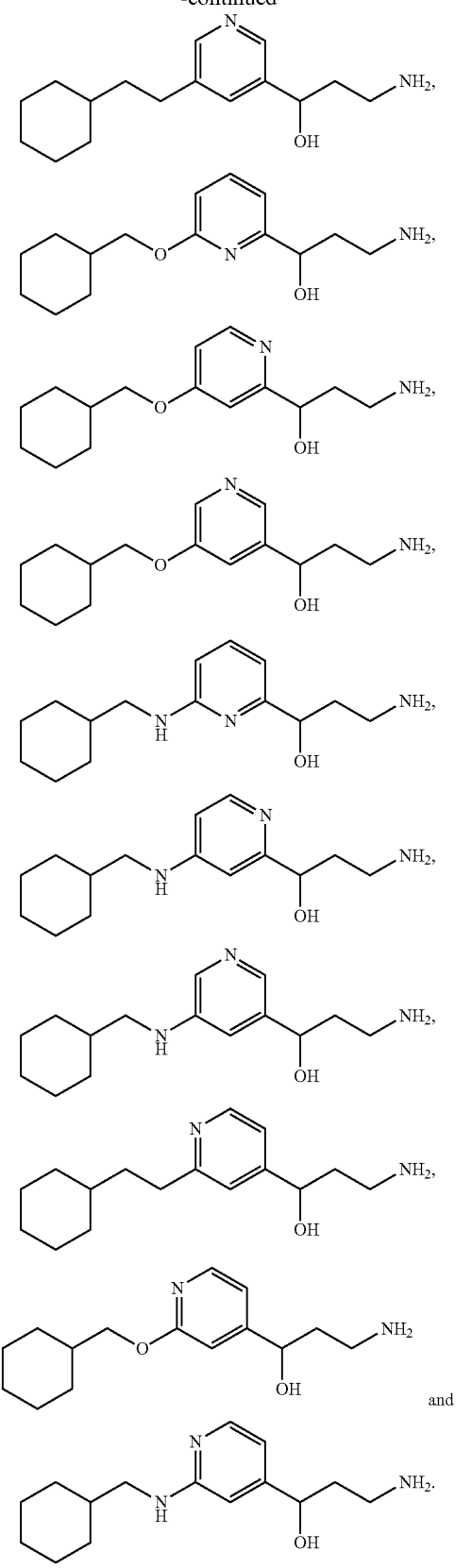
In additional embodiments, the compound of Formula (A) is selected from the group consisting of:

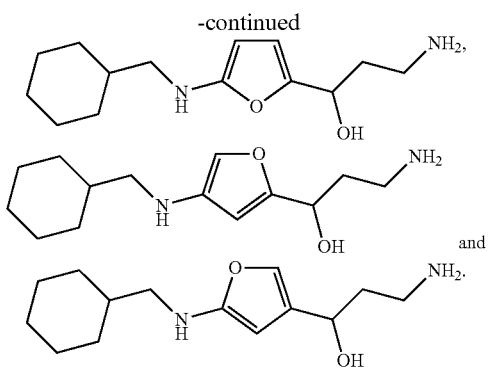

One embodiment provides a compound of Formula (B) or tautomer, stereoisomer, geometric isomer or a pharmaceutically acceptable solvate, hydrate, salt, or N-oxide thereof:

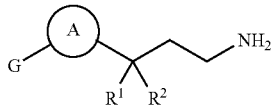

Formula (B)

wherein,

Ring A is selected from a 1,3-disubstituted heterocycle;

G is —X—Y;

X is selected from —O—, —S—, —NH—, or —CH$_2$—;

Y is selected from carbocyclyl, or heterocyclyl; and

R$^1$ and R$^2$ are each independently selected from hydrogen, or —OH; or R$^1$ and R$^2$ form an oxo.

For any and all of the embodiments, substituents are selected from among from a subset of the listed alternatives. For example, in some embodiments is provided a compound of Formula (B) or tautomer, stereoisomer, geometric isomer or a pharmaceutically acceptable solvate, hydrate, salt, or N-oxide thereof, wherein Ring A is selected from:

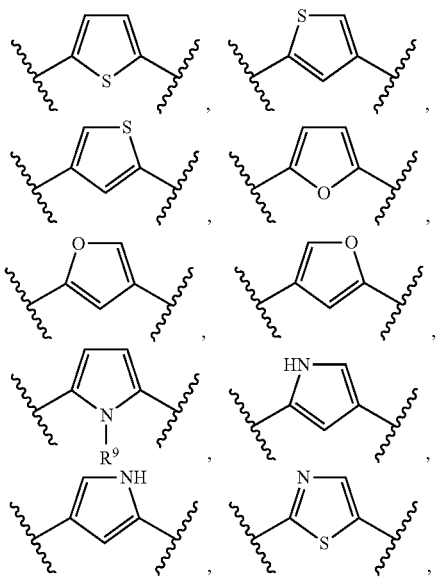

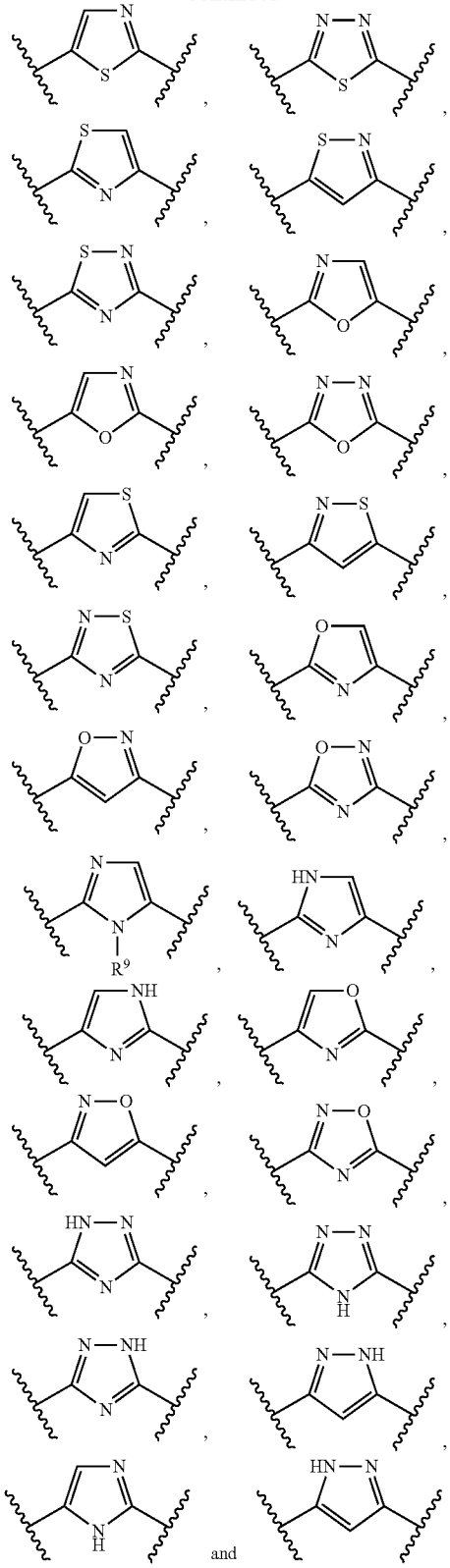

Another embodiment provides a compound of Formula (B) or tautomer, stereoisomer, geometric isomer or a pharmaceutically acceptable solvate, hydrate, salt, or N-oxide thereof, wherein Ring A is selected from:

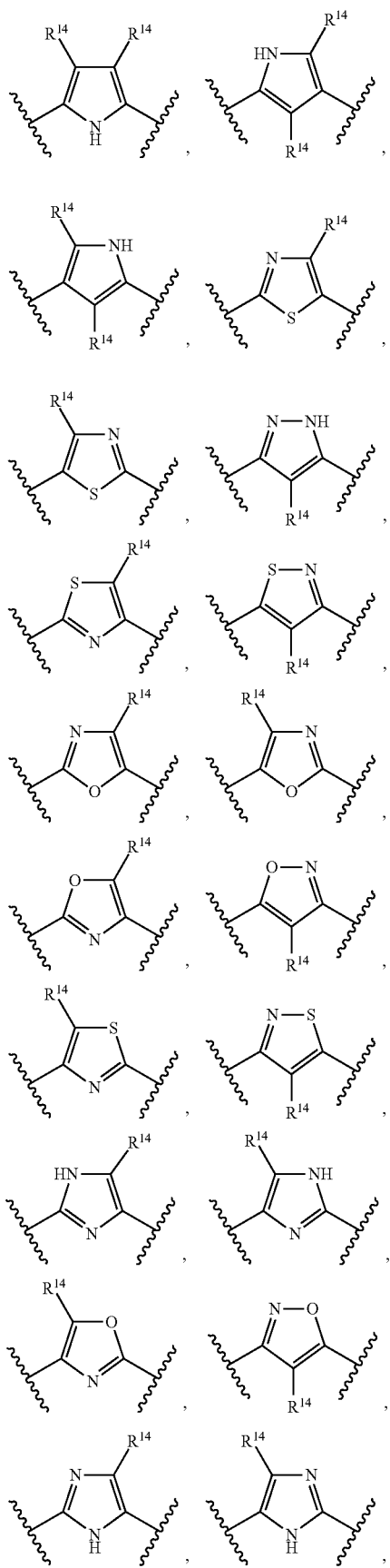
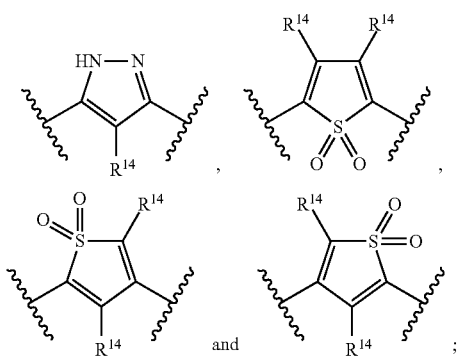

and each $R^{14}$ is independently selected from hydrogen, halogen, alkyl, or fluoroalkyl.

Another embodiment provides a compound of Formula (B) or tautomer, stereoisomer, geometric isomer or a pharmaceutically acceptable solvate, hydrate, salt, or N-oxide thereof, wherein Ring A is selected from:

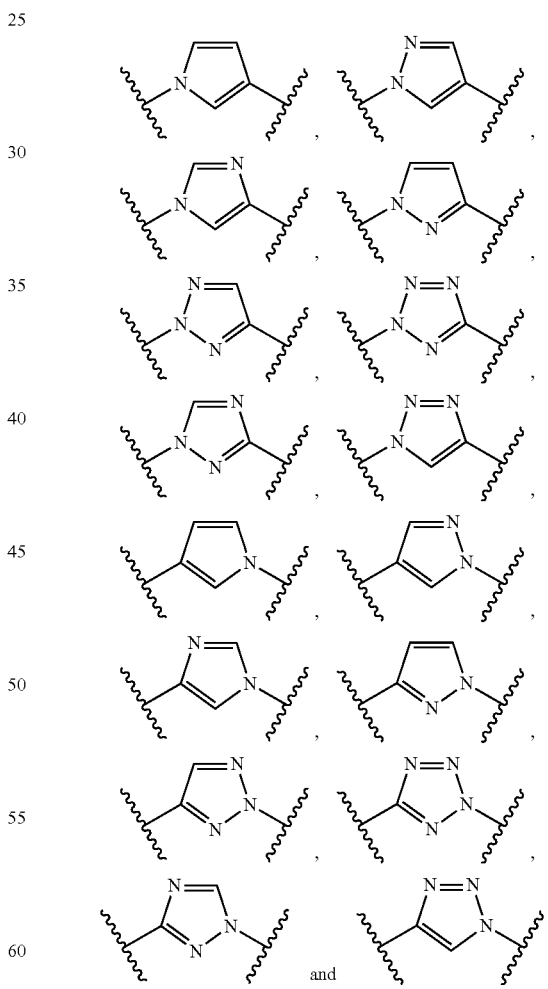

Another embodiment provides a compound of Formula (B) or tautomer, stereoisomer, geometric isomer or a pharmaceutically acceptable solvate, hydrate, salt, or N-oxide thereof, wherein Ring A is selected from:

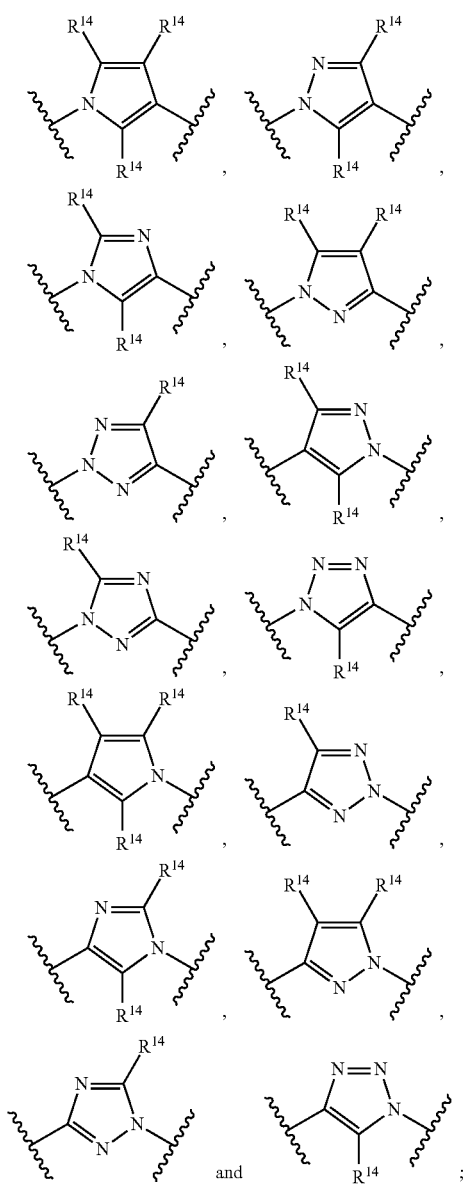

and each R[14] is independently selected from hydrogen, halogen, alkyl, or fluoroalkyl.

Another embodiment provides a compound of Formula (B) or tautomer, stereoisomer, geometric isomer or a pharmaceutically acceptable solvate, hydrate, salt, or N-oxide thereof, wherein Ring A is selected from:

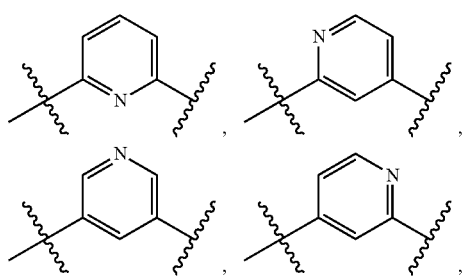

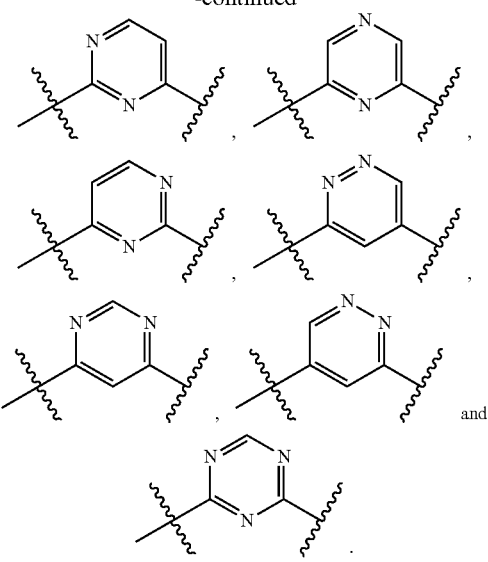

Another embodiment provides a compound of Formula (B) or tautomer, stereoisomer, geometric isomer or a pharmaceutically acceptable solvate, hydrate, salt, or N-oxide thereof, wherein Ring A is selected from:

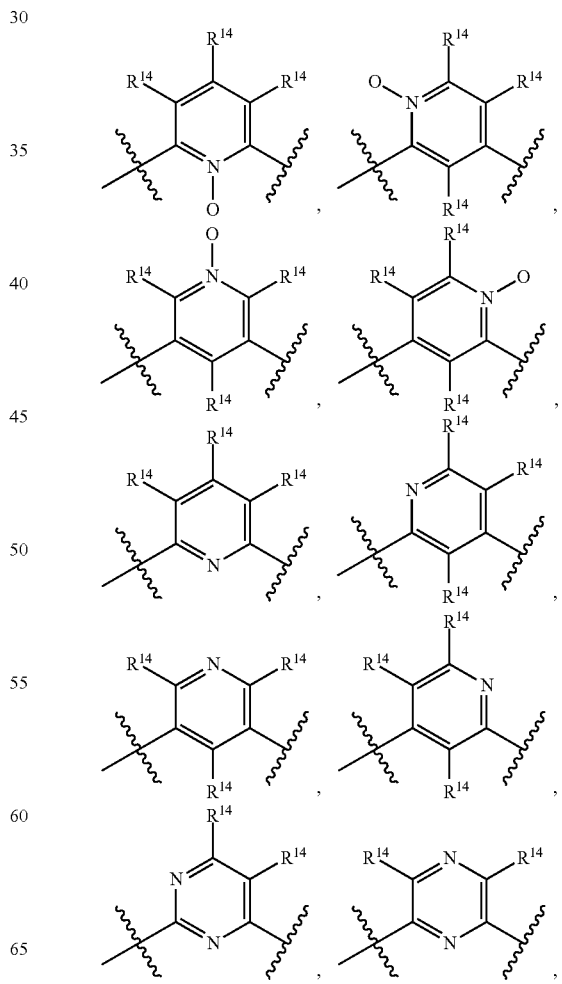

-continued

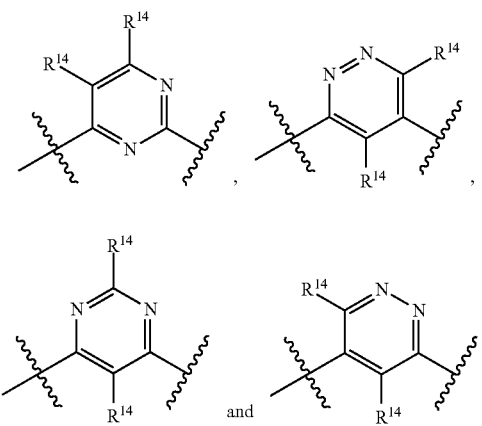

and each $R^{14}$ is independently selected from hydrogen, halogen, alkyl, or fluoroalkyl.

Another embodiment provides a compound of Formula (B) or tautomer, stereoisomer, geometric isomer or a pharmaceutically acceptable solvate, hydrate, salt, or N-oxide thereof, wherein Ring A is selected from:

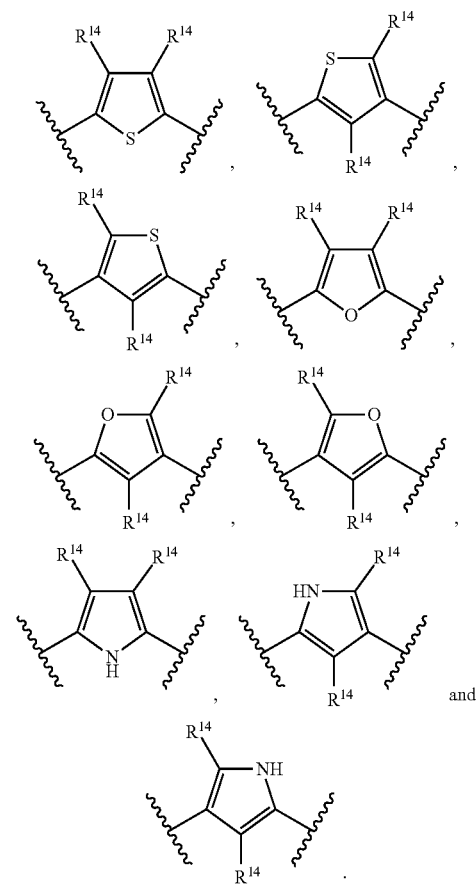

Another embodiment provides a compound of Formula (B) or tautomer, stereoisomer, geometric isomer or a pharmaceutically acceptable solvate, hydrate, salt, or N-oxide thereof, wherein Ring A is selected from:

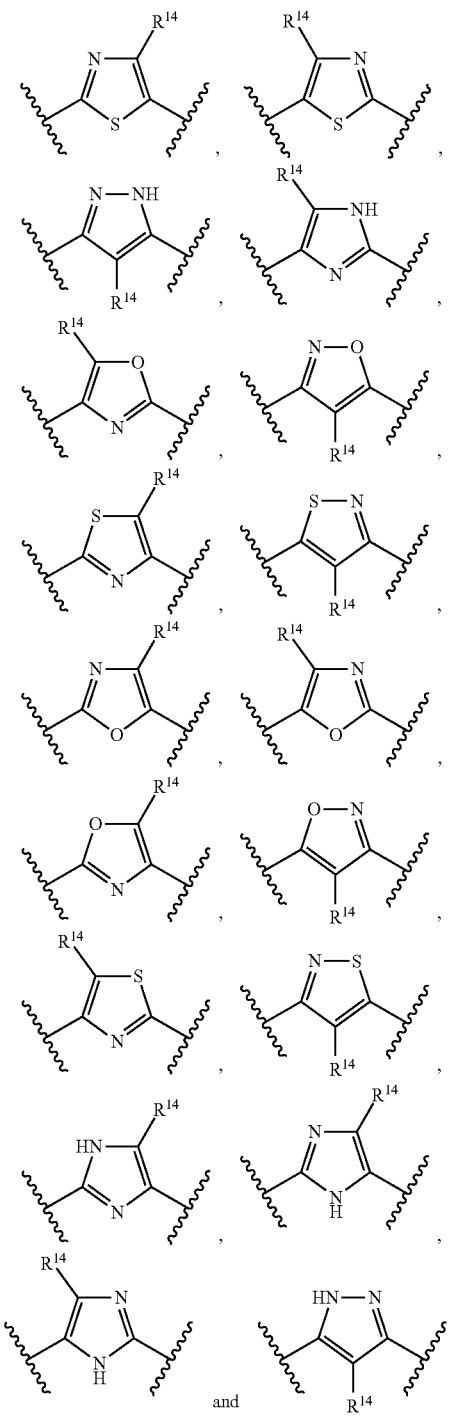

Another embodiment provides a compound of Formula (B) or tautomer, stereoisomer, geometric isomer or a pharmaceutically acceptable solvate, hydrate, salt, or N-oxide thereof, wherein Ring A is selected from:

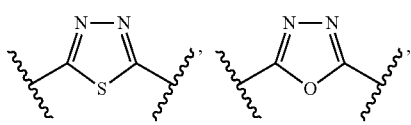

-continued

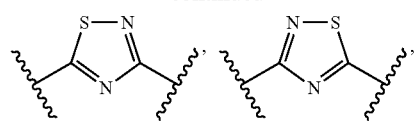

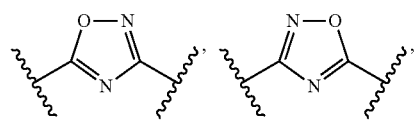

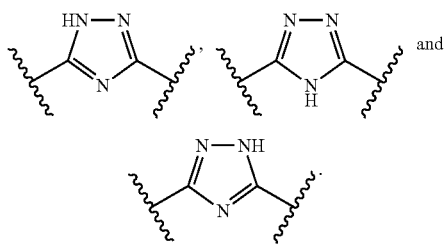

Another embodiment provides a compound of Formula (B) or tautomer, stereoisomer, geometric isomer or a pharmaceutically acceptable solvate, hydrate, salt, or N-oxide thereof, wherein Ring A is selected from:

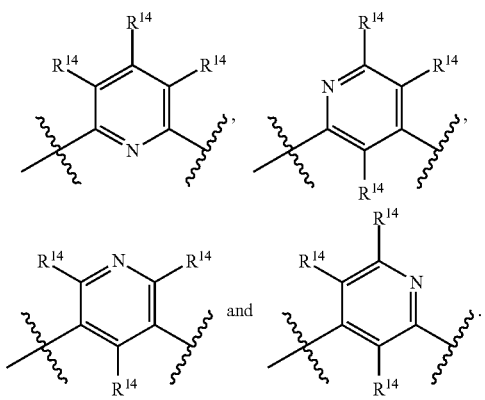

Another embodiment provides a compound of Formula (B) or tautomer, stereoisomer, geometric isomer or a pharmaceutically acceptable solvate, hydrate, salt, or N-oxide thereof, wherein Ring A is selected from:

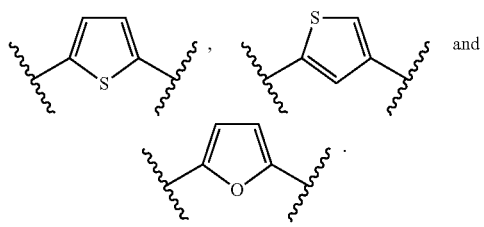

Another embodiment provides a compound of Formula (B) or tautomer, stereoisomer, geometric isomer or a pharmaceutically acceptable solvate, hydrate, salt, or N-oxide thereof, wherein Ring A is:

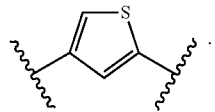 [SMILES: *c1csc(*)c1]

Another embodiment provides a compound of Formula (B) or tautomer, stereoisomer, geometric isomer or a pharmaceutically acceptable solvate, hydrate, salt, or N-oxide thereof, wherein Ring A is:

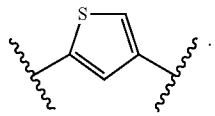 [SMILES: *c1csc(*)c1]

Another embodiment provides a compound of Formula (B) or tautomer, stereoisomer, geometric isomer or a pharmaceutically acceptable solvate, hydrate, salt, or N-oxide thereof, wherein Ring A is:

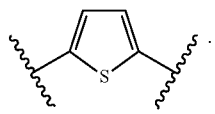

Another embodiment provides a compound of Formula (B) or tautomer, stereoisomer, geometric isomer or a pharmaceutically acceptable solvate, hydrate, salt, or N-oxide thereof, wherein Ring A is:

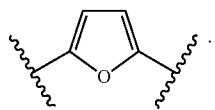 [SMILES: *c1ccc(*)o1]

Another embodiment provides a compound of Formula (B) or tautomer, stereoisomer, geometric isomer or a pharmaceutically acceptable solvate, hydrate, salt, or N-oxide thereof, wherein Ring A is:

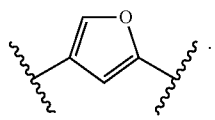 [SMILES: *c1coc(*)c1]

Another embodiment provides a compound of Formula (B) or tautomer, stereoisomer, geometric isomer or a pharmaceutically acceptable solvate, hydrate, salt, or N-oxide thereof, wherein Ring A is:

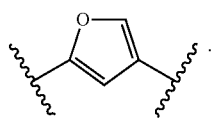 [SMILES: *c1coc(*)c1]

Another embodiment provides a compound of Formula (B) or tautomer, stereoisomer, geometric isomer or a pharmaceutically acceptable solvate, hydrate, salt, or N-oxide thereof, wherein Ring A is:

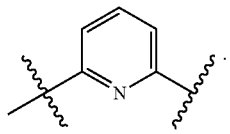

Another embodiment provides a compound of Formula (B) or tautomer, stereoisomer, geometric isomer or a pharmaceutically acceptable solvate, hydrate, salt, or N-oxide thereof, wherein Ring A is:

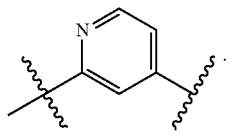 [SMILES: *c1ccnc(*)c1]

Another embodiment provides a compound of Formula (B) or tautomer, stereoisomer, geometric isomer or a pharmaceutically acceptable solvate, hydrate, salt, or N-oxide thereof, wherein Ring A is:

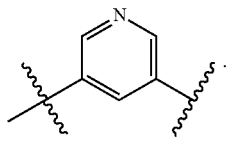 [SMILES: *c1cncc(*)c1]

Another embodiment provides a compound of Formula (B) or tautomer, stereoisomer, geometric isomer or a pharmaceutically acceptable solvate, hydrate, salt, or N-oxide thereof, wherein Ring A is:

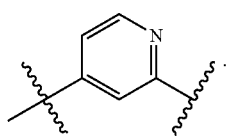 [SMILES: *c1ccnc(*)c1]

For any and all of the embodiments, substituents are selected from among from a subset of the listed alternatives. For example, in some embodiments is provided a compound of Formula (B) or tautomer, stereoisomer, geometric isomer or a pharmaceutically acceptable solvate, hydrate, salt, or N-oxide thereof, wherein Y is carbocyclyl. Another embodiment provides a compound of Formula (B) or tautomer, stereoisomer, geometric isomer or a pharmaceutically acceptable solvate, hydrate, salt, or N-oxide thereof, wherein Y is a 4-, 5-, 6-, or 7-membered carbocyclyl. Another embodiment provides a compound of Formula (B) or tautomer, stereoisomer, geometric isomer or a pharmaceutically acceptable solvate, hydrate, salt, or N-oxide thereof, wherein Y is cyclobutyl, cyclopentyl, cyclohexyl, or cycloheptyl.

Another embodiment provides a compound of Formula (B) or tautomer, stereoisomer, geometric isomer or a pharmaceutically acceptable solvate, hydrate, salt, or N-oxide thereof, wherein X is selected from —O—.

Another embodiment provides a compound of Formula (B) or tautomer, stereoisomer, geometric isomer or a pharmaceutically acceptable solvate, hydrate, salt, or N-oxide thereof, wherein X is selected from —S—.

Another embodiment provides a compound of Formula (B) or tautomer, stereoisomer, geometric isomer or a pharmaceutically acceptable solvate, hydrate, salt, or N-oxide thereof, wherein X is selected from —NH—.

Another embodiment provides a compound of Formula (B) or tautomer, stereoisomer, geometric isomer or a pharmaceutically acceptable solvate, hydrate, salt, or N-oxide thereof, wherein X is —CH$_2$—.

Another embodiment provides a compound of Formula (B) or tautomer, stereoisomer, geometric isomer or a pharmaceutically acceptable solvate, hydrate, salt, or N-oxide thereof, wherein X is selected from —O—, and Y is carbocyclyl. Another embodiment provides a compound of Formula (B) or tautomer, stereoisomer, geometric isomer or a pharmaceutically acceptable solvate, hydrate, salt, or N-oxide thereof, wherein X is selected from —O—, and Y is a 4-, 5-, 6-, or 7-membered carbocyclyl. Another embodiment provides a compound of Formula (B) or tautomer, stereoisomer, geometric isomer or a pharmaceutically acceptable solvate, hydrate, salt, or N-oxide thereof, wherein X is selected from —O—, and Y is cyclobutyl, cyclopentyl, cyclohexyl, or cycloheptyl.

Another embodiment provides a compound of Formula (B) or tautomer, stereoisomer, geometric isomer or a pharmaceutically acceptable solvate, hydrate, salt, or N-oxide thereof, wherein $R^1$ and $R^2$ are both hydrogen. Another embodiment provides a compound of Formula (B) or tautomer, stereoisomer, geometric isomer or a pharmaceutically acceptable solvate, hydrate, salt, or N-oxide thereof, wherein $R^1$ and $R^2$ are both hydrogen, X is selected from —O—, and Y is carbocyclyl. Another embodiment provides a compound of Formula (B) or tautomer, stereoisomer, geometric isomer or a pharmaceutically acceptable solvate, hydrate, salt, or N-oxide thereof, wherein $R^1$ and $R^2$ are both hydrogen, X is selected from —O—, and Y is a 4-, 5-, 6-, or 7-membered carbocyclyl. Another embodiment provides a compound of Formula (B) or tautomer, stereoisomer, geometric isomer or a pharmaceutically acceptable solvate, hydrate, salt, or N-oxide thereof, wherein $R^1$ and $R^2$ are both hydrogen, X is selected from —O—, and Y is cyclobutyl, cyclopentyl, cyclohexyl, or cycloheptyl.

Another embodiment provides a compound of Formula (B) or tautomer, stereoisomer, geometric isomer or a pharmaceutically acceptable solvate, hydrate, salt, or N-oxide thereof, wherein $R^1$ is hydrogen and $R^2$ is —OH. Another embodiment provides a compound of Formula (B) or tautomer, stereoisomer, geometric isomer or a pharmaceutically acceptable solvate, hydrate, salt, or N-oxide thereof, wherein $R^1$ is hydrogen and $R^2$ is —OH, X is selected from —O—, and Y is carbocyclyl. Another embodiment provides a compound of Formula (B) or tautomer, stereoisomer, geometric isomer or a pharmaceutically acceptable solvate, hydrate, salt, or N-oxide thereof, wherein $R^1$ is hydrogen and $R^2$ is —OH, X is selected from —O—, and Y is a 4-, 5-, 6-, or 7-membered carbocyclyl. Another embodiment provides a compound of Formula (B) or tautomer, stereoisomer, geometric isomer or a pharmaceutically acceptable solvate, hydrate, salt, or N-oxide thereof, wherein $R^1$ is hydrogen and $R^2$ is —OH, X is selected from —O—, and Y is cyclobutyl, cyclopentyl, cyclohexyl, or cycloheptyl.

Another embodiment provides a compound of Formula (B) or tautomer, stereoisomer, geometric isomer or a pharmaceutically acceptable solvate, hydrate, salt, or N-oxide thereof, wherein $R^1$ and $R^2$ together form an oxo. Another embodiment provides a compound of Formula (B) or tautomer, stereoisomer, geometric isomer or a pharmaceutically acceptable solvate, hydrate, salt, or N-oxide thereof, wherein $R^1$ and $R^2$ together form an oxo, X is selected from —O—, and Y is carbocyclyl. Another embodiment provides a compound of Formula (B) or tautomer, stereoisomer, geometric isomer or a pharmaceutically acceptable solvate, hydrate, salt, or N-oxide thereof, wherein $R^1$ and $R^2$ together form an oxo, X is selected from —O—, and Y is a 4-, 5-, 6-, or 7-membered carbocyclyl. Another embodiment provides a compound of Formula (B) or tautomer, stereoisomer, geometric isomer or a pharmaceutically acceptable solvate, hydrate, salt, or N-oxide thereof, wherein $R^1$ and $R^2$ together form an oxo, X is selected from —O—, and Y is a 4-, 5-, 6-, or 7-membered carbocyclyl.

Another embodiment provides a compound of Formula (B) or tautomer, stereoisomer, geometric isomer or a pharmaceutically acceptable solvate, hydrate, salt, or N-oxide thereof, wherein X is selected from —O—, and ring A is:

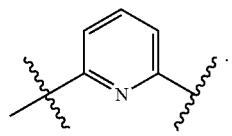 [SMILES: *c1cccc(*)n1]

Another embodiment provides a compound of Formula (B) or tautomer, stereoisomer, geometric isomer or a pharmaceutically acceptable solvate, hydrate, salt, or N-oxide thereof, wherein Y is carbocyclyl, and ring A is:

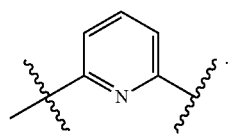

Another embodiment provides a compound of Formula (B) or tautomer, stereoisomer, geometric isomer or a pharmaceutically acceptable solvate, hydrate, salt, or N-oxide thereof, wherein Y is a 4-, 5-, 6-, or 7-membered carbocyclyl, and ring A is:

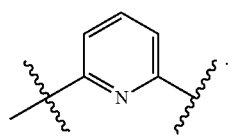

Another embodiment provides a compound of Formula (B) or tautomer, stereoisomer, geometric isomer or a pharmaceutically acceptable solvate, hydrate, salt, or N-oxide thereof, wherein Y is cyclobutyl, cyclopentyl, cyclohexyl, or cycloheptyl, and ring A is:

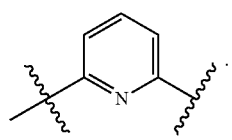 [SMILES: *c1cccc(*)n1]

Another embodiment provides a compound of Formula (B) or tautomer, stereoisomer, geometric isomer or a pharmaceutically acceptable solvate, hydrate, salt, or N-oxide thereof, wherein X is selected from —O—, Y is carbocyclyl, and ring A is:

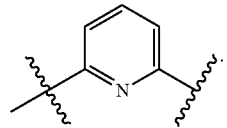 [SMILES: *c1cccc(*)n1]

Another embodiment provides a compound of Formula (B) or tautomer, stereoisomer, geometric isomer or a pharmaceutically acceptable solvate, hydrate, salt, or N-oxide thereof, wherein X is selected from —O—, Y is a 4-, 5-, 6-, or 7-membered carbocyclyl, and ring A is:

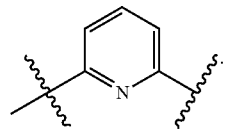 [SMILES: *c1cccc(*)n1]

Another embodiment provides a compound of Formula (B) or tautomer, stereoisomer, geometric isomer or a pharmaceutically acceptable solvate, hydrate, salt, or N-oxide thereof, wherein X is selected from —O—, Y is cyclobutyl, cyclopentyl, cyclohexyl, or cycloheptyl, and ring A is:

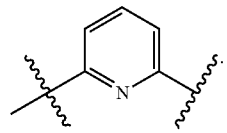 [SMILES: *c1cccc(*)n1]

Another embodiment provides a compound of Formula (B) or tautomer, stereoisomer, geometric isomer or a pharmaceutically acceptable solvate, hydrate, salt, or N-oxide thereof, wherein $R^1$ is hydrogen, $R^2$ is —OH, X is selected from —O—, Y is carbocyclyl, and ring A is:

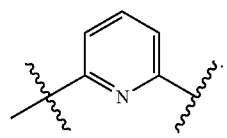

Another embodiment provides a compound of Formula (B) or tautomer, stereoisomer, geometric isomer or a pharmaceutically acceptable solvate, hydrate, salt, or N-oxide thereof, wherein $R^1$ is hydrogen, $R^2$ is —OH, X is selected from —O—, Y is a 4-, 5-, 6-, or 7-membered carbocyclyl, and ring A is:

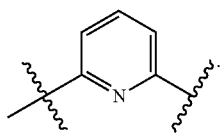 [SMILES: *c1cccc(*)n1]

Another embodiment provides a compound of Formula (B) or tautomer, stereoisomer, geometric isomer or a pharmaceutically acceptable solvate, hydrate, salt, or N-oxide thereof, wherein $R^1$ is hydrogen, $R^2$ is —OH, X is selected from —O—, Y is cyclobutyl, cyclopentyl, cyclohexyl, or cycloheptyl, and ring A is:

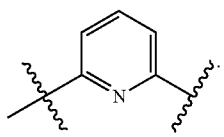

Any combination of the groups described above for the various variables is contemplated herein. Throughout the specification, groups and substituents thereof are chosen by one skilled in the field to provide stable moieties and compounds.

In some embodiments the compounds of Formula (B) disclosed herein have the structure provided in Table 1B.

TABLE 1B

| Synthesis Example | Structure | Name |
|---|---|---|
| 26 | 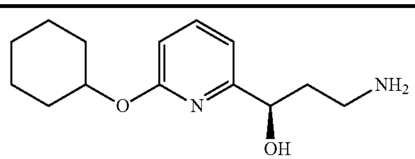 | (R)-3-Amino-1-(6-(cyclohexyloxy)pyridin-2-yl)propan-1-ol |
| 34 | 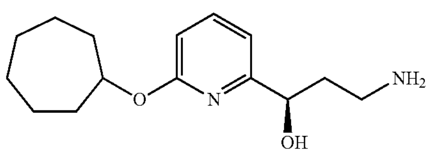 [SMILES: NCC[C@@H](O)c1cccc(OC2CCCCCC2)n1] | (R)-3-Amino-1-(6-(cycloheptyloxy)pyridin-2-yl)propan-1-ol |

Preparation of the Substituted Heterocyclic Amine Derivative Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted heterocyclic amine derivative compounds described herein is P. H. Stahl & C. G. Wermuth "Handbook of Pharmaceutical Salts", Verlag Helvetica Chimica Acta, Zurich, 2002.

Treatment of Ophthalmic Diseases and Disorders

One embodiment provides a method for treating an ophthalmic disease or disorder in a subject, comprising administering to the subject a pharmaceutical composition comprising a compound of Formula (A) or tautomer, stereoisomer, geometric isomer, or pharmaceutically acceptable solvate, hydrate, salt, or N-oxide thereof:

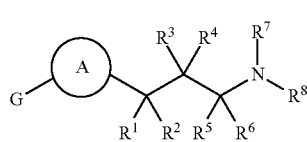

Formula (A)

wherein,
Ring A is selected from a 1,3-disubstituted heterocycle;
G is —X—Y;
X is selected from —O—C($R^9$)$_2$—, —O—C(=O)—, —S—C($R^9$)$_2$—, —S(O)—C($R^9$)$_2$—, —S(O)$_2$—C($R^9$)$_2$—, —SO$_2$(N$R^9$)—, —$NR^9$—C($R^9$)$_2$—, —$NR^9$—C(=O)—, —$NR^9$—S(O)$_2$—, —C($R^9$)$_2$—C($R^9$)$_2$—, —C(=O)—C($R^9$)$_2$—, —C($R^9$)$_2$—C(=O)—, —C($R^9$)=C($R^9$)—, —C≡C—, —C(=O)—N($R^9$)—, —C(=O)—O—, —C($R^9$)$_2$—O—, and —C($R^9$)$_2$—$NR^9$;
Y is selected from $C_3$-$C_{15}$ alkyl, carbocyclyl, carbocyclylalkyl, heterocyclyl, heterocyclylalkyl, aryl or aralkyl;
$R^1$ and $R^2$ are each independently selected from hydrogen, halogen, alkyl, fluoroalkyl, —$OR^9$, —$NR^{10}R^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;
$R^3$ and $R^4$ are each independently selected from hydrogen, halogen, $C_1$-$C_5$ alkyl, fluoroalkyl, —$OR^9$ or —$NR^{10}R^{11}$; or $R^3$ and $R^4$ together form an oxo;
$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;
$R^7$ and $R^8$ are each independently selected from hydrogen, alkyl, carbocyclyl, —C(=O)$R^{13}$, SO$_2R^{13}$, CO$_2R^{13}$ or SO$_2NR^{10}R^{11}$; or $R^7$ and $R^8$, together with the nitrogen atom to which they are attached, form an N-heterocyclyl;
each $R^9$ independently hydrogen or alkyl;
each $R^{10}$ and $R^{11}$ is independently selected from hydrogen, alkyl, carbocyclyl, heterocyclyl, —C(=O)$R^{13}$, SO$_2R^{13}$, CO$_2R^{13}$ or SO$_2NR^{10}R^{11}$; or $R^{10}$ and $R^{11}$ together with the nitrogen atom to which they are attached, form an N-heterocyclyl; and
each $R^{13}$ is independently selected from alkyl, heteroalkyl, alkenyl, aryl, aralkyl, carbocyclyl, heteroaryl or heterocyclyl.

One embodiment provides a method for treating an ophthalmic disease or disorder in a subject, wherein the ophthalmic disease or disorder is age-related macular degeneration or Stargardt's macular dystrophy.

One embodiment provides a method for treating an ophthalmic disease or disorder in a subject, wherein the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS.

Another embodiment provides a method for treating an ophthalmic disease or disorder in a subject resulting in a reduction of lipofuscin pigment accumulated in an eye of the subject.

Another embodiment provides a method for treating an ophthalmic disease or disorder in a subject resulting in a reduction of lipofuscin pigment accumulated in an eye of the subject wherein the lipofuscin pigment is N-retinylidene-N-retinyl-ethanolamine (A2E).

One embodiment provides a method for treating an ophthalmic disease or disorder in a subject, comprising administering to the subject a pharmaceutical composition comprising a compound of Formula (B) or tautomer, stereoisomer, geometric isomer or a pharmaceutically acceptable solvate, hydrate, salt, or N-oxide thereof:

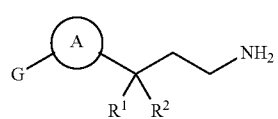

Formula (B)

wherein,
Ring A is selected from a 1,3-disubstituted heterocycle;
G is —X—Y;
X is selected from —O—, —S—, —NH—, or —CH$_2$—;
Y is selected from carbocyclyl, or heterocyclyl; and
$R^1$ and $R^2$ are each independently selected from hydrogen, or —OH; or $R^1$ and $R^2$ form an oxo. Another embodiment provides a method for treating an ophthalmic disease or disorder in a subject, comprising administering to the subject a pharmaceutical composition comprising a compound of Formula (B) or tautomer, stereoisomer, geometric isomer or a pharmaceutically acceptable solvate, hydrate, salt, or N-oxide thereof, wherein the ophthalmic disease or disorder is age-related macular degeneration or Stargardt's macular dystrophy.

One embodiment provides a method of modulating chromophore flux in a retinoid cycle comprising administering to the subject a pharmaceutical composition comprising a compound of Formula (A) or tautomer, stereoisomer, geometric isomer, or pharmaceutically acceptable solvate, hydrate, salt, or N-oxide thereof:

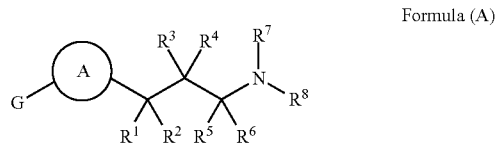

Formula (A)

wherein,

Ring A is selected from a 1,3-disubstituted heterocycle;

G is —X—Y;

X is selected from —O—C($R^9$)$_2$—, —O—C(=O)—, —S—C($R^9$)$_2$—, —S(O)—C($R^9$)$_2$—, —S(O)$_2$—C($R^9$)$_2$—, —SO$_2$(N$R^9$)—, —$NR^9$—C($R^9$)$_2$—, —$NR^9$—C(=O)—, —$NR^9$—S(O)$_2$—, —C($R^9$)$_2$—C($R^9$)$_2$—, —C(=O)—C($R^9$)$_2$—, —C($R^9$)$_2$—C(=O)—, —C($R^9$)=C($R^9$)—, —C≡C—, —C(=O)—N($R^9$)—, —C(=O)—O—, —C($R^9$)$_2$—O—, and —C($R^9$)$_2$—$NR^9$;

Y is selected from $C_3$-$C_{15}$ alkyl, carbocyclyl, carbocyclylalkyl, heterocyclyl, heterocyclylalkyl, aryl or aralkyl;

$R^1$ and $R^2$ are each independently selected from hydrogen, halogen, alkyl, fluoroalkyl, —$OR^9$, —$NR^{10}R^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;

$R^3$ and $R^4$ are each independently selected from hydrogen, halogen, $C_1$-$C_5$ alkyl, fluoroalkyl, —$OR^9$ or —$NR^{10}R^{11}$; or $R^3$ and $R^4$ together form an oxo;

$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;

$R^7$ and $R^8$ are each independently selected from hydrogen, alkyl, carbocyclyl, —C(=O)$R^{13}$, SO$_2$$R^{13}$, CO$_2$$R^{13}$ or SO$_2$$NR^{10}R^{11}$; or $R^7$ and $R^8$, together with the nitrogen atom to which they are attached, form an N-heterocyclyl;

each $R^9$ independently hydrogen or alkyl;

each $R^{10}$ and $R^{11}$ is independently selected from hydrogen, alkyl, carbocyclyl, heterocyclyl, —C(=O)$R^{13}$, SO$_2$$R^{13}$, CO$_2$$R^{13}$ or SO$_2$$NR^{10}R^{11}$; or $R^{10}$ and $R^{11}$ together with the nitrogen atom to which they are attached, form an N-heterocyclyl; and each $R^{13}$ is independently selected from alkyl, heteroalkyl, alkenyl, aryl, aralkyl, carbocyclyl, heteroaryl or heterocyclyl.

One embodiment provides a method of inhibiting dark adaptation of a rod photoreceptor cell of the retina comprising contacting the retina with a compound of Formula (A) or tautomer, stereoisomer, geometric isomer, or pharmaceutically acceptable solvate, hydrate, salt, or N-oxide thereof:

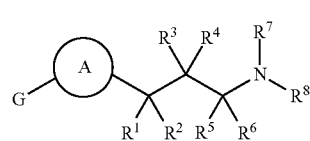

Formula (A)

wherein,

Ring A is selected from a 1,3-disubstituted heterocycle;

G is —X—Y;

X is selected from —O—C($R^9$)$_2$—, —O—C(=O)—, —S—C($R^9$)$_2$—, —S(O)—C($R^9$)$_2$—, —S(O)$_2$—C($R^9$)$_2$—, —SO$_2$(N$R^9$)—, —$NR^9$—C($R^9$)$_2$—, —$NR^9$—C(=O)—, —$NR^9$—S(O)$_2$—, —C($R^9$)$_2$—C($R^9$)$_2$—, —C(=O)—C($R^9$)$_2$—, —C($R^9$)$_2$—C(=O)—, —C($R^9$)=C($R^9$)—, —C≡C—, —C(=O)—N($R^9$)—, —C(=O)—O—, —C($R^9$)$_2$—O—, and —C($R^9$)$_2$—$NR^9$;

Y is selected from $C_3$-$C_{15}$ alkyl, carbocyclyl, carbocyclylalkyl, heterocyclyl, heterocyclylalkyl, aryl or aralkyl;

$R^1$ and $R^2$ are each independently selected from hydrogen, halogen, alkyl, fluoroalkyl, —$OR^9$, —$NR^{10}R^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;

$R^3$ and $R^4$ are each independently selected from hydrogen, halogen, $C_1$-$C_5$ alkyl, fluoroalkyl, —$OR^9$ or —$NR^{10}R^{11}$; or $R^3$ and $R^4$ together form an oxo;

$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;

$R^7$ and $R^8$ are each independently selected from hydrogen, alkyl, carbocyclyl, —C(=O)$R^{13}$, SO$_2$$R^{13}$, CO$_2$$R^{13}$ or SO$_2$$NR^{10}R^{11}$; or $R^7$ and $R^8$, together with the nitrogen atom to which they are attached, form an N-heterocyclyl;

each $R^9$ independently hydrogen or alkyl;

each $R^{10}$ and $R^{11}$ is independently selected from hydrogen, alkyl, carbocyclyl, heterocyclyl, —C(=O)$R^{13}$, SO$_2$$R^{13}$, CO$_2$$R^{13}$ or SO$_2$$NR^{10}R^{11}$; or $R^{10}$ and $R^{11}$ together with the nitrogen atom to which they are attached, form an N-heterocyclyl; and each $R^{13}$ is independently selected from alkyl, heteroalkyl, alkenyl, aryl, aralkyl, carbocyclyl, heteroaryl or heterocyclyl.

One embodiment provides a method of inhibiting regeneration of rhodopsin in a rod photoreceptor cell of the retina comprising contacting the retina with a compound of Formula (A) or tautomer, stereoisomer, geometric isomer, or pharmaceutically acceptable solvate, hydrate, salt, or N-oxide thereof:

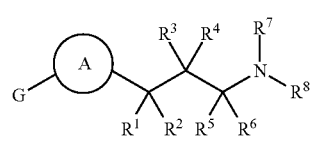

Formula (A)

wherein,
Ring A is selected from a 1,3-disubstituted heterocycle;
G is —X—Y;
X is selected from —O—C($R^9$)$_2$—, —O—C(=O)—, —S—C($R^9$)$_2$—, —S(O)—C($R^9$)$_2$—, —S(O)$_2$—C($R^9$)$_2$—, —SO$_2$(N$R^9$)—, —$NR^9$—C($R^9$)$_2$—, —$NR^9$—C(=O)—, —$NR^9$—S(O)$_2$—, —C($R^9$)$_2$—C($R^9$)$_2$—, —C(=O)—C($R^9$)$_2$—, —C($R^9$)$_2$—C(=O)—, —C($R^9$)=C($R^9$)—, —C≡C—, —C(=O)—N($R^9$)—, —C(=O)—O—, —C($R^9$)$_2$—O—, and —C($R^9$)$_2$—$NR^9$;

Y is selected from $C_3$-$C_{15}$ alkyl, carbocyclyl, carbocyclylalkyl, heterocyclyl, heterocyclylalkyl, aryl or aralkyl;

$R^1$ and $R^2$ are each independently selected from hydrogen, halogen, alkyl, fluoroalkyl, —$OR^9$, —$NR^{10}R^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;

$R^3$ and $R^4$ are each independently selected from hydrogen, halogen, $C_1$-$C_5$ alkyl, fluoroalkyl, —$OR^9$ or —$NR^{10}R^{11}$; or $R^3$ and $R^4$ together form an oxo;

$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;

$R^7$ and $R^8$ are each independently selected from hydrogen, alkyl, carbocyclyl, —C(=O)$R^{13}$, SO$_2R^{13}$, CO$_2R^{13}$ or SO$_2NR^{10}R^{11}$; or $R^7$ and $R^8$, together with the nitrogen atom to which they are attached, form an N-heterocyclyl;

each $R^9$ independently hydrogen or alkyl;

each $R^{10}$ and $R^{11}$ is independently selected from hydrogen, alkyl, carbocyclyl, heterocyclyl, —C(=O)$R^{13}$, SO$_2R^{13}$, CO$_2R^{13}$ or SO$_2NR^{10}R^{11}$; or $R^{10}$ and $R^{11}$ together with the nitrogen atom to which they are attached, form an N-heterocyclyl; and each $R^{13}$ is independently selected from alkyl, heteroalkyl, alkenyl, aryl, aralkyl, carbocyclyl, heteroaryl or heterocyclyl.

One embodiment provides a method of reducing ischemia in an eye of a subject comprising administering to the subject a pharmaceutical composition comprising a compound of Formula (A) or tautomer, stereoisomer, geometric isomer, or pharmaceutically acceptable solvate, hydrate, salt, or N-oxide thereof:

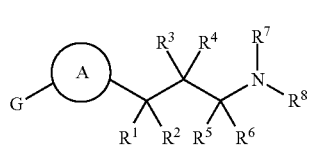

Formula (A)

wherein,
Ring A is selected from a 1,3-disubstituted heterocycle;
G is —X—Y;
X is selected from —O—C($R^9$)$_2$—, —O—C(=O)—, —S—C($R^9$)$_2$—, —S(O)—C($R^9$)$_2$—, —S(O)$_2$—C($R^9$)$_2$—, —SO$_2$(N$R^9$)—, —$NR^9$—C($R^9$)$_2$—, —$NR^9$—C(=O)—, —$NR^9$—S(O)$_2$—, —C($R^9$)$_2$—C($R^9$)$_2$—, —C(=O)—C($R^9$)$_2$—, —C($R^9$)$_2$—C(=O)—, —C($R^9$)=C($R^9$)—, —C≡C—, —C(=O)—N($R^9$)—, —C(=O)—O—, —C($R^9$)$_2$—O—, and —C($R^9$)$_2$—$NR^9$;

Y is selected from $C_3$-$C_{15}$ alkyl, carbocyclyl, carbocyclylalkyl, heterocyclyl, heterocyclylalkyl, aryl or aralkyl;

$R^1$ and $R^2$ are each independently selected from hydrogen, halogen, alkyl, fluoroalkyl, —$OR^9$, —$NR^{10}R^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;

$R^3$ and $R^4$ are each independently selected from hydrogen, halogen, $C_1$-$C_5$ alkyl, fluoroalkyl, —$OR^9$ or —$NR^{10}R^{11}$; or $R^3$ and $R^4$ together form an oxo;

$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;

$R^7$ and $R^8$ are each independently selected from hydrogen, alkyl, carbocyclyl, —C(=O)$R^{13}$, SO$_2R^{13}$, CO$_2R^{13}$ or SO$_2NR^{10}R^{11}$; or $R^7$ and $R^8$, together with the nitrogen atom to which they are attached, form an N-heterocyclyl;

each $R^9$ independently hydrogen or alkyl;

each $R^{10}$ and $R^{11}$ is independently selected from hydrogen, alkyl, carbocyclyl, heterocyclyl, —C(=O)$R^{13}$, SO$_2R^{13}$, CO$_2R^{13}$ or SO$_2NR^{10}R^{11}$; or $R^{10}$ and $R^{11}$ together with the nitrogen atom to which they are attached, form an N-heterocyclyl; and each $R^{13}$ is independently selected from alkyl, heteroalkyl, alkenyl, aryl, aralkyl, carbocyclyl, heteroaryl or heterocyclyl.

Another embodiment provides a method of reducing ischemia in an eye of a subject comprising administering to the subject a pharmaceutical composition comprising a compound of Formula (A) or tautomer, stereoisomer, geometric isomer, or pharmaceutically acceptable solvate, hydrate, salt, or N-oxide thereof, wherein the pharmaceutical composition is administered under conditions and at a time sufficient to inhibit dark adaptation of a rod photoreceptor cell, thereby reducing ischemia in the eye.

One embodiment provides a method of modulating chromophore flux in a retinoid cycle comprising administering to the subject a pharmaceutical composition comprising a compound of Formula (B) or tautomer, stereoisomer, geometric isomer or a pharmaceutically acceptable solvate, hydrate, salt, or N-oxide thereof:

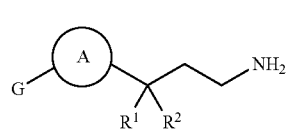

Formula (B)

wherein,
Ring A is selected from a 1,3-disubstituted heterocycle;
G is —X—Y;
X is selected from —O—, —S—, —NH—, or —CH$_2$—;
Y is selected from carbocyclyl, or heterocyclyl; and
$R^1$ and $R^2$ are each independently selected from hydrogen, or —OH; or $R^1$ and $R^2$ form an oxo.

One embodiment provides a method of inhibiting dark adaptation of a rod photoreceptor cell of the retina comprising contacting the retina with a compound of Formula (B) or tautomer, stereoisomer, geometric isomer or a pharmaceutically acceptable solvate, hydrate, salt, or N-oxide thereof:

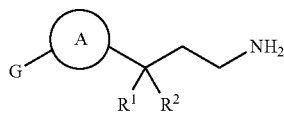

Formula (B)

wherein,
Ring A is selected from a 1,3-disubstituted heterocycle;
G is —X—Y;
X is selected from —O—, —S—, —NH—, or —CH$_2$—;
Y is selected from carbocyclyl, or heterocyclyl; and
$R^1$ and $R^2$ are each independently selected from hydrogen, or —OH; or $R^1$ and $R^2$ form an oxo.

One embodiment provides a method of inhibiting regeneration of rhodopsin in a rod photoreceptor cell of the retina comprising contacting the retina with a compound of Formula (B) or tautomer, stereoisomer, geometric isomer or a pharmaceutically acceptable solvate, hydrate, salt, or N-oxide thereof:

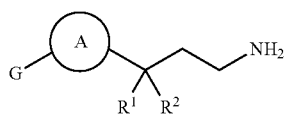

Formula (B)

wherein,
Ring A is selected from a 1,3-disubstituted heterocycle;
G is —X—Y;
X is selected from —O—, —S—, —NH—, or —CH$_2$—;
Y is selected from carbocyclyl, or heterocyclyl; and
$R^1$ and $R^2$ are each independently selected from hydrogen, or —OH; or $R^1$ and $R^2$ form an oxo.

One embodiment provides a method of reducing ischemia in an eye of a subject comprising administering to the subject a pharmaceutical composition comprising a compound of Formula (B) or tautomer, stereoisomer, geometric isomer or a pharmaceutically acceptable solvate, hydrate, salt, or N-oxide thereof:

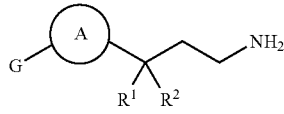

Formula (B)

wherein,
Ring A is selected from a 1,3-disubstituted heterocycle;
G is —X—Y;
X is selected from —O—, —S—, —NH—, or —CH$_2$—;
Y is selected from carbocyclyl, or heterocyclyl; and
$R^1$ and $R^2$ are each independently selected from hydrogen, or —OH; or $R^1$ and $R^2$ form an oxo.

One embodiment provides a method of inhibiting neovascularization in the retina of an eye of a subject comprising administering to the subject a pharmaceutical composition comprising a compound of Formula (A) or tautomer, stereoisomer, geometric isomer, or pharmaceutically acceptable solvate, hydrate, salt, or N-oxide thereof:

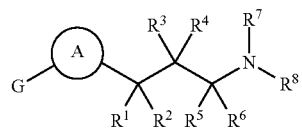

Formula (A)

wherein,
Ring A is selected from a 1,3-disubstituted heterocycle;
G is —X—Y;
X is selected from —O—C(R$^9$)$_2$—, —O—C(=O)—, —S—C(R$^9$)$_2$—, —S(O)—C(R$^9$)$_2$—, —S(O)$_2$—C(R$^9$)$_2$—, —SO$_2$(NR$^9$)—, —NR$^9$—C(R$^9$)$_2$—, —NR$^9$—C(=O)—, —NR$^9$—S(O)$_2$—, —C(R$^9$)$_2$—C(R$^9$)$_2$—, —C(=O)—C(R$^9$)$_2$—, —C(R$^9$)$_2$—C(=O)—, —C(R$^9$)=C(R$^9$)—, —C≡C—, —C(=O)—N(R$^9$)—, —C(=O)—O—, —C(R$^9$)$_2$—O—, and —C(R$^9$)$_2$—NR$^9$;
Y is selected from C$_3$-C$_{15}$ alkyl, carbocyclyl, carbocyclylalkyl, heterocyclyl, heterocyclylalkyl, aryl or aralkyl;
$R^1$ and $R^2$ are each independently selected from hydrogen, halogen, alkyl, fluoroalkyl, —OR$^9$, —NR$^{10}$R$^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;
$R^3$ and $R^4$ are each independently selected from hydrogen, halogen, C$_1$-C$_5$ alkyl, fluoroalkyl, —OR$^9$ or —NR$^{10}$R$^{11}$; or $R^3$ and $R^4$ together form an oxo;
$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;
$R^7$ and $R^8$ are each independently selected from hydrogen, alkyl, carbocyclyl, —C(=O)R$^{13}$, SO$_2$R$^{13}$, CO$_2$R$^{13}$ or SO$_2$NR$^{10}$R$^{11}$; or $R^7$ and $R^8$, together with the nitrogen atom to which they are attached, form an N-heterocyclyl;
each $R^9$ independently hydrogen or alkyl;
each $R^{10}$ and $R^{11}$ is independently selected from hydrogen, alkyl, carbocyclyl, heterocyclyl, —C(=O)R$^{13}$, SO$_2$R$^{13}$, CO$_2$R$^{13}$ or SO$_2$NR$^{10}$R$^{11}$; or $R^{10}$ and $R^{11}$ together with the nitrogen atom to which they are attached, form an N-heterocyclyl; and
each $R^{13}$ is independently selected from alkyl, heteroalkyl, alkenyl, aryl, aralkyl, carbocyclyl, heteroaryl or heterocyclyl.

One embodiment provides a method of inhibiting neovascularization in the retina of an eye of a subject comprising administering to the subject a pharmaceutical composition comprising a compound of Formula (A) or tautomer, stereoisomer, geometric isomer, or pharmaceutically acceptable solvate, hydrate, salt, or N-oxide thereof wherein the pharmaceutical composition is administered under conditions and at a time sufficient to inhibit dark adaptation of a rod photoreceptor cell, thereby inhibiting neovascularization in the retina.

One embodiment provides a method of inhibiting neovascularization in the retina of an eye of a subject comprising administering to the subject a pharmaceutical composition comprising a compound of Formula (B) or tautomer, stereoisomer, geometric isomer or a pharmaceutically acceptable solvate, hydrate, salt, or N-oxide thereof:

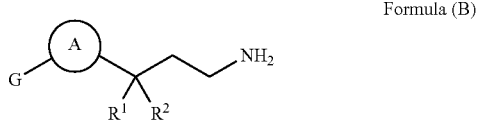

Formula (B)

wherein,
Ring A is selected from a 1,3-disubstituted heterocycle;
G is —X—Y;
X is selected from —O—, —S—, —NH—, or —CH$_2$—;
Y is selected from carbocyclyl, or heterocyclyl; and
$R^1$ and $R^2$ are each independently selected from hydrogen, or —OH; or $R^1$ and $R^2$ form an oxo.

One embodiment provides a method of inhibiting degeneration of a retinal cell in a retina comprising contacting the retina with a compound of Formula (A) or tautomer, stereoisomer, geometric isomer, or pharmaceutically acceptable solvate, hydrate, salt, or N-oxide thereof:

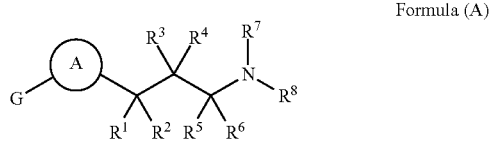

Formula (A)

wherein,
Ring A is selected from a 1,3-disubstituted heterocycle;
G is —X—Y;
X is selected from —O—C($R^9$)$_2$—, —O—C(=O)—, —S—C($R^9$)$_2$—, —S(O)—C($R^9$)$_2$—, —S(O)$_2$—C($R^9$)$_2$—, —SO$_2$(NR$^9$)—, —NR$^9$—C($R^9$)$_2$—, —NR$^9$—C(=O)—, —NR$^9$—S(O)$_2$—, —C($R^9$)$_2$—C($R^9$)$_2$—, —C(=O)—C($R^9$)$_2$—, —C($R^9$)$_2$—C(=O)—, —C($R^9$)=C($R^9$)—, —C≡C—, —C(=O)—N($R^9$)—, —C(=O)—O—, —C($R^9$)$_2$—O—, and —C($R^9$)$_2$—NR$^9$;
Y is selected from C$_3$-C$_{15}$ alkyl, carbocyclyl, carbocyclylalkyl, heterocyclyl, heterocyclylalkyl, aryl or aralkyl;
$R^1$ and $R^2$ are each independently selected from hydrogen, halogen, alkyl, fluoroalkyl, —OR$^9$, —NR$^{10}$R$^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;
$R^3$ and $R^4$ are each independently selected from hydrogen, halogen, C$_1$-C$_5$ alkyl, fluoroalkyl, —OR$^9$ or —NR$^{10}$R$^{11}$; or $R^3$ and $R^4$ together form an oxo;
$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;
$R^7$ and $R^8$ are each independently selected from hydrogen, alkyl, carbocyclyl, —C(=O)R$^{13}$, SO$_2$R$^{13}$, CO$_2$R$^{13}$ or SO$_2$NR$^{10}$R$^{11}$; or $R^7$ and $R^8$, together with the nitrogen atom to which they are attached, form an N-heterocyclyl;

each $R^9$ independently hydrogen or alkyl;
each $R^{10}$ and $R^{11}$ is independently selected from hydrogen, alkyl, carbocyclyl, heterocyclyl, —C(=O)R$^{13}$, SO$_2$R$^{13}$, CO$_2$R$^{13}$ or SO$_2$NR$^{10}$R$^{11}$; or $R^{10}$ and $R^{11}$ together with the nitrogen atom to which they are attached, form an N-heterocyclyl; and
each $R^{13}$ is independently selected from alkyl, heteroalkyl, alkenyl, aryl, aralkyl, carbocyclyl, heteroaryl or heterocyclyl.

One embodiment provides a method of inhibiting degeneration of a retinal cell in a retina comprising contacting the retina with a compound of Formula (A) or tautomer, stereoisomer, geometric isomer, or pharmaceutically acceptable solvate, hydrate, salt, or N-oxide thereof wherein the retinal cell is a retinal neuronal cell. One embodiment provides a method of inhibiting degeneration of a retinal cell in a retina comprising contacting the retina with a compound of Formula (A) or tautomer, stereoisomer, geometric isomer, or pharmaceutically acceptable solvate, hydrate, salt, or N-oxide thereof wherein the retinal neuronal cell is a photoreceptor cell.

One embodiment provides a method of inhibiting degeneration of a retinal cell in a retina comprising contacting the retina with a compound of Formula (B) or tautomer, stereoisomer, geometric isomer or a pharmaceutically acceptable solvate, hydrate, salt, or N-oxide thereof:

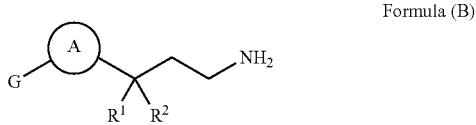

Formula (B)

wherein,
Ring A is selected from a 1,3-disubstituted heterocycle;
G is —X—Y;
X is selected from —O—, —S—, —NH—, or —CH$_2$—;
Y is selected from carbocyclyl, or heterocyclyl; and
$R^1$ and $R^2$ are each independently selected from hydrogen, or —OH; or $R^1$ and $R^2$ form an oxo.

Substituted heterocyclic amine derivative compounds as described in detail herein, including a compound having the structure as set forth in Formula (A) or Formula (B) and substructures thereof, and the specific substituted heterocyclic amine compounds described herein that are useful for treating an ophthalmic disease or disorder, inhibit one or more steps in the visual cycle, for example, by inhibiting or blocking a functional activity of a visual cycle trans-cis isomerase (also including a visual cycle trans-cis isomerohydrolase). The compounds described herein, inhibit, block, or in some manner interfere with the isomerization step in the visual cycle. In a particular embodiment, the compound inhibits isomerization of an all-trans-retinyl ester; in certain embodiments, the all-trans-retinyl ester is a fatty acid ester of all-trans-retinol, and the compound inhibits isomerization of all-trans-retinol to 11-cis-retinol. The compound binds to, or in some manner interact with, and inhibit the isomerase activity of at least one visual cycle isomerase, which is also referred to herein and in the art as a retinal isomerase or an isomerohydrolase. The compound blocks or inhibits binding of an all-trans-retinyl ester substrate to an isomerase. Alternatively, or in addition, the compound binds to the catalytic site or region of the isomerase, thereby inhibiting the capability of the enzyme to catalyze isomerization of an all-trans-retinyl ester substrate. On the basis of scientific data to date, at least one isomerase that catalyzes the isomerization of all-trans-retinyl esters is believed to be located in the cytoplasm of RPE cells. As discussed herein, each step, enzyme, substrate, intermediate, and product of the visual cycle is not yet elucidated (see, e.g., Moiseyev et al., *Proc. Natl. Acad. Sci. USA* 102:12413-18 (2004); Chen et al., *Invest. Ophthalmol. Vis. Sci.* 47:1177-84 (2006); Lamb et al. supra).

A method for determining the effect of a compound on isomerase activity is performed in vitro as described herein and in the art (Stecher et al., *J Biol Chem* 274:8577-85 (1999); see also Golczak et al., *Proc. Natl. Acad. Sci. USA* 102:8162-67 (2005)). Retinal pigment epithelium (RPE) microsome membranes isolated from an animal (such as bovine, porcine, human, for example) may serve as the source of the isomerase. The capability of the substituted heterocyclic amine derivative compounds to inhibit isomerase is also determined by an in vivo murine isomerase assay. Brief exposure of the eye to intense light ("photobleaching" of the visual pigment or simply "bleaching") is known to photo-isomerize almost all 11-cis-retinal in the retina. The recovery of 11-cis-retinal after bleaching can be used to estimate the activity of isomerase in vivo (see, e.g., Maeda et al., *J. Neurochem* 85:944-956 (2003); Van Hooser et al., *J Biol Chem* 277:19173-82, 2002). Electroretinographic (ERG) recording may be performed as previously described (Haeseleer et al., *Nat. Neurosci.* 7:1079-87 (2004); Sugitomo et al., *J. Toxicol. Sci.* 22 Suppl 2:315-25 (1997); Keating et al., *Documenta Ophthalmologica* 100: 77-92 (2000)). See also Deigner et al., *Science,* 244: 968-971 (1989); Gollapalli et al., *Biochim Biophys Acta.* 1651: 93-101 (2003); Parish, et al., *Proc. Natl. Acad. Sci. USA* 95:14609-13 (1998); Radu, et al., *Proc Natl Acad Sci USA* 101: 5928-33 (2004)). In certain embodiments, compounds that are useful for treating a subject who has or who is at risk of developing any one of the ophthalmic and retinal diseases or disorders described herein have $IC_{50}$ levels (compound concentration at which 50% of isomerase activity is inhibited) as measured in the isomerase assays described herein or known in the art that is less than about 1 µM; in other embodiments, the determined $IC_{50}$ level is less than about 10 nM; in other embodiments, the determined $IC_{50}$ level is less than about 50 nM; in certain other embodiments, the determined $IC_{50}$ level is less than about 100 nM; in other certain embodiments, the determined $IC_{50}$ level is less than about 10 µM; in other embodiments, the determined $IC_{50}$ level is less than about 50 µM; in other certain embodiments, the determined $IC_{50}$ level is less than about 100 µM or about 500 µM; in other embodiments, the determined $IC_{50}$ level is between about 1 µM and 10 µM; in other embodiments, the determined $IC_{50}$ level is between about 1 nM and 10 nM. When adminstered into a subject, one or more compounds of the present invention exhibits an $ED_{50}$ value of about 5 mg/kg, 5 mg/kg or less as ascertained by inhibition of an isomerase reaction that results in production of 11-cis retinol. In some embodiments, the compounds of the present invention have $ED_{50}$ values of about 1 mg/kg when administered into a subject. In other embodiments, the compounds of the present invention have $ED_{50}$ values of about 0.1 mg/kg when administered into a subject. The $ED_{50}$ values can be measured after about 2 hours, 4 hours, 6 hours, 8 hours or longer upon administering a subject compound or a pharmaceutical composition thereof.

The compounds described herein are useful for treating a subject who has an ophthalmic disease or disorder, particularly a retinal disease or disorder such as age-related macular degeneration or Stargardt's macular dystrophy. In one embodiment, the compounds described herein inhibit (i.e., prevent, reduce, slow, abrogate, or minimize) accumulation of lipofuscin pigments and lipofuscin-related and/or associated molecules in the eye. In another embodiment, the compounds inhibit (i.e., prevent, reduce, slow, abrogate, or minimize) N-retinylidene-N-retinylethanolamine (A2E) accumulation in the eye. The ophthalmic disease results, at least in part, from lipofuscin pigments accumulation and/or from accumulation of A2E in the eye. Accordingly, in certain embodiments, methods are provided for inhibiting or preventing accumulation of lipofuscin pigments and/or A2E in the eye of a subject. These methods comprise administering to the subject a composition comprising a pharmaceutically acceptable or suitable excipient (i.e., pharmaceutically acceptable or suitable carrier) and a substituted heterocyclic amine derivative compound as described in detail herein, including a compound having the structure as set forth in Formula (A) or Formula (B), and substructures thereof, and the specific substituted heterocyclic amine derivative compounds described herein.

Accumulation of lipofuscin pigments in retinal pigment epithelium (RPE) cells has been linked to progression of retinal diseases that result in blindness, including age-related macular degeneration (De Laey et al., *Retina* 15:399-406 (1995)). Lipofuscin granules are autofluorescent lysosomal residual bodies (also called age pigments). The major fluorescent species of lipofuscin is A2E (an orange-emitting fluorophore), which is a positively charged Schiff-base condensation-product formed by all-trans retinaldehyde with phosphatidylethanolamine (2:1 ratio) (see, e.g., Eldred et al., *Nature* 361:724-6 (1993); see also, Sparrow, *Proc. Natl. Acad. Sci. USA* 100:4353-54 (2003)). Much of the indigestible lipofuscin pigment is believed to originate in photoreceptor cells; deposition in the RPE occurs because the RPE internalize membranous debris that is discarded daily by the photoreceptor cells. Formation of this compound is not believed to occur by catalysis by any enzyme, but rather A2E forms by a spontaneous cyclization reaction. In addition, A2E has a pyridinium bisretinoid structure that once formed is resistant to enzymatic degradation. Lipofuscin, and thus A2E, accumulate with aging of the human eye and also accumulate in a juvenile form of macular degeneration called Stargardt's disease, and in several other congenital retinal dystrophies.

A2E may induce damage to the retina via several different mechanisms. At low concentrations, A2E inhibits normal proteolysis in lysosomes (Holz et al., *Invest. Ophthalmol. Vis. Sci.* 40:737-43 (1999)). At higher, sufficient concentrations, A2E may act as a positively charged lysosomotropic detergent, dissolving cellular membranes, and may alter lysosomal function, release proapoptotic proteins from mitochondria, and ultimately kill the RPE cell (see, e.g., Eldred et al., supra; Sparrow et al., *Invest. Ophthalmol. Vis. Sci.* 40:2988-95 (1999); Holz et al., supra; Finneman et al., *Proc. Natl. Acad. Sci. USA* 99:3842-347 (2002); Suter et al., *J. Biol. Chem.* 275:39625-30 (2000)). A2E is phototoxic and initiates blue light-induced apoptosis in RPE cells (see, e.g., Sparrow et al., *Invest. Ophthalmol. Vis. Sci.* 43:1222-27 (2002)). Upon exposure to blue light, photooxidative products of A2E are formed (e.g., epoxides) that damage cellular macromolecules, including DNA (Sparrow et al., *J. Biol. Chem.* 278(20):18207-13 (2003)). A2E self-generates singlet oxygen that reacts with A2E to generate epoxides at carbon-carbon double bonds (Sparrow et al., supra). Generation of oxygen reactive species upon photoexcitation of A2E causes oxidative damage to the cell, often resulting in cell death. An indirect method of blocking formation of A2E by inhibiting biosynthesis of the direct precursor of A2E, all-trans-retinal, has been described (see U.S. Patent Application Publication No. 2003/0032078). However, the usefulness of the method described therein is limited because generation of all-trans retinal is an important component of the visual cycle. Other therapies described include neutralizing damage caused by oxidative radical species by using superoxide-dismutase mimetics (see, e.g., U.S. Patent Application Publication No. 2004/0116403) and inhibiting A2E-induced cytochrome C oxidase in retinal cells with negatively charged phospholipids (see, e.g., U.S. Patent Application Publication No. 2003/0050283).

The substituted heterocyclic amine derivative compounds described herein is useful for preventing, reducing, inhibiting, or decreasing accumulation (i.e., deposition) of A2E and A2E-related and/or derived molecules in the RPE. Without wishing to be bound by theory, because the RPE is critical for the maintenance of the integrity of photoreceptor cells, preventing, reducing, or inhibiting damage to the RPE may inhibit degeneration (i.e., enhance the survival or increase or prolong cell viability) of retinal neuronal cells, particularly, photoreceptor cells. Compounds that bind specifically to or interact with A2E, A2E-related and/or derived molecules, or that affect A2E formation or accumulation may also reduce, inhibit, prevent, or decrease one or more toxic effects of A2E or of A2E-related and/or derived molecules that result in retinal neuronal cell (including a photoreceptor cell) damage, loss, or neurodegeneration, or in some manner decrease retinal neuronal cell viability. Such toxic effects include induction of apoptosis, self-generation of singlet oxygen and generation of oxygen reactive species; self-generation of singlet oxygen to form A2E-epoxides that induce DNA lesions, thus damaging cellular DNA and inducing cellular damage; dissolving cellular membranes; altering lysosomal function; and effecting release of proapoptotic proteins from mitochondria.

In other embodiments, the compounds described herein are useful for treating other ophthalmic diseases or disorders, for example, glaucoma, cone-rod dystrophy, retinal detachment, hemorrhagic or hypertensive retinopathy, retinitis pigmentosa, optic neuropathy, inflammatory retinal disease, proliferative vitreoretinopathy, genetic retinal dystrophies, traumatic injury to the optic nerve (such as by physical injury, excessive light exposure, or laser light), hereditary optic neuropathy, neuropathy due to a toxic agent or caused by adverse drug reactions or vitamin deficiency, Sorsby's fundus dystrophy, uveitis, a retinal disorder associated with Alzheimer's disease, a retinal disorder associated with multiple sclerosis; a retinal disorder associated with viral infection (cytomegalovirus or herpes simplex virus), a retinal disorder associated with Parkinson's disease, a retinal disorder associated with AIDS, or other forms of progressive retinal atrophy or degeneration. In another specific embodiment, the disease or disorder results from mechanical injury, chemical or drug-induced injury, thermal injury, radiation injury, light injury, laser injury. The subject compounds are useful for treating both hereditary and non-hereditary retinal dystrophy. These methods are also useful for preventing ophthalmic injury from environmental factors such as light-induced oxidative retinal damage, laser-induced retinal damage, "flash bomb injury," or "light dazzle", refractive errors including but not limited to myopia (see, e.g., Quinn G E et al. Nature 1999; 399:113-114; Zadnik K et al. Nature 2000; 404:143-144; Gwiazda J et al. Nature 2000; 404: 144), etc.

In other embodiments, methods are provided herein for inhibiting neovascularization (including but not limited to neovascular glycoma) in the retina using any one or more of the substituted heterocyclic amine derivative compound as described in detail herein, including a compound having the structure as set forth in Formula (A) or Formula (B), and substructures thereof, and the specific substituted heterocyclic amine derivative compounds described herein. In certain other embodiments, methods are provided for reducing hypoxia in the retina using the compounds described herein. These methods comprise administering to a subject, in need thereof, a composition comprising a pharmaceutically acceptable or suitable excipient (i.e., pharmaceutically acceptable or suitable carrier) and a substituted heterocyclic amine derivative compound as described in detail herein, including a compound having the structure as set forth in Formulae (A), and substructures thereof, and the specific substituted heterocyclic amine derivative compounds described herein.

Merely by way of explanation and without being bound by any theory, and as discussed in further detail herein, dark-adapted rod photoreceptors engender a very high metabolic demand (i.e., expenditure of energy (ATP consumption) and consumption of oxygen). The resultant hypoxia may cause and/or exacerbate retinal degeneration, which is likely exaggerated under conditions in which the retinal vasculature is already compromised, including, but not limited to, such conditions as diabetic retinopathy, macular edema, diabetic maculopathy, retinal blood vessel occlusion (which includes retinal venous occlusion and retinal arterial occlusion), retinopathy of prematurity, ischemia reperfusion related retinal injury, as well as in the wet form of age-related macular degeneration (AMD). Furthermore, retinal degeneration and hypoxia may lead to neovascularization, which in turn may worsen the extent of retinal degeneration. In some embodiments, the substituted heterocyclic amine derivative compounds described herein that modulate the visual cycle are administered to prevent, inhibit, and/or delay dark adaptation of rod photoreceptor cells, and therefore reduce metabolic demand, thereby reducing hypoxia and inhibiting neovascularization.

By way of background, oxygen is a critical metabolite for preservation of retinal function in mammals, and retinal hypoxia may be a factor in many retinal diseases and disorders that have ischemia as a component. In most mammals (including humans) with dual vascular supply to the retina, oxygenation of the inner retina is achieved through the intraretinal microvasculature, which is sparse compared to the choriocapillaris that supplies oxygen to the RPE and photoreceptors. The different vascular supply networks create an uneven oxygen tension across the thickness of the retina (Cringle et al., *Invest. Ophthalmol. Vis. Sci.* 43:1922-27 (2002)). Oxygen fluctuation across the retinal layers is related to both the differing capillary densities and disparity in oxygen consumption by various retinal neurons and glia.

Local oxygen tension can significantly affect the retina and its microvasculature by regulation of an array of vasoactive agents, including, for example, vascular endothelial growth factor (VEGF). (See, e.g., Werdich et al., *Exp. Eye Res.* 79:623 (2004); Arden et al., *Br. J. Ophthalmol.* 89:764 (2005)). Rod photoreceptors are believed to have the highest metabolic rate of any cell in the body (see, e.g., Arden et al., supra). During dark adaptation, the rod photoreceptors recover their high cytoplasmic calcium levels via cGMP-gated calcium channels with concomitant extrusion of sodium ions and water. The efflux of sodium from the cell is an ATP-dependent process, such that the retinal neurons consume up to an estimated five times more oxygen under scotopic (i.e., dark adapted), compared with photopic (i.e., light adapted) conditions. Thus, during characteristic dark adaptation of photoreceptors, the high metabolic demand leads to significant local reduction of oxygen levels in the dark-adapted retina (Ahmed et al, *Invest. Ophthalmol. Vis. Sci.* 34:516 (1993)).

Without being bound by any one theory, retinal hypoxia may be further increased in the retina of subjects who have diseases or conditions such as, for example, central retinal vein occlusion in which the retinal vasculature is already compromised. Increasing hypoxia may increase susceptibility to sight-threatening, retinal neovascularization. Neovascularization is the formation of new, functional microvascular networks with red blood cell perfusion, and is a characteristic of retinal degenerative disorders, including, but not limited to, diabetic retinopathy, retinopathy of prematurity, wet AMD and central retinal vein occlusions. Preventing or inhibiting dark adaptation of rod photoreceptor cells, thereby decreasing expenditure of energy and consumption of oxygen (i.e., reducing metabolic demand), may inhibit or slow retinal degeneration, and/or may promote regeneration of retinal cells, including rod photoreceptor cells and retinal pigment epithelial (RPE) cells, and may reduce hypoxia and may inhibit neovascularization.

Methods are described herein for inhibiting (i.e., reducing, preventing, slowing or retarding, in a biologically or statistically significant manner) degeneration of retinal cells (including retinal neuronal cells as described herein and RPE cells) and/or for reducing (i.e., preventing or slowing, inhibiting, abrogating in a biologically or statistically significant manner) retinal ischemia. Methods are also provided for inhibiting (i.e., reducing, preventing, slowing or retarding, in a biologically or statistically significant manner) neovascularization in the eye, particularly in the retina. Such methods comprise contacting the retina, and thus, contacting retinal cells (including retinal neuronal cells such as rod photoreceptor cells, and RPE cells) with at least one of the substituted heterocyclic amine derivative compounds described herein that inhibits at least one visual cycle trans-cis isomerase (which may include inhibition of isomerization of an all-trans-retinyl ester), under conditions and at a time that may prevent, inhibit, or delay dark adaptation of a rod photoreceptor cell in the retina. As described in further detail herein, in particular embodiments, the compound that contacts the retina interacts with an isomerase enzyme or enzymatic complex in a RPE cell in the retina and inhibits, blocks, or in some manner interferes with the catalytic activity of the isomerase. Thus, isomerization of an all-trans-retinyl ester is inhibited or reduced. The at least one substituted heterocyclic amine derivative compound (or composition comprising at least one compound) is administered to a subject who has developed and manifested an ophthalmic disease or disorder or who is at risk of developing an ophthalmic disease or disorder, or to a subject who presents or who is at risk of presenting a condition such as retinal neovascularization or retinal ischemia.

By way of background, the visual cycle (also called retinoid cycle) refers to the series of enzyme and light-mediated conversions between the 11-cis and all-trans forms of retinol/retinal that occur in the photoreceptor and retinal pigment epithelial (RPE) cells of the eye. In vertebrate photoreceptor cells, a photon causes isomerization of the 11-cis-retinylidene chromophore to all-trans-retinylidene coupled to the visual opsin receptors. This photoisomerization triggers conformational changes of opsins, which, in turn, initiate the biochemical chain of reactions termed phototransduction (Filipek et al., *Annu. Rev. Physiol.* 65 851-79 (2003)). After absorption of light and photoisomerization of 11-cis-retinal to all-trans retinal, regeneration of the visual chromophore is a critical step in restoring photoreceptors to their dark-adapted state. Regeneration of the visual pigment requires that the chromophore be converted back to the 11-cis-configuration (reviewed in McBee et al., *Prog. Retin. Eye Res.* 20:469-52 (2001)). The chromophore is released from the opsin and reduced in the photoreceptor by retinol dehydrogenases. The product, all-trans-retinol, is trapped in the adjacent retinal pigment epithelium (RPE) in the form of insoluble fatty acid esters in subcellular structures known as retinosomes (Imanishi et al., *J. Cell Biol.* 164:373-78 (2004)).

During the visual cycle in rod receptor cells, the 11-cis retinal chromophore within the visual pigment molecule, which is called rhodopsin, absorbs a photon of light and is isomerized to the all-trans configuration, thereby activating the phototransduction cascade. Rhodopsin is a G-protein coupled receptor (GPCR) that consists of seven membrane-spanning helices that are interconnected by extracellular and cytoplasmic loops. When the all-trans form of the retinoid is still covalently bound to the pigment molecule, the pigment is referred to as metarhodopsin, which exists in different forms (e.g., metarhodopsin I and metarhodopsin II). The all-trans retinoid is then hydrolyzed and the visual pigment is in the form of the apoprotein, opsin, which is also called apo-rhodopsin in the art and herein. This all-trans retinoid is transported or chaperoned out of the photoreceptor cell and across the extracellular space to the RPE cells, where the retinoid is converted to the 11-cis isomer. The movement of the retinoids between the RPE and photoreceptors cells is believed to be accomplished by different chaperone polypeptides in each of the cell types. See Lamb et al., *Progress in Retinal and Eye Research* 23:307-80 (2004).

Under light conditions, rhodopsin continually transitions through the three forms, rhodopsin, metarhodopsin, and apo-rhodopsin. When most of the visual pigment is in the rhodopsin form (i.e., bound with 11-cis retinal), the rod photoreceptor cell is in a "dark-adapted" state. When the visual pigment is predominantly in the metarhodopsin form (i.e., bound with all-trans-retinal), the state of the photoreceptor cell is referred to as a "light-adapted," and when the visual pigment is apo-rhodopsin (or opsin) and no longer has bound chromophore, the state of the photoreceptor cell is referred to as "rhodopsin-depleted." Each of the three states of the photoreceptor cell has different energy requirements, and differing levels of ATP and oxygen are consumed. In the dark-adapted state, rhodopsin has no regulatory effect on cation channels, which are open, resulting in an influx of cations ($Na^+/K^+$ and $Ca^{2+}$). To maintain the proper level of these cations in the cell during the dark state, the photoreceptor cells actively transport the cations out of the cell via ATP-dependent pumps. Thus maintenance of this "dark current" requires a large amount of energy, resulting in high metabolic demand. In the light-adapted state, metarhodopsin triggers an enzymatic cascade process that results in hydrolysis of GMP, which in turn, closes cation-specific channels in the photoreceptor cell membrane. In the rhodopsin-depleted state, the chromophore is hydrolyzed from metarhodopsin to form the apoprotein, opsin (apo-rhodopsin), which partially regulates the cation channels such that the rod photoreceptor cells exhibit an attenuated current compared with the photoreceptor in the dark-adapted state, resulting in a moderate metabolic demand.

Under normal light conditions, the incidence of rod photoreceptors in the dark adapted state is small, in general, 2% or less, and the cells are primarily in the light-adapted or rhodopsin-depleted states, which overall results in a relatively low metabolic demand compared with cells in the dark-adapted state. At night, however, the relative incidence of the dark-adapted photoreceptor state increases profoundly, due to the absence of light adaptation and to the continued operation of the "dark" visual cycle in RPE cells, which replenishes the rod photoreceptor cells with 11-cis-retinal. This shift to dark adaptation of the rod photoreceptor causes an increase in metabolic demand (that is, increased ATP and oxygen consumption), leading ultimately to retinal hypoxia and subsequent initiation of angiogenesis. Most ischaemic insults to the retina therefore occur in the dark, for example, at night during sleep.

Without being bound by any theory, therapeutic intervention during the "dark" visual cycle may prevent retinal hypoxia and neovascularization that are caused by high metabolic activity in the dark-adapted rod photoreceptor cell. Merely by way of one example, altering the "dark" visual cycle by administering any one of the compounds described herein, which is an isomerase inhibitor, rhodopsin (i.e., 11-cis retinal bound) may be reduced or depleted, preventing or inhibiting dark adaptation of rod photoreceptors. This in turn may reduce retinal metabolic demand, attenuating the nighttime risk of retinal ischemia and neovascularization, and thereby inhibiting or slowing retinal degeneration.

In one embodiment, at least one of the compounds described herein (i.e., a substituted heterocyclic amine derivative compound as described in detail herein, including a compound having the structure as set forth in Formula (A) or Formula (B) and substructures thereof, and the specific substituted heterocyclic amine derivative compounds described herein) that, for example, blocks, reduces, inhibits, or in some manner attenuates the catalytic activity of a visual cycle isomerase in a statistically or biologically significant manner, prevents, inhibits, or delays dark adaptation of a rod photoreceptor cell, thereby inhibiting (i.e., reducing, abrogating, preventing, slowing the progression of, or decreasing in a statistically or biologically significant manner) degeneration of retinal cells (or enhancing survival of retinal cells) of the retina of an eye. In another embodiment, the substituted heterocyclic amine derivative compounds prevents or inhibits dark adaptation of a rod photoreceptor cell, thereby reducing ischemia (i.e., decreasing, preventing, inhibiting, slowing the progression of ischemia in a statistically or biologically significant manner). In yet another embodiment, the substituted heterocyclic amine derivative compounds described herein prevent dark adaptation of a rod photoreceptor cell, thereby inhibiting neovascularization in the retina of an eye. Accordingly, methods are provided herein for inhibiting retinal cell degeneration, for inhibiting neovascularization in the retina of an eye of a subject, and for reducing ischemia in an eye of a subject wherein the methods comprise administering at least one substituted heterocyclic amine derivative compound described herein, under conditions and at a time sufficient to prevent, inhibit, or delay dark adaptation of a rod photoreceptor cell. These methods and compositions are therefore useful for treating an ophthalmic disease or disorder including, but not limited to, diabetic retinopathy, diabetic maculopathy, retinal blood vessel occlusion, retinopathy of prematurity, or ischemia reperfusion related retinal injury.

The substituted heterocyclic amine derivative compounds described herein (i.e., a substituted heterocyclic amine derivative compound as described in detail herein, including a compound having the structure as set forth in Formula (A) or Formula (B), and substructures thereof, and the specific substituted heterocyclic amine derivative compounds described herein) prevent (i.e., delay, slow, inhibit, or decrease) recovery of the visual pigment chromophore, which prevents or inhibits or retards the formation of retinals and increases the level of retinal esters, which perturbs the visual cycle, inhibiting regeneration of rhodopsin, and which prevents, slows, delays or inhibits dark adaptation of a rod photoreceptor cell. In certain embodiments, when dark adaptation of rod photoreceptor cells is prevented in the presence of the compound, dark adaptation is substantially prevented, and the number or percent of rod photoreceptor cells that are rhodopsin-depleted or light adapted is increased compared with the number or percent of cells that are rhodopsin-depleted or light-adapted in the absence of the agent. Thus, in certain embodiments when dark adaptation of rod photoreceptor cells is prevented (i.e., substantially prevented), only at least 2% of rod photoreceptor cells are dark-adapted, similar to the percent or number of cells that are in a dark-adapted state during normal, light conditions. In other certain embodiments, at least 5-10%, 10-20%, 20-30%, 30-40%, 40-50%, 50-60%, or 60-70% of rod photoreceptor cells are dark-adapted after administration of an agent. In other embodiments, the compound acts to delay dark adaptation, and in the presence of the compound dark adaptation of rod photoreceptor cells is delayed 30 minutes, one hour, two hours, three hours, or four hours compared to dark adaptation of rod photoreceptors in the absence of the compound. By contrast, when a substituted heterocyclic amine derivative compound is administered such that the compound effectively inhibits isomerization of substrate during light-adapted conditions, the compound is administered in such a manner to minimize the percent of rod photoreceptor cells that are dark-adapted, for example, only 2%, 5%, 10%, 20%, or 25% of rod photoreceptors are dark-adapted (see e.g., U.S. Patent Application Publication No. 2006/0069078; Patent Application No. PCT/US2007/002330).

In the retina in the presence of at least one substituted heterocyclic amine derivative compound, regeneration of rhodopsin in a rod photoreceptor cell is inhibited or the rate of regeneration is reduced (i.e., inhibited, reduced, or decreased in a statistically or biologically significant manner), at least in part, by preventing the formation of retinals, reducing the level of retinals, and/or increasing the level of retinyl esters. To determine the level of regeneration of rhodopsin in a rod photoreceptor cell, the level of regeneration of rhodopsin (which may be called a first level) is determined prior to permitting contact between the compound and the retina (i.e., prior to administration of the agent). After a time sufficient for the compound and the retina and cells of the retina to interact, (i.e., after administration of the compound), the level of regeneration of rhodopsin (which may be called a second level) is determined. A decrease in the second level compared with the first level indicates that the compound inhibits regeneration of rhodopsin. The level of rhodopsin generation may be determined after each dose, or after any number of doses, and ongoing throughout the therapeutic regimen to characterize the effect of the agent on regeneration of rhodopsin.

In certain embodiments, the subject in need of the treatments described herein, has a disease or disorder that results in or causes impairment of the capability of rod photoreceptors to regenerate rhodopsin in the retina. By way of example, inhibition of rhodopsin regeneration (or reduction of the rate of rhodopsin regeneration) may be symptomatic in patients with diabetes. In addition to determining the level of regeneration of rhodopsin in the subject who has diabetes before and after administration of a substituted heterocyclic amine derivative compound described herein, the effect of the compound is also characterized by comparing inhibition of rhodopsin regeneration in a first subject (or a first group or plurality of subjects) to whom the compound is administered, to a second subject (or second group or plurality of subjects) who has diabetes but who does not receive the agent.

In another embodiment, a method is provided for preventing or inhibiting dark adaptation of a rod photoreceptor cell (or a plurality of rod photoreceptor cells) in a retina comprising contacting the retina and at least one of the substituted heterocyclic amine derivative compounds described herein (i.e., a compound as described in detail herein, including a compound having the structure as set forth in Formula (A) or Formula (B), and substructures thereof, and the specific substituted heterocyclic amine derivative compounds described herein), under conditions and at a time sufficient to permit interaction between the agent and an isomerase present in a retinal cell (such as an RPE cell). A first level of 11-cis-retinal in a rod photoreceptor cell in the presence of the compound is determined and compared to a second level of 11-cis-retinal in a rod photoreceptor cell in the absence of the compound. Prevention or inhibition of dark adaptation of the rod photoreceptor cell is indicated when the first level of 11-cis-retinal is less than the second level of 11-cis-retinal.

Inhibiting regeneration of rhodopsin also includes increasing the level of 11-cis-retinyl esters present in the RPE cell in the presence of the compound compared with the level of 11-cis-retinyl esters present in the RPE cell in the absence of the compound (i.e., prior to administration of the agent). A two-photon imaging technique is used to view and analyze retinosome structures in the RPE, which structures are believed to store retinyl esters (see, e.g., Imanishi et al., *J. Cell Biol.* 164:373-83 (2004), Epub 2004 Jan. 26). A first level of retinyl esters may be determined prior to administration of the compound, and a second level of retinyl esters may be determined after administration of a first dose or any subsequent dose, wherein an increase in the second level compared to the first level indicates that the compound inhibits regeneration of rhodopsin.

Retinyl esters are analyzed by gradient HPLC according to methods practiced in the art (see, for example, Mata et al., *Neuron* 36:69-80 (2002); Trevino et al. *J. Exp. Biol.* 208: 4151-57 (2005)). To measure 11-cis and all-trans retinals, retinoids are extracted by a formaldehyde method (see, e.g., Suzuki et al., *Vis. Res.* 28:1061-70 (1988); Okajima and Pepperberg, *Exp. Eye Res.* 65:331-40 (1997)) or by a hydroxylamine method (see, e.g., Groenendijk et al., *Biochim. Biophys. Acta.* 617:430-38 (1980)) before being analyzed on isocratic HPLC (see, e.g., Trevino et al., supra). The retinoids are monitored spectrophotometrically (see, e.g., Maeda et al., *J. Neurochem.* 85:944-956 (2003); Van Hooser et al., *J. Biol. Chem.* 277:19173-82 (2002)).

In another embodiment of the methods described herein for treating an ophthalmic disease or disorder, for inhibiting retinal cell degeneration (or enhancing retinal cell survival), for inhibiting neovascularization, and for reducing ischemia in the retina, preventing or inhibiting dark adaptation of a rod photoreceptor cell in the retina comprises increasing the level of apo-rhodopsin (also called opsin) in the photoreceptor cell. The total level of the visual pigment approximates the sum of rhodopsin and apo-rhodopsin and the total level remains constant. Therefore, preventing, delaying, or inhibiting dark adaptation of the rod photoreceptor cell may alter the ratio of apo-rhodopsin to rhodopsin. In particular embodiments, preventing, delaying, or inhibiting dark adaptation by administering a substituted heterocyclic amine derivative compound described herein may increase the ratio of the level of apo-rhodopsin to the level of rhodopsin compared to the ratio in the absence of the agent (for example, prior to administration of the agent). An increase in the ratio (i.e., a statistically or biologically significant increase) of apo-rhodopsin to rhodopsin indicates that the percent or number of rod photoreceptor cells that are rhodopsin-depleted is increased and that the percent or number of rod photoreceptor cells that are dark-adapted is decreased. The ratio of apo-rhodopsin to rhodopsin may be determined throughout the course of therapy to monitor the effect of the agent.

Determining or characterizing the capability of compound to prevent, delay, or inhibit dark adaptation of a rod photoreceptor cell may be determined in animal model studies. The level of rhodopsin and the ratio of apo-rhodopsin to rhodopsin may be determined prior to administration (which may be called a first level or first ratio, respectively) of the agent and then after administration of a first or any subsequent dose of the agent (which may be called a second level or second ratio, respectively) to determine and to demonstrate that the level of apo-rhodopsin is greater than the level of apo-rhodopsin in the retina of animals that did not receive the agent. The level of rhodopsin in rod photoreceptor cells may be performed according to methods practiced in the art and provided herein (see, e.g., Yan et al. *J. Biol. Chem.* 279:48189-96 (2004)).

A subject in need of such treatment is a human or is a non-human primate or other animal (i.e., veterinary use) who has developed symptoms of an ophthalmic disease or disorder or who is at risk for developing an ophthalmic disease or disorder. Examples of non-human primates and other animals include but are not limited to farm animals, pets, and zoo animals (e.g., horses, cows, buffalo, llamas, goats, rabbits, cats, dogs, chimpanzees, orangutans, gorillas, monkeys, elephants, bears, large cats, etc.).

Also provided herein are methods for inhibiting (reducing, slowing, preventing) degeneration and enhancing retinal neuronal cell survival (or prolonging cell viability) comprising administering to a subject a composition comprising a pharmaceutically acceptable carrier and a substituted heterocyclic amine derivative compound described in detail herein, including a compound having any one of the structures set forth in Formula (A) or Formula (B), substructures thereof, and specific substituted heterocyclic amine derivative compounds recited herein. Retinal neuronal cells include photoreceptor cells, bipolar cells, horizontal cells, ganglion cells, and amacrine cells. In another embodiment, methods are provided for enhancing survival or inhibiting degeneration of a mature retinal cell such as a RPE cell or a Müller glial cell. In other embodiments, a method for preventing or inhibiting photoreceptor degeneration in an eye of a subject are provided. A method that prevents or inhibits photoreceptor degeneration may include a method for restoring photoreceptor function in an eye of a subject. Such methods comprise administering to the subject a composition comprising a substituted heterocyclic amine derivative compound as described herein and a pharmaceutically or acceptable carrier (i.e., excipient or vehicle). More specifically, these methods comprise administering to a subject a pharmaceutically acceptable excipient and a substituted heterocyclic amine derivative compound described herein, including a compound having the structures set forth in Formula (A) or Formula (B) or substructures thereof described herein. Without wishing to be bound by theory, the compounds described herein may inhibit an isomerization step of the retinoid cycle (i.e., visual cycle) and/or may slow chromophore flux in a retinoid cycle in the eye.

The ophthalmic disease may result, at least in part, from lipofuscin pigment(s) accumulation and/or from accumulation of N-retinylidene-N-retinylethanolamine (A2E) in the eye. Accordingly, in certain embodiments, methods are provided for inhibiting or preventing accumulation of lipofuscin pigment(s) and/or A2E in the eye of a subject. These methods comprise administering to the subject a composition comprising a pharmaceutically acceptable carrier and a substituted heterocyclic amine derivative compound as described in detail herein, including a compound having the structure as set forth in Formulae (A) or substructures thereof.

In some embodiments, a substituted heterocyclic amine derivative compound is administered to a subject who has an excess of a retinoid in an eye (e.g., an excess of 11-cis-retinol or 11-cis-retinal), an excess of retinoid waste products or intermediates in the recycling of all-trans-retinal, or the like. Methods described herein and practiced in the art may be used to determine whether the level of one or more endogenous retinoids in a subject are altered (increased or decreased in a statistically significant or biologically significant manner) during or after administration of any one of the compounds described herein. Rhodopsin, which is composed of the protein opsin and retinal (a vitamin A form), is located in the membrane of the photoreceptor cell in the retina of the eye and catalyzes the only light-sensitive step in vision. The 11-cis-retinal chromophore lies in a pocket of the protein and is isomerized to all-trans retinal when light is absorbed. The isomerization of retinal leads to a change of the shape of rhodopsin, which triggers a cascade of reactions that lead to a nerve impulse that is transmitted to the brain by the optic nerve.

Methods of determining endogenous retinoid levels in a vertebrate eye, and an excess or deficiency of such retinoids, are disclosed in, for example, U.S. Patent Application Publication No: 2005/0159662 (the disclosure of which is incorporated by reference herein in its entirety). Other methods of determining endogenous retinoid levels in a subject, which is useful for determining whether levels of such retinoids are above the normal range, and include for example, analysis by high pressure liquid chromatography (HPLC) of retinoids in a biological sample from a subject. For example, retinoid levels can be determined in a biological sample that is a blood sample (which includes serum or plasma) from a subject. A biological sample may also include vitreous fluid, aqueous humor, intraocular fluid, subretinal fluid, or tears.

For example, a blood sample can be obtained from a subject, and different retinoid compounds and levels of one or more of the retinoid compounds in the sample can be separated and analyzed by normal phase high pressure liquid chromatography (HPLC) (e.g., with a HP1100 HPLC and a Beckman, Ultrasphere-Si, 4.6 mm×250 mm column using 10% ethyl acetate/90% hexane at a flow rate of 1.4 ml/minute). The retinoids can be detected by, for example, detection at 325 nm using a diode-array detector and HP Chemstation A.03.03 software. An excess in retinoids can be determined, for example, by comparison of the profile of retinoids (i.e., qualitative, e.g., identity of specific compounds, and quantitative, e.g., the level of each specific compound) in the sample with a sample from a normal subject. Persons skilled in the art who are familiar with such assays and techniques will readily understand that appropriate controls are included.

As used herein, increased or excessive levels of endogenous retinoid, such as 11-cis-retinol or 11-cis-retinal, refer to levels of endogenous retinoid higher than those found in a healthy eye of a young vertebrate of the same species. Administration of a substituted heterocyclic amine derivative compound can reduce or eliminate the requirement for endogenous retinoid. In certain embodiments, the level of endogenous retinoid may be compared before and after any one or more doses of a substituted heterocyclic amine derivative compound is administered to a subject to determine the effect of the compound on the level of endogenous retinoids in the subject.

In another embodiment, the methods described herein for treating an ophthalmic disease or disorder, for inhibiting neovascularization, and for reducing ischemia in the retina comprise administering at least one of the substituted heterocyclic amine derivative compounds described herein, thereby effecting a decrease in metabolic demand, which includes effecting a reduction in ATP consumption and in oxygen consumption in rod photoreceptor cells. As described herein, consumption of ATP and oxygen in a dark-adapted rod photoreceptor cell is greater than in rod photoreceptor cells that are light-adapted or rhodopsin-depleted; thus, use of the compounds in the methods described herein reduces the consumption of ATP in the rod photoreceptor cells that are prevented, inhibited, or delayed from dark adaptation compared with rod photoreceptor cells that are dark-adapted (such as the cells prior to administration or contact with the compound or cells that are never exposed to the compound).

The methods described herein prevent or inhibit dark adaptation of a rod photoreceptor cell therefore reduce hypoxia (i.e., reduce in a statistically or biologically significant manner) in the retina. For example, the level of hypoxia (a first level) may be determined prior to initiation of the treatment regimen, that is, prior to the first dosing of the compound (or a composition, as described herein, comprising the compound). The level of hypoxia (for example, a second level) may be determined after the first dosing, and/or after any second or subsequent dosing to monitor and characterize hypoxia throughout the treatment regimen. A decrease (reduction) in the second (or any subsequent) level of hypoxia compared to the level of hypoxia prior to initial administration indicates that the compound and the treatment regiment prevent dark adaptation of the rod photoreceptor cells and may be used for treating ophthalmic diseases and disorders. Consumption of oxygen, oxygenation of the retina, and/or hypoxia in the retina may be determined using methods practiced in the art. For example, oxygenation of the retina may be determined by measuring the fluorescence of flavoproteins in the retina (see, e.g., U.S. Pat. No. 4,569,354). Another exemplary method is retinal oximetry that measures blood oxygen saturation in the large vessels of the retina near the optic disc. Such methods may be used to identify and determine the extent of retinal hypoxia before changes in retinal vessel architecture can be detected.

A biological sample is a blood sample (from which serum or plasma may be prepared), biopsy specimen, body fluids (e.g., vitreous fluid, aqueous humor, intraocular fluid, subretinal fluid, or tears), tissue explant, organ culture, or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. The subject or biological source may be a human or non-human animal, a primary cell culture (e.g., a retinal cell culture), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like. Mature retinal cells, including retinal neuronal cells, RPE cells, and Müller glial cells, may be present in or isolated from a biological sample as described herein. For example, the mature retinal cell may be obtained from a primary or long-term cell culture or may be present in or isolated from a biological sample obtained from a subject (human or non-human animal).

Retinal Cells

The retina is a thin layer of nervous tissue located between the vitreous body and choroid in the eye. Major landmarks in the retina are the fovea, the macula, and the optic disc. The retina is thickest near the posterior sections and becomes thinner near the periphery. The macula is located in the posterior retina and contains the fovea and foveola. The foveola contains the area of maximal cone density and, thus, imparts the highest visual acuity in the retina. The foveola is contained within the fovea, which is contained within the macula.

The peripheral portion of the retina increases the field of vision. The peripheral retina extends anterior to the ciliary body and is divided into four regions: the near periphery (most posterior), the mid-periphery, the far periphery, and the ora serrata (most anterior). The ora serrata denotes the termination of the retina.

The term neuron (or nerve cell) as understood in the art and used herein denotes a cell that arises from neuroepithelial cell precursors. Mature neurons (i.e., fully differentiated cells) display several specific antigenic markers. Neurons may be classified functionally into four groups: (1) afferent neurons (or sensory neurons) that transmit information into the brain for conscious perception and motor coordination; (2) motor neurons that transmit commands to muscles and glands; (3) interneurons that are responsible for local circuitry; and (4) projection interneurons that relay information from one region of the brain to anther region and therefore have long axons. Interneurons process information within specific subregions of the brain and have relatively shorter axons. A neuron typically has four defined regions: the cell body (or soma); an axon; dendrites; and presynaptic terminals. The dendrites serve as the primary input of information from other neural cells. The axon carries the electrical signals that are initiated in the cell body to other neurons or to effector organs. At the presynaptic terminals, the neuron transmits information to another cell (the postsynaptic cell), which may be another neuron, a muscle cell, or a secretory cell.

The retina is composed of several types of neuronal cells. As described herein, the types of retinal neuronal cells that may be cultured in vitro by this method include photoreceptor cells, ganglion cells, and interneurons such as bipolar cells, horizontal cells, and amacrine cells. Photoreceptors are specialized light-reactive neural cells and comprise two major classes, rods and cones. Rods are involved in scotopic or dim light vision, whereas photopic or bright light vision originates in the cones. Many neurodegenerative diseases, such as AMD, that result in blindness affect photoreceptors.

Extending from their cell bodies, the photoreceptors have two morphologically distinct regions, the inner and outer segments. The outer segment lies furthermost from the photoreceptor cell body and contains disks that convert incoming light energy into electrical impulses (phototransduction). The outer segment is attached to the inner segment with a very small and fragile cilium. The size and shape of the outer segments vary between rods and cones and are dependent upon position within the retina. See Hogan, "Retina" in *Histology of the Human Eye: an Atlas and Text Book* (Hogan et al. (eds). WB Saunders; Philadelphia, Pa. (1971)); *Eye and Orbit*, $8^{th}$ Ed., Bron et al., (Chapman and Hall, 1997).

Ganglion cells are output neurons that convey information from the retinal interneurons (including horizontal cells, bipolar cells, amacrine cells) to the brain. Bipolar cells are named according to their morphology, and receive input from the photoreceptors, connect with amacrine cells, and send output radially to the ganglion cells. Amacrine cells have processes parallel to the plane of the retina and have typically inhibitory output to ganglion cells. Amacrine cells are often subclassified by neurotransmitter or neuromodulator or peptide (such as calretinin or calbindin) and interact with each other, with bipolar cells, and with photoreceptors. Bipolar cells are retinal interneurons that are named according to their morphology; bipolar cells receive input from the photoreceptors and sent the input to the ganglion cells. Horizontal cells modulate and transform visual information from large numbers of photoreceptors and have horizontal integration (whereas bipolar cells relay information radially through the retina).

Other retinal cells that may be present in the retinal cell cultures described herein include glial cells, such as Müller glial cells, and retinal pigment epithelial cells (RPE). Glial cells surround nerve cell bodies and axons. The glial cells do not carry electrical impulses but contribute to maintenance of normal brain function. Müller glia, the predominant type of glial cell within the retina, provide structural support of the retina and are involved in the metabolism of the retina (e.g., contribute to regulation of ionic concentrations, degradation of neurotransmitters, and remove certain metabolites (see, e.g., Kljavin et al., *J. Neurosci.* 11:2985 (1991))). Müller's fibers (also known as sustentacular fibers of retina) are sustentacular neuroglial cells of the retina that run through the thickness of the retina from the internal limiting membrane to the bases of the rods and cones where they form a row of junctional complexes.

Retinal pigment epithelial (RPE) cells form the outermost layer of the retina, separated from the blood vessel-enriched choroids by Bruch's membrane. RPE cells are a type of phagocytic epithelial cell, with some functions that are macrophage-like, which lies immediately below the retinal photoreceptors. The dorsal surface of the RPE cell is closely apposed to the ends of the rods, and as discs are shed from the rod outer segment they are internalized and digested by RPE cells. Similar process occurs with the disc of the cones. RPE cells also produce, store, and transport a variety of factors that contribute to the normal function and survival of photoreceptors. Another function of RPE cells is to recycle vitamin A as it moves between photoreceptors and the RPE during light and dark adaptation in the process known as the visual cycle.

Described herein is an exemplary long-term in vitro cell culture system that permits and promotes the survival in culture of mature retinal cells, including retinal neurons, for at least 2-4 weeks, over 2 months, or for as long as 6 months. The cell culture system may be used for identifying and characterizing the substituted heterocyclic amine derivative compounds that are useful in the methods described herein for treating and/or preventing an ophthalmic disease or disorder or for preventing or inhibiting accumulation in the eye of lipofuscin(s) and/or A2E. Retinal cells are isolated from non-embryonic, non-tumorigenic tissue and have not been immortalized by any method such as, for example, transformation or infection with an oncogenic virus. The cell culture system comprises all the major retinal neuronal cell types (photoreceptors, bipolar cells, horizontal cells, amacrine cells, and ganglion cells), and also may include other mature retinal cells such as retinal pigment epithelial cells and Müller glial cells.

For example, a blood sample can be obtained from a subject, and different retinoid compounds and levels of one or more of the retinoid compounds in the sample can be separated and analyzed by normal phase high pressure liquid chromatography (HPLC) (e.g., with a HP1100 HPLC and a Beckman, Ultrasphere-Si, 4.6 mm×250 mm column using 10% ethyl acetate/90% hexane at a flow rate of 1.4 ml/minute). The retinoids can be detected by, for example, detection at 325 nm using a diode-array detector and HP Chemstation A.03.03 software. An excess in retinoids can be determined, for example, by comparison of the profile of retinoids (i.e., qualitative, e.g., identity of specific compounds, and quantitative, e.g., the level of each specific compound) in the sample with a sample from a normal subject. Persons skilled in the art who are familiar with such assays and techniques and will readily understand that appropriate controls are included.

As used herein, increased or excessive levels of endogenous retinoid, such as 11-cis-retinol or 11-cis-retinal, refer to levels of endogenous retinoid higher than those found in a healthy eye of a young vertebrate of the same species. In some embodiments, administration of a substituted heterocyclic amine derivative compound will reduce or eliminate the requirement for endogenous retinoid.

In Vivo and In Vitro Methods for Determining Therapeutic Effectiveness of Compounds In one embodiment, methods are provided for using the compounds described herein for enhancing or prolonging retinal cell survival, including retinal neuronal cell survival and RPE cell survival. Also provided herein are methods for inhibiting or preventing degeneration of a retinal cell, including a retinal neuronal cell (e.g., a photoreceptor cell, an amacrine cell, a horizontal cell, a bipolar cell, and a ganglion cell) and other mature retinal cells such as retinal pigment epithelial cells and Müller glial cells using the compounds described herein. Such methods comprise, in certain embodiments, administration of a substituted heterocyclic amine derivative compound as described herein. Such a compound is useful for enhancing retinal cell survival, including photoreceptor cell survival and retinal pigment epithelia survival, inhibiting or slowing degeneration of a retinal cell, and thus increasing retinal cell viability, which can result in slowing or halting the progression of an ophthalmic disease or disorder or retinal injury, which are described herein.

The effect of a substituted heterocyclic amine derivative compound on retinal cell survival (and/or retinal cell degeneration) may be determined by using cell culture models, animal models, and other methods that are described herein and practiced by persons skilled in the art. By way of example, and not limitation, such methods and assays include those described in Oglivie et al., *Exp. Neurol.* 161:675-856 (2000); U.S. Pat. No. 6,406,840; WO 01/81551; WO 98/12303; U.S. Patent Application No. 2002/0009713; WO 00/40699; U.S. Pat. No. 6,117,675; U.S. Pat. No. 5,736,516; WO 99/29279; WO 01/83714; WO 01/42784; U.S. Pat. No. 6,183,735; U.S. Pat. No. 6,090,624; WO 01/09327; U.S. Pat. No. 5,641,750; U.S. Patent Application Publication No. 2004/0147019; and U.S. Patent Application Publication No. 2005/0059148.

Compounds described herein that are useful for treating an ophthalmic disease or disorder (including a retinal disease or disorder) inhibit, block, impair, or in some manner interfere with one or more steps in the visual cycle (also called the retinoid cycle herein and in the art). Without wishing to be bound by a particular theory, a substituted heterocyclic amine derivative compound inhibits or blocks an isomerization step in the visual cycle, for example, by inhibiting or blocking a functional activity of a visual cycle trans-cis isomerase. The compounds described herein inhibit, directly or indirectly, isomerization of all-trans-retinol to 11-cis-retinol. The compounds bind to, or in some manner interact with, and inhibit the isomerase activity of at least one isomerase in a retinal cell. The compounds described herein also directly or indirectly inhibit or reduce the activity of an isomerase that is involved in the visual cycle. The compound blocks or inhibits the capability of the isomerase to bind to one or more substrates, including but not limited to, an all-trans-retinyl ester substrate or all-trans-retinol. Alternatively, or in addition, the compound may bind to the catalytic site or region of the isomerase, thereby inhibiting the capability of the enzyme to catalyze isomerization of at least one substrate. On the basis of scientific data to date, and at least one isomerase that catalyzes the isomerization of a substrate during the visual cycle is believed to be located in the cytoplasm of RPE cells. As discussed herein, each step, enzyme, substrate, intermediate, and product of the visual cycle is not yet elucidated. While a polypeptide called RPE65, which has been found in the cytoplasm and membrane bound in RPE cells, is hypothesized to have isomerase activity (and has also been referred to in the art as having isomerohydrolase activity) (see, e.g., Moiseyev et al., *Proc. Natl. Acad. Sci. USA* 102:12413-18 (2004); Chen et al., *Invest. Ophthalmol. Vis. Sci.* 47:1177-84 (2006)), other persons skilled in the art believe that the RPE65 acts primarily as a chaperone for all-trans-retinyl esters (see, e.g., Lamb et al. supra).

Exemplary methods are described herein and practiced by persons skilled in the art for determining the level of enzymatic activity of a visual cycle isomerase in the presence of any one of the compounds described herein. A compound that decreases isomerase activity is useful for treating an ophthalmic disease or disorder. Thus, methods are provided herein for detecting inhibition of isomerase activity comprising contacting (i.e., mixing, combining, or in some manner permitting the compound and isomerase to interact) a biological sample comprising the isomerase and a substituted heterocyclic amine derivative compound described herein and then determining the level of enzymatic activity of the isomerase. A person having skill in the art will appreciate that as a control, the level of activity of the isomerase in the absence of a compound or in the presence of a compound known not to alter the enzymatic activity of the isomerase can be determined and compared to the level of activity in the presence of the compound. A decrease in the level of isomerase activity in the presence of the compound compared to the level of isomerase activity in the absence of the compound indicates that the compound is useful for treating an ophthalmic disease or disorder, such as age-related macular degeneration or Stargardt's disease. A decrease in the level of isomerase activity in the presence of the compound compared to the level of isomerase activity in the absence of the compound indicates that the compound is also useful in the methods described herein for inhibiting or preventing dark adaptation, inhibiting neovascularization and reducing hypoxia and thus useful for treating an ophthalmic disease or disorder, for example, diabetic retinopathy, diabetic maculopathy, retinal blood vessel occlusion, retinopathy of prematurity, or ischemia reperfusion related retinal injury.

The capability of a substituted heterocyclic amine derivative compound described herein to inhibit or to prevent dark adaptation of a rod photoreceptor cell by inhibiting regeneration of rhodopsin is determined by in vitro assays and/or in vivo animal models. By way of example, inhibition of regeneration is determined in a mouse model in which a diabetes-like condition is induced chemically or in a diabetic mouse model (see, e.g., Phipps et al., *Invest. Ophthalmol. Vis. Sci.* 47:3187-94 (2006); Ramsey et al., *Invest. Ophthalmol. Vis. Sci.* 47:5116-24 (2006)). The level of rhodopsin (a first level) may be determined (for example, spectrophotometrically) in the retina of animals prior to administration of the agent and compared with the level (a second level) of rhodopsin measured in the retina of animals after administration of the agent. A decrease in the second level of rhodopsin compared with the first level of rhodopsin indicates that the agent inhibits regeneration of rhodopsin. The appropriate controls and study design to determine whether regeneration of rhodopsin is inhibited in a statistically significant or biologically significant manner can be readily determined and implemented by persons skilled in the art.

Methods and techniques for determining or characterizing the effect of any one of the compounds described herein on dark adaptation and rhodopsin regeneration in rod photoreceptor cells in a mammal, including a human, may be performed according to procedures described herein and practiced in the art. For example, detection of a visual stimulus after exposure to light (i.e., photobleaching) versus time in darkness may be determined before administration of the first dose of the compound and at a time after the first dose and/or any subsequent dose. A second method for determining prevention or inhibition of dark adaptation by the rod photoreceptor cells includes measurement of the amplitude of at least one, at least two, at least three, or more electroretinogram components, which include, for example, the a-wave and the b-wave. See, for example, Lamb et al., supra; Asi et al., *Documenta Ophthalmologica* 79:125-39 (1992).

Inhibiting regeneration of rhodopsin by a substituted heterocyclic amine derivative compound described herein comprises reducing the level of the chromophore, 11-cis-retinal, that is produced and present in the RPE cell, and consequently reducing the level of 11-cis-retinal that is present in the photoreceptor cell. Thus, the compound, when permitted to contact the retina under suitable conditions and at a time sufficient to prevent dark adaptation of a rod photoreceptor cell and to inhibit regeneration of rhodopsin in the rod photoreceptor cell, effects a reduction in the level of 11-cis-retinal in a rod photoreceptor cell (i.e., a statistically significant or biologically significant reduction). That is, the level of 11-cis retinal in a rod photoreceptor cell is greater prior to administration of the compound when compared with the level of 11-cis-retinal in the photoreceptor cell after the first and/or any subsequent administration of the compound. A first level of 11-cis-retinal may be determined prior to administration of the compound, and a second level of 11-cis-retinal may be determined after administration of a first dose or any subsequent dose to monitor the effect of the compound. A decrease in the second level compared to the first level indicates that the compound inhibits regeneration of rhodopsin and thus inhibits or prevents dark adaptation of the rod photoreceptor cells.

An exemplary method for determining or characterizing the capability of a substituted heterocyclic amine derivative compound to reduce retinal hypoxia includes measuring the level of retinal oxygenation, for example, by Magnetic Resonance Imaging (MRI) to measure changes in oxygen pressure (see, e.g., Luan et al., *Invest. Ophthalmol. Vis. Sci.* 47:320-28 (2006)). Methods are also available and routinely practiced in the art to determine or characterize the capability of compounds described herein to inhibit degeneration of a retinal cell (see, e.g., Wenzel et al., *Prog. Retin. Eye Res.* 24:275-306 (2005)).

Animal models may be used to characterize and identify compounds that may be used to treat retinal diseases and disorders. A recently developed animal model may be useful for evaluating treatments for macular degeneration has been described by Ambati et al. (*Nat. Med.* 9:1390-97 (2003); Epub 2003 Oct. 19). This animal model is one of only a few exemplary animal models presently available for evaluating a compound or any molecule for use in treating (including preventing) progression or development of a retinal disease or disorder. Animal models in which the ABCR gene, which encodes an ATP-binding cassette transporter located in the rims of photoreceptor outer segment discs, may be used to evaluate the effect of a compound. Mutations in the ABCR gene are associated with Stargardt's disease, and heterozygous mutations in ABCR have been associated with AMD. Accordingly, animals have been generated with partial or total loss of ABCR function and may used to characterize the substituted heterocyclic amine derivative compound described herein. (See, e.g., Mata et al., *Invest. Ophthalmol. Sci.* 42:1685-90 (2001); Weng et al., *Cell* 98:13-23 (1999); Mata et al., *Proc. Natl. Acad. Sci. USA* 97:7154-49 (2000); US 2003/0032078; U.S. Pat. No. 6,713,300). Other animal models include the use of mutant ELOVL4 transgenic mice to determine lipofuscin accumulation, electrophysiology, and photoreceptor degeneration, or prevention or inhibition thereof (see, e.g., Karan et al., *Proc. Natl. Acad. Sci. USA* 102:4164-69 (2005)).

The effect of any one of the compounds described herein may be determined in a diabetic retinopathy animal model, such as described in Luan et al. or may be determined in a normal animal model, in which the animals have been light or dark adapted in the presence and absence of any one of the compounds described herein. Another exemplary method for determining the capability of the agent to reduce retinal hypoxia measures retinal hypoxia by deposition of a hydroxyprobe (see, e.g., de Gooyer et al. (*Invest. Ophthalmol. Vis. Sci.* 47:5553-60 (2006)). Such a technique may be performed in an animal model using $Rho^-/Rho^-$ knockout mice (see de Gooyer et al., supra) in which at least one compound described herein is administered to group(s) of animals in the presence and absence of the at least one compound, or may be performed in normal, wildtype animals in which at least one compound described herein is administered to group(s) of animals in the presence and absence of the at least one compound. Other animal models include models for determining photoreceptor function, such as rat models that measure elctroretinographic (ERG) oscillatory potentials (see, e.g., Liu et al., *Invest. Ophthalmol. Vis. Sci.* 47:5447-52 (2006); Akula et al., *Invest. Ophthalmol. Vis. Sci.* 48:4351-59 (2007); Liu et al., *Invest. Ophthalmol. Vis. Sci.* 47:2639-47 (2006); Dembinska et al., *Invest. Ophthalmol. Vis. Sci.* 43:2481-90 (2002); Penn et al., *Invest. Ophthalmol. Vis. Sci.* 35:3429-35 (1994); Hancock et al., *Invest. Ophthalmol. Vis. Sci.* 45:1002-1008 (2004)).

A method for determining the effect of a compound on isomerase activity is performed in vitro as described herein and in the art (Stecher et al., *J. Biol. Chem.* 274:8577-85 (1999); see also Golczak et al., *Proc. Natl. Acad. Sci. USA* 102:8162-67 (2005)). Retinal pigment epithelium (RPE) microsome membranes isolated from an animal (such as bovine, porcine, human, for example) serves as the source of the isomerase. The capability of the substituted heterocyclic amine derivative compounds to inhibit isomerase is also determined by an in vivo murine isomerase assay. Brief exposure of the eye to intense light ("photobleaching" of the visual pigment or simply "bleaching") is known to photoisomerize almost all 11-cis-retinal in the retina. The recovery of 11-cis-retinal after bleaching can be used to estimate the activity of isomerase in vivo (see, e.g., Maeda et al., *J. Neurochem.* 85:944-956 (2003); Van Hooser et al., *J. Biol. Chem.* 277:19173-82, 2002). Electroretinographic (ERG) recording is performed as previously described (Haeseleer et al., *Nat. Neurosci.* 7:1079-87 (2004); Sugitomo et al., *J. Toxicol. Sci.* 22 Suppl 2:315-25 (1997); Keating et al., *Documenta Ophthalmologica* 100:77-92 (2000)). See also Deigner et al., *Science,* 244: 968-971 (1989); Gollapalli et al., *Biochim. Biophys. Acta* 1651: 93-101 (2003); Parish, et al., *Proc. Natl. Acad. Sci. USA* 95:14609-13 (1998); Radu et al., *Proc Natl Acad Sci USA* 101: 5928-33 (2004).

Cell culture methods, such as the method described herein, are also useful for determining the effect of a compound described herein on retinal neuronal cell survival. Exemplary cell culture models are described herein and described in detail in U.S. Patent Application Publication No. US 2005-0059148 and U.S. Patent Application Publication No. US2004-0147019 (which are incorporated by reference in their entirety), which are useful for determining the capability of a substituted heterocyclic amine derivative compound as described herein to enhance or prolong survival of neuronal cells, particularly retinal neuronal cells, and of retinal pigment epithelial cells, and inhibit, prevent, slow, or retard degeneration of an eye, or the retina or retinal cells thereof, or the RPE, and which compounds are useful for treating ophthalmic diseases and disorders.

The cell culture model comprises a long-term or extended culture of mature retinal cells, including retinal neuronal cells (e.g., photoreceptor cells, amacrine cells, ganglion cells, horizontal cells, and bipolar cells). The cell culture system and methods for producing the cell culture system provide extended culture of photoreceptor cells. The cell culture system may also comprise retinal pigment epithelial (RPE) cells and Müller glial cells.

The retinal cell culture system may also comprise a cell stressor. The application or the presence of the stressor affects the mature retinal cells, including the retinal neuronal cells, in vitro, in a manner that is useful for studying disease pathology that is observed in a retinal disease or disorder. The cell culture model provides an in vitro neuronal cell culture system that will be useful in the identification and biological testing of a substituted heterocyclic amine derivative compound that is suitable for treatment of neurological diseases or disorders in general, and for treatment of degenerative diseases of the eye and brain in particular. The ability to maintain primary, in vitro-cultured cells from mature retinal tissue, including retinal neurons over an extended period of time in the presence of a stressor enables examination of cell-to-cell interactions, selection and analysis of neuroactive compounds and materials, use of a controlled cell culture system for in vitro CNS and ophthalmic tests, and analysis of the effects on single cells from a consistent retinal cell population.

The cell culture system and the retinal cell stress model comprise cultured mature retinal cells, retinal neurons, and a retinal cell stressor, which may be used for screening and characterizing a substituted heterocyclic amine derivative compound that are capable of inducing or stimulating the regeneration of CNS tissue that has been damaged by disease. The cell culture system provides a mature retinal cell culture that is a mixture of mature retinal neuronal cells and non-neuronal retinal cells. The cell culture system comprises all the major retinal neuronal cell types (photoreceptors, bipolar cells, horizontal cells, amacrine cells, and ganglion cells), and may also include other mature retinal cells such as RPE and Müller glial cells. By incorporating these different types of cells into the in vitro culture system, the system essentially resembles an "artificial organ" that is more akin to the natural in vivo state of the retina.

Viability of one or more of the mature retinal cell types that are isolated (harvested) from retinal tissue and plated for tissue culture may be maintained for an extended period of time, for example, from two weeks up to six months. Viability of the retinal cells may be determined according to methods described herein and known in the art. Retinal neuronal cells, similar to neuronal cells in general, are not actively dividing cells in vivo and thus cell division of retinal neuronal cells would not necessarily be indicative of viability. An advantage of the cell culture system is the ability to culture amacrine cells, photoreceptors, and associated ganglion projection neurons and other mature retinal cells for extended periods of time, thereby providing an opportunity to determine the effectiveness of a substituted heterocyclic amine derivative compound described herein for treatment of retinal disease.

The biological source of the retinal cells or retinal tissue may be mammalian (e.g., human, non-human primate, ungulate, rodent, canine, porcine, bovine, or other mammalian source), avian, or from other genera. Retinal cells including retinal neurons from post-natal non-human primates, post-natal pigs, or post-natal chickens may be used, but any adult or post-natal retinal tissue may be suitable for use in this retinal cell culture system.

In certain instances, the cell culture system may provide for robust long-term survival of retinal cells without inclusion of cells derived from or isolated or purified from non-retinal tissue. Such a cell culture system comprises cells isolated solely from the retina of the eye and thus is substantially free of types of cells from other parts or regions of the eye that are separate from the retina, such as the ciliary body, iris, choroid, and vitreous. Other cell culture methods include the addition of non-retinal cells, such as ciliary body cell and/or stem cells (which may or may not be retinal stem cells) and/or additional purified glial cells.

The in vitro retinal cell culture systems described herein may serve as physiological retinal models that can be used to characterize aspects of the physiology of the retina. This physiological retinal model may also be used as a broader general neurobiology model. A cell stressor may be included in the model cell culture system. A cell stressor, which as described herein is a retinal cell stressor, adversely affects the viability or reduces the viability of one or more of the different retinal cell types, including types of retinal neuronal cells, in the cell culture system. A person skilled in the art would readily appreciate and understand that as described herein a retinal cell that exhibits reduced viability means that the length of time that a retinal cell survives in the cell culture system is reduced or decreased (decreased lifespan) and/or that the retinal cell exhibits a decrease, inhibition, or adverse effect of a biological or biochemical function (e.g., decreased or abnormal metabolism; initiation of apoptosis; etc.) compared with a retinal cell cultured in an appropriate control cell system (e.g., the cell culture system described herein in the absence of the cell stressor). Reduced viability of a retinal cell may be indicated by cell death; an alteration or change in cell structure or morphology; induction and/or progression of apoptosis; initiation, enhancement, and/or acceleration of retinal neuronal cell neurodegeneration (or neuronal cell injury).

Methods and techniques for determining cell viability are described in detail herein and are those with which skilled artisans are familiar. These methods and techniques for determining cell viability may be used for monitoring the health and status of retinal cells in the cell culture system and for determining the capability of the substituted heterocyclic amine derivative compounds described herein to alter (preferably increase, prolong, enhance, improve) retinal cell or retinal pigment epithelial cell viability or retinal cell survival.

The addition of a cell stressor to the cell culture system is useful for determining the capability of a substituted heterocyclic amine derivative compound to abrogate, inhibit, eliminate, or lessen the effect of the stressor. The retinal cell culture system may include a cell stressor that is chemical (e.g., A2E, cigarette smoke concentrate); biological (for example, toxin exposure; beta-amyloid; lipopolysaccharides); or non-chemical, such as a physical stressor, environmental stressor, or a mechanical force (e.g., increased pressure or light exposure) (see, e.g., US 2005-0059148).

The retinal cell stressor model system may also include a cell stressor such as, but not limited to, a stressor that may be a risk factor in a disease or disorder or that may contribute to the development or progression of a disease or disorder, including but not limited to, light of varying wavelengths and intensities; A2E; cigarette smoke condensate exposure; oxidative stress (e.g., stress related to the presence of or exposure to hydrogen peroxide, nitroprusside, Zn++, or Fe++); increased pressure (e.g., atmospheric pressure or hydrostatic pressure), glutamate or glutamate agonist (e.g., N-methyl-D-aspartate (NMDA); alpha-amino-3-hydroxy-5-methylisoxazole-4-proprionate (AMPA); kainic acid; quisqualic acid; ibotenic acid; quinolinic acid; aspartate; trans-1-aminocyclopentyl-1,3-dicarboxylate (ACPD)); amino acids (e.g., aspartate, L-cysteine; beta-N-methylamine-L-alanine); heavy metals (such as lead); various toxins (for example, mitochondrial toxins (e.g., malonate, 3-nitropropionic acid; rotenone, cyanide); MPTP (1-methyl-4-phenyl-1,2,3,6,-tetrahydropyridine), which metabolizes to its active, toxic metabolite MPP+ (1-methyl-4-phenylpryidine)); 6-hydroxydopamine; alpha-synuclein; protein kinase C activators (e.g., phorbol myristate acetate); biogenic amino stimulants (for example, methamphetamine, MDMA (3-4 methylenedioxymethamphetamine)); or a combination of one or more stressors. Useful retinal cell stressors include those that mimic a neurodegenerative disease that affects any one or more of the mature retinal cells described herein. A chronic disease model is of particular importance because most neurodegenerative diseases are chronic. Through use of this in vitro cell culture system, the earliest events in long-term disease development processes may be identified because an extended period of time is available for cellular analysis.

A retinal cell stressor may alter (i.e., increase or decrease in a statistically significant manner) viability of retinal cells such as by altering survival of retinal cells, including retinal neuronal cells and RPE cells, or by altering neurodegeneration of retinal neuronal cells and/or RPE cells. Preferably, a retinal cell stressor adversely affects a retinal neuronal cell or RPE cell such that survival of a retinal neuronal cell or RPE cell is decreased or adversely affected (i.e., the length of time during which the cells are viable is decreased in the presence of the stressor) or neurodegeneration (or neuron cell injury) of the cell is increased or enhanced. The stressor may affect only a single retinal cell type in the retinal cell culture or the stressor may affect two, three, four, or more of the different cell types. For example, a stressor may alter viability and survival of photoreceptor cells but not affect all the other major cell types (e.g., ganglion cells, amacrine cells, horizontal cells, bipolar cells, RPE, and Müller glia). Stressors may shorten the survival time of a retinal cell (in vivo or in vitro), increase the rapidity or extent of neurodegeneration of a retinal cell, or in some other manner adversely affect the viability, morphology, maturity, or lifespan of the retinal cell.

The effect of a cell stressor (in the presence and absence of a substituted heterocyclic amine derivative compound) on the viability of retinal cells in the cell culture system may be determined for one or more of the different retinal cell types. Determination of cell viability may include evaluating structure and/or a function of a retinal cell continually at intervals over a length of time or at a particular time point after the retinal cell culture is prepared. Viability or long term survival of one or more different retinal cell types or one or more different retinal neuronal cell types may be examined according to one or more biochemical or biological parameters that are indicative of reduced viability, such as apoptosis or a decrease in a metabolic function, prior to observation of a morphological or structural alteration.

A chemical, biological, or physical cell stressor may reduce viability of one or more of the retinal cell types present in the cell culture system when the stressor is added to the cell culture under conditions described herein for maintaining the long-term cell culture. Alternatively, one or more culture conditions may be adjusted so that the effect of the stressor on the retinal cells can be more readily observed. For example, the concentration or percent of fetal bovine serum may be reduced or eliminated from the cell culture when cells are exposed to a particular cell stressor (see, e.g., US 2005-0059148). Alternatively, retinal cells cultured in media containing serum at a particular concentration for maintenance of the cells may be abruptly exposed to media that does not contain any level of serum.

The retinal cell culture may be exposed to a cell stressor for a period of time that is determined to reduce the viability of one or more retinal cell types in the retinal cell culture system. The cells may be exposed to a cell stressor immediately upon plating of the retinal cells after isolation from retinal tissue. Alternatively, the retinal cell culture may be exposed to a stressor after the culture is established, or any time thereafter. When two or more cell stressors are included in the retinal cell culture system, each stressor may be added to the cell culture system concurrently and for the same length of time or may be added separately at different time points for the same length of time or for differing lengths of time during the culturing of the retinal cell system. A substituted heterocyclic amine derivative compound may be added before the retinal cell culture is exposed to a cell stressor, may be added concurrently with the cell stressor, or may be added after exposure of the retinal cell culture to the stressor.

Photoreceptors may be identified using antibodies that specifically bind to photoreceptor-specific proteins such as opsins, peripherins, and the like. Photoreceptors in cell culture may also be identified as a morphologic subset of immunocytochemically labeled cells by using a pan-neuronal marker or may be identified morphologically in enhanced contrast images of live cultures. Outer segments can be detected morphologically as attachments to photoreceptors.

Retinal cells including photoreceptors can also be detected by functional analysis. For example, electrophysiology methods and techniques may be used for measuring the response of photoreceptors to light. Photoreceptors exhibit specific kinetics in a graded response to light. Calcium-sensitive dyes may also be used to detect graded responses to light within cultures containing active photoreceptors. For analyzing stress-inducing compounds or potential neurotherapeutics, retinal cell cultures can be processed for immunocytochemistry, and photoreceptors and/or other retinal cells can be counted manually or by computer software using photomicroscopy and imaging techniques. Other immunoassays known in the art (e.g., ELISA, immunoblotting, flow cytometry) may also be useful for identifying and characterizing the retinal cells and retinal neuronal cells of the cell culture model system described herein.

The retinal cell culture stress models may also be useful for identification of both direct and indirect pharmacologic agent effects by the bioactive agent of interest, such as a substituted heterocyclic amine derivative compound as described herein. For example, a bioactive agent added to the cell culture system in the presence of one or more retinal cell stressors may stimulate one cell type in a manner that enhances or decreases the survival of other cell types. Cell/cell interactions and cell/extracellular component interactions may be important in understanding mechanisms of disease and drug function. For example, one neuronal cell type may secrete trophic factors that affect growth or survival of another neuronal cell type (see, e.g., WO 99/29279).

In another embodiment, a substituted heterocyclic amine derivative compound is incorporated into screening assays comprising the retinal cell culture stress model system described herein to determine whether and/or to what level or degree the compound increases or prolongs viability (i.e., increases in a statistically significant or biologically significant manner) of a plurality of retinal cells. A person skilled in the art would readily appreciate and understand that as described herein a retinal cell that exhibits increased viability means that the length of time that a retinal cell survives in the cell culture system is increased (increased lifespan) and/or that the retinal cell maintains a biological or biochemical function (normal metabolism and organelle function; lack of apoptosis; etc.) compared with a retinal cell cultured in an appropriate control cell system (e.g., the cell culture system described herein in the absence of the compound). Increased viability of a retinal cell may be indicated by delayed cell death or a reduced number of dead or dying cells; maintenance of structure and/or morphology; lack of or delayed initiation of apoptosis; delay, inhibition, slowed progression, and/or abrogation of retinal neuronal cell neurodegeneration or delaying or abrogating or preventing the effects of neuronal cell injury. Methods and techniques for determining viability of a retinal cell and thus whether a retinal cell exhibits increased viability are described in greater detail herein and are known to persons skilled in the art.

In certain embodiments, a method is provided for determining whether a substituted heterocyclic amine derivative compound, enhances survival of photoreceptor cells. One method comprises contacting a retinal cell culture system as described herein with an substituted heterocyclic amine derivative compound under conditions and for a time sufficient to permit interaction between the retinal neuronal cells and the compound. Enhanced survival (prolonged survival) may be measured according to methods described herein and known in the art, including detecting expression of rhodopsin.

The capability of a substituted heterocyclic amine derivative compound to increase retinal cell viability and/or to enhance, promote, or prolong cell survival (that is, to extend the time period in which retinal cells, including retinal neuronal cells, are viable), and/or impair, inhibit, or impede degeneration as a direct or indirect result of the herein described stress may be determined by any one of several methods known to those skilled in the art. For example, changes in cell morphology in the absence and presence of the compound may be determined by visual inspection such as by light microscopy, confocal microscopy, or other microscopy methods known in the art. Survival of cells can also be determined by counting viable and/or nonviable cells, for instance. Immunochemical or immunohistological techniques (such as fixed cell staining or flow cytometry) may be used to identify and evaluate cytoskeletal structure (e.g., by using antibodies specific for cytoskeletal proteins such as glial fibrillary acidic protein, fibronectin, actin, vimentin, tubulin, or the like) or to evaluate expression of cell markers as described herein. The effect of a substituted heterocyclic amine derivative compound on cell integrity, morphology, and/or survival may also be determined by measuring the phosphorylation state of neuronal cell polypeptides, for example, cytoskeletal polypeptides (see, e.g., Sharma et al., *J. Biol. Chem.* 274:9600-06 (1999); Li et al., *J. Neurosci.* 20:6055-62 (2000)). Cell survival or, alternatively cell death, may also be determined according to methods described herein and known in the art for measuring apoptosis (for example, annexin V binding, DNA fragmentation assays, caspase activation, marker analysis, e.g., poly(ADP-ribose) polymerase (PARP), etc.).

In the vertebrate eye, for example, a mammalian eye, the formation of A2E is a light-dependent process and its accumulation leads to a number of negative effects in the eye. These include destabilization of retinal pigment epithelium (RPE) membranes, sensitization of cells to blue-light damage, and impaired degradation of phospholipids. Products of the oxidation of A2E (and A2E related molecules) by molecular oxygen (oxiranes) were shown to induce DNA damage in cultured RPE cells. All these factors lead to a gradual decrease in visual acuity and eventually to vision loss. If reducing the formation of retinals during vision processes were possible, this reduction would lead to decreased amounts of A2E in the eye. Without wishing to be bound by theory, decreased accumulation of A2E may reduce or delay degenerative processes in the RPE and retina and thus may slow down or prevent vision loss in dry AMD and Stargardt's Disease.

In another embodiment, methods are provided for treating and/or preventing degenerative diseases and disorders, including neurodegenerative retinal diseases and ophthalmic diseases, and retinal diseases and disorders as described herein. A subject in need of such treatment is a human or non-human primate or other animal who has developed symptoms of a degenerative retinal disease or who is at risk for developing a degenerative retinal disease. As described herein a method is provided for treating (which includes preventing or prophylaxis) an ophthalmic disease or disorder by administrating to a subject a composition comprising a pharmaceutically acceptable carrier and a substituted heterocyclic amine derivative compound (e.g., a compound having the structure of Formula (A) or Formula (B), and substructures thereof.) As described herein, a method is provided for enhancing survival of neuronal cells such as retinal neuronal cells, including photoreceptor cells, and/or inhibiting degeneration of retinal neuronal cells by administering the pharmaceutical compositions described herein comprising a substituted heterocyclic amine derivative compound.

Enhanced survival (or prolonged or extended survival) of one or more retinal cell types in the presence of a substituted heterocyclic amine derivative compound indicates that the compound is an effective agent for treatment of a degenerative disease, particularly a retinal disease or disorder, and including a neurodegenerative retinal disease or disorder. Cell survival and enhanced cell survival may be determined according to methods described herein and known to a skilled artisan including viability assays and assays for detecting expression of retinal cell marker proteins. For determining enhanced survival of photoreceptor cells, opsins may be detected, for instance, including the protein rhodopsin that is expressed by rods.

In another embodiment, the subject is being treated for Stargardt's disease or Stargardt's macular degeneration. In Stargardt's disease, which is associated with mutations in the ABCA4 (also called ABCR) transporter, the accumulation of all-trans-retinal has been proposed to be responsible for the formation of a lipofuscin pigment, A2E, which is toxic towards retinal cells and causes retinal degeneration and consequently loss of vision.

In yet another embodiment, the subject is being treated for age-related macular degeneration (AMD). In various embodiments, AMD can be wet- or dry-form. In AMD, vision loss primarily occurs when complications late in the disease either cause new blood vessels to grow under the macula or the macula atrophies. Without intending to be bound by any particular theory, the accumulation of all-trans-retinal has been proposed to be responsible for the formation of a lipofuscin pigment, N-retinylidene-N-retinylethanolamine (A2E) and A2E related molecules, which are toxic towards RPE and retinal cells and cause retinal degeneration and consequently loss of vision.

A neurodegenerative retinal disease or disorder for which the compounds and methods described herein may be used for treating, curing, preventing, ameliorating the symptoms of, or slowing, inhibiting, or stopping the progression of, is a disease or disorder that leads to or is characterized by retinal neuronal cell loss, which is the cause of visual impairment. Such a disease or disorder includes but is not limited to age-related macular degeneration (including dry-form and wet-form of macular degeneration) and Stargardt's macular dystrophy.

Age-related macular degeneration as described herein is a disorder that affects the macula (central region of the retina) and results in the decline and loss of central vision. Age-related macular degeneration occurs typically in individuals over the age of 55 years. The etiology of age-related macular degeneration may include both environmental influences and genetic components (see, e.g., Lyengar et al., *Am. J. Hum. Genet.* 74:20-39 (2004) (Epub 2003 Dec. 19); Kenealy et al., *Mol. Vis.* 10:57-61 (2004); Gorin et al., *Mol. Vis.* 5:29 (1999)). More rarely, macular degeneration occurs in younger individuals, including children and infants, and generally, these disorders results from a genetic mutation. Types of juvenile macular degeneration include Stargardt's disease (see, e.g., Glazer et al., *Ophthalmol. Clin. North Am.* 15:93-100, viii (2002); Weng et al., *Cell* 98:13-23 (1999)); Doyne's honeycomb retinal dystrophy (see, e.g., Kermani et al., *Hum. Genet.* 104:77-82 (1999)); Sorsby's fundus dystrophy, Malattia Levintinese, fundus flavimaculatus, and autosomal dominant hemorrhagic macular dystrophy (see also Seddon et al., *Ophthalmology* 108:2060-67 (2001); Yates et al., *J. Med. Genet.* 37:83-7 (2000); Jaakson et al., *Hum. Mutat.* 22:395-403 (2003)). Geographic atrophy of the RPE is an advanced form of non-neovascular dry-type age-related macular degeneration, and is associated with atrophy of the choriocapillaris, RPE, and retina.

Stargardt's macular degeneration, a recessive inherited disease, is an inherited blinding disease of children. The primary pathologic defect in Stargardt's disease is also an accumulation of toxic lipofuscin pigments such as A2E in cells of the retinal pigment epithelium (RPE). This accumulation appears to be responsible for the photoreceptor death and severe visual loss found in Stargardt's patients. The compounds described herein slow the synthesis of 11-cis-retinaldehyde (11 cRAL or retinal) and regeneration of rhodopsin by inhibiting isomerase in the visual cycle. Light activation of rhodopsin results in its release of all-trans-retinal, which constitutes the first reactant in A2E biosynthesis. Treatment with substituted heterocyclic amine derivative compounds inhibits lipofuscin accumulation and thus delays the onset of visual loss in Stargardt's and AMD patients without toxic effects that would preclude treatment with a substituted heterocyclic amine derivative compound. The compounds described herein are used for effective treatment of other forms of retinal or macular degeneration associated with lipofuscin accumulation.

Administration of a substituted heterocyclic amine derivative compound to a subject can prevent formation of the lipofuscin pigment, A2E (and A2E related molecules), that is toxic towards retinal cells and causes retinal degeneration. In certain embodiments, administration of a substituted heterocyclic amine derivative compound reduces the production of waste products, e.g., lipofuscin pigment, A2E (and A2E related molecules), ameliorate the development of AMD (e.g., dry-form) and Stargardt's disease, and reduce or slow vision loss (e.g., choroidal neovascularization and/or chorioretinal atrophy). In previous studies, with 13-cis-retinoic acid (Accutane® or Isotretinoin), a drug commonly used for the treatment of acne and an inhibitor of 11-cis-retinol dehydrogenase, has been administered to patients to prevent A2E accumulation in the RPE. However, a major drawback in this proposed treatment is that 13-cis-retinoic acid can easily isomerize to all-trans-retinoic acid. All-trans-retinoic acid is a very potent teratogenic compound that adversely affects cell proliferation and development. Retinoic acid also accumulates in the liver and may be a contributing factor in liver diseases.

In yet other embodiments, a substituted heterocyclic amine derivative compound is administered to a subject such as a human with a mutation in the ABCA4 transporter in the eye. In some embodiments, the substituted heterocyclic amine derivative compound is administered to an aging subject. As used herein, an aging human subject is typically at least 45, or at least 50, or at least 60, or at least 65 years old. In Stargardt's disease, which is associated with mutations in the ABCA4 transporter, the accumulation of all-trans-retinal has been proposed to be responsible for the formation of a lipofuscin pigment, A2E (and A2E related molecules), that is toxic towards retinal cells and causes retinal degeneration and consequently loss of vision. Without wishing to be bound by theory, a substituted heterocyclic amine derivative compound described herein is a strong inhibitor of an isomerase involved in the visual cycle. Treating patients with a substituted heterocyclic amine derivative compound as described herein prevents or slows the formation of A2E (and A2E related molecules) and can has protective properties for normal vision.

In other certain embodiments, one or more of the compounds described herein are used for treating other ophthalmic diseases or disorders, for example, glaucoma, retinal detachment, hemorrhagic retinopathy, retinitis pigmentosa, an inflammatory retinal disease, proliferative vitreoretinopathy, retinal dystrophy, hereditary optic neuropathy, Sorsby's fundus dystrophy, uveitis, a retinal injury, optical neuropathy, and retinal disorders associated with other neurodegenerative diseases such as Alzheimer's disease, multiple sclerosis, Parkinson's disease or other neurodegenerative diseases that affect brain cells, a retinal disorder associated with viral infection, or other conditions such as AIDS. A retinal disorder also includes light damage to the retina that is related to increased light exposure (i.e., overexposure to light), for example, accidental strong or intense light exposure during surgery; strong, intense, or prolonged sunlight exposure, such as at a desert or snow covered terrain; during combat, for example, when observing a flare or explosion or from a laser device, and the like. Retinal diseases can be of degenerative or non-degenerative nature. Non-limiting examples of degenerative retinal diseases include age-related macular degeneration, and Stargardt's macular dystrophy. Examples of non-degenerative retinal diseases include but are not limited hemorrhagic retinopathy, retinitis pigmentosa, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, and a retinal disorder associated with AIDS.

In other certain embodiments, at least one of the compounds described herein is used for treating, curing, preventing, ameliorating the symptoms of, or slowing, inhibiting, or stopping the progression of, certain ophthalmic diseases and disorders including but not limited to diabetic retinopathy, diabetic maculopathy, diabetic macular edema, retinal ischemia, ischemia-reperfusion related retinal injury, and retinal blood vessel occlusion (including venous occlusion and arterial occlusion).

Diabetic retinopathy is a leading cause of blindness in humans and is a complication of diabetes. Diabetic retinopathy occurs when diabetes damages blood vessels inside the retina. Non-proliferative retinopathy is a common, usually mild form that generally does not interfere with vision. Abnormalities are limited to the retina, and vision is impaired only if the macula is involved. If left untreated retinopathy can progress to proliferative retinopathy, the more serious form of diabetic retinopathy. Proliferative retinopathy occurs when new blood vessels proliferate in and around the retina. Consequently, bleeding into the vitreous, swelling of the retina, and/or retinal detachment may occur, leading to blindness.

Other ophthalmic diseases and disorders that may be treated using the methods and compositions described herein include diseases, disorders, and conditions that are associated with, exacerbated by, or caused by ischemia in the retina. Retinal ischemia includes ischemia of the inner retina and the outer retina. Retinal ischemia can occur from either choroidal or retinal vascular diseases, such as central or branch retinal vision occlusion, collagen vascular diseases and thrombocytopenic purpura. Retinal vasculitis and occlusion is seen with Eales disease and systemic lupus erythematosus.

Retinal ischemia may be associated with retinal blood vessel occlusion. In the United States, both branch and central retinal vein occlusions are the second most common retinal vascular diseases after diabetic retinopathy. About 7%-10% of patients who have retinal venous occlusive disease in one eye eventually have bilateral disease. Visual field loss commonly occurs from macular edema, ischemia, or vitreous hemorrhage secondary to disc or retinal neovascularization induced by the release of vascular endothelial growth factor.

Arteriolosclerosis at sites of retinal arteriovenous crossings (areas in which arteries and veins share a common adventitial sheath) causes constriction of the wall of a retinal vein by a crossing artery. The constriction results in thrombus formation and subsequent occlusion of the vein. The blocked vein may lead to macular edema and hemorrhage secondary to breakdown in the blood-retina barrier in the area drained by the vein, disruption of circulation with turbulence in venous flow, endothelial damage, and ischemia. Clinically, areas of ischemic retina appear as feathery white patches called cotton-wool spots.

Branch retinal vein occlusions with abundant ischemia cause acute central and paracentral visual field loss corresponding to the location of the involved retinal quadrants. Retinal neovascularization due to ischemia may lead to vitreous hemorrhage and subacute or acute vision loss.

Two types of central retinal vein occlusion, ischemic and nonischemic, may occur depending on whether widespread retinal ischemia is present. Even in the nonischemic type, the macula may still be ischemic. Approximately 25% central retinal vein occlusion is ischemic. Diagnosis of central retinal vein occlusion can usually be made on the basis of characteristic ophthalmoscopic findings, including retinal hemorrhage in all quadrants, dilated and tortuous veins, and cotton-wool spots. Macular edema and foveal ischemia can lead to vision loss. Extracellular fluid increases interstitial pressure, which may result in areas of retinal capillary closure (i.e., patchy ischemic retinal whitening) or occlusion of a cilioretinal artery.

Patients with ischemic central retinal vein occlusion are more likely to present with a sudden onset of vision loss and have visual acuity of less than 20/200, a relative afferent pupillary defect, abundant intraretinal hemorrhages, and extensive nonperfusion on fluorescein angiography. The natural history of ischemic central retinal vein occlusion is associated with poor outcomes: eventually, approximately two-thirds of patients who have ischemic central retinal vein occlusion will have ocular neovascularization and one-third will have neovascular glaucoma. The latter condition is a severe type of glaucoma that may lead to rapid visual field and vision loss, epithelial edema of the cornea with secondary epithelial erosion and predisposition to bacterial keratitis, severe pain, nausea and vomiting, and, eventually, phthisis bulbi (atrophy of the globe with no light perception).

As used herein, a patient (or subject) is any mammal, including a human, that is afflicted with a neurodegenerative disease or condition, including an ophthalmic disease or disorder, or that may be free of detectable disease. Accordingly, the treatment may be administered to a subject who has an existing disease, or the treatment may be prophylactic, administered to a subject who is at risk for developing the disease or condition. Treating or treatment refers to any indicia of success in the treatment or amelioration of an injury, pathology or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being.

The treatment or amelioration of symptoms can be based on objective or subjective parameters; including the results of a physical examination. Accordingly, the term "treating" includes the administration of the compounds or agents described herein to treat pain, hyperalgesia, allodynia, or nociceptive events and to prevent or delay, to alleviate, or to arrest or inhibit development of the symptoms or conditions associated with pain, hyperalgesia, allodynia, nociceptive events, or other disorders. The term "therapeutic effect" refers to the reduction, elimination, or prevention of the disease, symptoms of the disease, or sequelae of the disease in the subject. Treatment also includes restoring or improving retinal neuronal cell functions (including photoreceptor function) in a vertebrate visual system, for example, such as visual acuity and visual field testing etc., as measured over time (e.g., as measured in weeks or months). Treatment also includes stabilizing disease progression (i.e., slowing, minimizing, or halting the progression of an ophthalmic disease and associated symptoms) and minimizing additional degeneration of a vertebrate visual system. Treatment also includes prophylaxis and refers to the administration of a substituted heterocyclic amine derivative compound to a subject to prevent degeneration or further degeneration or deterioration or further deterioration of the vertebrate visual system of the subject and to prevent or inhibit development of the disease and/or related symptoms and sequelae.

Various methods and techniques practiced by a person skilled in the medical and ophthalmological arts to determine and evaluate a disease state and/or to monitor and assess a therapeutic regimen include, for example, fluorescein angiogram, fundus photography, indocyanine green dye tracking of the choroidal circulatory system, opthalmoscopy, optical coherence tomography (OCT), and visual acuity testing.

A fluorescein angiogram involves injecting a fluorescein dye intravenously and then observing any leakage of the dye as it circulates through the eye. Intravenous injection of indocyanine green dye may also be used to determine if vessels in the eye are compromised, particularly in the choroidal circulatory system that is just behind the retina. Fundus photography may be used for examining the optic nerve, macula, blood vessels, retina, and the vitreous. Microaneurysms are visible lesions in diabetic retinopathy that may be detected in digital fundus images early in the disease (see, e.g., U.S. Patent Application Publication No. 2007/0002275). An ophthalmoscope may be used to examine the retina and vitreous. Opthalmoscopy is usually performed with dilated pupils, to allow the best view inside the eye. Two types of ophthalmoscopes may be used: direct and indirect. The direct ophthalmoscope is generally used to view the optic nerve and the central retina. The periphery, or entire retina, may be viewed by using an indirect ophthalmoscope. Optical coherence tomography (OCT) produces high resolution, high speed, non-invasive, cross-sectional images of body tissue. OCT is noninvasive and provides detection of microscopic early signs of disruption in tissues.

A subject or patient refers to any vertebrate or mammalian patient or subject to whom the compositions described herein is administered. The term "vertebrate" or "mammal" includes humans and non-human primates, as well as experimental animals such as rabbits, rats, and mice, and other animals, such as domestic pets (such as cats, dogs, horses), farm animals, and zoo animals. Subjects in need of treatment using the methods described herein may be identified according to accepted screening methods in the medical art that are employed to determine risk factors or symptoms associated with an ophthalmic disease or condition described herein or to determine the status of an existing ophthalmic disease or condition in a subject. These and other routine methods allow the clinician to select patients in need of therapy using the methods and formulations described herein.

Pharmaceutical Compositions

In certain embodiments, a substituted heterocyclic amine derivative compound is administered as a pure chemical. In other embodiments, the substituted heterocyclic amine derivative compound is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)), the disclosure of which is hereby incorporated herein by reference, in its entirety.

Accordingly, provided herein is a pharmaceutical composition comprising one or more a substituted heterocyclic amine derivative compounds, or a stereoisomer, prodrug, pharmaceutically acceptable salt, hydrate, solvate, acid salt hydrate, N-oxide or isomorphic crystalline form thereof, of a compound described herein, together with one or more pharmaceutically acceptable carriers and, optionally, other therapeutic and/or prophylactic ingredients. The carrier(s) (or excipient(s)) is acceptable or suitable if the carrier is compatible with the other ingredients of the composition and not deleterious to the recipient (i.e., the subject) of the composition. A pharmaceutically acceptable or suitable composition includes an ophthalmologically suitable or acceptable composition.

One embodiment provides a pharmaceutical composition comprising a pharmaceutically acceptable carrier and a compound of Formula (A) or tautomer, stereoisomer, geometric isomer, or pharmaceutically acceptable solvate, hydrate, salt, or N-oxide thereof:

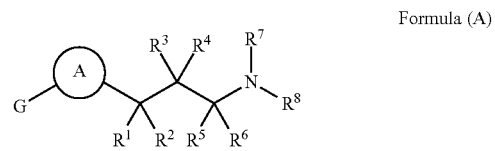

Formula (A)

wherein,
Ring A is selected from a 1,3-disubstituted heterocycle;
G is —X—Y;
X is selected from —O—C(R$^9$)$_2$—, —O—C(=O)—, —S—C(R$^9$)$_2$—, —S(O)—C(R$^9$)$_2$—, —S(O)$_2$—C(R$^9$)$_2$—, —SO$_2$(NR$^9$)—, —NR$^9$—C(R$^9$)$_2$—, —NR$^9$—C(=O)—, —NR$^9$—S(O)$_2$—, —C(R$^9$)$_2$—C(R$^9$)$_2$—, —C(=O)—C(R$^9$)$_2$—, —C(R$^9$)$_2$—C(=O)—, —C(R$^9$)=C(R$^9$)—, —C≡C—, —C(=O)—N(R$^9$)—, —C(=O)—O—, —C(R$^9$)$_2$—O—, and —C(R$^9$)$_2$—NR$^9$;
Y is selected from C$_3$-C$_{15}$ alkyl, carbocyclyl, carbocyclylalkyl, heterocyclyl, heterocyclylalkyl, aryl or aralkyl;

$R^1$ and $R^2$ are each independently selected from hydrogen, halogen, alkyl, fluoroalkyl, —$OR^9$, —$NR^{10}R^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;

$R^3$ and $R^4$ are each independently selected from hydrogen, halogen, $C_1$-$C_5$ alkyl, fluoroalkyl, —$OR^9$ or —$NR^{10}R^{11}$; or $R^3$ and $R^4$ together form an oxo;

$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;

$R^7$ and $R^8$ are each independently selected from hydrogen, alkyl, carbocyclyl, —C(=O)$R^{13}$, $SO_2R^{13}$, $CO_2R^{13}$ or $SO_2NR^{10}R^{11}$; or $R^7$ and $R^8$, together with the nitrogen atom to which they are attached, form an N-heterocyclyl;

each $R^9$ independently hydrogen or alkyl;

each $R^{10}$ and $R^{11}$ is independently selected from hydrogen, alkyl, carbocyclyl, heterocyclyl, —C(=O)$R^{13}$, $SO_2R^{13}$, $CO_2R^{13}$ or $SO_2NR^{10}R^{11}$; or $R^{10}$ and $R^{11}$ together with the nitrogen atom to which they are attached, form an N-heterocyclyl; and each $R^{13}$ is independently selected from alkyl, heteroalkyl, alkenyl, aryl, aralkyl, carbocyclyl, heteroaryl or heterocyclyl.

One embodiment provides a pharmaceutical composition comprising a pharmaceutically acceptable carrier and a compound of Formula (B) or tautomer, stereoisomer, geometric isomer or a pharmaceutically acceptable solvate, hydrate, salt, or N-oxide thereof:

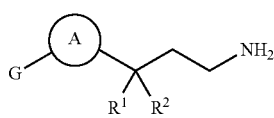

Formula (B)

wherein,

Ring A is selected from a 1,3-disubstituted heterocycle;

G is —X—Y;

X is selected from —O—, —S—, —NH—, or —$CH_2$—;

Y is selected from carbocyclyl, or heterocyclyl; and $R^1$ and $R^2$ are each independently selected from hydrogen, or —OH; or $R^1$ and $R^2$ form an oxo.

A pharmaceutical composition (e.g., for oral administration or delivery by injection, or combined devices, or for application as an eye drop) may be in the form of a liquid or solid. A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. Physiological saline is commonly used as an excipient, and an injectable pharmaceutical composition or a composition that is delivered ocularly is preferably sterile.

In certain embodiments, the compound is substantially pure, in that it contains less than about 5% or less than about 1%, or less than about 0.1%, of other organic small molecules, such as contaminating intermediates or by-products that are created, for example, in one or more of the steps of a synthesis method. In other embodiments, a combination of one or more substituted heterocyclic amine derivative compounds is administered.

In some embodiments, a substituted heterocyclic amine derivative compound is delivered to a subject by any suitable means, including, for example, orally, parenterally, intraocularly, intravenously, intraperitoneally, intranasally (or other delivery methods to the mucous membranes, for example, of the nose, throat, and bronchial tubes), or by local administration to the eye, or by an intraocular or periocular device. Modes of local administration include, for example, eye drops, intraocular injection or periocular injection. Periocular injection typically involves injection of the synthetic isomerization inhibitor, i.e., substituted heterocyclic amine derivative compound under the conjunctiva or into the Tennon's space (beneath the fibrous tissue overlying the eye). Intraocular injection typically involves injection of the substituted heterocyclic amine derivative compound into the vitreous. In certain embodiments, the administration is non-invasive, such as by eye drops or oral dosage form, or as a combined device.

In some embodiments, a substituted heterocyclic amine derivative compound is formulated for administration using pharmaceutically acceptable (suitable) carriers or vehicles as well as techniques routinely used in the art. A pharmaceutically acceptable or suitable carrier includes an ophthalmologically suitable or acceptable carrier. A carrier is selected according to the solubility of the substituted heterocyclic amine derivative compound. Suitable ophthalmological compositions include those that are administrable locally to the eye, such as by eye drops, injection or the like. In the case of eye drops, the formulation also optionally includes, for example, ophthalmologically compatible agents such as isotonizing agents such as sodium chloride, concentrated glycerin, and the like; buffering agents such as sodium phosphate, sodium acetate, and the like; surfactants such as polyoxyethylene sorbitan mono-oleate (also referred to as Polysorbate 80), polyoxyl stearate 40, polyoxyethylene hydrogenated castor oil, and the like; stabilization agents such as sodium citrate, sodium edentate, and the like; preservatives such as benzalkonium chloride, parabens, and the like; and other ingredients. Preservatives can be employed, for example, at a level of from about 0.001 to about 1.0% weight/volume. The pH of the formulation is usually within the range acceptable to ophthalmologic formulations, such as within the range of about pH 4 to 8.

For injection, the substituted heterocyclic amine derivative compound is provided in an injection grade saline solution, in the form of an injectable liposome solution, slow-release polymer system or the like. Intraocular and periocular injections are known to those skilled in the art and are described in numerous publications including, for example, Spaeth, Ed., *Ophthalmic Surgery Principles of Practice*, W. B. Sanders Co., Philadelphia, Pa., 85-87, 1990.

For delivery of a composition comprising at least one of the compounds described herein via a mucosal route, which includes delivery to the nasal passages, throat, and airways, the composition may be delivered in the form of an aerosol. The compound may be in a liquid or powder form for intramucosal delivery. For example, the composition may be delivered via a pressurized aerosol container with a suitable propellant, such as a hydrocarbon propellant (e.g., propane, butane, isobutene). The composition may be delivered via a non-pressurized delivery system such as a nebulizer or atomizer.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

The substituted heterocyclic amine derivative compounds described herein, in some embodiments, are formulated for sustained or slow-release. Such compositions may generally be prepared using well known technology and administered by, for example, oral, periocular, intraocular, rectal or subcutaneous implantation, or by implantation at the desired target site. Sustained-release formulations may contain an agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained-release formulation depends upon the site of implantation, the rate and expected duration of release, and the nature of the condition to be treated or prevented.

Systemic drug absorption of a drug or composition administered via an ocular route is known to those skilled in the art (see, e.g., Lee et al., *Int. J. Pharm.* 233:1-18 (2002)). In one embodiment, a substituted heterocyclic amine derivative compound is delivered by a topical ocular delivery method (see, e.g., *Curr. Drug Metab.* 4:213-22 (2003)). The composition, in some embodiments, is in the form of an eye drop, salve, or ointment or the like, such as, aqueous eye drops, aqueous ophthalmic suspensions, non-aqueous eye drops, and non-aqueous ophthalmic suspensions, gels, ophthalmic ointments, etc. For preparing a gel, for example, carboxyvinyl polymer, methyl cellulose, sodium alginate, hydroxypropyl cellulose, ethylene maleic anhydride polymer and the like can be used.

The dose of the composition comprising at least one of the substituted heterocyclic amine derivative compounds described herein differs, depending upon the patient's (e.g., human) condition, that is, stage of the disease, general health status, age, and other factors that a person skilled in the medical art will use to determine dose. When the composition is used as eye drops, for example, one to several drops per unit dose, preferably 1 or 2 drops (about 50 μl per 1 drop), may be applied about 1 to about 6 times daily.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with neurodegeneration of retinal neuronal cells and/or degeneration of other mature retinal cells such as RPE cells. Optimal doses may generally be determined using experimental models and/or clinical trials. The optimal dose may depend upon the body mass, weight, or blood volume of the patient.

The doses of the substituted heterocyclic amine derivative compound is suitably selected depending on the clinical status, condition and age of the subject, dosage form and the like. In the case of eye drops, a substituted heterocyclic amine derivative compound is administered, for example, from about 0.01 mg, about 0.1 mg, or about 1 mg, to about 25 mg, to about 50 mg, to about 90 mg per single dose. Eye drops are administered one or more times per day, as needed. In the case of injections, suitable doses are, for example, about 0.0001 mg, about 0.001 mg, about 0.01 mg, or about 0.1 mg to about 10 mg, to about 25 mg, to about 50 mg, or to about 90 mg of the substituted heterocyclic amine derivative compound, one to seven times per week. In other embodiments, about 1.0 to about 30 mg of the substituted heterocyclic amine derivative compound is administered one to seven times per week.

Oral doses typically range from 1.0 to 1000 mg, one to four times, or more, per day. An exemplary dosing range for oral administration is from 10 to 250 mg one to three times per day. If the composition is a liquid formulation, the composition comprises at least 0.1% active compound at particular mass or weight (e.g., from 1.0 to 1000 mg) per unit volume of carrier, for example, from about 2%-about 60%.

In certain embodiments, at least one substituted heterocyclic amine derivative compound described herein is administered under conditions and at a time that inhibits or prevents dark adaptation of rod photoreceptor cells. In certain embodiments, the compound is administered to a subject at least 30 minutes (half hour), 60 minutes (one hour), 90 minutes (1.5 hour), or 120 minutes (2 hours) prior to sleeping. In certain embodiments, the compound is administered at night before the subject sleeps. In other embodiments, a light stimulus may be blocked or removed during the day or under normal light conditions by placing the subject in an environment in which light is removed, such as placing the subject in a darkened room or by applying an eye mask over the eyes of the subject. When the light stimulus is removed in such a manner or by other means contemplated in the art, the agent may be administered prior to sleeping.

The doses of the compounds that are administered to prevent or inhibit dark adaptation of a rod photoreceptor cell can be suitably selected depending on the clinical status, condition and age of the subject, dosage form and the like. In the case of eye drops, the compound (or the composition comprising the compound) can be administered, for example, from about 0.01 mg, about 0.1 mg, or about 1 mg, to about 25 mg, to about 50 mg, to about 90 mg per single dose. In the case of injections, suitable doses are, for example, about 0.0001 mg, about 0.001 mg, about 0.01 mg, or about 0.1 mg to about 10 mg, to about 25 mg, to about 50 mg, or to about 90 mg of the compound, administered any number of days between one to seven days per week prior to sleeping or prior to removing the subject from all light sources. In certain other embodiments, for administration of the compound by eye drops or injection, the dose is between 1-10 mg (compound)/kg (body weight of subject) (i.e., for example, 80-800 mg total per dose for a subject weighing 80 kg). In other embodiments, about 1.0 to about 30 mg of compound is administered one to seven times per week. Oral doses typically range from about 1.0 to about 1000 mg, administered any number of days between one to seven days per week. An exemplary dosing range for oral administration is from about 10 to about 800 mg once per day prior to sleeping. In other embodiments, the composition is delivered by intravitreal administration.

Also provided are methods of manufacturing the compounds and pharmaceutical compositions described herein. A composition comprising a pharmaceutically acceptable excipient or carrier and at least one of the substituted heterocyclic amine derivative compounds described herein is prepared by synthesizing the compound according to any one of the methods described herein or practiced in the art and then formulating the compound with a pharmaceutically acceptable carrier. Formulation of the composition will be appropriate and dependent on several factors, including but not limited to, the delivery route, dose, and stability of the compound.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Flash column chromatography and thin layer chromatography (TLC) were performed on silica gel unless otherwise noted. Proton and carbon nuclear magnetic resonance spectra were obtained with a Varian VnmrJ 400 at 400 MHz for proton. Spectra are given in ppm (δ) and coupling constants J are reported in Hertz. For proton spectra the solvent peak was used as the reference peak. HPLC/LC-MS was performed using the following method: Agilent HP 1100 system with diode array detection at 220 nm on Phenomenex Gemini 4.6×150 mm 5µ column, mobile phase $CH_3CN$—$H_2O$ with 0.05% TFA (10%-70% for 15 mins, 70%-95% for 2 mins, 95% for 3 min, then 10% for 4 min) with mass-spectral detection using electrospray ionization (ESI+) mode.

Example 1

Preparation of 3-amino-1-(5-(cyclohexylmethoxy)thiophen-2-yl)propan-1-ol

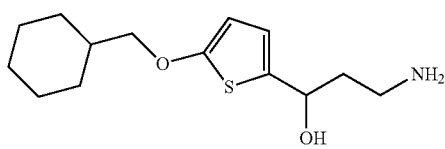

3-Amino-1-(5-(cyclohexylmethoxy)thiophen-2-yl)propan-1-ol was prepared following the method shown in Scheme 1.

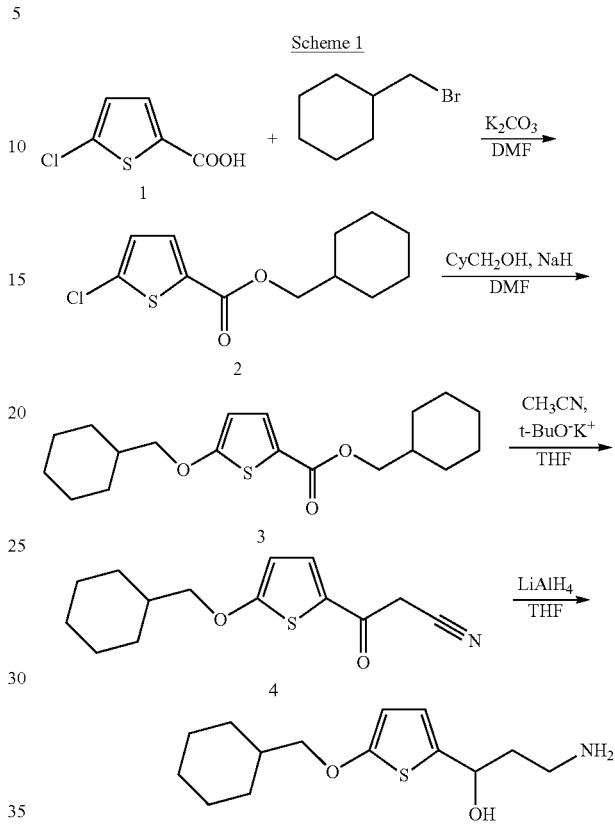

Step 1: A mixture of 5-chlorothiophene-2-carboxylic acid (3.01 g, 19.0 mmol), cyclohexylmethyl bromide (3.51 g, 19.8 mmol) and potassium carbonate (2.81 g, 20.33 mmol) was stirred under Ar at +85° C. for 3 days and cooled to room temperature. Reaction mixture was diluted with water and extracted with hexanes three times. Combined organic layers were dried over anhydrous $MgSO_4$ and concentrated under reduced pressure. Purification by flash chromatography (2%-15% EtOAc—hexanes gradient) gave cyclohexylmethyl 5-chlorothiophene-2-carboxylate as a colorless oil. Yield (4.76 g, 97%); $^1$H NMR (400 MHz, $CDCl_3$) δ 7.56-7.60 (m, 1H), 6.90-6.94 (m, 1H), 4.08 (d, J=6.10 Hz, 2H), 1.64-1.82 (m, 6H), 1.10-1.34 (m, 3H), 0.97-1.10 (m, 2H).

Step 2: Cyclohexylmethanol (1.0 mL, 8.13 mmol) was added under Ar at room temperature to a stirred suspension of NaH (0.19 g, 7.92 mmol) in anhydrous DMF (3 mL). The mixture was stirred for 5 hrs and then chloride (2) (1.20 g, 4.64 mmol) was added. The reaction mixture was stirred at +65° C. for 1 h, quenched with aqueous 25% NH4Cl and extracted with MBTE twice. Combined organic layers were washed with brine and concentrated under reduced pressure. Purification by flash chromatography (1%-5% EtOAc—hexanes gradient) gave ether (3) as a light yellow solid. Yield (0.90 g, 58%); $^1$H NMR (400 MHz, DMSO-$d_6$) δ 7.49-7.53 (m, 1H), 6.38-6.43 (m, 1H), 3.98 (d, J=6.07 Hz, 2H), 3.94 (d, J=5.87 Hz, 2H), 1.56-1.80 (m, 12H), 1.17-1.28 (m, 6H), 0.90-1.16 (m, 4H).

Step 3: Anhydrous $CH_3CN$ (0.07 mL, 1.34 mmol) was added under Ar to a cold (−50° C.) solution of t-BuO$^-$K$^+$ (1M/THF, 1.5 mL, 1.5 mmol), the mixture was stirred for 10 min after which a solution of ester (3) (0.303 g, 0.90 mmol) in anhydrous THF (2 mL) was added. The reaction mixture was stirred under Ar while gradually warming to 0° C. over 3 hrs and then stirred on ice bath for 1 h. 5% Aqueous NaHSO$_4$ was added to the reaction mixture and the resulting mixture was extracted twice with EtOAc. Combined organic layers were washed with brine. Purification by flash chromatography (5%-30% EtOAc—hexanes gradient) gave ketonitrile (4) as a white solid. Yield (0.12 g, 51%); $^1$H NMR (400 MHz, DMSO-d$_6$) δ 7.75-7.79 (m, 1H), 6.51-6.55 (m, 1H), 4.52 (s, 2H), 4.00 (d, J=6.10 Hz, 2H), 1.58-1.80 (m, 6H), 1.10-1.27 (m, 3H), 0.96-1.08 (m, 2H).

Step 4: A solution of LiAlH$_4$ (1M/THF, 0.7 mL, 0.7 mmol) was added under Ar to a solution of ketonitrile (4) (0.12 g, 0.456 mmol) in anhydrous THF (8 mL) at 0° C. under Ar. The reaction mixture was stirred for 30 min at 0° C. and quenched by slow addition of saturated aqueous Na$_2$SO$_4$. Filtration throught Celite, followed by concentration under reduced pressure and flash chromatography purification (2%-20% 7N NH$_3$/MeOH—CH$_2$Cl$_2$ gradient) gave Example 1 as a light yellow solid. Yield (0.015 g, 12%); $^1$H NMR (400 MHz, CD$_3$OD) δ 6.54-6.59 (m, 1H), 6.00-6.40 (m, 1H), 4.77 (t, J=7.24 Hz, 1H), 3.80 (d, J=5.87 Hz, 2H), 2.86-2.77 (m, 2H), 1.65-1.96 (m, 8H), 1.18-1.36 (m, 3H), 1.00-1.12 (m, 2H); RP-HPLC t$_R$=10.12 min; ESI-MS m/z 252.2 [M–H$_2$O+H]$^+$.

Example 2

Preparation of 3-amino-1-(6-(cyclohexylmethoxy)pyridin-2-yl)propan-1-ol

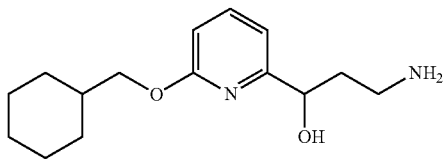 [SMILES: NCCC(O)c1cccc(OCC2CCCCC2)n1]

3-Amino-1-(6-(cyclohexylmethoxy)pyridin-2-yl)propan-1-ol was prepared following the method shown in Scheme 2.

SCHEME 2

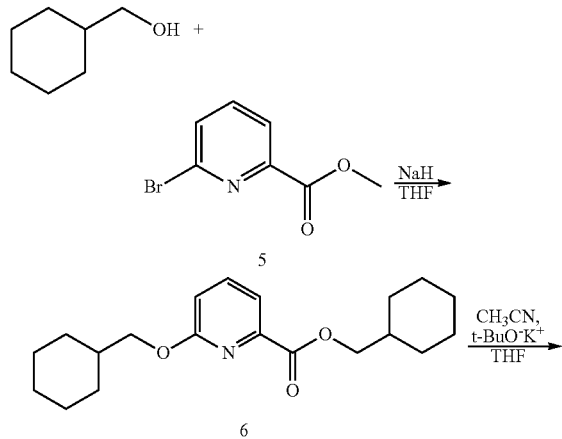

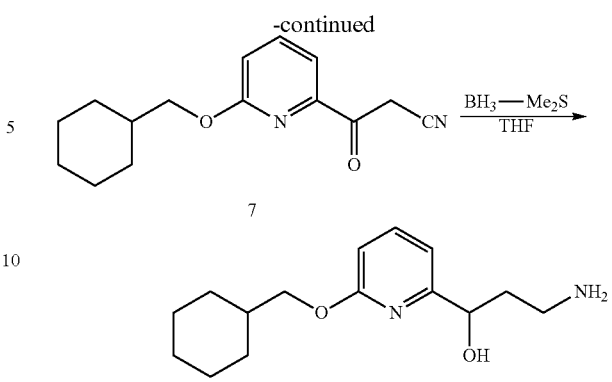

Step 1: NaH (0.15 g, 6.90 mmol) was added to a solution of cyclohexylmethanol (0.79 g, 6.90 mmol) in anhydrous THF (20 mL) at room temperature. The reaction mixture was stirred at 60° C. for 1 hour and then methyl 6-bromopicolinate (5) (1.0 g, 4.60 mmol) was added. The reaction mixture was stirred at 60° C. for 18 hours, cooled to room temperature, filtered through Celite and concentrated under reduced pressure. Purification by flash chromatography (30%-50% EtOAc—hexanes gradient) gave ether (6) as a colorless oil. Yield (0.60 g, 41%); $^1$H NMR (400 MHz, DMSO-d$_6$) δ 7.83 (t, J=8.0 Hz, 1H), 7.63 (d, J=8.0 Hz, 1H), 7.03 (d, J=8.4 Hz, 1H), 4.08 (d, J=6.0 Hz, 2H), 3.79 (d, J=6.0 Hz, 2H), 1.84-1.58 (m, 12H), 0.88-1.26 (m, 10H).

Step 2: CH$_3$CN (0.22 g, 5.46 mmol) was added to a solution of potassium tert-butoxide (1 M/THF, 6.4 mL, 6.40 mmol) in THF (20 mL) at −35° C. The reaction mixture was stirred at this temperature for 15 min and then ester (6) (0.6 g, 1.84 mmol) in THF (15 ml) was added dropwise. The reaction mixture was stirred at 0° C. for 1 hour, quenched by acetic acid (0.42 ml, 6.4 mmol), diluted with sat. NH$_4$Cl (30 ml). The mixture was extracted with ethyl acetate (50 ml), dried over anhydrous Na$_2$SO$_4$ and concentrated under reduced pressure. Purification by flash chromatography (30%-50% EtOAc—hexanes gradient) gave ketonitrile (7) as a yellow oil. Yield (0.20 g, 42%); $^1$H NMR (400 MHz, CDCl$_3$) δ 7.12 (t, J=8.0 Hz, 1H), 7.67 (d, J=7.2 Hz, 1H), 6.99 (d, J=8.0 Hz, 1H), 4.26 (s, 2H), 1.88-1.64 (m, 6H), 1.08-1.02 (m, 5H).

Step 3: BH$_3$.Me$_2$S (0.22 g, 2.96 mmol) was added to a stirred solution of ketonitrile (7) (0.2 g, 0.74 mmol) in anhydrous THF (20 mL). The reaction mixture was stirred at 60° C. for 2 hours and at room temperature for 60 hours, quenched 3N HCl (pH=0). The resulting mixture was stirred at room temperature for 12 hours, diluted with water (20 ml) and MTBE (40 ml) and pH was adjusted to 14 with concentrated NaOH. Organic layer was separated, dried over Na$_2$SO$_4$ and concentrated under reduced pressure. Purification by flash chromatography (5%-20% 7N NH$_3$-MeOH—CH$_2$Cl$_2$ gradient) gave Example 2 as a yellow oil. Yield (0.05 g, 4%): $^1$H NMR (400 MHz, CD$_3$OD) δ 7.64 (t, J=8.0 Hz, 1H), 7.03 (d, J=7.6 Hz, 1H), 6.63 (d, J=8.0 Hz, 1H), 4.72-4.66 (m, 1H), 4.06 (d, J=6.4 Hz, 2H), 2.86 (t, J=6.1 Hz, 2H), 1.92-1.68 (m, 8H), 1.38-1.02 (m, 5H); RP-HPLC t$_R$=9.02 min; ESI-MS m/z 265.2 [M+H]$^+$.

Example 3

Preparation of (E)-3-amino-1-(6-(2-cyclohexylvinyl)pyridin-2-yl)propan-1-ol

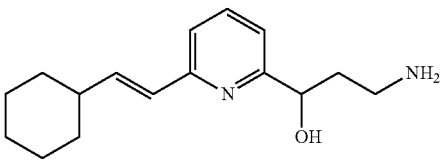 [SMILES: NCCC(O)c1cccc(/C=C/C2CCCCC2)n1]

(E)-3-Amino-1-(6-(2-cyclohexylvinyl)pyridin-2-yl)propan-1-ol was prepared following the method shown in Scheme 3.

SCHEME 3

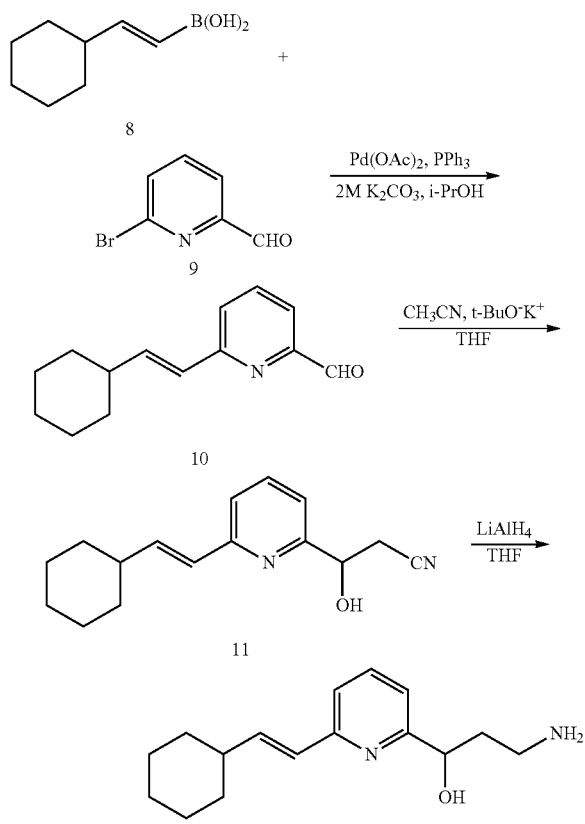

Step 1: To an argon saturated mixture of (E)-(2-cyclohexylvinyl)boronic acid (8) (2.74 g, 16.0 mmol), 6-bromopicolinaldehyde (9) (3.0 g, 16 mmol), Pd(OAc)$_2$ (0.04 g, 0.18 mmol), K$_2$CO$_3$ (2M in i-PrOH, 30 mmol) was added PPh$_3$ (0.20 g, 0.76 mmol). The reaction mixture was stirred at 70° C. for 20 hours under N$_2$, concentrated under reduced pressure and partitioned between H$_2$O (80 ml) and ethyl acetate (80 ml). Organic layer was dried over anhydrous Na$_2$SO$_4$ and concentrated under reduced pressure. Purification by flash chromatography (30%-50% EtOAc—hexanes gradient) gave alkene (10) as a pale yellow oil. Yield (3.1 g, 90%); $^1$H NMR (400 MHz, DMSO-d$_6$) δ 9.34 (s, 1H), 7.93 (t, J=7.6 Hz, 1H), 7.71 (d, J=8.4 Hz, 1H), 7.69 (d, J=8.4 Hz, 1H), 7.86 (dd, J=6.8, 16.0 Hz, 1H), 6.54 (d, J=16 Hz, 1H), 2.26-2.16 (m, 1H), 1.84-1.58 (m, 5H), 1.36-1.10 (m, 5H).

Step 2: CH$_3$CN (0.56 g, 15.8 mmol) was added to a solution of potassium tert-butoxide (1 M in THF, 15 mL, 15.0 mmol) in THF (20 mL) at −35° C. The reaction mixture was stirred at this temperature for 15 min and then aldehyde (10) (1.0 g, 4.6 mmol) in anhydrous THF (15 ml) was added dropwise. The reaction mixture was stirred at −35° C. for 30 min and quenched by aqueous NH$_4$Cl (30 ml), extracted with ethyl acetate (50 ml), dried over anhydrous Na$_2$SO$_4$ and concentrated under reduced pressure. Purification by flash chromatography (30%-50% EtOAc—hexanes gradient) gave hydroxynitrile (11) as a yellow oil. Yield (0.55 g, 46%); $^1$H NMR (400 MHz, CDCl$_3$) δ 7.37 (t, J=7.6 Hz, 1H), 7.34 (d, J=7.6 Hz, 1H), 7.28 (d, J=7.6 Hz, 1H), 6.73 (dd, J=6.8, 16.0 Hz, 1H), 6.40 (d, J=16 Hz, 1H), 6.16-6.06 (m, 1H), 4.90-4.80 (m, 1H), 3.04-2.87 (m, 2H), 2.21-2.08 (m, 1H), 1.82-1.58 (m, 5H), 1.36-1.10 (m, 5H).

Step 3: LiAlH$_4$ (1M in THF, 2.6 mL, 2.6 mmol) was added to a solution of hydroxynitrile (11) (0.55 g, 2.15 mmol) in diethyl ether (20 mL) at 0° C. under argon flow. The reaction mixture was stirred at 0° C. for 20 min, quenched by slow addition of saturated Na$_2$SO$_4$ and stirred at room temperature for 2 hours. Organic layer was separated, dried over Na$_2$SO$_4$ and concentrated under reduced pressure. Purification by flash chromatography (5%-20% 7N NH$_3$-MeOH—CH$_2$Cl$_2$ gradient) gave Example 3 as a pale yellow oil. Yield (0.3 g, 54%); $^1$H NMR (400 MHz, CD$_3$OD) δ 7.71 (t, J=7.6 Hz, 1H), 7.34-7.30 (m, 2H), 6.66 (dd, J=16 and 6.8 Hz, 1H), 6.45 (d, J=16 Hz, 1H), 6.16-6.06 (m, 1H), 4.78-4.76 (m, 1H), 2.24-2.16 (m, 2H), 2.21-2.08 (m, 1H), 2.04-1.66 (m, 5H), 1.44-1.16 (m, 5H); RP-HPLC t$_R$=6.54 min; ESI-MS m/z 261.2 [M+H]$^+$.

Example 4

Preparation of 3-amino-1-(6-(2-cyclohexylethyl)pyridin-2-yl)propan-1-ol

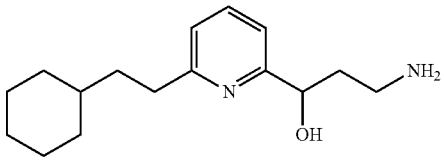 [SMILES: NCCC(O)c1cccc(CCC2CCCCC2)n1]

3-Amino-1-(6-(2-cyclohexylethyl)pyridin-2-yl)propan-1-ol was prepared following the method described below.

Step 1: Pd/C (10% wt, 0.015 g) was added to a solution of Example 3 (0.28 g, 1.22 mmol) in MeOH (20 mL) saturated with argon. The resulting mixture was stirred under H$_2$ (1 atm) for 20 hours. The reaction mixture was filtered and the filtrate was concentrated under reduced pressure. Purification by flash chromatography (5%-20% 7N NH$_3$/MeOH—CH$_2$Cl$_2$ gradient) gave Example 4 as a pale yellow oil. Yield (0.20 g, 71%); $^1$H NMR (400 MHz, CD$_3$OD) δ 7.71 (t, J=7.6 Hz, 1H), 7.35 (d, J=7.6 Hz, 1H), 7.13 (d, J=8.0 Hz, 1H), 4.78-4.76 (m, 1H), 2.83-2.76 (m, 4H), 1.84-1.56 (m, 9H), 1.36-0.95 (m, 6H); RP-HPLC t$_R$=6.46 min; ESI-MS m/z 263.2 [M+H]$^+$.

Example 5

Preparation of (R)-3-amino-1-(5-(cyclohexylmethoxy)thiophen-2-yl)propan-1-ol

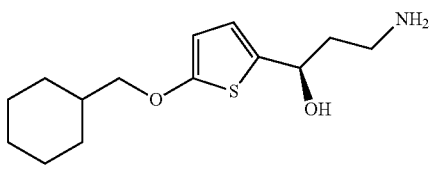 [SMILES: NCC[C@@H](O)c1ccc(OCC2CCCCC2)s1]

(R)-3-Amino-1-(5-(cyclohexylmethoxy)thiophen-2-yl)propan-1-ol was prepared following the method described in Example 1 and below.

Step 1: (1R,2R)—RuCl(TsDPEN)(p-cymene) (6.3 mg, 0.01 mmol) was added to a degassed solution of 3-(5-(cyclohexylmethoxy)thiophen-2-yl)-3-oxopropanenitrile (4) (0.27 g, 1.03 mmol) in HCOOH:Et$_3$N (1:1, 4.0 M in EtOH) and the reaction mixture was stirred at room temperature for 24 hrs. Aqueous NH$_4$Cl (25%) was added and the mixture was extracted twice with MTBE. Combined organic layers were washed with brine and concentrated under reduced pressure. Purification by flash chromatography gave (R)-3-(5-(cyclohexylmethoxy)thiophen-2-yl)-3-hydroxypropanenitrile as an off-white solid which was used directly in the next step. Yield (0.21 g, 77%); $^1$H NMR (400 MHz, CD$_3$OD) δ 6.64-6.78 (m, 1H), 6.02-6.10 (m, 1H), 4.99-5.09 (m, 1H), 3.79-3.88 (m, 2H), 2.79-2.91 (m, 2H), 1.62-1.90 (m, 6H), 1.12-1.39 (m, 3H), 0.98-1.12 (m, 2H).

Step 2: Reduction of (R)-3-(5-(cyclohexylmethoxy)thiophen-2-yl)-3-hydroxypropanenitrile following the method used in Example 1, with the exception that Et$_2$O was used as the solvent, gave after purification by flash chromatography (4%-20% 7N NH$_3$/MeOH—CH$_2$Cl$_2$ gradient) Example 5 as a colorless oil. Yield (0.0185 g, 9%); $^1$H NMR (400 MHz, CD$_3$OD) δ 6.54-6.59 (m, 1H), 6.00-6.40 (m, 1H), 4.77 (t, J=7.2 Hz, 1H), 3.80 (d, J=5.9 Hz, 2H), 2.86-2.77 (m, 2H), 1.65-1.96 (m, 8H), 1.18-1.36 (m, 3H), 1.00-1.12 (m, 2H); RP-HPLC t$_R$=10.01 min; ESI-MS m/z 252.2 [M−H$_2$O+H]$^+$.

Example 6

Preparation of (R)-3-amino-1-(6-(cyclohexylmethoxy)pyridin-2-yl)propan-1-ol

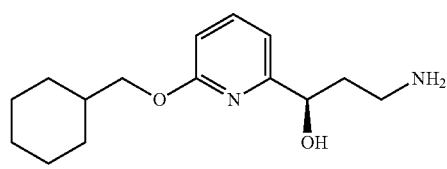 [SMILES: NCC[C@@H](O)c1cccc(OCC2CCCCC2)n1]

(R)-3-Amino-1-(6-(cyclohexylmethoxy)pyridin-2-yl)propan-1-ol was prepared following the method shown in Scheme 4.

SCHEME 4.

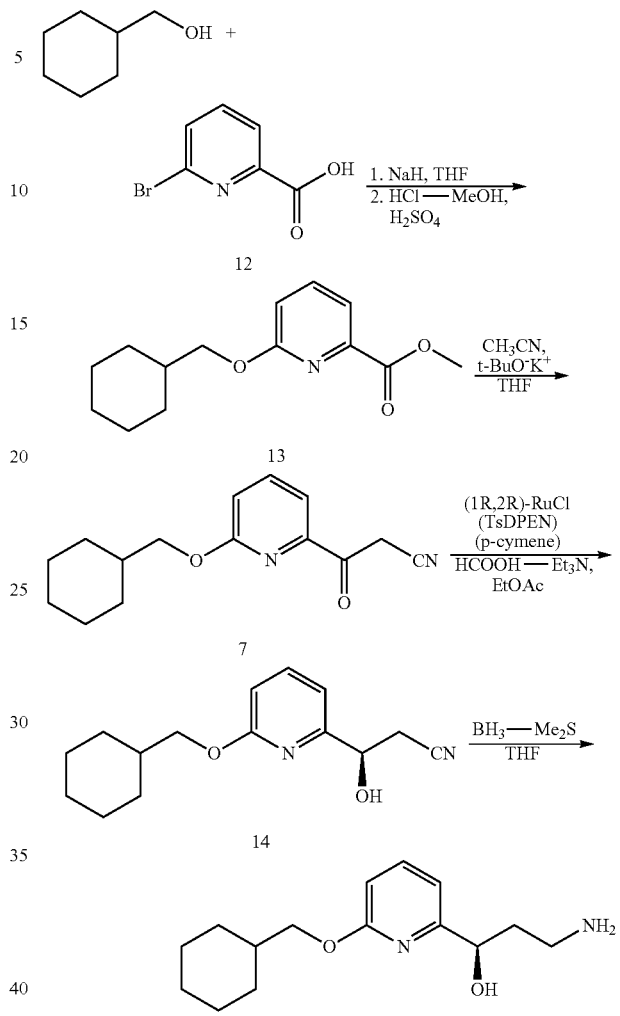

Step 1: NaH (0.355 g, 15 mmol) was added to a suspension of 6-bromopicolinic acid (12) (1.0 g, 4.9 mmol) and cyclohexylmethanol (0.79 g, 6.90 mmol) in THF (20 mL) at room temperature. The reaction mixture was stirred at 60° C. for 18 hours then concentrated under reduced pressure. Methanol (20 ml) was added to the residue followed by 1.25 M HCl/MeOH (10 ml) and conc. H$_2$SO$_4$ (1 ml). The resulting mixture was stirred at 60° C. for 18 hours, concentrated under reduced pressure, partitioned between saturated NaHCO$_3$ (50 ml) and ethyl acetate (100 ml). Organic layer was separated, dried over anhydrous Na$_2$SO$_4$ and concentrated under reduced pressure. Crude methyl 6-(cyclohexylmethoxy)picolinate (13) was used in next reaction without purification. Yield (1.22 g, quant.); $^1$H NMR (400 MHz, DMSO-d$_6$) δ 7.84 (t, J=8.0 Hz, 1H), 7.63 (d, J=8.0 Hz, 1H), 7.03 (d, J=8.4 Hz, 1H), 4.08 (d, J=6.0 Hz, 2H), 3.84 (s, 3H), 1.84-1.58 (m, 6H), 0.88-1.26 (m, 5H).

Step 2: CH$_3$CN (0.41 g, 10 mmol) was added to a solution of potassium tert-butoxide (1M in THF, 11 mL, 11 mmol) in THF (20 mL) at −35° C. The reaction mixture was stirred at this temperature for 15 min. Methyl 6-(cyclohexylmethoxy)picolinate (4.9 mmol) in THF (15 ml) was added dropwise to the reaction mixture. The reaction mixture was stirred at 0° C. for 1 hour and quenched by addition of aqueous HCl (1M, 11 ml, 11 mmol), washed with saturated aqueous NH₄Cl (30 ml), extracted with ethyl acetate (50 ml). Combined organic layers were dried over anhydrous Na₂SO₄ and concentrated under reduced pressure. Crude ketonitrile 7 was used in the next step without purification. Yield (1.26 g, quant.); $^1$H NMR (400 MHz, DMSO-d₆) δ 7.90 (t, J=7.6 Hz, 1H), 7.60 (d, J=7.6 Hz, 1H), 7.13 (d, J=8.4 Hz, 1H), 4.66 (s, 2H), 4.15 (d, J=6.4 Hz, 2H), 1.84-1.58 (m, 6H), 0.88-1.26 (m, 5H).

Step 3: Solution of HCOOH-Et₃N (4 M) in EtOH (5 mL) was added to a solution of ketonitrile 7 (4.9 mmol) in EtOAc (5 ml), followed by triethylamine (1 ml) and (1R,2R)—RuCl (TsDPEN)(p-cymene) (30 mg, 0.047 mmol). The mixture was saturated with argon, stirred at room temperature for 18 hr, quenched by addition of aqueous HCl (1N, 11 ml, 11 mmol), washed with saturated NH₄Cl (30 ml), extracted with ethyl acetate (50 ml), dried over anhydrous Na₂SO₄ and concentrated under reduced pressure. Purification by flash chromatography (30%-50% EtOAc—hexane gradient) gave (R)-hydroxynitrile 14 as a pale yellow oil. Yield (1.1 g, 87%); $^1$H NMR (400 MHz, CD₃OD) δ 7.66 (t, J=7.6 Hz, 1H), 7.11 (d, J=7.6 Hz, 1H), 6.67 (d, J=8.0 Hz, 1H), 4.88 (t, J=5.2 Hz, 1H), 4.09 (d, J=6.8 Hz, 2H), 3.04-2.86 (m, 2H), 1.88-1.66 (m, 6H), 1.38-1.02 (m, 5H).

Step 4: Reduction of (R)-hydroxynitrile 14 with BH₃-Me₂S following the method used in Example 2 gave Example 6 as a colorless oil. Yield (1.0 g, 89%); $^1$H NMR (400 MHz, CD₃OD) δ 7.63 (t, J=7.6 Hz, 1H), 7.02 (d, J=7.2 Hz, 1H), 6.61 (d, J=8.0 Hz, 1H), 4.69-4.66 (m, 1H), 4.07 (d, J=6.4 Hz, 2H), 2.79 (t, J=6.4 Hz, 2H), 1.92-1.64 (m, 8H), 1.38-1.02 (m, 5H); RP-HPLC $t_R$=8.99 min; ESI-MS m/z 265.2 [M+H]⁺.

Example 7

Preparation of 3-amino-1-(2-(cyclohexylmethoxy)pyridin-4-yl)propan-1-ol

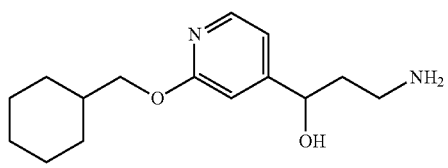 [SMILES: NCCC(O)c1ccnc(OCC2CCCCC2)c1]

3-Amino-1-(2-(cyclohexylmethoxy)pyridin-4-yl)propan-1-ol was prepared following the method described in Examples 2 and 6.

Step 1: Reaction between 2-bromoisonicotinic acid and cyclohexylmethanol following the method used in Example 6 gave methyl 2-(cyclohexylmethoxy)isonicotinate which was used in the next step without additional purification. Yield (1.27 g, quant.); $^1$H NMR (400 MHz, DMSO-d₆) δ 8.31 (d, J=4.2 Hz, 1H), 7.38-7.40 (m, 1H), 7.17 (s, 1H), 4.08 (d, J=6.4 Hz, 2H), 3.86 (s, 3H), 1.80-1.54 (m, 6H), 1.30-0.96 (m, 5H).

Step 2: Addition of CH₃CN to methyl 2-(cyclohexylmethoxy)isonicotinate following the method used in Example 2 gave after flash chromatography purification (50%-60% EtOAc—hexanes gradient) 3-(2-(cyclohexylmethoxy)pyridin-4-yl)-3-oxopropanenitrile as a yellow oil. Yield (0.65 g, 51%); $^1$H NMR (400 MHz, CD₃OD) δ 8.29 (d, J=5.2 Hz, 1H), 7.34 (d, J=5.6 Hz, 1H), 7.23 (s, 1H), 4.13 (d, J=6.0 Hz, 2H), 3.34-3.30 (m, 2H), 1.88-1.64 (m, 6H), 1.08-1.02 (m, 5H).

Step 3: Reduction of 3-(2-(cyclohexylmethoxy)pyridin-4-yl)-3-oxopropanenitrile following the method described in Example 2 gave after flash chromatography purification (5%-20% 7N NH₃/MeOH—CH₂Cl₂ gradient) Example 7 and Example 8 (see below) as yellow oils. Yield (0.16 g, 24%); $^1$H NMR (400 MHz, CD₃OD) δ 8.02-8.00 (m, 1H), 6.92 (d, J=5.2 Hz, 1H), 6.79 (s, 1H), 4.76-4.71 (m, 1H), 4.04-4.01 (m, 2H), 2.78 (t, J=6.8 Hz, 2H), 1.90-1.66 (m, 8H), 1.40-1.02 (m, 5H); RP-HPLC $t_R$=6.79 min; ESI-MS m/z 265.2 [M+H]⁺.

Example 8

Preparation of (E)-3-(2-(cyclohexylmethoxy)pyridin-4-yl)prop-2-en-1-amine

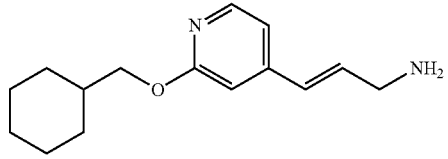 [SMILES: NC/C=C/c1ccnc(OCC2CCCCC2)c1]

(E)-3-(2-(Cyclohexylmethoxy)pyridin-4-yl)prop-2-en-1-amine was prepared following the method described in Example 7.

Step 1: Example 8 was prepared following the method used in Example 7 and isolated during step 3 chromatography (see above). Yield (0.04 g, 6%); $^1$H NMR (400 MHz, CD₃OD) δ 7.98 (d, J=5.2 Hz, 1H), 6.97 (d, J=5.6 Hz, 1H), 6.73 (s, 1H), 6.63-6.53 (m, 1H), 6.47 (d, J=16 Hz, 1H), 4.01 (d, J=5.6 Hz, 2H), 3.41 (d, J=6.0 Hz, 2H), 1.88-1.66 (m, 6H), 1.38-1.02 (m, 5H); RP-HPLC $t_R$=7.79 min; ESI-MS m/z 247.2 [M+H]⁺.

Example 9

Preparation of 1-((5-(3-amino-1-hydroxypropyl)thiophen-3-yl)ethynyl)cyclohexanol

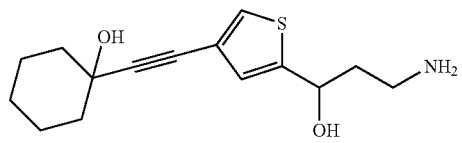 [SMILES: NCCC(O)c1cc(C#CC2(O)CCCCC2)cs1]

1-((5-(3-Amino-1-hydroxypropyl)thiophen-3-yl)ethynyl)cyclohexanol was prepared following the method described below.

Step 1: Addition of CH₃CN to 4-bromothiophene-2-carbaldehyde following the method used in Example 2 gave 3-(4-bromothiophen-2-yl)-3-hydroxypropanenitrile as a light brown oil which was used in the next step without additional purification. Yield (1.95 g, 80%).

Step 2: LiAlH₄ reduction of 3-(4-bromothiophen-2-yl)-3-hydroxypropanenitrile following the method used in Example 1 gave after flash chromatography purification (2%-10% 7N NH₃/MeOH—CH₂Cl₂ gradient) 3-amino-1-(4-bromothiophen-2-yl)propan-1-ol with was used directly in the next step. $^1$H NMR (400 MHz, CD₃OD) δ 7.26 (d, J=1.5 Hz, 1H), 6.85-6.92 (m, 1H), 4.94 (t, J=5.0 Hz, 1H), 2.70-2.80 (m, 2H), 1.86-1.94 (m, 2H).

Step 3: 3-Amino-1-(4-bromothiophen-2-yl)propan-1-ol and ethyl trifluoroacetate (2.0 mL) were stirred in CH₂Cl₂ (10 mL) at room temperature overnight. Concentration under reduced pressure gave N-(3-(4-bromothiophen-2-yl)-3-hydroxypropyl)-2,2,2-trifluoroacetamide which was used in the next step without additional purification. Yield (0.77 g, 28% in three steps); $^1$H NMR (400 MHz, DMSO-d₆) δ 9.36 (br.s, 1H), 7.51 (d, J=1.5 Hz, 1H), 6.90-7.00 (m, 1H), 5.86 (d, J=5.0 Hz, 1H), 4.75-4.83 (m, 1H), 3.20-3.30 (m, 2H), 1.80-1.94 (m, 2H).

Step 4: Solution of N-(3-(4-bromothiophen-2-yl)-3-hydroxypropyl)-2,2,2-trifluoroacetamide (0.77 g, 2.32 mmol) and 1-ethynylcyclohexanol (0.48 g, 3.87 mmol) in Et₃N (10 mL) was degassed by bubbling Ar for 5 min. CuI (0.0482 g, 0.253 mmol) and PdCl₂($^P$h₃P)₂ (0.0874 g, 0.125 mmol) were added to the reaction mixture and degassed by alternating vacuum/Ar once. The reaction mixture was stirred at +80° C. overnight, partitioned between EtOAc and aqueous NH₄Cl (25%). Aqueous layer was additionally extracted with EtOAc and combined organic layers were washed with brine. Concentration under reduced pressure followed by flash chromatography purification (10%-75% EtOAc—hexanes gradient) gave 2,2,2-trifluoro-N-(3-hydroxy-3-(4-((1-hydroxycyclohexyl)ethynyl)thiophen-2-yl)propyl)acetamide as a light yellow oil. Yield (0.52 g, 60%); $^1$H NMR (400 MHz, DMSO-d₆) δ 9.37 (br.s, 1H), 7.52 (d, J=1.3 Hz, 1H), 6.92 (d, J=1.3 Hz, 1H), 5.78 (d, J=4.7 Hz, 1H), 5.34 (s, 1H), 4.74-4.81 (m, 1H), 3.20-3.30 (m, 2H), 1.84-1.91 (m, 2H), 1.74-1.84 (m, 2H), 1.56-1.65 (m, 2H), 1.38-1.56 (m, 6H).

Step 5: A mixture of 2,2,2-trifluoro-N-(3-hydroxy-3-(4-((1-hydroxycyclohexyl)ethynyl)thiophen-2-yl)propyl)acetamide (0.52 g, 1.39 mmol) and K₂CO₃ (0.43 g, 3.11 mmol) in MeOH:H₂O (3:1, 16 mL) was stirred at room temperature overnight and concentrated under reduced pressure. Purification by flash chromatography (7%-20% 7N NH₃/MeOH—CH₂Cl₂ gradient) gave Example 9 as a light yellow oil. Yield (0.105 g, 27%); $^1$H NMR (400 MHz, CD₃OD) δ 7.37 (d, J=1.5 Hz, 1H), 6.94 (s, 1H), 4.93 (dd, J=5.8, 7.3 Hz, 1H), 2.70-2.80 (m, 2H), 1.86-2.00 (m, 4H), 1.67-1.76 (m, 2H), 1.52-1.67 (m, 5H), 1.22-1.36 (m, 1H); RP-HPLC $t_R$=6.98 min; ESI-MS m/z 280.2 [M−H₂O+H]⁺.

Example 10

Preparation of (E)-3-amino-1-(5-(2-cyclohexylvinyl)pyridin-3-yl)propan-1-ol

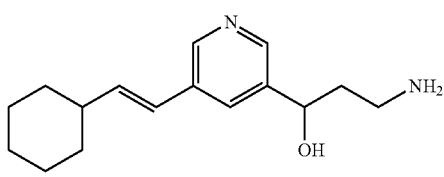 [SMILES: NCCC(O)c1cncc(/C=C/C2CCCCC2)c1]

(E)-3-Amino-1-(5-(2-cyclohexylvinyl)pyridin-3-yl)propan-1-ol was prepared following the method described in Example 3 and below.

Step 1: Coupling of (E)-(2-cyclohexylvinyl)boronic acid with 5-bromonicotinaldehyde following the method used in Example 3 gave (E)-5-(2-cyclohexylvinyl)nicotinaldehyde as a yellow oil. Yield (0.8 g, 69%); $^1$H NMR (400 MHz, DMSO-d₆) δ 10.08 (s, 1H), 8.32 (s, 1H), 8.75 (s, 1H), 8.28 (s, 1H), 6.51-6.38 (m, 2H), 2.26-2.13 (m, 1H), 1.88-1.58 (m, 5H), 1.42-1.18 (m, 5H).

Step 2: Addition of CH₃CN to (E)-5-(2-cyclohexylvinyl)nicotinaldehyde following the method used in Example 3 gave (E)-3-(5-(2-cyclohexylvinyl)pyridin-3-yl)-3-hydroxypropanenitrile as a yellow oil. Yield (0.9 g, 95%); $^1$H NMR (400 MHz, CDCl₃) δ 8.43 (s, 1H), 8.41 (s, 1H), 7.93 (s, 1H), 6.42 (s, 2H), 5.05 (t, J=5.6 Hz, 1H), 2.98-2.82 (m, 2H), 2.24-2.12 (m, 1H), 1.88-1.66 (m, 5H), 1.42-1.18 (m, 5H).

Step 3: LiAlH₄ reduction of (E)-3-(5-(2-cyclohexylvinyl)pyridin-3-yl)-3-hydroxypropanenitrile following the method used in Example 3 gave after flash chromatography purification (10%-30% 7N NH₃/MeOH—CH₂Cl₂ gradient) Example 10 as a light yellow oil. Yield (0.5 g, 59%); $^1$H NMR (400 MHz, CD₃OD) δ 8.37 (d, J=2.0 Hz, 1H), 8.33 (d, J=1.5 Hz, 1H), 7.85 (t, J=2.0 Hz, 1H), 6.40-6.38 (m, 2H), 4.84-4.76 (m, 1H), 2.86-2.78 (m, 2H), 2.24-2.08 (m, 1H), 1.98-1.66 (m, 7H), 1.44-1.28 (m, 5H); RP-HPLC $t_R$=6.23 min; ESI-MS m/z 261.2 [M+H]⁺.

Example 11

Preparation of 3-amino-1-(5-(2-cyclohexylethyl)pyridin-3-yl)propan-1-ol

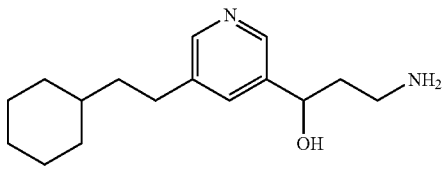 [SMILES: NCCC(O)c1cncc(CCC2CCCCC2)c1]

3-Amino-1-(5-(2-cyclohexylethyl)pyridin-3-yl)propan-1-ol was prepared following the method described in Example 10 and below.

Step 1: A solution of (E)-3-amino-1-(5-(2-cyclohexylvinyl)pyridin-3-yl)propan-1-ol (0.40 g, 1.54 mmol), Pd/C (10% wt, 30 mg) in methanol (20 ml) was stirred under hydrogen atmosphere at room temperature and for 18 hrs. The reaction mixture was filtered and concentrated under reduced pressure. The residue was purified by flash chromatography (20%-30% 7N NH₃/MeOH—CH₂Cl₂ (gradient) to give Example 11 as a pale yellow oil. Yield (0.14 g, 34%); $^1$H NMR (400 MHz, CD₃OD) δ 8.30 (s, 1H), 8.24 (s, 1H), 7.50 (s, 1H), 4.70-4.67 (m, 1H), 2.64-2.60 (m, 4H), 1.78-1.56 (m, 8H), 1.50-1.38 (m, 2H), 1.24-0.95 (m, 5H), 0.98-0.82 (m, 2H); RP-HPLC $t_R$=6.28 min; ESI-MS: m/z 263.2 [M+H]⁺.

Example 12

Preparation of 3-amino-1-(4-(cyclohexylmethoxy)pyridin-2-yl)propan-1-ol

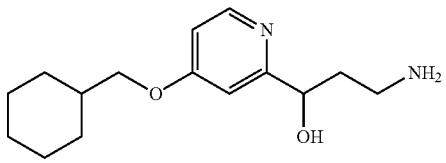 [SMILES: NCCC(O)c1cc(OCC2CCCCC2)ccn1]

3-Amino-1-(4-(cyclohexylmethoxy)pyridin-2-yl)propan-1-ol was prepared following the method shown in Scheme 5.

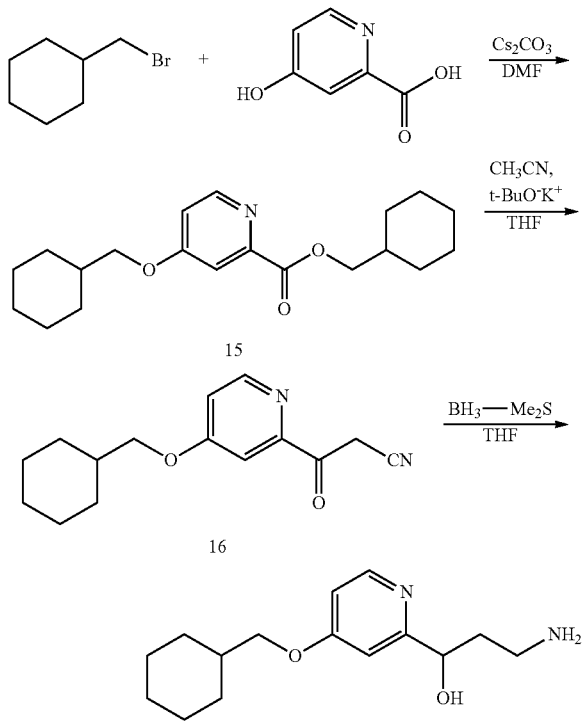

Step 1: Cs$_2$CO$_3$ (11.8 g, 36.7 mmol) was added to a mixture of 4-hydroxypicolinic acid (1.0 g, 7.2 mmol) and (bromomethyl)cyclohexane (3.25 g, 18.4 mmol) in DMF (30 ml). The resulting mixture was stirred at 80° C. for 18 hrs and concentrated under reduced pressure. EtOAc (50 ml) was added to the residue, sonicated, filtered, concentrated under reduced pressure. Purification by flash chromatography (50%-75% EtOAc—hexane gradient) gave ester 15 as a colorless oil. Yield (0.66 g, 28%); $^1$H NMR (400 MHz, DMSO-d$_6$) δ 8.46 (d, J=4.9 Hz, 1H), 7.46 (d, J=2.3 Hz, 1H), 7.18 (dd, J=5.5, 2.3 Hz, 1H), 4.08 (d, J=6.2 Hz, 2H), 3.92 (d, J=6.2 Hz, 2H), 1.82-1.58 (m, 12H), 1.28-1.00 (m, 10H).

Step 2: Addition of CH$_3$CN to ester 15 following the method used in Example 2 gave ketonitrile 16 as a yellow oil. Yield (0.30 g, 59%); $^1$H NMR (400 MHz, DMSO-d$_6$) δ 8.47 (d, J=4.9 Hz, 1H), 7.46 (d, J=2.3 Hz, 1H), 7.18 (dd, J=5.5, 2.3 Hz, 1H), 4.48 (s, 2H), 3.94 (d, J=5.8 Hz, 2H), 1.82-1.58 (m, 6H), 1.28-1.02 (m, 5H).

Step 3: Reduction of 3-(4-(cyclohexylmethoxy)pyridin-2-yl)-3-oxopropanenitrile with borane-dimethylsulfide following the method used in Example 2 gave after flash chromatography purification (20%-30% 7N NH$_3$/MeOH—CH$_2$Cl$_2$ gradient) Example 12 as a yellow oil. Yield (0.13 g, 43%); $^1$H NMR (400 MHz, DMSO-d$_6$) δ 8.22 (d, J=4.5 Hz, 1H), 6.98 (d, J=2.3 Hz, 1H), 6.76 (dd, J=5.9, 2.8 Hz, 1H), 4.62-4.58 (m, 1H), 3.94 (d, J=5.8 Hz, 2H), 2.72-2.58 (m, 2H), 1.88-1.58 (m, 8H), 1.40-1.02 (m, 5H); RP-HPLC t$_R$=5.91 min; ESI-MS m/z 265.2 [M+H]$^+$.

Example 13

Preparation of (E)-3-amino-1-(4-(2-cyclohexylvinyl)thiophen-2-yl)propan-1-ol

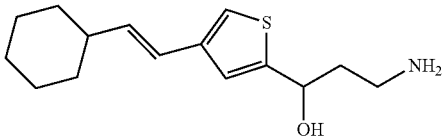 [SMILES: NCCC(O)c1cc(/C=C/C2CCCCC2)cs1]

(E)-3-Amino-1-(4-(2-cyclohexylvinyl)thiophen-2-yl)propan-1-ol was prepared following the method described in Example 3.

Step 1: Coupling of (E)-(2-cyclohexylvinyl)boronic acid with 4-bromothiophene-2-carbaldehyde following the method used in Example 3 gave after flash chromatography purification (30%-40% EtOAc—hexanes gradient) (E)-4-(2-cyclohexylvinyl)thiophene-2-carbaldehyde as a yellow oil. Yield (1.2 g, 91%); $^1$H NMR (400 MHz, DMSO-d$_6$) δ 9.88 (d, J=1.6 Hz, 1H), 8.15 (d, J=1.6 Hz, 1H), 7.89 (s, 1H), 6.37 (d, J=16.8 Hz, 1H), 6.22 (dd, J=16.8, 6.8 Hz, 1H), 2.08-2.02 (m, 1H), 1.80-1.58 (m, 5H), 1.32-1.18 (m, 5H).

Step 2: Addition of CH$_3$CN to (E)-4-(2-cyclohexylvinyl)thiophene-2-carbaldehyde following the method used in Example 3 gave after flash chromatography purification (10%-50% EtOAc—hexanes gradient) (E)-3-(4-(2-cyclohexylvinyl)thiophen-2-yl)-3-hydroxypropanenitrile as a yellow oil. Yield (1.2 g, 84%); $^1$H NMR (400 MHz, DMSO-d$_6$) δ 7.19 (s, 1H), 7.17 (s, 1H), 6.27 (d, J=16.8 Hz, 1H), 6.29-6.26 (m, 1H), 6.00 (dd, J=16.0, 6.4 Hz, 1H), 5.05 (q, J=5.6 Hz, 1H), 3.0-2.86 (m, 2H), 2.24-2.12 (m, 1H), 1.78-1.56 (m, 5H), 1.38-1.08 (m, 5H).

Step 3: LiAlH$_4$ reduction of (E)-2-(4-(2-cyclohexylvinyl)thiophen-2-yl)-2-hydroxyacetonitrile following the method used in Example 3 gave after flash chromatography purification (20%-30% 7N NH$_3$/MeOH—CH$_2$Cl$_2$ gradient) Example 13 as a light yellow oil. Yield (0.44 g, 36%); $^1$H NMR (400 MHz, DMSO-d$_6$) δ 7.19 (s, 1H), 7.13 (s, 1H), 6.25 (d, J=16.8 Hz, 1H), 5.98 (dd, J=16.0, 6.4 Hz, 1H), 4.84 (t, J=6.0 Hz, 1H), 2.72-2.58 (m, 2H), 2.24-2.08 (m, 1H), 1.78-1.58 (m, 7H), 1.38-1.02 (m, 5H); RP-HPLC t$_R$=10.49 min; ESI-MS m/z 219.1.2 [M+H]$^+$.

Example 14

Preparation of (E)-3-amino-1-(5-(2-cyclohexylvinyl)furan-2-yl)propan-1-ol

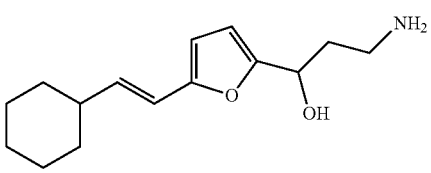 [SMILES: NCCC(O)c1ccc(/C=C/C2CCCCC2)o1]

(E)-3-Amino-1-(5-(2-cyclohexylvinyl)furan-2-yl)propan-1-ol was prepared following the method described in Example 3 and below.

Step 1: A mixture of 5-bromofuran-2-carbaldehyde (1.03 g, 5.89 mmol), vinylcyclohexane (0.86 g, 7.80 mmol), P(o-Tol)$_3$ (0.089 g, 0.29 mmol), Pd(OAc)$_2$ (0.070 g, 0.31 mmol) and Et₃N (2.0 mL) in anhydrous DMF (3.0 mL) was degassed by bubbling Ar then alternating vacuum/Ar three times. The reaction mixture was heated under inert atmosphere at +90° C. for 20 hrs and cooled to room temperature. Aqueous NH₄Cl was added to the reaction mixture and the mixture was extracted twice with hexanes and EtOAc. Combined organic layers were washed with brine, concentrated under reduced pressure. Purification by flash chromatography (3%-8% EtOAc—hexanes gradient) gave (E)-5-(2-cyclohexylvinyl)furan-2-carbaldehyde as a yellow oil. Yield (0.40 g, 33%); $^1$H NMR (400 MHz, CDCl₃) δ 9.53 (s, 1H), 7.19 (d, J=3.8 Hz, 1H), 6.55 (dd, J=7.0, 16.1 Hz, 1H), 6.34 (d, J=3.5 Hz, 1H), 6.19-6.26 (m, 1H), 2.10-2.19 (m, 1H), 1.52-1.92 (m, 6H), 1.10-1.42 (m, 4H).

Step 2: Acetonitrile addition to (E)-5-(2-cyclohexylvinyl)furan-2-carbaldehyde following the method used in Example 3 gave after flash chromatography purification (10%-50% EtOAc—hexanes gradient) (E)-3-(5-(2-cyclohexylvinyl)furan-2-yl)-3-hydroxypropanenitrile as a yellow oil. Yield (0.45 g, 94%); $^1$H NMR (400 MHz, DMSO-d₆) δ 6.32 (d, J=2.9 Hz, 1H), 6.23 (d, J=3.5 Hz, 1H), 6.15 (m, 1H), 6.05 (dd, J=3.9, 17.6 Hz, 1H), 4.76-4.87 (m, 1H), 2.84-3.00 (m, 2H), 2.02-2.14 (m, 1H), 1.40-1.80 (m, 4H), 1.02-1.36 (m, 6H).

Step 3: Reduction of (E)-3-(5-(2-cyclohexylvinyl)furan-2-yl)-3-hydroxypropanenitrile following the method used in Example 1, with the exception that Et₂O was used as the solvent, gave after flash chromatography purification (2%-16% 7N NH₃/MeOH—CH₂Cl₂ gradient) crude (E)-3-amino-1-(5-(2-cyclohexylvinyl)furan-2-yl)propan-1-ol which was additionally purified as described below. Yield (0.25 g, 55%).

Step 4: (E)-3-amino-1-(5-(2-cyclohexylvinyl)furan-2-yl)propan-1-ol (0.25 g, 1.0 mmol) was dissolved in CH₂Cl₂ (5 mL) and ethyl trifluoroacetate (0.5 mL) was added. The reaction mixture was stirred at room temperature for 30 min and concentrated under reduced pressure. Purification by flash chromatography (10%-50% EtOAc—hexanes gradient) gave (E)-N-(3-(5-(2-cyclohexylvinyl)furan-2-yl)-3-hydroxypropyl)-2,2,2-trifluoroacetamide as a colorless oil. Yield (0.26 g, 75%). (E)-N-(3-(5-(2-Cyclohexylvinyl)furan-2-yl)-3-hydroxypropyl)-2,2,2-trifluoroacetamide (0.15 g, 0.434 mmol) was dissolved in MeOH:H₂O (3:1, 8 mL) and K₂CO₃ (0.13 g, 0.94 mmol) was added. The reaction mixture was stirred at room temperature overnight and concentrated under reduced pressure. Flash chromatography purification (2%-16% 7N NH₃/MeOH—CH₂Cl₂ gradient) gave Example 14 as a light yellow oil. Yield (0.025 g, 23%); $^1$H NMR (400 MHz, CD₃OD) δ 6.00-6.40 (m, 4H), 4.64-4.74 (m, 1H), 2.70-2.80 (m, 2H), 2.01-2.14 (m, 1H), 1.90-2.00 (m, 2H), 1.50-1.80 (m, 5H), 1.10-1.40 (m, 5H); RP-HPLC $t_R$=10.06 min; ESI-MS m/z 232.2 [M−H₂O+H]⁺.

Example 15

Preparation of 3-amino-1-(5-(2-cyclohexylethyl)tetrahydrofuran-2-yl)propan-1-ol

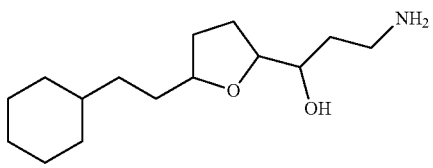 [SMILES: NCCC(O)C1CCC(CCC2CCCCC2)O1]

3-Amino-1-(5-(2-cyclohexylethyl)tetrahydrofuran-2-yl)propan-1-ol was prepared following the method described in Example 14 and below.

Step 1: A mixture of (E)-N-(3-(5-(2-cyclohexylvinyl)furan-2-yl)-3-hydroxypropyl)-2,2,2-trifluoroacetamide (0.11 g, 0.319 mmol) and Pd/C (10% wt, 0.037 g) in EtOAc (10 mL) was degassed by alternating vacuum/H₂ three times and then stirred under H₂ atmosphere at room temperature for 40 hrs, filtered through Celite and concentrated under reduced pressure to give N-(3-(5-(2-cyclohexylethyl)tetrahydrofuran-2-yl)-3-hydroxypropyl)-2,2,2-trifluoroacetamide which was used directly in the next step without additional purification.

Step 2: Deprotection of N-(3-(5-(2-cyclohexylethyl)tetrahydrofuran-2-yl)-3-hydroxypropyl)-2,2,2-trifluoroacetamide following the method used in Example 14 gave after flash chromatography purification (4%-16% 7N NH₃/MeOH—CH₂Cl₂ gradient) Example 15 as a colorless oil. Yield (0.033 g, 40%); $^1$H NMR (400 MHz, CD₃OD) δ 3.62-3.84 (m, 2H), 3.45-3.57 (m, 2H), 2.71-2.88 (m, 2H), 1.80-2.05 (m, 2H), 1.39-1.80 (m, 10H), 1.09-1.37 (m, 6H), 0.87-0.99 (m, 2H); RP-HPLC $t_R$=9.75 min; ESI-MS m/z 256.3 [M+H]⁺.

Example 16

Preparation of 1-(2-(5-(3-amino-1-hydroxypropyl)thiophen-3-yl)ethyl)cyclohexanol

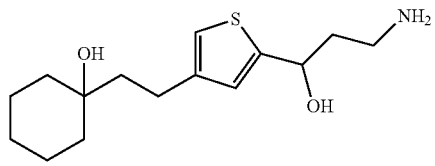 [SMILES: NCCC(O)c1cc(CCC2(O)CCCCC2)cs1]

1-(2-(5-(3-Amino-1-hydroxypropyl)thiophen-3-yl)ethyl)cyclohexanol was prepared following the method described in Example 11.

Step 1: Hydrogenation of Example 9 following the method used in Example 15, except that EtOH was used as the solvent, gave after filtration throught Celite and concentration under reduced pressure Example 16 as a colorless oil. Yield (0.055 g, 77%); $^1$H NMR (400 MHz, CD₃OD) δ 6.88 (s, 1H), 6.85 (s, 1H), 4.91 (dd, J=5.8, 7.8 Hz, 1H), 2.68-2.80 (m, 2H), 2.58-2.68 (m, 2H), 1.86-2.05 (m, 2H), 1.40-1.78 (m, 12H), 1.2-1.4 (m, 1H); RP-HPLC $t_R$=7.25 min; ESI-MS m/z 284.2 [M+H]⁺.

Example 17

Preparation of 3-amino-1-(4-(2-cyclohexylethyl)thiophen-2-yl)propan-1-ol

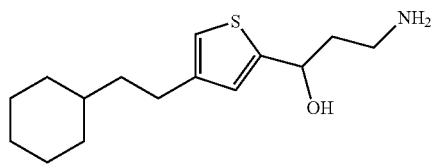 [SMILES: NCCC(O)c1cc(CCC2CCCCC2)cs1]

3-Amino-1-(4-(2-cyclohexylethyl)thiophen-2-yl)propan-1-ol was prepared following the method described in Examples 11 and 13.

Hydrogenation of (E)-3-amino-1-(4-(2-cyclohexylvinyl)thiophen-2-yl)propan-1-ol (Example 13) following the method used in Example 11 gave Example 17 as a pale yellow oil. Yield (0.3 g, 75%); $^1$H NMR (400 MHz, DMSO-$d_6$) δ 6.89 (s, 1H), 6.73 (s, 1H), 4.82 (t, J=6.0 Hz, 1H), 2.72-2.58 (m, 4H), 1.78-1.56 (m, 9H), 1.46-1.36 (m, 2H), 1.24-1.06 (m, 5H), 0.98-0.80 (m, 2H); RP-HPLC $t_R$=10.85 min; ESI-MS m/z 221.2 [M+H]$^+$.

Example 18

Preparation of 3-amino-1-(4-(cyclohexylmethoxy)thiophen-2-yl)propan-1-ol

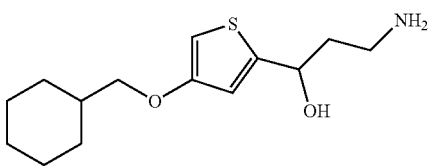 [SMILES: NCCC(O)c1cc(OCC2CCCCC2)cs1]

3-Amino-1-(4-(cyclohexylmethoxy)thiophen-2-yl)propan-1-ol was prepared following the method described in Examples 1, 2 and below.

Step 1: A solution of oxalyl chloride (1.4 mL, 16.1 mmol) in anhydrous $CH_2Cl_2$ (10 mL) was added dropwise to a solution of 4-bromothiophene-2-carboxylic acid (3.08 g, 14.9 mmol) and DMF (0.2 mL) in anhydrous $CH_2Cl_2$ (40 mL) over 30 mins. The reaction mixture was stirred at room temperature for 35 min then concentrated under reduced pressure. $CH_2Cl_2$ (30 mL) was added to the residue followed by cyclohexylmethanol (1.9 mL, 15.44 mmol) and $Et_3N$ (2.5 mL, 17.94 mmol). The reaction mixture was stirred at room temperature overnight and partitioned between EtOAc and aqueous 25% $NH_4Cl$. Organic layer was washed with brine, concentrated under reduced pressure and purified by flash chromatography (2%-20% EtOAc—hexanes gradient) to give cyclohexylmethyl 4-bromothiophene-2-carboxylate as a colorless oil which was directly used in the next step. Yield (3.61 g, 80%).

Step 2: Cyclohexylmethanol (0.50 mL, 4.06 mmol) was added to a suspension of NaH (0.080 g, 3.33 mmol) in anhydrous THF (5 mL). Then cyclohexylmethyl 4-bromothiophene-2-carboxylate (0.56 g, 1.847 mmol) was added to the reaction mixture followed by CuI (0.34 g, 1.79 mmol). The reaction mixture was stirred at room temperature for 12 days then aqueous $NH_4Cl$ (25%) was added. Aqueous layer was extracted with EtOAc and combined organic layers were washed with brine, dried over anhydrous $MgSO_4$ and concentrated under reduced pressure. Flash chromatography purification (2%-10% EtOAc—hexanes gradient) gave cyclohexylmethyl 4-(cyclohexylmethoxy)thiophene-2-carboxylate as a colorless oil. Yield (0.17 g, 27%); $^1$H NMR (400 MHz, $CD_3OD$) δ 7.35 (d, J=1.7 Hz, 1H), 6.75 (d, J=1.7 Hz, 1H), 4.07 (d, J=6.3 Hz, 2H), 3.78 (d, J=6.3 Hz, 2H), 1.65-1.90 (m, 12H), 1.15-1.38 (m, 6H), 1.00-1.15 (m, 4H).

Step 3: Acetonitrile addition to cyclohexylmethyl 4-(cyclohexylmethoxy)thiophene-2-carboxylate following the method used in Example 1 gave after flash chromatography purification (5%-20% EtOAc—hexanes gradient) 3-(4-(cyclohexylmethoxy)thiophen-2-yl)-3-oxopropanenitrile as a white solid. Yield (0.084 g, 63%); $^1$H NMR (400 MHz, $CDCl_3$) δ 7.38 (d, J=2 Hz, 1H), 6.72 (d, J=1.5 Hz, 1H), 3.93 (s, 2H), 3.76 (d, J=5.9 Hz, 2H), 1.67-1.86 (m, 6H), 1.13-1.38 (m, 3H), 0.95-1.13 (m, 2H).

Step 4: Borane-dimethylsulfide reduction of 3-(4-(cyclohexylmethoxy)thiophen-2-yl)-3-oxopropanenitrile following the method used in Example 2 gave after flash chromatography purification (2%-20% 7N $NH_3$/MeOH—$CH_2Cl_2$ gradient) Example 18 as a colorless oil. Yield (0.037 g, 43%); $^1$H NMR (400 MHz, $CD_3OD$) δ 6.62 (dm J=1 Hz, 1H), 6.22 (d, J=1.4 Hz, 1H), 4.85 (m, 1H), 3.71 (d, J=6.3 Hz, 2H), 2.71-2.78 (m, 2H), 1.64-1.97 (m, 8H), 1.15-1.37 (m, 3H), 1.05-1.15 (m, 2H); RP-HPLC $t_R$=9.63 min; ESI-MS m/z 223.1 $[C_{13}H_{18}OS_2.+H]^+$ or $[M-H_2O-CH_2NH_2+H]^+$.

Example 19

Preparation of (R)-3-amino-1-(6-((2-propylpentyl)oxy)pyridin-2-yl)propan-1-ol

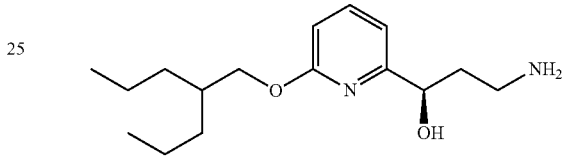

(R)-3-Amino-1-(6-((2-propylpentyl)oxy)pyridin-2-yl)propan-1-ol was prepared following the method described in Example 6.

Step 1: Reaction of 6-bromopicolinic acid with 2-propylpentan-1-ol following the method used in Example 6 gave methyl 6-((2-propylpentyl)oxy)picolinate as an off-white solid which was directly used in next reaction without further purification. Yield (1.29 g, quant.); $^1$H NMR (400 MHz, DMSO-$d_6$) δ 7.84 (t, J=8.3 Hz, 1H), 7.63 (d, J=7.2 Hz, 1H), 7.04 (d, J=8.4 Hz, 1H), 4.18 (d, J=6.0 Hz, 2H), 3.84 (s, 3H), 1.84-1.58 (m, 1H), 1.40-1.20 (m, 8H), 0.91-0.80 (m, 6H).

Step 2: $CH_3CN$ addition to methyl 6-((2-propylpentyl)oxy)picolinate following the method used in Example 6 gave 3-oxo-3-(6-((2-propylpentyl)oxy)pyridin-2-yl)propanenitrile in quantitative yield as a solid which was directly used in next reaction without further purification.

Step 3: Chiral reduction of 3-oxo-3-(6-((2-propylpentyl)oxy)pyridin-2-yl)propanenitrile following the method used in Example 6 gave (R)-3-hydroxy-3-(6-((2-propylpentyl)oxy)pyridin-2-yl)propanenitrile as an off-white solid which was directly used in next reaction without further purification. Yield (1.34 g, quant.); $^1$H NMR (400 MHz, DMSO-$d_6$) δ 7.69 (t, J=8.0 Hz, 1H), 7.09 (d, J=6.8 Hz, 1H), 6.68 (d, J=8.4 Hz, 1H), 6.09 (d, J=5.2 Hz, 1H), 4.80-4.75 (m, 1H), 4.20-4.08 (m, 2H), 3.01-2.81 (m, 2H), 1.80-1.68 (m, 1H), 1.40-1.21 (m, 8H), 0.92-0.80 (m, 6H).

Step 4: Reduction of (R)-3-hydroxy-3-(6-((2-propylpentyl)oxy)pyridin-2-yl)propanenitrile following the method used in Example 6 gave Example 19 as a colorless oil. Yield (0.5 g, 39%); $^1$H NMR (400 MHz, DMSO-$d_6$) δ 7.62 (t, J=8.0 Hz, 1H), 7.02 (d, J=7.6 Hz, 1H), 6.58 (d, J=8.0 Hz, 1H), 4.56-4.52 (m, 1H), 4.08-4.11 (m, 2H), 3.18-3.44 (br.m, 2H), 2.65-2.74 (m, 2H), 1.78-1.84 (m, 2H), 1.64-1.56 (m, 1H), 1.38-1.20 (m, 10H), 0.92-0.78 (m, 6H); RP-HPLC $t_R$=10.56 min; ESI-MS m/z 281.3 [M+H]$^+$.

Example 20

Preparation of (E)-3-amino-1-(5-(2-cyclohexylvinyl)thiophen-3-yl)propan-1-ol

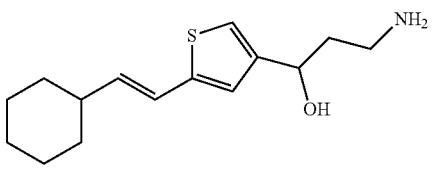 [SMILES: NCCC(O)c1csc(/C=C/C2CCCCC2)c1]

(E)-3-Amino-1-(5-(2-cyclohexylvinyl)thiophen-3-yl)propan-1-ol was prepared following the method described in Example 3.

Step 1: Coupling of (E)-(2-cyclohexylvinyl)boronic acid with 5-chlorothiophene-3-carbaldehyde in the presence of tetrabutylamonium bromide (1.2 g, 3.72 mmol) following the method used in Example 3 gave after flash chromatography purification (10%-50% EtOAc—hexanes gradient) (E)-5-(2-cyclohexylvinyl)thiophene-3-carbaldehyde as a yellow oil. Yield (0.4 g, 53%); $^1$H NMR (400 MHz, DMSO-$d_6$) δ 9.77 (s, 1H), 8.38 (s, 1H), 7.29 (s, 1H), 6.55 (d, J=8.0 Hz, 1H), 6.13 (dd, J=16.4, 6.8 Hz, 1H), 2.08-2.02 (m, 1H), 1.80-1.58 (m, 5H), 1.38-1.08 (m, 5H).

Step 2: Addition of $CH_3CN$ to (E)-5-(2-cyclohexylvinyl)thiophene-3-carbaldehyde following the method used in Example 3 gave (E)-3-(5-(2-cyclohexylvinyl)thiophen-3-yl)-3-hydroxypropanenitrile as a yellow oil which was used in the next step without further purification. Yield (0.47 g, quant.).

Step 3: $LiAlH_4$ reduction of (E)-3-(5-(2-cyclohexylvinyl)thiophen-3-yl)-3-hydroxypropanenitrile following the method used in Example 3 gave Example 20 as a light yellow oil. Yield (0.2 g, 49%); $^1$H NMR (400 MHz, DMSO-$d_6$) δ 6.99 (s, 1H), 6.88 (s, 1H), 6.45 (d, J=16.8 Hz, 1H), 5.91 (dd, J=16.0, 6.8 Hz, 1H), 4.60 (t, J=6.4 Hz, 1H), 2.66-2.56 (m, 2H), 2.18-2.08 (m, 1H), 1.78-1.58 (m, 7H), 1.38-1.02 (m, 5H); RP-HPLC $t_R$=10.62 min; ESI-MS m/z 219.1 [M+H]$^+$.

Example 21

Preparation of 3-amino-1-(5-(2-cyclohexylethyl)thiophen-3-yl)propan-1-ol

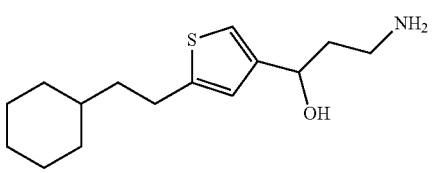 [SMILES: NCCC(O)c1csc(CCC2CCCCC2)c1]

3-Amino-1-(5-(2-cyclohexylethyl)thiophen-3-yl)propan-1-ol was prepared following the method described in 20 and 11.

Step 1: Hydrogenation of (E)-3-amino-1-(5-(2-cyclohexylvinyl)thiophen-3-yl)propan-1-ol following the method used in Example 11 gave Example 21 as a pale yellow oil. Yield (0.08 g, 90%); $^1$H NMR (400 MHz, DMSO-$d_6$) δ 6.99 (s, 1H), 6.78 (s, 1H), 4.72 (t, J=6.0 Hz, 1H), 2.82-2.68 (m, 4H), 1.98-1.82 (m, 2H), 1.81-1.61 (m, 6H), 1.58-1.46 (m, 2H), 1.38-1.06 (m, 3H), 0.98-0.80 (m, 2H); RP-HPLC $t_R$=10.78 min; ESI-MS m/z 221.1 [M+H]$^+$.

Example 22

Preparation of (E)-3-amino-1-(4-(2-cyclohexylvinyl)furan-2-yl)propan-1-ol

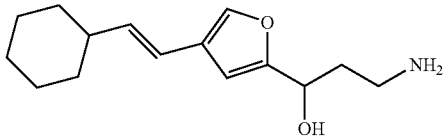

(E)-3-Amino-1-(4-(2-cyclohexylvinyl)furan-2-yl)propan-1-ol was prepared following the method described in Examples 1 and 3.

Step 1: Suzuki coupling between (E)-(2-cyclohexylvinyl)boronic acid and 4-bromofuran-2-carbaldehyde following the method used in Example 3 gave after flash chromatography purification (1%-15% EtOAc—hexanes gradient) (E)-4-(2-cyclohexylvinyl)furan-2-carbaldehyde as a yellow oil. Yield (0.18 g, 21%).

Step 2: Acetonitrile addition to (E)-4-(2-cyclohexylvinyl)furan-2-carbaldehyde following the method used in Example 3 gave after flash chromatography purification (10%-50% EtOAc—hexanes gradient) (E)-3-(4-(2-cyclohexylvinyl)furan-2-yl)-3-hydroxypropanenitrile as a light yellow oil. Yield (0.13 g, 60%); $^1$H NMR (400 MHz, $CD_3OD$) δ 7.38 (s, 1H), 6.53 (s, 1H), 6.17 (d, J=16.1 Hz, 1H), 5.90 (dd, J=6.9, 16.2 Hz, 1H), 4.90 (t, J=6.3 Hz, 1H), 2.84-2.97 (m, 2H), 1.99-2.12 (m, 1H), 1.63-1.81 (m, 5H), 1.10-1.40 (m, 5H).

Step 3: $LiAlH_4$ reduction of (E)-3-(4-(2-cyclohexylvinyl)furan-2-yl)-3-hydroxypropanenitrile following the method used in Example 1 gave after flash chromatography purification (2%-20% 7N $NH_3$/MeOH—$CH_2Cl_2$ gradient) Example 22 as a colorless oil. Yield (0.07 g, 53%); $^1$H NMR (400 MHz, $CD_3OD$) δ 7.34 (s, 1H), 6.41 (s, 1H), 6.17 (d, J=17.2 Hz, 1H), 5.88 (dd, J=7.3, 16.1 Hz, 1H), 4.67 (t, J=6.9 Hz, 1H), 2.67-2.80 (m, 2H), 2.00-2.10 9m, 1H), 1.90-2.00 (m, 2H), 1.63-1.81 (m, 5H), 1.10-1.40 (m, 5H); RP-HPLC $t_R$=10.42 min; ESI-MS m/z 232.2 [M–$H_2O$+H]$^+$.

Example 23

Preparation of 3-amino-1-(5-(cyclohexylethynyl)furan-2-yl)propan-1-ol

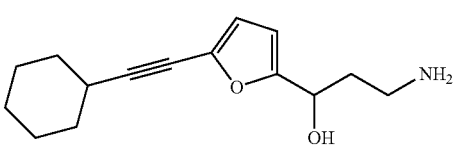 [SMILES: NCCC(O)c1ccc(C#CC2CCCCC2)o1]

3-Amino-1-(5-(cyclohexylethynyl)furan-2-yl)propan-1-ol was prepared following the method described in Example 1 and below.

Step 1: A mixture of 5-bromofuran-2-carboxylic acid (2.64 g, 13.8 mmol), (cyclohexylmethyl)bromide (2.62 g, 14.8 mmol), $K_2CO_3$ (2.30 g, 16.64 mmol) in anhydrous NMP was stirred under Ar at +70° C. for 8 hrs after which additional (cyclohexylmethyl)bromide (1.55 g, 8.75 mmol) was added. Stirring continued overnight then the reaction mixture was concentrated under reduced pressure. The residue was partitioned between aqueous NaHCO$_3$ (10%) and hexanes, and then aqueous layer was extracted with hexanes. Combined organic layers were washed with brine, dried over anhydrous MgSO$_4$ and concentrated under reduced pressure to give cyclohexylmethyl 5-bromofuran-2-carboxylate as a light yellow oil. Yield (2.22 g, 56%); $^1$H NMR (400 MHz, CDCl$_3$) δ 7.10 (d, J=3.9 Hz, 1H), 6.44 (d, J=3.4 Hz, 1H), 4.10 (d, J=6.4 Hz, 2H), 1.64-1.84 (m, 6H), 1.12-1.34 (m, 3H), 0.95-1.09 (m, 2H).

Step 2: A mixture of cyclohexylmethyl 5-bromofuran-2-carboxylate (0.63 g, 2.19 mmol) and ethynylcyclohexane (0.32 g, 2.96 mmol) in Et$_3$N (10 mL) was degassed by bubbling Ar. CuI (0.023 g, 0.119 mmol) and PdCl$_2$(Ph$_3$P)$_2$ (0.0412 g, 0.0587 mmol) were added and the reaction mixture was degassed by alternating vac/Ar three 3 times. The reaction mixture was stirred at +70° C. under Ar overnight and concentrated under reduced pressure. The residue was partitioned between hexanes and aqueous NH$_4$Cl (25%) and aqueous layer was extracted twice with hexanes. Combined organic layers were washed with brine, treated with activated charcoal and dried over anhydrous MgSO$_4$. Concentration under reduced pressure gave cyclohexylmethyl 5-(cyclohexylethynyl)furan-2-carboxylate as an orange solid which was used directly in the next step without additional purification. Yield (0.75 g, quant.); $^1$H NMR (400 MHz, CDCl$_3$) δ 7.10 (d, J=3.9 Hz, 1H), 6.50 (d, J=3.9 Hz, 1H), 4.10 (d, J=6.4 Hz, 2H), 1.56-2.66 (m, 1H), 1.63-1.84 (m, 9H), 1.42-1.60 (m, 4H), 1.10-1.40 (m, 6H), 0.96-1.10 (m, 2H).

Step 3: Acetonitrile addition to cyclohexylmethyl 5-(cyclohexylethynyl)furan-2-carboxylate following the method used in Example 1 gave after flash chromatography purification (10%-75% EtOAc—hexanes gradient) 3-(5-(cyclohexylethynyl)furan-2-yl)-3-oxopropanenitrile an orange solid which was directly used in the next step without additional purification. Yield (0.64 g, quant.).

Step 4: LiAlH$_4$ reduction of 3-(5-(cyclohexylethynyl)furan-2-yl)-3-oxopropanenitrile following the method used in Example 1 gave after flash chromatography purification (2%-20% 7N NH$_3$/MeOH—CH$_2$Cl$_2$ gradient) followed by treatment with activated charcoal Example 23 as a light yellow oil. Yield (0.14 g, 26%); $^1$H NMR (400 MHz, CD$_3$OD) δ 6.39 (d, J=3.4 Hz, 1H), 6.24 (d, J=3.9 Hz, 1H), 4.68 (t, J=6.8 Hz, 1H), 2.69-2.79 (m, 2H), 2.56-2.64 (m, 1H), 1.90-1.98 (m, 2H), 1.81-1.90 (m, 2H), 1.68-1.80 (m, 2H), 1.28-1.68 (m, 6H); RP-HPLC t$_R$=9.95 min; ESI-MS m/z 230.2 [M−H$_2$O+H]$^+$.

Example 24

Preparation of 3-amino-1-(5-(cyclohexylmethoxy)furan-2-yl)propan-1-ol

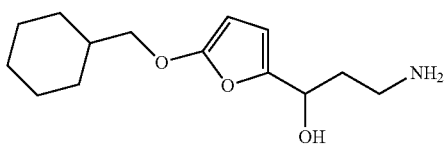

3-Amino-1-(5-(cyclohexylmethoxy)furan-2-yl)propan-1-ol was prepared following the method described in Examples 1, 23 and below.

Step 1: Cyclohexylmethanol (1.60 g, 14.0 mmol) was slowly added to a cooled (0° C.) suspension of sodium hydride (0.30 g, 12.5 mmol) in anhydrous NMP (5 mL) under Ar. A solution of cyclohexylmethyl 5-bromofuran-2-carboxylate (1.79 g, 6.23 mmol) in anhydrous NMP (6 mL) was added to the reaction mixture and stirred overnight at room temperature. The reaction mixture was partitioned between aqueous NH$_4$Cl (25%) and hexanes. Aqueous layer was extracted with hexanes and combined organic layers were washed with brine and concentrated under reduced pressure. Purification by flash chromatography (2%-10% EtOAc—hexanes gradient) gave cyclohexylmethyl 5-(cyclohexylmethoxy)furan-2-carboxylate as a colorless oil. Yield (1.05 g, 53%); $^1$H NMR (400 MHz, CDCl$_3$) δ 7.10 (d, J=3.4 Hz, 1H), 5.27 (d, J=3.9 Hz, 1H), 4.05 (d, J=6.4 Hz, 2H), 3.91 (d, J=5.9 Hz, 2H), 1.62-1.85 (m, 12H), 1.10-1.33 (m, 6H), 0.94-1.10 (m, 4H).

Step 2: LiAlH$_4$ reduction of cyclohexylmethyl 5-(cyclohexylmethoxy)furan-2-carboxylate following the method used in Example 1 gave after flash chromatography purification (10%-50% EtOAc—hexanes gradient) (5-(cyclohexylmethoxy)furan-2-yl)methanol as a mixture with cyclohexylmethanol which was used in the next step without further purification. Yield (0.75 g, quant.); $^1$H NMR (400 MHz, DMSO-d$_6$) δ 6.09 (d, J=3.4 Hz, 1H), 5.17 (d, J=2.9 Hz, 1H), 4.98 (t, J=5.4 Hz, 1H), 4.19 (d, J=5.9 Hz, 2H), 3.77 (d, J=5.9 Hz, 2H), 1.55-1.77 (m, 6H), 1.05-1.25 (m, 3H), 0.94-1.05 (m, 2H).

Step 3: A mixture of (5-(cyclohexylmethoxy)furan-2-yl)methanol and cyclohexylmethanol (0.75 g) and MnO$_2$ (3.16 g, 36.3 mmol) in anhydrous CH$_2$Cl$_2$ (16 mL) was stirred at room temperature for 3 days. The reaction mixture was filtered through Celite and concentrated under reduced pressure. Flash chromatography purification (10%-50% EtOAc—hexanes gradient) gave 5-(cyclohexylmethoxy)furan-2-carbaldehyde with cyclohexylmethanol as an impurity as a light yellow. Yield (0.68 g, 99%); $^1$H NMR (400 MHz, DMSO-d$_6$) δ 9.20 (s, 1H), 7.52 (d, J=3.8 Hz, 1H), 5.79 (d, J=3.8 Hz, 1H), 4.03 (d, J=5.8 Hz, 2H), 1.55-1.80 (m, 6H), 0.96-1.25 (m, 5H).

Step 4: Acetonitrile addition to 5-(cyclohexylmethoxy)furan-2-carbaldehyde following the method used in Example 3 gave after flash chromatography purification (10%-50% EtOAc—hexanes gradient) followed by treatment with activated charcoal 3-(5-(cyclohexylmethoxy)furan-2-yl)-3-hydroxypropanenitrile as a colorless oil which was directly used in the next step. Yield (0.56 g, 69%).

Step 5: LiAlH$_4$ reduction of 3-(5-(cyclohexyl$^m$ethoxy)furan-2-yl)-3-hydroxypropanenitrile following the method used in Example 1 gave after flash chromatography purification (2%-20% 7N NH$_3$/MeOH—CH$_2$Cl$_2$ gradient) Example 24 as a light yellow oil which solidified upon standing. Yield (0.26 g, 46%); $^1$H NMR (400 MHz, CD$_3$OD) δ 6.11 (d, J=3.4 Hz, 1H), 5.10 (d, J=3.4 Hz, 1H), 4.56 (t, J=6.8 Hz, 1H), 3.79 (d, J=6.3 Hz, 2H), 2.65-2.77 (m, 2H), 1.82-1.96 (m, 2H), 1.66-1.82 (m, 6H), 1.15-1.37 (m, 3H), 1.00-1.13 (m, 2H); ESI-MS m/z 254.2 [M+H]$^+$.

Example 25

Preparation of (R)-3-amino-1-(6-((cyclohexylmethyl)thio)pyridin-2-yl)propan-1-ol

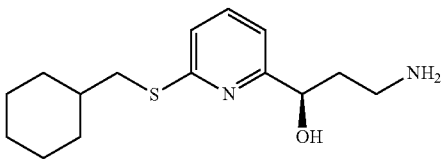 [SMILES: NCC[C@@H](O)c1cccc(SCC2CCCCC2)n1]

(R)-3-Amino-1-(6-((cyclohexylmethyl)thio)pyridin-2-yl)propan-1-ol was prepared following the method described in Example 6 and below.

Step 1: A suspension of (bromomethyl)cyclohexane (0.95 g, 5.4 mmol) and AcSK (0.65, 5.4 mmol) in DMF was degassed by bubbling Ar and stirred at 60° C. for 4 hrs. $Cs_2CO_3$ (3.1 g, 10.8 mmol), followed by MeOH (1 ml) and 6-bromopicolinic acid (1.0 g, 4.9 mmol) were then added to the reaction mixture. Stirring was continued at 70° C. for 18 hr. The reaction mixture was filtered through celite and concentrated under reduced pressure. Methanol (20 ml) followed by 1.25 M HCl-MeOH (10 ml) and conc. $H_2SO_4$ (1 ml) was added to the residue. The resulting mixture was stirred at 60° C. for 18 hours, concentrated, partitioned between saturated $NaHCO_3$ (50 ml) and ethyl acetate (100 ml). Organic layer was separated, dried over anhydrous $Na_2SO_4$ and concentrated under reduced pressure. Purification by flash chromatography (30%-50% EtOAc—hexane gradient) gave methyl 6-((cyclohexylmethyl)thio)picolinate. Yield (0.6 g, 46%); $^1$H NMR (400 MHz, $CDCl_3$) δ 7.76 (d, J=8.0 Hz, 1H), 7.58 (t, J=8.0 Hz, 1H), 7.31 (d, J=8.0 Hz, 1H), 3.96 (s, 3H), 3.14 (d, J=6.4 Hz, 2H), 1.96-1.84 (m, 2H), 1.78-1.58 (m, 4H), 1.26-1.00 (m, 5H).

Step 2: Addition of $CH_3CN$ to methyl 6-((cyclohexylmethyl)thio)picolinate following the method used in Example 6 gave 3-(6-((cyclohexylmethyl)thio)pyridin-2-yl)-3-oxopropanenitrile as a yellow oil which was used in the next step without further purification. Yield (0.63 g, quant.).

Step 3: Chiral reduction of 3-(6-((cyclohexylmethyl)thio)pyridin-2-yl)-3-oxopropanenitrile following the method described in Example 6 gave (R)-3-(6-((cyclohexylmethyl)thio)pyridin-2-yl)-3-hydroxypropanenitrile as a yellow oil which was used in the next step without further purification. Yield (0.63 g, quant.).

Step 4: Reduction of (R)-3-(6-((cyclohexylmethyl)thio)pyridin-2-yl)-3-hydroxypropanenitrile following the method described in Example 6 gave after flash chromatography purification (15%-20% 7N $NH_3$/MeOH—$CH_2Cl_2$ gradient) Example 25 as a colorless oil. Yield (0.3 g, 43%); $^1$H NMR (400 MHz, $CD_3OD$) δ 7.56 (t, J=7.6 Hz, 1H), 7.17 (d, J=7.6 Hz, 1H), 7.09 (d, J=8.0 Hz, 1H), 4.75-4.72 (m, 1H), 3.04 (d, J=7.2 Hz, 2H), 2.80 (t, J=7.6 Hz, 2H), 2.03-1.98 (m, 1H), 1.94-1.54 (m, 7H), 1.30-0.99 (m, 5H); RP-HPLC $t_R$=9.63 min; ESI-MS m/z 281.2 [M+H]$^+$.

Example 26

Preparation of (R)-3-amino-1-(6-(cyclohexyloxy)pyridin-2-yl)propan-1-ol

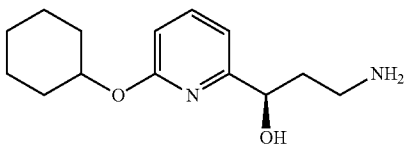 [SMILES: NCC[C@@H](O)c1cccc(OC2CCCCC2)n1]

(R)-3-Amino-1-(6-(cyclohexyloxy)pyridin-2-yl)propan-1-ol was prepared following the method described in Example 6.

Step 1: Reaction of 6-bromopicolinic acid with cyclohexanol following the method used in Example 6 gave methyl 6-(cyclohexyloxy)picolinate as a yellow oil which was used in the next step without additional purification. Yield (1.15 g, quant.).

Step 2: $CH_3CN$ addition to methyl 6-(cyclohexyloxy)picolinate following the method described in Example 6 gave 3-(6-(cyclohexyloxy)pyridin-2-yl)-3-oxopropanenitrile as a yellow oil which was used in the next step without further purification. Yield (1.2 g, quant.).

Step 3: Chiral reduction of 3-(6-(cyclohexyloxy)pyridin-2-yl)-3-oxopropanenitrile following the method described in Example 6 gave (R)-3-(6-(cyclohexyloxy)pyridin-2-yl)-3-hydroxypropanenitrile as a yellow oil which was used in the next step without further purification. Yield (1.2 g, quant.); $^1$H NMR (400 MHz, DMSO-$d_6$) δ 7.77 (t, J=7.6 Hz, 1H), 7.06 (d, J=7.6 Hz, 1H), 6.63 (d, J=8.4 Hz, 1H), 6.07 (d, J=5.2 Hz, 1H), 5.02-4.92 (m, 1H), 4.76 (q, J=5.6 Hz, 1H), 3.0-2.86 (m, 2H), 2.0-1.06 (m, 10H).

Step 4: Reduction of (R)-3-(6-(cyclohexyloxy)pyridin-2-yl)-3-hydroxypropanenitrile following the method described in Example 6 gave after flash chromatography purification (15%-25% 7N $NH_3$/MeOH—$CH_2Cl_2$ gradient) Example 26 as a colorless oil. Yield (0.4 g, 33%); $^1$H NMR (400 MHz, $CD_3OD$) δ 7.61 (t, J=7.8 Hz, 1H), 7.00 (d, J=7.6 Hz, 1H), 6.58 (d, J=8.4 Hz, 1H), 5.05-4.96 (m, 1H), 4.40-4.28 (m, 1H), 2.84 (t, J=6.8 Hz, 2H), 2.08-1.74 (m, 6H), 1.62-1.32 (m, 6H); RP-HPLC $t_R$=7.04 min; ESI-MS m/z 251.2 [M+H]$^+$.

Example 27

Preparation of (R)-3-amino-1-(6-((cyclohexylmethyl)sulfonyl)pyridin-2-yl)propan-1-ol

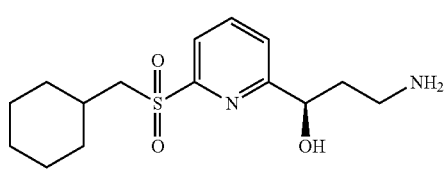 [SMILES: NCC[C@@H](O)c1cccc(S(=O)(=O)CC2CCCCC2)n1]

(R)-3-Amino-1-(6-((cyclohexylmethyl)sulfonyl)pyridin-2-yl)propan-1-ol was prepared following the method shown in Scheme 6

SCHEME 6.

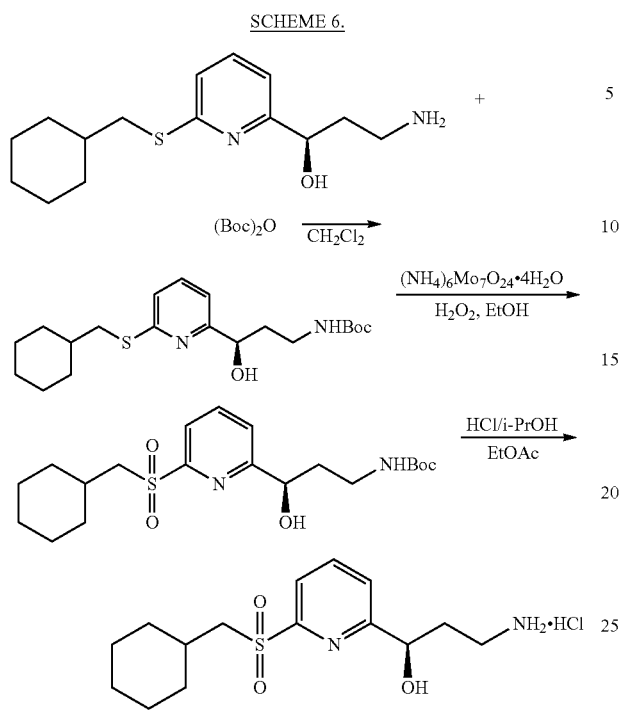

Step 1: A mixture of Example 25 (0.2 g, 0.71 mmol) and di-tert-butyl carbonate (0.17 g, 0.78 mmol) in DCM (10 ml) was stirred at room temperature for 18 hrs. Concentration under reduced pressure gave carbamate 18 as a pale yellow oil which was used in the next step without further purification. Yield (0.27 g, quant.).

Step 2: Hydrogen peroxide (1 ml, 30%) was added to a mixture of thioether 18 (0.27 g, 0.71 mmol) and ammonium molybdate tetrahydrate (0.28 g, 0.22 mmol) in ethanol (10 ml). The reaction mixture was stirred at room temperature for 18 hrs, diluted with water (15 ml), concentrated under reduced pressure. Aqueous layer was extracted with EtOAc (3×20 ml) and combined organic layers were dried over anhydrous $Na_2SO_4$ and concentrated under reduced pressure. Purification by flash chromatography (60%-75% EtOAc—hexanes gradient) gave sulfone 19 as a colorless oil. Yield (0.16 g, 55%); $^1$H NMR (400 MHz, $CD_3OD$) δ 8.10 (t, J=7.6 Hz, 1H), 7.95 (d, J=7.6 Hz, 1H), 7.83 (d, J=7.6 Hz, 1H), 4.84-4.81 (m, 1H), 3.47-3.42 (m, 2H), 3.30-3.12 (m, 2H), 2.10-1.98 (m, 1H), 1.94-1.54 (m, 7H), 1.43 (s, 9H), 1.30-0.99 (m, 5H).

Step 3: A mixture of carbamate 19 (0.16 g, 0.39 mmol) and HCl/i-PrOH (2.0 ml, 11 mmol) in EtOAc (5 ml) was stirred at room temperature for 18 hrs and concentrated under reduced pressure to give Example 27 hydrochloride as a colorless oil. Yield (0.12 g, 88%); $^1$H NMR (400 MHz, $CD_3OD$) δ 8.10 (t, J=6.8 Hz, 1H), 7.95 (d, J=7.2 Hz, 1H), 7.83 (d, J=8.0 Hz, 1H), 4.94-4.86 (m, 1H), 3.14-3.04 (m, 2H), 2.24-2.14 (m, 1H), 2.06-1.96 (m, 1H), 1.94-1.54 (m, 7H), 1.30-0.99 (m, 6H); RP-HPLC $t_R$=7.82 min; ESI-MS: m/z 313.2 [M+H]$^+$.

Example 28

Preparation of (R,E)-5-(2-(6-(3-amino-1-hydroxypropyl)pyridin-2-yl)vinyl)nonan-5-ol (R,E)-5-(2-(6-(3-Amino-1-hydroxypropyl)pyridin-2-yl)vinyl)nonan-5-ol was prepared following the method shown in Scheme 7.

SCHEME 7.

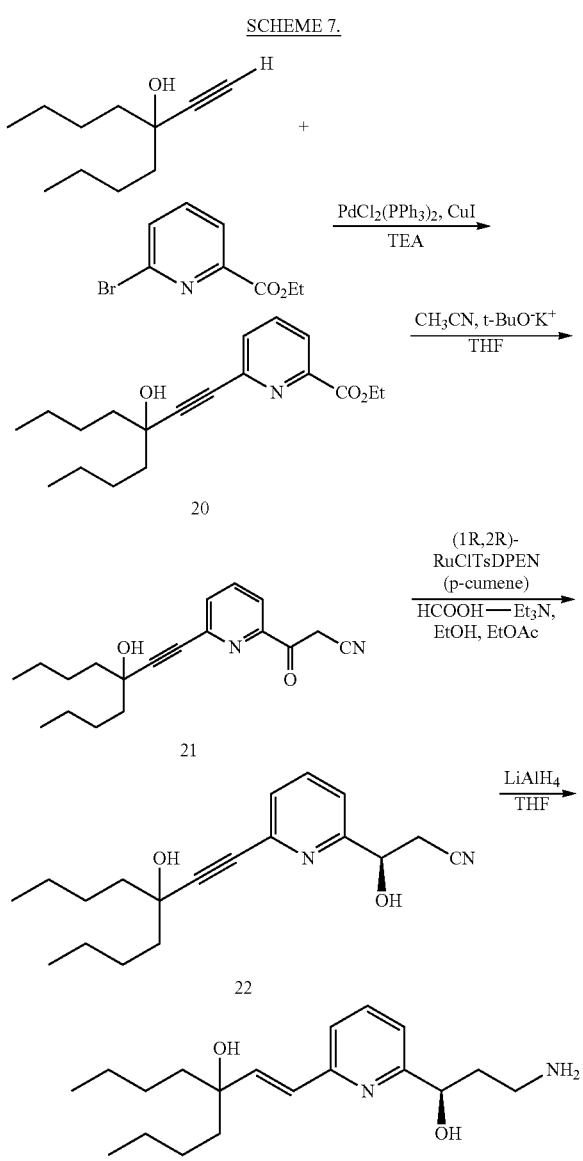

Step 1: CuI (0.07 g, 0.37 mmol) was added to a mixture of 5-ethynylnonan-5-ol (0.76 g, 5.0 mmol), ethyl 6-bromopicolinate (1.0 g, 5.0 mmol) and $PdCl_2$ $(PPh)_2$ (0.1 g, 0.14 mmol) in TEA (20 ml). The reaction mixture was bubbled with argon and then stirred at +70° C. for 18 hrs, cooled to room temperature, diluted with EtOAc (40 ml) and filtered through Celite. Concentration under reduced pressure gave alkyne 20 with was used in the next step without further purification. Yield (1.59 g, quant.).

Step 2: CH$_3$CN addition to ester 20 following the method described in Example 6 gave ketonitrile 21 as a yellow oil which was used in the next step without further purification. Yield (1.63 g, quant.).

Step 3: Chiral reduction of ketonitrile 21 following the method used in Example 6 gave after purification by flash chromatography (35%-50% EtOAc—hexanes gradient) (R)-hydroxynitrile 22 as a white solid. Yield (1.20 g, 70%); $^1$H NMR (400 MHz, DMSO-d$_6$) δ 7.85 (t, J=8.0 Hz, 1H), 7.49 (d, J=7.6 Hz, 1H), 7.33 (d, J=8.0 Hz, 1H), 4.88-4.82 (m, 1H), 3.02-2.82 (m, 2H), 1.66-1.52 (m, 4H), 1.50-1.34 (m, 4H), 1.32-1.22 (m, 4H), 0.92-0.80 (m, 6H).

Step 4: LiAlH$_4$ reduction of (R)-hydroxynitrile 22 following the method used in Example 3 gave after flash chromatography purification (20%-30% 7N NH$_3$/MeOH—CH$_2$Cl$_2$ gradient) Example 28 as a light yellow oil. Yield (0.23 g, 21%); $^1$H NMR (400 MHz, DMSO-d$_6$) δ 7.65 (t, J=7.80 Hz, 1H), 7.26-7.20 (m, 2H), 6.63 (d, J=16 Hz, 1H), 6.50 (d, J=16 Hz, 1H), 4.65-4.56 (m, 1H), 2.72-2.58 (m, 2H), 1.82-1.72 (m, 2H), 1.50-1.38 (m, 4H), 1.32-1.10 (m, 8H), 0.86-0.76 (m, 6H); RP-HPLC t$_R$=7.62 min; ESI-MS m/z 321.1 [M+H]$^+$.

Example 29

Preparation of (R)-5-(2-(6-(3-amino-1-hydroxypropyl)pyridin-2-yl)ethyl)nonan-5-ol

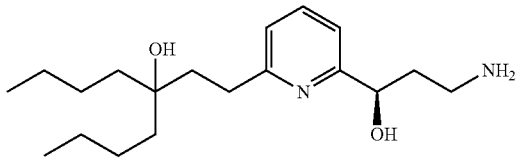 [SMILES: CCCCC(O)(CCCC)CCc1cccc([C@H](O)CCN)n1]

(R)-5-(2-(6-(3-Amino-1-hydroxypropyl)pyridin-2-yl)ethyl)nonan-5-ol was prepared following the method described in Example 11 and below.

Step 1: Hydrogenation of Example 28 following the method used in Example 11 gave Example 29 as pale yellow oil. Yield (0.09 g, 90%); $^1$H NMR (400 MHz, DMSO-d$_6$) δ 7.60 (t, J=7.80 Hz, 1H), 7.24 (d, J=8.0 Hz, 1H), 7.04 (d, J=8.0 Hz, 1H), 4.65-4.56 (m, 1H), 2.72-2.58 (m, 4H), 1.84-1.68 (m, 2H), 1.66-1.54 (m, 2H), 1.36-1.26 (m, 4H), 1.25-1.14 (m, 8H), 0.88-0.78 (m, 6H); RP-HPLC t$_R$=7.50 min; ESI-MS m/z 323.3 [M+H].

Example 30

Preparation of (R)-3-amino-1-(6-(2-ethylbutoxy)pyridin-2-yl)propan-1-ol

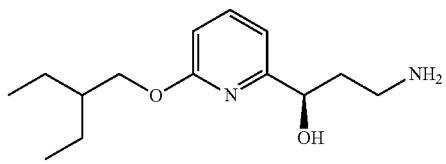 [SMILES: CCC(CC)COc1cccc([C@H](O)CCN)n1]

(R)-3-amino-1-(6-(2-ethylbutoxy)pyridin-2-yl)propan-1-ol was prepared following the method described in Example 6.

Step 1: Reaction of 6-bromopicolinic acid with 2-ethylbutan-1-ol following the method used in Example 6 gave methyl 6-(2-ethylbutoxy)picolinate as a yellow oil which was used in the next step without further purification. Yield (1.19 g, quant.); $^1$H NMR (400 MHz, DMSO-d$_6$) δ 7.83 (t, J=8.0 Hz, 1H), 7.62 (d, J=7.6 Hz, 1H), 7.02 (d, J=8.0 Hz, 1H), 4.18 (d, J=6.0 Hz, 2H), 3.82 (s, 3H), 1.66-1.56 (m, 1H), 1.42-1.32 (m, 4H), 0.86 (t, J=7.6 Hz, 6H).

Step 2: CH$_3$CN addition to methyl 6-(2-ethylbutoxy)picolinate following the method described in Example 6 gave 3-(6-(2-ethylbutoxy)pyridin-2-yl)-3-oxopropanenitrile as a yellow oil which was used in the next step without further purification. Yield (1.2 g, quant.).

Step 3: Borane reduction of 3-(6-(2-ethylbutoxy)pyridin-2-yl)-3-oxopropanenitrile following the method described in Example 6 gave after flash chromatography purification (25%-30% 7N NH$_3$/MeOH—CH$_2$Cl$_2$ gradient) Example 30 as a colorless oil. Yield (0.11 g, 25%); $^1$H NMR (400 MHz, DMSO-d$_6$) δ 7.61 (t, J=7.6 Hz, 1H), 7.0 (d, J=7.6 Hz, 1H), 6.57 (d, J=8.4 Hz, 1H), 4.57-4.50 (m, 1H), 4.15-4.06 (m, 2H), 2.70-2.58 (m, 2H), 1.84-1.76 (m, 1H), 1.64-1.52 (m, 2H), 1.42-1.28 (m, 4H), 0.85 (t, J=7.2 Hz, 6H); RP-HPLC t$_R$=8.51 min; ESI-MS m/z 253.2 [M+H]$^+$.

Example 31

Preparation of (R)-3-amino-1-(6-(cycloheptylmethoxy)pyridin-2-yl)propan-1-ol

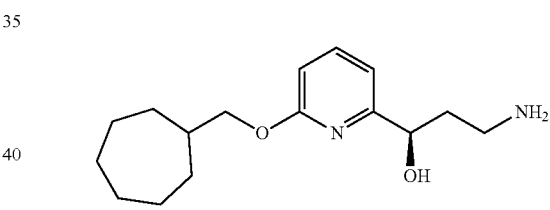

(R)-3-Amino-1-(6-(cycloheptylmethoxy)pyridin-2-yl)propan-1-ol was prepared following the method described in Example 6.

Step 1: Reaction of 6-bromopicolinic acid with cycloheptylmethanol following the method used in Example 6 gave methyl 6-(cycloheptylmethoxy)picolinate as a yellow oil which was used in the next step without further purification. Yield (2.0 g, quant.); $^1$H NMR (400 MHz, DMSO-d$_6$) δ 7.82 (t, J=8.0 Hz, 1H), 7.61 (d, J=7.2 Hz, 1H), 7.03 (d, J=8.0 Hz, 1H), 4.05 (d, J=6.4 Hz, 2H), 3.82 (s, 3H), 1.99-1.01 (m, 13H).

Step 2: CH$_3$CN addition to methyl 6-(cycloheptylmethoxy)picolinate following the method used in Example 6 gave 3-(6-(cycloheptylmethoxy)pyridin-2-yl)-3-oxopropanenitrile as a yellow oil which was used in the next step without further purification. Yield (2.12 g, quant.).

Step 3: Chiral reduction of 3-(6-(cycloheptylmethoxy)pyridin-2-yl)-3-oxopropanenitrile following the method described in Example 6 gave (R)-3-(6-(cycloheptylmethoxy)pyridin-2-yl)-3-hydroxypropanenitrile as a yellow oil after purification by flash chromatography (30%-50% EtOAc—hexanes gradient). Yield (0.77 g, 36%); $^1$H NMR (400 MHz, DMSO-d$_6$) δ 7.67 (t, J=8.0 Hz, 1H), 7.06 (d, J=7.4 Hz, 1H), 6.66 (d, J=8.2 Hz, 1H), 6.05 (d, J=5.0 Hz, 1H), 4.78-4.70 (m, 1H), 4.18-3.96 (m, 2H), 3.01-2.82 (m, 2H), 1.99-1.01 (m, 13H).

Step 4: LiAlH₄ reduction of (R)-3-(6-(cycloheptylmethoxy)pyridin-2-yl)-3-hydroxypropanenitrile following the method described in Example 1 gave after flash chromatography purification (20%-30% 7N NH₃/MeOH—CH₂Cl₂ gradient) Example 31 as a colorless oil. Yield (0.11 g, 25%); ¹H NMR (400 MHz, DMSO-d₆) δ 7.60 (t, J=8.0 Hz, 1H), 7.00 (d, J=6.8 Hz, 1H), 6.67 (d, J=7.6 Hz, 1H), 4.56-4.50 (m, 1H), 4.02-3.98 (m, 2H), 2.72-2.60 (m, 2H), 1.92-1.6 (m, 15H); RP-HPLC $t_R$=9.59 min; ESI-MS m/z 279.2 [M+H]⁺.

Example 32

Preparation of (R)-3-amino-1-(5-((2-propylpentyl)oxy)furan-2-yl)propan-1-ol

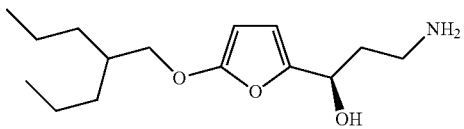 [SMILES: CCCC(CCC)COc1ccc([C@H](O)CCN)o1]

(R)-3-Amino-1-(5-((2-propylpentyl)oxy)furan-2-yl)propan-1-ol was prepared following the method described in Examples 5, 18 and below.

Step 1: Esterification of 5-bromofuran-2-carboxylic acid with 2-propylpentan-1-ol following the method used in Example 18 gave after flash chromatography purification (5%-20% EtOAc—hexanes gradient) 2-propylpentyl 5-bromofuran-2-carboxylate as a colorless oil. Yield (4.85 g, 98%); ¹H NMR (400 MHz, CDCl₃) δ 7.07 (d, J=3.9 Hz, 1H), 6.43 (d, J=3.4 Hz, 1H), 4.18 (d, J=5.9 Hz, 2H), 1.70-1.80 (m, 1H), 1.25-1.40 (m, 8H), 0.83-0.95 (m, 6H).

Step 2: Reaction between 2-propylpentan-1-ol and 2-propylpentyl 5-bromofuran-2-carboxylate following the method used in Example 18, except that NMP was used as the solvent, no CuI was used and the reaction mixture was heated at +50° C. under Ar for 1.5 hrs, gave after flash chromatography purification (2%-5% EtOAc—hexanes gradient) 2-propylpentyl 5-((2-propylpentyl)oxy)furan-2-carboxylate as a colorless oil. Yield (0.62 g, 48%); ¹H NMR (400 MHz, CD₃OD) δ 7.15 (d, J=3.9 Hz, 1H), 5.47 (d, J=3.9 Hz, 1H), 4.14 (d, J=5.9 Hz, 2H), 4.06 (d, J=5.9 Hz, 2H), 1.70-1.84 (m, 2H), 1.28-1.44 (m, 16H), 0.86-0.97 (m, 12H).

Step 3: 2-Propylpentyl 5-((2-propylpentyl)oxy)furan-2-carboxylate (0.62 g, 1.76 mmol), NaOMe (30% in MeOH, 2 mL) in anhydrous MeOH (75 mL) were stirred at room temperature overnight then concentrated under reduced pressure. The residue was partitioned between aqueous NH₄Cl (25%) and hexanes. Organic layer was washed with brine, dried over anhydrous MgSO₄, concentrated under reduced pressure. Flash chromatography purification (5%-20% EtOAc—hexanes gradient) gave methyl 5-((2-propylpentyl)oxy)furan-2-carboxylate as a colorless oil. Yield (0.38 g, 85%); ¹H NMR (400 MHz, CDCl₃) δ 7.12 (d, J=4.0 Hz, 1H), 5.27 (d, J=3.5 Hz, 1H), 3.99 (d, J=5.9 Hz, 2H), 3.03 (s, 3H), 1.74-1.83 (m, 1H), 1.20-1.40 (8H), 0.86-0.94 (m, 6H).

Step 4: Anhydrous CH₃CN (0.15 mL, 2.87 mmol) was added to a solution of LiHMDS (1M/THF, 3.0 mL, 3.0 mmol) at −75° C. under inert atmosphere and the reaction mixture was stirred for 5 min. A solution of methyl 5-((2-propylpentyl)oxy)furan-2-carboxylate (1.337 mmol) in anhydrous THF (7 mL) was added to the reaction mixture and the reaction mixture was stirred under inert atmosphere while slowly warming to 0° C. for over 75 min. The reaction mixture was partitioned between aqueous NaHSO₄ (10%) and EtOAc. Organic layer was washed with brine, concentrated under reduced pressure. Flash chromatography purification (10%-50% EtOAc—hexanes gradient) gave 3-oxo-3-(5-((2-propylpentyl)oxy)furan-2-yl)propanenitrile as an off-white solid. Yield (0.23 g, 66%); ¹H NMR (400 MHz, DMSO-d₆) δ 7.57 (d, J=3.8 Hz, 1H), 5.78 (d, J=3.8 Hz, 1H), 4.30 (s, 2H), 4.08 (d, J=5.6 Hz, 2H), 1.69-1.79 (m, 1H), 1.23-1.35 (m, 8H), 0.80-0.88 (m, 6H).

Step 5: Chiral reduction of 3-oxo-3-(5-((2-propylpentyl)oxy)furan-2-yl)propanenitrile following the method used in Example 5 gave after flash chromatography purification (20%-100% EtOAc—hexanes gradient) (R)-3-hydroxy-3-(5-((2-propylpentyl)oxy)furan-2-yl)propanenitrile as a yellow oil. Yield (0.14 g, 61%); ¹H NMR (400 MHz, DMSO-d₆) δ 6.19 (d, J=2.4 Hz, 1H), 5.86 (d, J=5.4 Hz, 1H), 5.22 (d, J=3.4 Hz, 1H), 4.67 (q, J=5.8 Hz, 1H), 3.84 (d, J=5.4 Hz, 2H), 2.77-2.91 (m, 2H), 1.64-1.75 (m, 1H), 1.20-1.35 (m, 8H), 0.78-0.90 (m, 6H).

Step 6: LiAlH₄ reduction of (R)-3-hydroxy-3-(5-((2-propylpentyl)oxy)furan-2-yl)propanenitrile following the method used in Example 1 gave after flash chromatography purification (2%-20% 7N NH₃/MeOH—CH₂Cl₂ gradient) Example 32 as a colorless oil. Yield (0.080 g, 61%); ¹H NMR (400 MHz, CD₃OD) δ .6.11 (d, J=2.9 Hz, 1H), 5.11 (d, J=2.9 Hz, 1H), 4.56 (t, J=6.9 Hz, 1H), 3.88 (d, J=5.9 Hz, 2H), 2.65-2.78 (m, 2H), 1.88-1.96 (m, 2H), 1.70-1.80 (m, 1H), 1.30-1.44 (m, 8H), 0.085-0.97 (m, 6H); ESI-MS 270.2 m/z [M+H]⁺.

Example 33

Preparation of (R)-3-amino-1-(6-(cyclopentylmethoxy)pyridin-2-yl)propan-1-ol

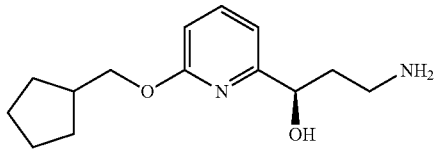 [SMILES: NCC[C@@H](O)c1cccc(OCC2CCCC2)n1]

(R)-3-Amino-1-(6-(cyclopentylmethoxy)pyridin-2-yl)propan-1-ol was prepared following the method described in Example 6.

Step 1: Reaction of 6-bromopicolinic acid with cyclopentylmethanol following the method used in Example 6 gave methyl 6-(cyclopentylmethoxy)picolinate as a yellow oil which was used in the next step without further purification. Yield (1.1 g, quant.); ¹H NMR (400 MHz, DMSO-d₆) δ 7.83 (t, J=8.0 Hz, 1H), 7.62 (d, J=7.2 Hz, 1H), 7.03 (d, J=8.0 Hz, 1H), 4.14 (d, J=6.4 Hz, 2H), 3.82 (s, 3H), 2.32-2.22 (m, 1H), 1.80-1.62 (m, 2H), 1.60-1.44 (m, 4H), 1.38-1.21 (m, 2H).

Step 2: CH₃CN addition to methyl 6-(cyclopentylmethoxy)picolinate following the method described in Example 6 gave 3-(6-(cyclopentylmethoxy)pyridin-2-yl)-3-oxopropanenitrile as a yellow oil which was used in the next step without further purification. Yield (1.22 g, quant.).

Step 3: Chiral reduction of 3-(6-(cyclopentylmethoxy)pyridin-2-yl)-3-oxopropanenitrile following the method described in Example 6 gave (R)-3-(6-(cyclopentylmethoxy)pyridin-2-yl)-3-hydroxypropanenitrile as a yellow oil which was used in the next step without further purification. Yield (1.22 g, quant.); $^1$H NMR (400 MHz, DMSO-d$_6$) δ 7.68 (t, J=7.6 Hz, 1H), 7.07 (d, J=7.6 Hz, 1H), 6.66 (d, J=8.0 Hz, 1H), 6.06 (d, J=5.6 Hz, 1H), 4.78-4.72 (m, 1H), 4.18-4.04 (m, 2H), 3.01-2.82 (m, 2H), 2.32-2.02 (m, 1H), 1.78-1.62 (m, 2H), 1.60-1.42 (m, 4H), 1.36-1.21 (m, 2H).

Step 4: LiAlH$_4$ reduction of (R)-3-(6-(cyclopentylmethoxy)pyridin-2-yl)-3-hydroxypropanenitrile following the method described in Example 1 gave after flash chromatography purification (20%-30% 7N NH$_3$/MeOH—CH$_2$Cl$_2$ gradient) Example 33 as a colorless oil. Yield (0.33 g, 24%); $^1$H NMR (400 MHz, DMSO-d$_6$) δ 7.60 (t, J=7.6 Hz, 1H), 7.00 (d, J=6.8 Hz, 1H), 6.56 (d, J=8.0 Hz, 1H), 4.57-4.51 (m, 1H), 4.10-4.04 (m, 2H), 2.71-2.58 (m, 2H), 2.30-2.02 (m, 1H), 1.82-1.21 (m, 10H); RP-HPLC t$_R$=7.71 min; ESI-MS m/z 251.3 [M+H]$^+$.

Example 34

Preparation of (R)-3-amino-1-(6-(cycloheptyloxy)pyridin-2-yl)propan-1-ol

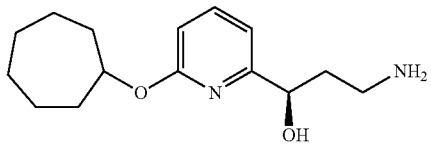 [SMILES: NCC[C@@H](O)c1cccc(OC2CCCCCC2)n1]

(R)-3-Amino-1-(6-(cycloheptyloxy)pyridin-2-yl)propan-1-ol was prepared following the method described in Example 6.

Step 1: Reaction of 6-bromopicolinic acid with cycloheptanol following the method used in Example 6 gave methyl 6-(cycloheptyloxy)picolinate as a yellow oil which was used in the next step without further purification. Yield (1.24 g, quant.); $^1$H NMR (400 MHz, DMSO-d$_6$) δ 7.80 (t, J=8.0 Hz, 1H), 7.58 (d, J=7.2 Hz, 1H), 6.57 (d, J=8.8 Hz, 1H), 5.25-5.15 (m, 1H), 3.80 (s, 3H), 2.0-1.82 (m, 2H), 1.76-1.40 (m, 10H).

Step 2: CH$_3$CN addition to methyl 6-(cycloheptyloxy)picolinate following the method described in Example 6 gave 3-(6-(cycloheptyloxy)pyridin-2-yl)-3-oxopropanenitrile as a yellow oil which was used in the next step without further purification. Yield (1.29 g, quant.).

Step 3: Chiral reduction of 3-(6-(cycloheptyloxy)pyridin-2-yl)-3-oxopropanenitrile following the method described in Example 6 gave (R)-3-(6-(cycloheptyloxy)pyridin-2-yl)-3-hydroxypropanenitrile as a yellow oil which was used in the next step without further purification. Yield (1.29 g, quant.).

Step 4: LiAlH$_4$ reduction of (R)-3-(6-(cycloheptyloxy)pyridin-2-yl)-3-hydroxypropanenitrile following the method described in Example 1 gave after flash chromatography purification (20%-30% 7N NH$_3$/MeOH—CH$_2$Cl$_2$ gradient) Example 34 as a colorless oil. Yield (0.19 g, 14%); $^1$H NMR (400 MHz, DMSO-d$_6$) δ 7.58 (t, J=8.0 Hz, 1H), 6.97 (d, J=7.2 Hz, 1H), 6.51 (d, J=8.0 Hz, 1H), 5.16-5.08 (m, 1H), 4.56-4.48 (m, 1H), 2.72-2.56 (m, 2H), 1.98-1.36 (m, 14H); RP-HPLC t$_R$=7.98 min; ESI-MS m/z 265.2 [M+H]$^+$.

Example 35

Preparation of (R)-ethyl 4-(((6-(3-amino-1-hydroxypropyl)pyridin-2-yl)oxy)methyl)piperidine-1-carboxylate

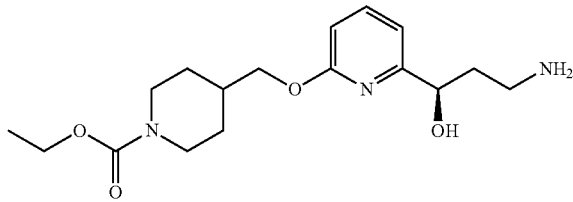 [SMILES: CCOC(=O)N1CCC(COc2cccc([C@H](O)CCN)n2)CC1]

(R)-Ethyl 4-(((6-(3-amino-1-hydroxypropyl)pyridin-2-yl)oxy)methyl)piperidine-1-carboxylate was prepared following the method described in Example 6 and below.

Step 1: Reaction of 6-bromopicolinic acid with piperidin-4-ylmethanol following the method used in Example 6 gave methyl 6-(piperidin-4-ylmethoxy)picolinate as a yellow oil. Yield (0.3 g, 24%); $^1$H NMR (400 MHz, DMSO-d$_6$) δ 7.82 (t, J=8.0 Hz, 1H), 7.62 (d, J=7.4 Hz, 1H), 7.02 (d, J=8.0 Hz, 1H), 4.08 (d, J=6.4 Hz, 2H), 3.82 (s, 3H), 2.98-2.86 (m, 2H), 2.51-2.28 (m, 2H), 1.84-1.71 (m, 1H), 1.66-1.58 (m, 2H), 1.20-1.06 (m, 24H).

Step 2: To a mixture of methyl 6-(piperidin-4-ylmethoxy)picolinate (0.3 g, 1.2 mmol), Et$_3$N (0.2 g, 1.8 mmol) in DCM (10 ml) was added ethyl chloroformate (0.2 g, 1.8 mmol) at 0° C. The reaction was warmed to room temperature, washed with 1N HCl (20 ml), dried over Na$_2$SO$_4$ and concentrated under reduced pressure to give methyl 6-((1-(ethoxycarbonyl)piperidin-4-yl)methoxy)picolinate which used in the next step without further purification. Yield (0.38 g, quant.).

Step 3: CH$_3$CN addition to methyl 6-((1-(ethoxycarbonyl)piperidin-4-yl)methoxy)picolinate following the method described in Example 6 gave ethyl 4-(((6-(2-cyanoacetyl)pyridin-2-yl)oxy)methyl)piperidine-1-carboxylate in ethyl acetate solution which was used in the next step without further purification.

Step 4: Chiral reduction of ethyl 4-(((6-(2-cyanoacetyl)pyridin-2-yl)oxy)methyl)piperidine-1-carboxylate following the method described in Example 6 gave after flash chromatography purification (20%-75% EtOAc—hexanes gradient) (R)-ethyl 4-(((6-(2-cyano-1-hydroxyethyl)pyridin-2-yl)oxy)methyl)piperidine-1-carboxylate as a yellow oil. Yield (0.27 g, 81%); $^1$H NMR (400 MHz, DMSO-d$_6$) δ 7.67 (t, J=8.0 Hz, 1H), 7.12 (d, J=7.2 Hz, 1H), 6.68 (d, J=8.4 Hz, 1H), 4.92-4.83 (m, 1H), 4.21-4.04 (m, 6H), 3.02-2.68 (m, 4H), 2.04-1.98 (m, 1H), 1.88-1.78 (m, 2H), 1.38-1.21 (m, 5H).

Step 5: A mixture of (R)-ethyl 4-(((6-(2-cyano-1-hydroxyethyl)pyridin-2-yl)oxy)methyl)piperidine-1-carboxylate (0.27 g, 0.81 mmol), Sponge Nickel catalyst A-4000 (0.1 g, Johnson Mathey) in 7N NH$_3$/MeOH (20 ml) was shaked under H$_2$ at 50 psi pressure at 50° C. in a Parr hydrogenator for 18 hrs, cooled to room temperature, filtered, concentrated under reduced pressure. Purification by flash chromatography (20%-30% 7N NH$_3$/MeOH—CH$_2$Cl$_2$ gradient) gave Example 35 as a light yellow oil. Yield (0.26 g, 95%); $^1$H NMR (400 MHz, CD$_3$OD) δ 7.64 (t, J=8.4 Hz, 1H), 7.04 (d, J=8.4 Hz, 1H), 6.63 (d, J=8.0 Hz, 1H), 4.70-4.62 (m, 1H), 4.18-4.08 (m, 6H), 2.82-2.78 (m, 4H), 2.08-1.81 (m, 5H), 1.25-1.21 (m, 5H); RP-HPLC $t_R$=6.99 min; ESI-MS m/z 338.3 [M+H]$^+$.

Example 36

Preparation of (R)-benzyl 4-(((6-(3-amino-1-hydroxypropyl)pyridin-2-yl)oxy)methyl)piperidine-1-carboxylate

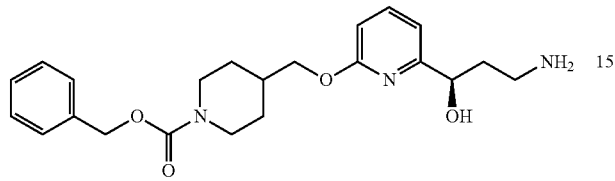

(R)-Benzyl 4-(((6-(3-amino-1-hydroxypropyl)pyridin-2-yl)oxy)methyl)piperidine-1-carboxylate was prepared following the method described in Example 6 and 35.

Step 1: Reaction of methyl 6-(piperidin-4-ylmethoxy)picolinate with benzyoxy chloroformate following the method described in Example 35 gave after flash chromatography purification (30%-50% EtOAc—hexanes gradient) methyl 6-((1-((benzyloxy)carbonyl)piperidin-4-yl)methoxy)picolinate. Yield (1.5 g, 61%); $^1$H NMR (400 MHz, DMSO-d$_6$) δ 7.84 (t, J=8.4 Hz, 1H), 7.63 (d, J=8.0 Hz, 1H), 7.36-7.24 (m, 5H), 7.04 (d, J=8.0 Hz, 1H), 5.04 (s, 2H), 4.12 (d, J=6.8 Hz, 2H), 4.07-3.96 (m, 4H), 3.02 (s, 3H), 2.01-1.81 (m, 1H), 1.78-1.66 (m, 2H), 1.21-1.12 (m, 2H).

Step 2: CH$_3$CN addition to 6-((1-((benzyloxy)carbonyl)piperidin-4-yl)methoxy)picolinate following the method described in Example 6 gave benzyl 4-(((6-(2-cyanoacetyl)pyridin-2-yl)oxy)methyl)piperidine-1-carboxylate in which was used in the next step without further purification. Yield (1.53 g, quant).

Step 3: Chiral reduction of benzyl 4-(((6-(2-cyanoacetyl)pyridin-2-yl)oxy)methyl)piperidine-1-carboxylate following the method described in Example 6 gave after flash chromatography purification (50%-75% EtOAc—hexanes gradient) (R)-benzyl 4-(((6-(2-cyano-1-hydroxyethyl)pyridin-2-yl)oxy)methyl)piperidine-1-carboxylate as a yellow oil. Yield (1.0 g, 65%); $^1$H NMR (400 MHz, CD$_3$OD) δ 7.66 (t, J=8.0 Hz, 1H), 7.36-7.25 (m, 5H), 7.12 (d, J=7.2 Hz, 1H), 6.67 (d, J=8.4 Hz, 1H), 5.10 (s, 2H), 4.87 (t, J=6.0 Hz, 1H), 4.21-4.10 (m, 4H), 3.02-2.76 (m, 4H), 2.06-1.98 (m, 1H), 1.90-1.78 (m, 2H), 1.36-1.20 (m, 2H).

Step 4: Borane-dimethylsulfide reduction of (R)-benzyl 4-(((6-(2-cyano-1-hydroxyethyl)pyridin-2-yl)oxy)methyl)piperidine-1-carboxylate following the method described in Example 2 gave after flash chromatography purification (30%-40% 7N NH$_3$/MeOH—CH$_2$Cl$_2$ gradient) Example 36 as a colorless oil. Yield (0.27 g, 27%); $^1$H NMR (400 MHz, CD$_3$OD) δ 7.63 (t, J=8.4 Hz, 1H), 7.38-7.25 (m, 5H), 7.03 (d, J=7.2 Hz, 1H), 6.62 (d, J=8.0 Hz, 1H), 5.10 (s, 2H), 4.70-4.62 (m, 1H), 4.21-4.10 (m, 4H), 2.88-2.78 (m, 4H), 2.02-1.70 (m, 5H), 1.34-1.20 (m, 2H); RP-HPLC $t_R$=9.40 min; ESI-MS m/z 400.3 [M+H]$^+$.

Example 37

Preparation of 3-amino-1-(6-((2-propylpentyl)oxy)pyridin-2-yl)propan-1-one

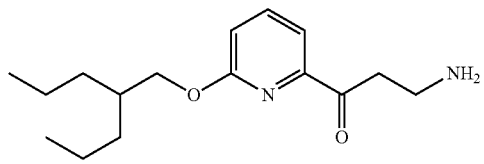 [SMILES: CCCC(CCC)COc1cccc(C(=O)CCN)n1]

3-Amino-1-(6-((2-propylpentyl)oxy)pyridin-2-yl)propan-1-one was prepared following the method used in Example 27 and below.

Step 1: Reaction of Example 19 with di-tert-butyl carbonate following the method described in Example 27 gave (R)-tert-butyl (3-hydroxy-3-(6-((2-propylpentyl)oxy)pyridin-2-yl)propyl)carbamate in solution which was treated in situ with PCC (0.16 g, 0.76 mmol) at room temperature for 18 hrs. The reaction mixture was filtered via Celite, concentrated under reduced pressure, purified by flash chromatography (50%-75% EtOAc—hexanes gradient) to give tert-butyl (3-oxo-3-(6-((2-propylpentyl)oxy)pyridin-2-yl)propyl)carbamate as a pale yellow oil without further purification. Yield (0.03 g, 21%); $^1$H NMR (400 MHz, CD$_3$OD) δ 7.80 (t, J=8.4 Hz, 1H), 7.58 (d, J=7.2 Hz, 1H), 6.97 (d, J=8.0 Hz, 1H), 4.31 (d, J=5.6 Hz, 2H), 3.48-3.40 (m, 2H), 3.38-3.32 (m, 2H), 1.91-1.84 (m, 1H), 1.48-1.35 (m, 17H), 0.92-0.82 (m, 6H).

Step 2: Deprotection of tert-butyl (3-oxo-3-(6-((2-propylpentyl)oxy)pyridin-2-yl)propyl)carbamate following the method described in Example 27 gave Example 37 hydrochloride as a colorless oil. Yield (0.01 g, 38%); $^1$H NMR (400 MHz, CD$_3$OD) δ 7.84 (t, J=8.4 Hz, 1H), 7.66 (d, J=8.0 Hz, 1H), 7.04 (d, J=8.4 Hz, 1H), 4.30 (d, J=5.6 Hz, 2H), 3.60 (t, J=6.4 Hz, 2H), 3.38-3.32 (m, 2H), 1.92-1.82 (m, 1H), 1.54-1.35 (m, 8H), 0.92-0.82 (m, 6H); RP-HPLC $t_R$=11.33 min; ESI-MS m/z 279.3 [M+H]$^+$.

Example 38

Preparation of 3-amino-1-(6-((tetrahydro-2H-pyran-4-yl)methoxy)pyridin-2-yl)propan-1-ol

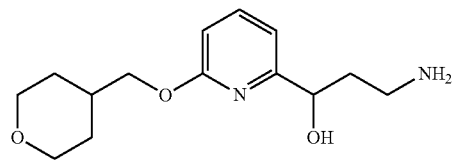 [SMILES: NCCC(O)c1cccc(OCC2CCOCC2)n1]

3-Amino-1-(6-((tetrahydro-2H-pyran-4-yl)methoxy)pyridin-2-yl)propan-1-ol is prepared following the method used in Examples 2 and 6.

Step 1: Reaction between (tetrahydro-2H-pyran-4-yl)methanol and NaH followed by addition of 6-bromopicolinic acid 12 following the method used in Example 6 gives, after esterification with HCl/MeOH, methyl 6-((tetrahydro-2H-pyran-4-yl)methoxy)picolinate.

Step 2: Reaction between methyl 6-((tetrahydro-2H-pyran-4-yl)methoxy)picolinate and CH$_3$CN following the method used in Example 6 gives 3-oxo-3-(6-((tetrahydro-2H-pyran-4-yl)methoxy)pyridin-2-yl)propanenitrile.

Step 3: Reduction of 3-oxo-3-(6-((tetrahydro-2H-pyran-4-yl)methoxy)pyridin-2-yl)propanenitrile by LiAlH₄ following the method used in Example 2 gives Example 38.

Example 39

Preparation of (S)-3-amino-1-(6-((2-propylpentyl)oxy)pyridin-2-yl)propan-1-ol

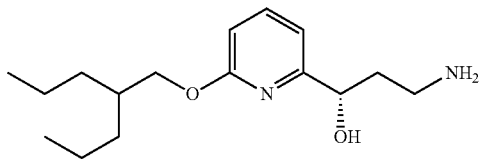 [SMILES: CCCC(CCC)COc1cccc([C@@H](O)CCN)n1]

(S)-3-Amino-1-(6-((2-propylpentyl)oxy)pyridin-2-yl)propan-1-ol was prepared following the method used in Example 6.

Step 1: Chiral reduction of 3-oxo-3-(6-((2-propylpentyl)oxy)pyridin-2-yl)propanenitrile following the method used in Example 6 using (1S,2S)—RuCl(TsDPEN)(p-cymene) as the catalyst gave (S)-3-hydroxy-3-(6-((2-propylpentyl)oxy)pyridin-2-yl)propanenitrile as an off-white solid which was used directly in next step without purification. Yield (0.83 g, quant.).

Step 2: Reduction of (S)-3-hydroxy-3-(6-((2-propylpentyl)oxy)pyridin-2-yl)propanenitrile following the method used in Example 6 followed by treating with HCl-MeOH gave Example 39 as a colorless oil. Yield (0.25 g, 39%); $^1$H NMR (400 MHz, DMSO-d₆) δ 7.63 (t, J=8.4 Hz, 1H), 7.03 (d, J=8.0 Hz, 1H), 6.62 (d, J=7.6 Hz, 1H), 4.70-4.66 (m, 1H), 4.20-4.14 (m, 2H), 2.82-2.78 (m, 2H), 2.02-1.78 (m, 3H), 1.44-1.38 (m, 8H), 0.98-0.84 (m, 6H); RP-HPLC $t_R$=10.38 min; ESI-MS m/z 281.2 [M+H]⁺.

Example 40

Preparation of (R)-3-amino-1-(6-(piperidin-4-ylmethoxy)pyridin-2-yl)propan-1-ol

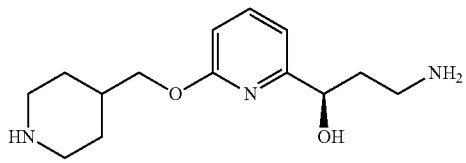 [SMILES: NCC[C@@H](O)c1cccc(OCC2CCNCC2)n1]

(R)-3-amino-1-(6-(piperidin-4-ylmethoxy)pyridin-2-yl)propan-1-ol was prepared following the method described in Example 6 and below.

Step 1: Reaction of Example 36 with di-tert-butyl carbonate following the method used in Example 27 gave after flash chromatography purification (50%-75% EtOAc—hexanes gradient) (R)-benzyl 4-(((6-(3-((tert-butoxycarbonyl)amino)-1-hydroxypropyl)pyridin-2-yl)oxy)methyl)piperidine-1-carboxylate as a colorless oil. Yield (0.3 g, 61%); $^1$H NMR (400 MHz, CD₃OD) δ 7.62 (t, J=8.4 Hz, 1H), 7.36-7.28 (m, 5H), 7.01 (d, J=7.6 Hz, 1H), 6.61 (d, J=7.6 Hz, 1H), 5.10 (s, 2H), 4.64-4.57 (m, 1H), 4.21-4.04 (m, 4H), 3.22-3.08 (m, 2H), 2.98-2.78 (m, 2H), 2.08-1.98 (m, 1H), 1.88-1.66 (m, 2H), 1.42 (s, 9H), 1.36-1.08 (m, 2H).

Step 2: Deprotection of (R)-benzyl 4-(((6-(3-((tert-butoxycarbonyl)amino)-1-hydroxypropyl)pyridin-2-yl)oxy)methyl)piperidine-1-carboxylate by hydrogenation following the method used in Example 11 gave (R)-tert-butyl (3-hydroxy-3-(6-(piperidin-4-ylmethoxy)pyridin-2-yl)propyl)carbamate as a colorless oil. Yield (0.25 g, quant); $^1$H NMR (400 MHz, CD₃OD) δ 7.62 (t, J=8.4 Hz, 1H), 7.02 (d, J=6.8 Hz, 1H), 6.61 (d, J=7.6 Hz, 1H), 4.64-4.58 (m, 1H), 4.18-4.12 (m, 2H), 3.10-3.06 (m, 2H), 2.72-2.61 (m, 2H), 2.06-1.84 (m, 3H), 1.86-1.78 (m, 4H), 1.45-1.20 (m, 11H); ESI-MS m/z 366.3 [M+H]⁺.

Step 3: Deprotection of (R)-tert-butyl (3-hydroxy-3-(6-(piperidin-4-ylmethoxy)pyridin-2-yl)propyl)carbamate following the method described in Example 27 except 2M HCl-Et₂O and CH₂Cl₂ as the solvent were used, gave Example 40 hydrochloride as a colorless oil. Yield (0.16 g, 86%); $^1$H NMR (400 MHz, CD₃OD) δ 8.30 (t, J=8.0 Hz, 1H), 7.47 (d, J=7.6 Hz, 1H), 7.34 (d, J=8.8 Hz, 1H), 5.06-5.03 (m, 1H), 4.38 (d, J=6.4 Hz, 2H), 3.52-3.44 (m, 2H), 3.18-3.14 (m, 2H), 3.10-3.04 (m, 2H), 2.36-2.02 (m, 5H), 1.78-1.64 (m, 2H); RP-HPLC $t_R$=1.69 min; ESI-MS m/z 266.2 [M+H]⁺.

Example 41

Preparation of (R)-3-amino-1-(6-phenethoxypyridin-2-yl)propan-1-ol

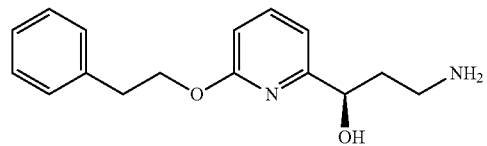 [SMILES: NCC[C@@H](O)c1cccc(OCCc2ccccc2)n1]

(R)-3-Amino-1-(6-phenethoxypyridin-2-yl)propan-1-ol was prepared following the method described in Example 6.

Step 1: Reaction of 6-bromopicolinic acid with 2-phenylethanol following the method used in Example 6 gave methyl 6-phenethoxypicolinate as a yellow oil which was used in the next step without further purification. Yield (1.28 g, quant.); $^1$H NMR (400 MHz, DMSO-d₆) δ 7.85 (t, J=8.4 Hz, 1H), 7.65 (d, J=8.4 Hz, 1H), 7.15-7.35 (m, 5H), 7.04 (d, J=8.0 Hz, 1H), 4.48 (t, J=7.2 Hz, 2H), 3.84 (s, 3H), 3.04 (t, J=6.8 Hz, 2H).

Step 2: CH₃CN addition to methyl 6-phenethoxypicolinate following the method described in Example 6 gave 3-oxo-3-(6-phenethoxypyridin-2-yl)propanenitrile as a yellow oil which was used in the next step without further purification. Yield (1.33 g, quant.).

Step 3: Chiral reduction of 3-oxo-3-(6-phenethoxypyridin-2-yl)propanenitrile following the method described in Example 6 gave after flash chromatography purification (40%-50% EtOAc—hexanes gradient) (R)-3-hydroxy-3-(6-phenethoxypyridin-2-yl)propanenitrile as a colorless oil. Yield (0.6 g, 45%); $^1$H NMR (400 MHz, CD₃OD) δ 7.66 (t, J=8.0 Hz, 1H), 7.30-7.15 (m, 5H), 7.11 (d, J=8.0 Hz, 1H), 6.65 (d, J=8.0 Hz, 1H), 4.90-4.86 (m, 1H), 4.55-4.51 (m, 2H), 3.08-2.84 (m, 4H).

Step 4: LiAlH₄ reduction of (R)-3-hydroxy-3-(6-phenethoxypyridin-2-yl)propanenitrile following the method described in Example 1 gave after flash chromatography purification (20%-30% 7N NH₃/MeOH—CH₂Cl₂ gradient) Example 41 as a colorless oil. Yield (0.13 g, 21%); $^1$H NMR (400 MHz, DMSO-d$_6$) δ 7.62 (t, J=8.0 Hz, 1H), 7.28-7.16 (m, 5H), 7.02 (d, J=8.0 Hz, 1H), 6.60 (d, J=8.0 Hz, 1H), 4.70-4.68 (m, 1H), 4.78 (t, J=7.2 Hz, 2H), 3.05 (t, J=7.2 Hz, 2H), 2.78 (t, J=6.8 Hz, 2H), 2.04-1.82 (m, 2H); RP-HPLC t$_R$=7.83 min; ESI-MS m/z 273.2 [M+H]$^+$.

Example 42

Preparation of 3-(6-(cyclohexylmethoxy)pyridin-2-yl)prop-2-yn-1-amine

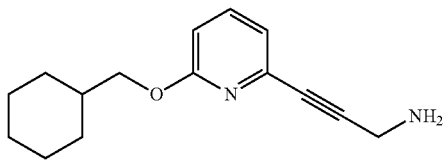 [SMILES: NCC#Cc1cccc(OCC2CCCCC2)n1]

3-(6-(cyclohexylmethoxy)pyridin-2-yl)prop-2-yn-1-amine was prepared following the method shown in Scheme 8.

SCHEME 8.

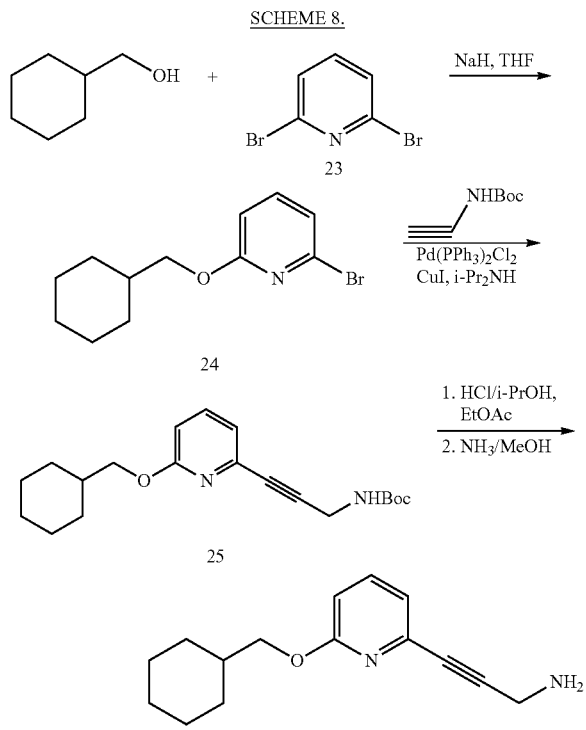

Step 1: Reaction of 2,6-dibromopyridine (23) with cyclohexylmethanol following the method used in Example 6 gave alkoxypyridine 24 as a yellow oil which was used in the next step without additional purification. Yield (1.34 g, quant.); $^1$H NMR (400 MHz, DMSO-d$_6$) δ 7.61 (t, J=8.0 Hz, 1H), 7.17 (d, J=8.0 Hz, 1H), 6.82 (d, J=8.4 Hz, 1H), 4.00 (d, J=6.0 Hz, 2H), 1.80-1.61 (m, 6H), 1.24-0.98 (m, 5H).

Step 2: A solution of 2-bromopyridine 24 (0.68 g, 2.53 mmol), Pd(PPh$_3$)$_2$Cl$_2$ (0.09 g, 0.12 mmol), CuI (0.03 g, 0.15 mmol) in i-Pr$_2$NH (15 ml) was saturated with nitrogen and tert-butyl prop-2-yn-1-ylcarbamate (0.35 g, 2.25 mmol) was added to the reaction mixture. The resulting mixture was stirred at 50° C. for 18 hr, concentrated under reduced pressure, partitioned between 1N HCl (10 ml), NH$_4$Cl (30 ml) and EtOAc (80 ml). Organic layer was dried over Na$_2$SO$_4$, concentrated under reduced pressure and purified by flash chromatography (50%-75% EtOAc—hexanes gradient) to give propargylpyridine 25 as a light yellow oil. Yield (0.38 g, 44%); $^1$H NMR (400 MHz, CD$_3$OD) δ 7.59 (t, J=8.0 Hz, 1H), 7.01 (d, J=7.2 Hz, 1H), 6.72 (d, J=8.4 Hz, 1H), 4.08-4.02 (m, 4H), 1.88-1.66 (m, 6H), 1.46 (s, 9H), 1.38-1.02 (m, 5H).

Step 3: Hydrogen chloride deprotection of carbamate 25 following the method used in Example 27 gave after flash chromatography purification (15%-25% 7N NH$_3$/MeOH—CH$_2$Cl$_2$ gradient) Example 42 as a yellow oil. Yield (0.03 g, 27%); $^1$H NMR (400 MHz, CD$_3$OD) δ 7.62 (t, J=8.0 Hz, 1H), 7.36 (d, J=7.6 Hz, 1H), 6.64 (d, J=8.8 Hz, 1H), 4.09 (d, J=6.4 Hz, 2H), 3.54 (s, 2H), 1.86-1.64 (m, 6H), 1.28-1.02 (m, 5H); RP-HPLC t$_R$=10.42 min; ESI-MS m/z 281.1 [M+H]$^+$.

Example 43

Preparation of 3-(methylamino)-1-(6-((2-propylpentyl)oxy)pyridin-2-yl)propan-1-ol

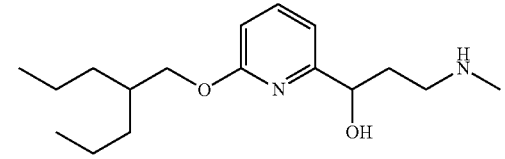 [SMILES: CCCC(CCC)COc1cccc(C(O)CCNC)n1]

3-(Methylamino)-1-(6-((2-propylpentyl)oxy)pyridin-2-yl)propan-1-ol was prepared following the method described in Example 6.

Step 1: Reduction of 3-oxo-3-(6-((2-propylpentyl)oxy)pyridin-2-yl)propanenitrile following the method used in Example 6 gave after flash chromatography (20%-30% 7N NH$_3$/MeOH—CH$_2$Cl$_2$ gradient) 3-amino-1-(6-((2-propylpentyl)oxy)pyridin-2-yl)propan-1-ol as a colorless oil. Yield (0.16 g, 28%); $^1$H NMR (400 MHz, CD$_3$OD) δ 7.63 (t, J=8.4 Hz, 1H), 7.03 (d, J=8.0 Hz, 1H), 6.62 (d, J=8.0 Hz, 1H), 4.70-4.67 (m, 1H), 4.21-4.14 (m, 2H), 2.82-2.78 (m, 2H), 2.06-1.78 (m, 3H), 1.48-1.28 (m, 8H), 0.98-0.86 (m, 6H); ESI-MS m/z 281.2 [M+H]$^+$.

Step 2: Reaction of 3-amino-1-(6-((2-propylpentyl)oxy)pyridin-2-yl)propan-1-ol with di-tert-butyl carbonate following the method described in Example 27 gave after flash chromatography purification (50%-75% EtOAc—hexanes gradient) tert-butyl (3-hydroxy-3-(6-((2-propylpentyl)oxy)pyridin-2-yl)propyl)carbamate as a colorless oil which was used in the next step without purification. Yield (0.09 g, 41%).

Step 3: LiAlH$_4$ reduction of tert-butyl (3-hydroxy-3-(6-((2-propylpentyl)oxy)pyridin-2-yl)propyl)carbamate following the method described in Example 1 gave after flash chromatography purification (30%-40% 7N NH$_3$/MeOH—CH$_2$Cl$_2$ gradient) Example 43 as a colorless oil; Yield (0.04 g, 62%); $^1$H NMR (400 MHz, DMSO-d$_6$) δ 7.63 (t, J=8.4 Hz, 1H), 7.03 (d, J=8.0 Hz, 1H), 6.62 (d, J=8.0 Hz, 1H), 4.69-4.66 (m, 1H), 4.18-4.16 (m, 2H), 2.76-2.72 (m, 2H), 2.40 (s, 3H), 2.10-1.68 (m, 3H), 1.46-1.26 (m, 8H), 0.96-0.88 (m, 6H); RP-HPLC t$_R$=10.66 min; ESI-MS m/z 295.3 [M+H]$^+$.

Example 44

Preparation of N-(3-hydroxy-3-(6-((2-propylpentyl)oxy)pyridin-2-yl)propyl)acetamide

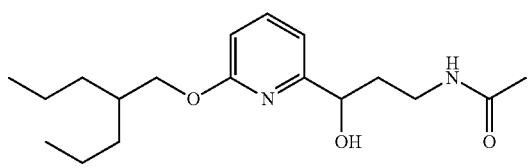 [SMILES: CCCC(CCC)COc1cccc(C(O)CCNC(C)=O)n1]

N-(3-Hydroxy-3-(6-((2-propylpentyl)oxy)pyridin-2-yl)propyl)acetamide is prepared following the method used in Example 43 and below.

Step 1: Acetylation of 3-amino-1-(6-((2-propylpentyl)oxy)pyridin-2-yl)propan-1-ol with Ac₂O or AcCl in the presence of tertiary base, such as Et₃N, in an appropriate solvent gives Example 44.

Example 45

Preparation of 3-amino-1-(2-(cyclohexylmethoxy)pyrimidin-4-yl)propan-1-ol

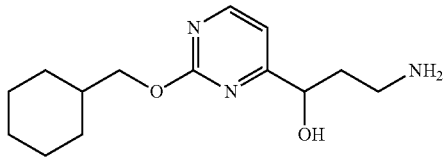 [SMILES: NCCC(O)c1ccnc(OCC2CCCCC2)n1]

3-Amino-1-(2-(cyclohexylmethoxy)pyrimidin-4-yl)propan-1-ol is prepared following the method described in Example 6 and shown in Scheme 9.

Scheme 9.

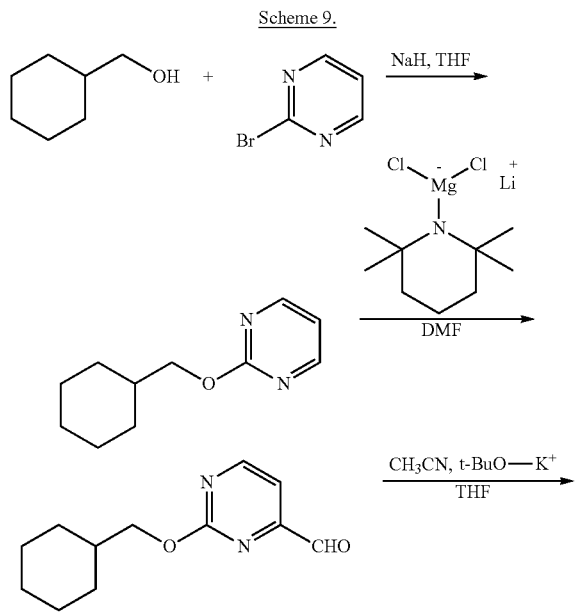

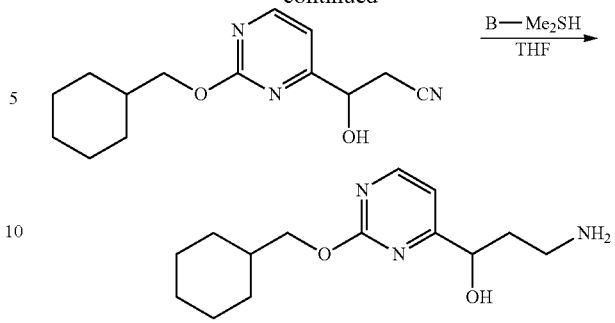

Step 1: NaH (1.1 equivalent) is added to an equimolar mixture of 2-bromopyrimidine and cyclohexylmethanol in THF. The reaction mixture is stirred at +60° C. for 18 hours, cooled to room temperature, partitioned between H₂O and ethyl acetate. Organic portion is separated, dried over anhydrous Na₂SO₄ and concentrated under reduced pressure to give 2-(cyclohexylmethoxy)pyrimidine.

Step 2: Knochel-Hauser reagent (2,2,6,6-tetramethylpiperidinylmagnesium chloride lithium chloride complex) is added to a mixture of 2-(cyclohexylmethoxy)pyrimidine in THF at −78° C., stirred for 15 min, then DMF is added. The reaction mixture is stirred at −30° C., quenched by aqueous NH₄Cl, extracted with ethyl acetate. Combined organic layers are dried over anhydrous Na₂SO₄ and concentrated under reduced pressure to give 2-(cyclohexylmethoxy)-pyrimidine-4-carbaldehyde.

Step 3: CH₃CN addition to 2-(cyclohexylmethoxy)pyrimidine-4-carbaldehyde following the method described in Example 6 gives 3-(2-(cyclohexylmethoxy)pyrimidin-4-yl)-3-hydroxypropanenitrile.

Step 4: Reduction of 3-(2-(cyclohexylmethoxy)pyrimidin-4-yl)-3-hydroxypropanenitrile with BH₃-Me₂S following the method described in Example 2 gives Example 45.

Example 46

Preparation of (R)-3-amino-1-(4-(cyclohexylmethoxy)pyrimidin-2-yl)propan-1-ol

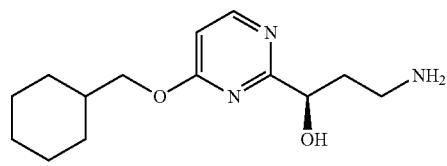 [SMILES: NCC[C@@H](O)c1nccc(OCC2CCCCC2)n1]

(R)-3-Amino-1-(4-(cyclohexylmethoxy)pyrimidin-2-yl)propan-1-ol is prepared following the method described in Example 6.

Step 1: Reaction of cyclohexylmethanol and 4-bromopyrimidine-2-carboxylic acid following the method described in Example 6 gives methyl 4-(cyclohexylmethoxy)pyrimidine-2-carboxylate.

Step 2: CH₃CN addition to methyl 4-(cyclohexylmethoxy)pyrimidine-2-carboxylate following the method described in Example 6 gives 3-(4-(cyclohexylmethoxy)pyrimidin-2-yl)-3-oxopropanenitrile.

Step 3: Chiral reduction of 3-(4-(cyclohexylmethoxy)pyrimidin-2-yl)-3-oxopropanenitrile following the method described in Example 6 gives (R)-3-(4-(cyclohexylmethoxy)pyrimidin-2-yl)-3-hydroxypropanenitrile Step 4: Reduction of (R)-3-(4-(cyclohexylmethoxy)pyrimidin-2-yl)-3-hydroxypropanenitrile with $BH_3$-$Me_2S$ following the method described in Example 2 gives Example 46.

II. Biological Evaluation

Example 1

In Vitro Isomerase Inhibition

The capability of compounds disclosed herein to inhibit the activity of a visual cycle isomerase was determined. In particular, the human in vitro isomerase assay was performed essentially as in Golczak et al. Proc. Natl. Acad. Sci. (2005) 102, 8162-8167, and in Imanishi, et al. J. Cell Biol. (2004), 164, 373-383.

Isolation of Human Apo Cellular Retinaldehyde-Binding Protein (CRALBP)

Recombinant human apo cellular retinaldehyde-binding protein (CRALBP) was cloned and expressed according to standard molecular biology methods (see Crabb et al., *Protein Science* 7:746-57 (1998); Crabb et al., *J. Biol. Chem.* 263:18688-92 (1988)). Briefly, total RNA was prepared from confluent ARPE19 cells (American Type Culture Collection, Manassas, Va.), cDNA was synthesized using an oligo(dT)$_{12-18}$ primer, and then DNA encoding CRALBP was amplified by two sequential polymerase chain reactions (see Crabb et al., *J. Biol. Chem.* 263:18688-92 (1988); Intres, et al., *J. Biol. Chem.* 269:25411-18 (1994); GenBank Accession No. L34219.1). The PCR product was sub-cloned into pTrcHis2-TOPO TA vector according to the manufacturer's protocol (Invitrogen Inc., Carlsbad, Calif.; catalog no. K4400-01), and then the sequence was confirmed according to standard nucleotide sequencing techniques. Recombinant 6×His-tagged human CRALBP was expressed in One Shot TOP 10 chemically competent *E. coli* cells (Invitrogen), and the recombinant polypeptide was isolated from *E. coli* cell lysates by nickel affinity chromatography using nickel (Ni) Sepharose XK16-20 columns for HPLC (Amersham Bioscience, Pittsburgh, Pa.; catalog no. 17-5268-02). The purified 6×His-tagged human CRALBP was dialyzed against 10 mM bis-tris-Propane (BTP) and analyzed by SDS-PAGE. The molecular weight of the recombinant human CRALBP was approximately 39 kDal.

Isomerase Assay

Compounds disclosed herein and control compounds were reconstituted in ethanol to 0.1 M. Ten-fold serial dilutions ($10^{-2}$, $10^{-3}$, $10^{-4}$, $10^{-5}$, $10^{-6}$ M) in ethanol of each compound were prepared for analysis in the isomerase assay.

A homogenate of HEK293 cell clone expressing recombinant human RPE65 and LRAT were the source of the visual enzymes, and exogenous all-trans-retinol (about 20 µM) was used as the substrate. Recombinant human CRALBP (about 80 ug/mL) was added to enhance the formation of 11-cis-retinal. The 200 µL Bis-Tris Phosphate buffer (10 mM, pH 7.2) based reaction mixture also contains 0.5% BSA, and 1 mM NaPPi. In this assay, the reaction was carried out at 37° C. in duplicates for one hour and was terminated by addition of 300 µL methanol. The amount of reaction product, 11-cis-retinol, was measured by HPLC analysis following Heptane extraction of the reaction mixture. The Peak Area Units (PAUs) corresponding to 11-cis-retinol in the HPLC chromatograms were recorded and concentration dependent curves analyzed by GraphPad Prism for $IC_{50}$ values. The ability of the compounds disclosed herein to inhibit isomerization reaction was quantified and the respective $IC_{50}$ value was determined. Tables 2 below summarize the $IC_{50}$ values of various compounds disclosed herein determined as described above.

TABLE 2

Human in vitro Inhibition data

| $IC_{50}$ (µM) | Example Number |
|---|---|
| ≤0.1 µM | 1, 2, 3, 4, 5, 6, 10, 11, 12, 13, 14, 16, 17, 18, 19, 20, 21, 22, 23, 24, 25, 26, 28, 30, 31, 32, 33, 34, 35, 36, 37, 39, 41, 43 |
| >0.1 µM-≤1 µM | 7, 8, 9, 15, 27, 29 |
| >1 µM-≤10 µM | 40 |
| >10 µM | |
| No detectable activity | |

Example 2

In Vivo Murine Isomerase Assay

The capability of compounds described herein to inhibit isomerase was determined by an in vivo murine isomerase assay. Brief exposure of the eye to intense light ("photobleaching" of the visual pigment or simply "bleaching") is known to photo-isomerize almost all 11-cis-retinal in the retina. The recovery of 11-cis-retinal after bleaching was used to estimate the activity of isomerase in vivo. Delayed recovery, as represented by lower 11-cis-retinal oxime levels, indicates inhibition of isomerization reaction. Procedures were performed essentially as described by Golczak et al., *Proc. Natl. Acad. Sci. USA* 102:8162-67 (2005). See also Deigner et al., *Science,* 244: 968-71 (1989); Gollapalli et al., *Biochim Biophys Acta.* 1651: 93-101 (2003); Parish, et al., *Proc. Natl. Acad. Sci. USA,* 14609-13 (1998); Radu, et al., *Proc Natl Acad Sci USA* 101: 5928-33 (2004).

Six-week old dark-adapted CD-1 (albino) male mice were orally gavaged with compound (0.03-3 mg/kg) dissolved in 100 µl corn oil containing 10% ethanol (five animals per group). After 2-24 hours in the dark, the mice were exposed to photobleaching of 5,000 lux of white light for 10 minutes. The mice were allowed to recover 2 hours in the dark. The animals were then sacrificed by carbon dioxide inhalation. Retinoids were extracted from the eye and the regeneration of 11-cis-retinal was assessed at various time intervals.

Eye Retinoid Extraction

All steps were performed in darkness with minimal redlight illumination (low light darkroom lights and red-filtered flashlights for spot illumination as needed) (see, e.g., Maeda et al., *J. Neurochem* 85:944-956, 2003; Van Hooser et al., *J Biol Chem* 277:19173-82, 2002). After the mice were sacrificed, the eyes were immediately removed and placed in liquid nitrogen for storage.

The eyes were placed in 500 µL of bis-tris propane buffer (10 mM, pH ~7.3) and 20 µL of 0.8M hydroxile amine (pH~7.3). The eyes were cut up into small pieces with small iris scissors and then thoroughly homogenized at 30000 rpm with a mechanical homogenizer (Polytron PT 1300 D) in the tube until no visible tissue remained. 500 µL of methanol and 500 µL of heptane were added to each tube. The tubes were attached to a vortexer so that the contents were mixed thoroughly for 15 minutes in room temperature. The organic phase was separated from the aqueous phase by centrifugation for 10 min at 13K rpm, 4° C. 240 µL of the solution from the top layer (organic phase) was removed and transferred to clean 300 µl glass inserts in HPLC vials using glass pipette and the vials were crimped shut tightly.

The samples were analyzed on an Agilent 1100 HPLC system with normal phase column: SILICA (Beckman Coutlier, dp 5 µm, 4.6 mM×250 mM). The running method had a flow rate of 1.5 ml/min; solvent components are 15% solvent 1 (1% isopropanol in ethyl acetate), and 85% solvent 2 (100% hexanes). Loading volume for each sample was 100 µl; detection wavelength is 360 nm. The area under the curve for 11-cis retinal oxime was calculated by Agilent Chemstation software and was recorded manually. Data processing was performed using Prizm software.

Positive control mice (no compound administered) were sacrificed fully dark-adapted and the eye retinoids analyzed. Light (bleached) control mice (no compound administered) were sacrificed and retinoids isolated and analyzed immediately after light treatment.

A time course study was performed to determine the isomerase inhibitory activity of the test compound. Male Balb/c mice (4/group) receive test compound orally by gavage. The animals were then "photo-bleached" (5000 Lux white light for 10 minutes) at 2, 4, 8, 16 and 24 hours after dosing, and returned to darkness to allow recovery of the 11-cis-retinal content of the eyes. Mice were sacrificed 2 hours after bleaching, eyes were enucleated, and retinoid content was analyzed by HPLC.

Recovery control mice (vehicle-only treated) were light-treated and left to recover for 2 hours in the dark before sacrifice and analysis. Light control mice (vehicle only treated) were sacrificed for analysis immediately after photo-bleaching.

Table 3 provides in vivo murine isomerase assay results of various compounds disclosed herein at the dose and time point indicated.

TABLE 3

In Vivo Murine Isomerase Assay data

| Synthesis Example | Inhibition, % | Dose (mg/kg) | Time (hour) |
|---|---|---|---|
| 1 | 0 | 1 | 2 |
| 1 | 0 | 1 | 4 |
| 3 | 0 | 1 | 2 |
| 4 | 29.3 ± 4.3 | 1 | 2 |
| 5 | 0 | 1 | 2 |
| 6 | 68.9 ± 6.5 | 1 | 2 |
| 6 | 37.7 ± 14.9 | 1 | 4 |
| 6 | 93.2 ± 0.9 | 3 | 2 |
| 6 | 85.5 ± 2.9 | 3 | 4 |
| 6 | 62.3 ± 3.8 | 3 | 6 |
| 6 | 30.8 ± 9.9 | 3 | 8 |
| 6 | 0 | 3 | 16 |
| 6 | 0 | 3 | 24 |
| 9 | 8.6 ± 4.2 | 1 | 2 |
| 12 | 0 | 1 | 2 |
| 19 | 98.2 ± 2.3 | 1 | 4 |
| 19 | 90.7 ± 3.3 | 1 | 8 |

Example 3

In Vivo Light Damage Mouse Model

This Example describes the effect of a compound disclosed herein in an in vivo light damage mouse model.

Exposure of the eye to intense white light can cause photo-damage to the retina. The extent of damage after light treatment is evaluated by measuring cytoplasmic histone-associated-DNA-fragment (mono- and oligonucleosomes) content in the eye (see, e.g., Wenzel et al., Prog. Retin. Eye Res. 24:275-306 (2005)).

Dark adapted male Balb/c (albino, 10/group) mice are gavaged with text compound at various doses (0.03, 0.1, 0.3, 1, and 3 mg/kg) or vehicle only was administered. Six hours after dosing, the animals are subjected to light treatment (8,000 lux of white light for 1 hour). Mice are sacrificed after 40 hours of recovery in dark, and retinas are dissected. A cell death detection ELISA assay is performed according to the manufacturer's instructions (ROCHE APPLIED SCIENCE, Cell Death Detection ELISA plus Kit). Contents of fragmented DNA in the retinas are measured to estimate the retinal-protective activity of the test compound.

Example 4

Electroretinographic (ERG) Study

ERG experiments are performed using 11-16 week old BALB/c mice of both genders (n=5). All studies involve the pharmacodynamic assessment of dark-adapted (scotopic, rod-dominated) and light-adapted (photopic, cone-dominated) ERG responses. Experiments are performed using test compound. All recording procedures are performed according to the same protocol and with the same equipment. Data are aggregated across individual studies to generate summary graphs.

Results from four independent studies are combined to build the dose-response function between administration of test compound and changes in the amplitude of the scotopic b-wave (0.01 cd·s/m$^2$), 4 hours after single oral administration of the test compound (dissolved in corn oil).

The effect on the cone system is estimated based on recording and measurement of the ERG b-wave intensity-response function under photopic conditions. In such studies, two parameters are typically evaluated: maximal response ($V_{max}$), measured in microvolts, and semi-saturation constant (k), measured in cd·s/m$^2$.

Results from three independent studies are combined to estimate the effect of single dosing of test compound on the photopic ERG (11-16 week old BALB/c mice of both genders, n=5).

III. Preparation of Dosage Forms

Example 1

Parenteral Composition

To prepare a parenteral pharmaceutical composition suitable for administration by injection, 100 mg of a water-soluble salt of a compound of Formula (A) is dissolved in sterile water and then mixed with 10 mL of 0.9% sterile saline. The mixture is incorporated into a dosage unit form suitable for administration by injection.

Example 2

Oral Composition

To prepare a pharmaceutical composition for oral delivery, 100 mg of a compound of Formula (A) is mixed with 750 mg of starch. The mixture is incorporated into an oral dosage unit, such as a hard gelatin capsule, which is suitable for oral administration.

Example 3

Sublingual (Hard Lozenge) Composition

To prepare a pharmaceutical composition for buccal delivery, such as a hard lozenge, combine 100 mg of a compound of Formula (A) with 420 mg of powdered sugar, 1.6 mL of light corn syrup, 2.4 mL distilled water, and 0.42 mL mint extract. The mixture is gently blended and poured into a mold to form a lozenge suitable for buccal administration.

Example 4

Fast-Disintegrating Sublingual Tablet

A fast-disintegrating sublingual tablet is prepared by mixing 48.5% by weigh of a compound of Formula (A), 44.5% by weight of microcrystalline cellulose (KG-802), 5% by weight of low-substituted hydroxypropyl cellulose (50 μm), and 2% by weight of magnesium stearate. Tablets are prepared by direct compression (AAPS PharmSciTech. 2006; 7(2):E41). The total weight of the compressed tablets is maintained at 150 mg. The formulation is prepared by mixing the amount of compound of Formula (A) with the total quantity of microcrystalline cellulose (MCC) and two-thirds of the quantity of low-substituted hydroxypropyl cellulose (L-HPC) by using a three dimensional manual mixer (Lnversina®, Bioengineering AG, Switzerland) for 4.5 minutes. All of the magnesium stearate (MS) and the remaining one-third of the quantity of L-HPC are added 30 seconds before the end of mixing.

Example 5

Inhalation Composition

To prepare a pharmaceutical composition for inhalation delivery, 20 mg of a compound of Formula (A) is mixed with 50 mg of anhydrous citric acid and 100 mL of 0.9% sodium chloride solution. The mixture is incorporated into an inhalation delivery unit, such as a nebulizer, which is suitable for inhalation administration.

Example 6

Rectal Gel Composition

To prepare a pharmaceutical composition for rectal delivery, 100 mg of a compound of Formula (A) is mixed with 2.5 g of methylcelluose (1500 mPa), 100 mg of methylparaben, 5 g of glycerin and 100 mL of purified water. The resulting gel mixture is then incorporated into rectal delivery units, such as syringes, which are suitable for rectal administration.

Example 7

Topical Gel Composition

To prepare a pharmaceutical topical gel composition, 100 mg of a compound of Formula (A) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 8

Ophthalmic Solution Composition

To prepare a pharmaceutical opthalmic solution composition, 100 mg of a compound of Formula (A) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 9

Nasal Spray Solution

To prepare a pharmaceutical nasal spray solution, 10 g of a compound of Formula (A) is mixed with 30 mL of a 0.05M phosphate buffer solution (pH 4.4). The solution is placed in a nasal administrator designed to deliver 100 μl of spray for each application.

VI. Clinical Trial

Example 1

Phase 1A Study of Safety and Pharmacodynamics Effect

A single-center, randomized, double masked, placebo controlled, dose-escalating Phase 1A study to determine the safety and pharmacodynamic effect of single oral dose of a compound of Formula (A) such as 3-amino-1-(6-(2-cyclohexylethyl)pyridin-2-yl)propan-1-ol (example 4), measured by dark-adapted electroretinogram (ERG), is performed. Study participants are healthy volunteers of both genders, aged 55-80, weighing between 50 and 110 kg. Major exclusion criteria include other ocular conditions (e.g. cataracts, glaucoma, uveitis, diabetic retinopathy, active conjunctivitis), change in prescription chronic medications within the preceeding 28 days, treatment with a retinoid compound within the last year, treatment with sildenafil citrate, tadalafil, or vardenafil citrate within the last week, or concomitant treatment with hypnotics, anti-depressants, psychoactive substances, digitalis glycosides, L-DOPA, chloroquine, hydroxychloroquine, systemic corticosteroids, topical anti-glaucoma medications, or medications for the treatment of wet AMD. Eight cohorts are randomized 5:1/drug:placebo and assigned to dosage cohorts of 2 mg, 7 mg, 10 mg, 20 mg, 40 mg, 60 mg, and 75 mg. Plasma concentration versus time is determined. Peak plasma concentrations ($C_{max}$), time of peak plasma concentration ($T_{max}$) and mean terminal elimination half-life ($t_{1/2}$) will be determined across all doses.

ERG studies are performed prior to dosing, 4-6 hours post-dose (Day 1 ERG), 24 hours post-dose (Day 2 ERG), Day 4, and on Day 7. For patients given placebo, the ERG readout will be monitored for a rapid rise in amplitude such that the response is 90% recovered by about 20 minutes. For patients given a test compound of Formula (A) such as such as 3-amino-1-(6-(2-cyclohexylethyl)pyridin-2-yl)propan-1-ol (example 4), the ERG readout will be monitored for a clear dose-related slowing of the rate of recovery; i.e. the slope of the recovery function became slower with increasing dose.

Example 2

Treatment of Dry-Form Age Related Macular Degeneration

An individual diagnosed with dry-form age related macular degeneration is treated with an oral dose of 5 mg of the test compound of Formula (A) such as 3-amino-1-(6-(2-cyclohexylethyl)pyridin-2-yl)propan-1-ol (example 4). On days 2, 4, 6, 8, 12, 18, 24 and 30 the individual is subjected to an electroretinogram determination to evaluate treatment response and the individual is monitored for instances of delayed dark adaptation and achromatopsia, as well as systemic adverse effects.

When ranges are used herein for physical properties, such as molecular weight, or chemical properties, such as chemical formulae, all combinations and subcombinations of ranges and specific embodiments therein are intended to be included.

The various embodiments described herein can be combined to provide further embodiments. All U.S. patents, U.S. patent application publications, U.S. patent applications, foreign patents, foreign patent applications, and non-patent publications referred to in this specification and/or listed in the Application Data Sheet, are incorporated herein by reference in their entireties.

From the foregoing it will be appreciated that, although specific embodiments have been described herein for purposes of illustration, various modifications may be made. Those skilled in the art will recognize, or be able to ascertain, using no more than routine experimentation, many equivalents to the specific embodiments described herein. Such equivalents are intended to be encompassed by the following claims. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. A compound of Formula (A) or tautomer, stereoisomer, geometric isomer or a pharmaceutically acceptable salt, or N-oxide thereof:

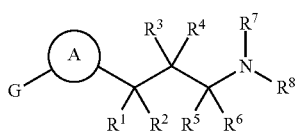

Formula (A)

wherein,
Ring A is a 1,3-disubstituted pyridine selected from the group consisting of:

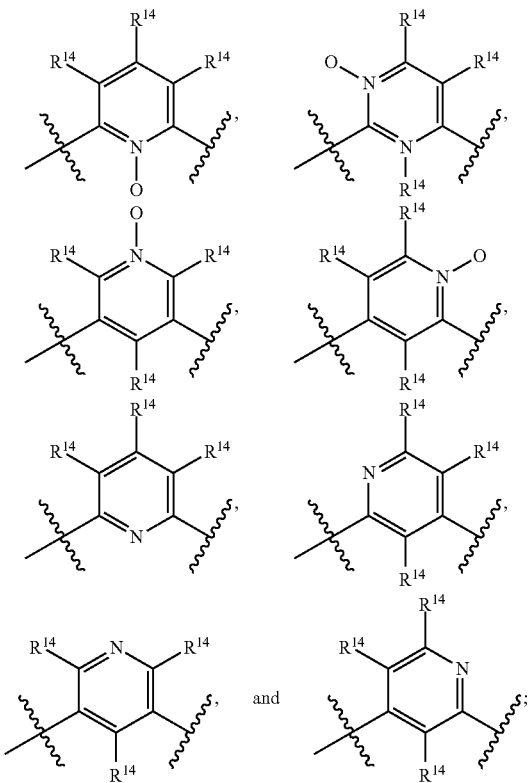

each $R^{14}$ is independently selected from hydrogen, halogen, $OR^9$, alkyl, or fluoroalkyl;
G is —X—Y;
X is selected from —C($R^9$)$_2$—C($R^9$)$_2$—, —C($R^9$)=C($R^9$)—, —C≡C—, and —C($R^9$)$_2$—O—;
Y is selected from:
  $C_3$-$C_{15}$ alkyl optionally substituted with a substituent chosen from halo, hydroxy, alkoxy, or fluoroalkyl;
  $C_3$-$C_{10}$ carbocyclyl optionally substituted with a substituent chosen from halo, hydroxy, alkyl, alkoxy, or fluoroalkyl;
  carbocyclylalkyl optionally substituted with a substituent chosen from halo, hydroxy, alkyl, alkoxy, or fluoroalkyl;
  aryl optionally substituted with a substituent chosen from halo, hydroxy, alkyl, alkoxy, or fluoroalkyl; or
  aralkyl optionally substituted with a substituent chosen from halo, hydroxy, alkyl, alkoxy, or fluoroalkyl;
$R^1$ and $R^2$ are each independently selected from hydrogen, or —$OR^9$; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;
$R^3$ and $R^4$ are hydrogen;
$R^5$ and $R^6$ are hydrogen;
$R^7$ and $R^8$ are each independently selected from hydrogen, $C_1$-$C_3$ alkyl, or —C(=O)$R^{13}$;
$R^9$ is hydrogen;
$R^{13}$ is $C_1$-$C_3$ alkyl.

2. The compound of claim 1, or a pharmaceutically acceptable salt or N-oxide thereof, wherein Ring A is selected from:

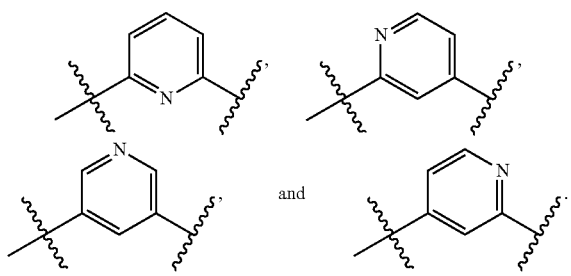

3. The compound of claim 1, or a pharmaceutically acceptable salt or N-oxide thereof, wherein Ring A is selected from:

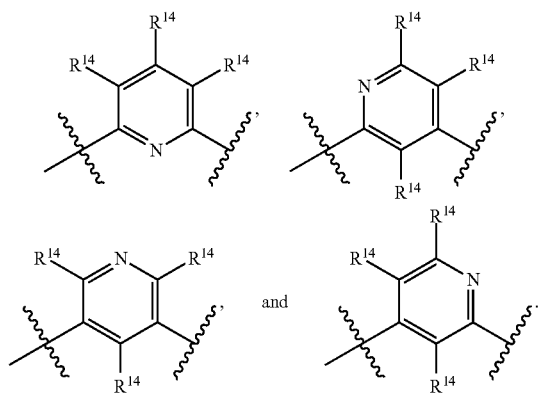

4. The compound of claim 1, or a pharmaceutically acceptable salt or N-oxide thereof, wherein Y is a $C_3$-$C_{15}$ alkyl optionally substituted with a substituent chosen from halo, hydroxy, alkoxy, or fluoroalkyl, or a $C_3$-$C_{10}$ carbocyclyl optionally substituted with a substituent chosen from halo, hydroxy, alkyl, alkoxy, or fluoroalkyl.

5. The compound of claim 4, or a pharmaceutically acceptable salt or N-oxide thereof, wherein Y is an optionally substituted $C_3$-$C_{15}$ alkyl having the formula: —C($R^{16}$)($R^{17}$)($R^{18}$); wherein $R^{16}$ and $R^{17}$ are each independently selected from hydrogen, $C_1$-$C_5$ alkyl, halo or fluoroalkyl; and $R^{18}$ is selected from a hydrogen, alkyl, alkoxy, hydroxy, halo, or fluoroalkyl.

6. The compound of claim 4, or a pharmaceutically acceptable salt or N-oxide thereof, wherein Y is an optionally substituted $C_3$-$C_{10}$ carbocyclyl having the formula: —C($R^{16}$)($R^{17}$)($R^{18}$); wherein $R^{16}$ and $R^{17}$ are each independently $C_1$-$C_5$ alkyl and $R^{16}$ and $R^{17}$ together with the carbon to which they are attached form a carbocyclyl; and $R^{18}$ is selected from a hydrogen, alkyl, alkoxy, hydroxy, halo, or fluoroalkyl.

7. The compound of claim 6, or a pharmaceutically acceptable salt or N-oxide thereof, wherein $R^{16}$ and $R^{17}$, together with the carbon to which they are attached, form a cyclobutyl, cyclopentyl, cyclohexyl, cycloheptyl, or cyclooctyl, and $R^{18}$ is hydrogen or hydroxy.

8. The compound of claim 7, or a pharmaceutically acceptable salt or N-oxide thereof, wherein $R^{16}$ and $R^{17}$, together with the carbon to which they are attached, form a cyclopentyl, cyclohexyl, or cycloheptyl, and $R^{18}$ is hydrogen or hydroxy.

9. The compound of claim 5, or a pharmaceutically acceptable salt or N-oxide thereof, wherein $R^{16}$ and $R^{17}$ is independently selected from $C_1$-$C_5$ alkyl; and $R^{18}$ is hydrogen, hydroxy or alkoxy.

10. The compound of claim 1, or a pharmaceutically acceptable salt or N-oxide thereof, wherein X is selected from —C($R^9$)$_2$—C($R^9$)$_2$—, or —C($R^9$)$_2$—O—.

11. The compound of claim 1, or a pharmaceutically acceptable salt or N-oxide thereof, wherein $R^1$ and $R^2$ are both hydrogen.

12. The compound of claim 1, or a pharmaceutically acceptable salt or N-oxide thereof, wherein $R^1$ is hydrogen and $R^2$ is —OH.

13. The compound of claim 1, or a pharmaceutically acceptable salt or N-oxide thereof, wherein $R^1$ and $R^2$ together form an oxo.

14. The compound of claim 1, or a pharmaceutically acceptable salt or N-oxide thereof, wherein $R^7$ and $R^8$ are both hydrogen.

15. The compound of claim 1, or a pharmaceutically acceptable salt or N-oxide thereof, wherein $R^7$ is hydrogen and $R^8$ is —C(=O)$R^{13}$.

16. The compound of claim 15, or a pharmaceutically acceptable salt or N-oxide thereof, wherein $R^{13}$ is methyl.

17. A compound, or tautomer, stereoisomer, geometric isomer, or pharmaceutically acceptable salt, or N-oxide thereof, selected from the group consisting of:

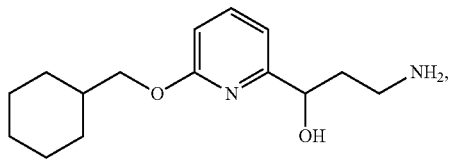

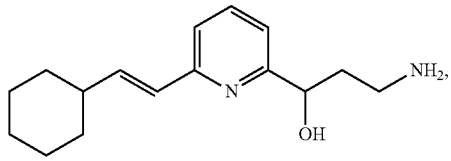

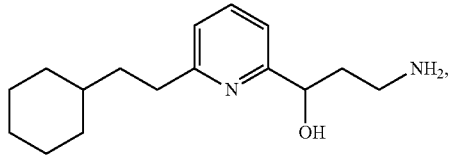

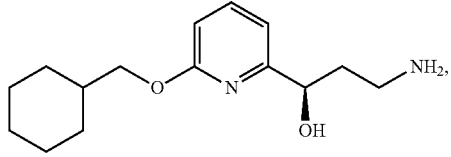

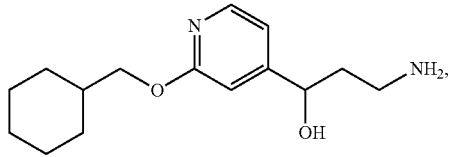

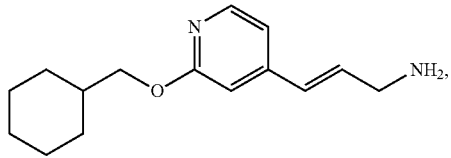

-continued
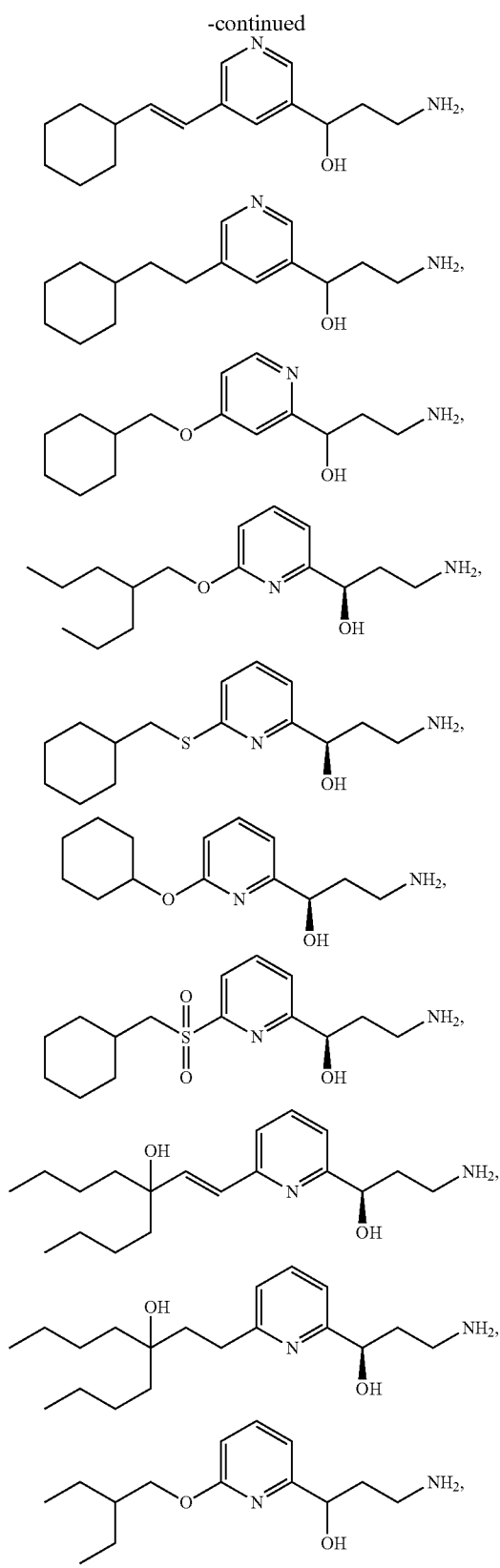
-continued
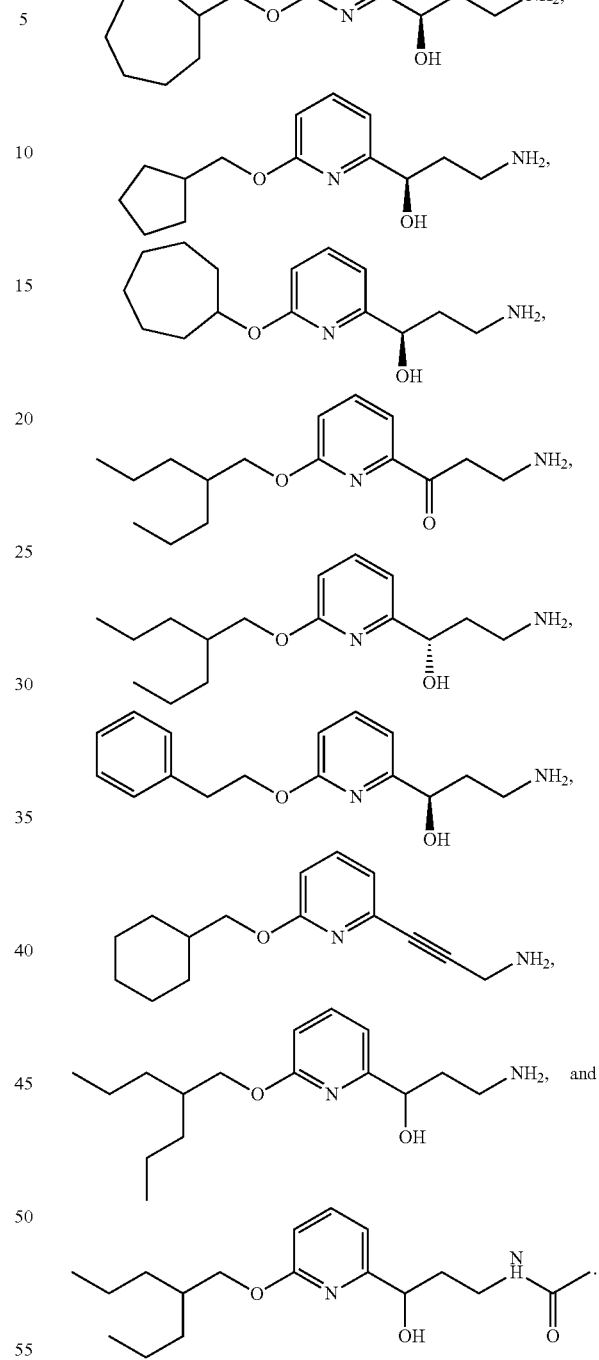
18. A pharmaceutical composition comprising a pharmaceutically acceptable carrier and a compound of Formula (A) as described in claim 1, or tautomer, stereoisomer, geometric isomer, or pharmaceutically acceptable salt, or N-oxide thereof.
* * * * *